US007811992B2

(12) United States Patent
Skinner et al.

(10) Patent No.: US 7,811,992 B2
(45) Date of Patent: Oct. 12, 2010

(54) ANTI-INFARCTION MOLECULES

(75) Inventors: James E. Skinner, Bangor, PA (US); Jerry M. Anchin, Deerfield Beach, FL (US)

(73) Assignee: Stasys Technologies, Inc., Boca Raton, FL (US)

( * ) Notice: Subject to any disclaimer, the term of this patent is extended or adjusted under 35 U.S.C. 154(b) by 959 days.

(21) Appl. No.: 10/359,363

(22) Filed: Feb. 5, 2003

(65) Prior Publication Data

US 2003/0228371 A1  Dec. 11, 2003

Related U.S. Application Data

(60) Provisional application No. 60/354,678, filed on Feb. 6, 2002, provisional application No. 60/392,133, filed on Jun. 28, 2002, provisional application No. 60/429,278, filed on Nov. 25, 2002.

(51) Int. Cl.
*A61K 38/10* (2006.01)
(52) U.S. Cl. ........................................ 514/13
(58) Field of Classification Search ....................... None
See application file for complete search history.

(56) References Cited

U.S. PATENT DOCUMENTS

| 4,187,217 | A  | 2/1980  | Chipens et al. |
| 5,648,331 | A  | 7/1997  | Koudsi et al. |
| 5,767,269 | A  | 6/1998  | Hirsh et al. |
| 6,294,519 | B1 | 9/2001  | Oeltgen et al. ............. 514/16 |
| 6,815,425 | B1 | 11/2004 | Meyerhoff et al. |

FOREIGN PATENT DOCUMENTS

| WO | WO 99/56766 | 11/1999 |
| WO | WO 99/56767 | 11/1999 |

OTHER PUBLICATIONS

Channabasavaiah, K., et al. "Fibrinopeptides. IV. Synthesis of human fibrinopeptide A." Int. J. Pept. Pro. Res. 1976, 8(3), 323-9.*
Scherer R., et al. "The effect of fibrinopeptides A and B on experimental allergic encephalomyelitis." Clin. Exp. Immunol. 1980, 40, 49-59.*
Miller, B.A., et al. "Cerebral protection by hypoxic preconditioning in a murine model of focal ischemia-reperfusion." Neurophys. Bas. Clin. 2001, 12(8), 1663-9.*
Smith, P. "Oral anticoagulants are effective long term after acute myocardial infarction." J. Int. Med. 1999, 245, 383-387.*
Ginalski et al. "Practical lessons from protein structure prediction." Nuc. Ac. Res., 2005, 33, 1874-1891.*
Rudinger "Characteristic of the amino acids as components of a peptide hormone sequence." (Peptide Hormones (Ed. J.A. Parson). University Park Press. Baltimore, 1976, pp. 1-7.*
Pitt et al. "Single amino acid substitution mutants of Klebsiella pneumoniae singma54 defective in transcription" Nuc. Ac. Res., 2000, 28, 4419-4427.*
Bradley et al. "Limits of Cooperativity in a Structurally Modular Protein: Response of the Notch Ankyrin Domain to Analogous Alanine Subsitutions in Each Repeat" J. Mol. Biol., 2002, 324, 373-386.*
Flanagan et al. "Truncated staphyloccal nuclease is compact but disordered" Proc. Natl. Acad. Sci. USA, 1992, 89, 748-752.*
Sawai et al. "Impact of single-residue mutations on the structure and function of ovispirin/novispirin antimicrobial peptides" Prot. Engin., 2002, 15, 225-232.*
Schnog et al. "Sickle cell disease; a general overview" J. Med., 2004, 62, 364-374.*
Becker "Anticoagulation and the Heart," J. Thrombosis and Thrombolysis, 2001, 12, 41-52.*
Aarts et al. Treatment of Ischemic Brain Damage by Perturbing NMDA Receptor-PSD-95 Protein Interactions. *Science* 298:846-850 (2002).
Andrews et al. Low-temperature carbon utilization is regulated by novel gene activity in the heart of a hibernating mammal. *PNAS* 95:8392-8397 (1998).
Ayaka et al. Molecular Mapping of Thrombin-Receptor Interactions. *Proteins: Structure, Function and Genetics* 45:107-116 (2001).
Bitting et al. C-fos MRNA increases in the ground squirrel suprachiasmatic nucleus during arousal from hibernation. *Neurosci Lett*, 165:117-21 (1994).
Bolli R. The late phase of preconditioning. *Circ Res* 87(11):972-83 (2000).
Bolling et al. Hibernation triggers and myocardial protection. *Circulation* 98(19 Suppl):II220-3; discussion II223-4 (Nov. 10, 1998).
Bolling et al. Use of "natural" hibernation induction triggers for myocardial protection. *Ann Thorac Surg* 64(3):623-7 (Sep. 1997).
Bruce et al. Circannual variations in bear plasma albumin and its opiod-like effects on guinea pig ileum. *Pharmacol Biochem Behav* 53:885-9 (1996).
Bruce et al. Is the Polar Bear (*Ursus maritimus*) a Hibernator?: Continued Studies on Opioids and Hibernation. *Pharmacol Biochem Behav* 35:705-711 (1990).
Bruce et al. Suppression of guinea pig ileum induced contractility by plasma albumin of hibernators. *Pharmacol Biochem Behav* Sep;43(1):199-203 (1992).
Cantwell and Di Cera, Rational Design of a Potent Anticoagulant Thrombin. *J. of Biol. Chem.* 275(51):39827-39830 (Dec. 2000).
Chen et al. The protective effect of ceramide in immature rat brain hypoxia-ischemia involves up-regulation of bcl-s and reduction of TUNEL-positive cells. J Cereb Blood Flow Metaqb 21:34-40 (2001).
Chien et al. Extension of tissue survival time in multiorgan block preparation with a delta opioid DADLE ([D-Ala$^2$, D-Leu$^5$]-enkephalin) *J Thorac Cardiovasc Surg* Mar;107(3):964-7 (1994).
Chien et al. Two-day preservation of major organs with autoperfusion multiorgan preparation and hibernation induction trigger. *J. Thorac Cardiovascular Surg* 102:224-34 (1991).
Cooper HA and Braunwald E., Clinical importance of stunned and hibernating myocardium. *Coron Artery Dis* 12:387-92 (2001).

(Continued)

*Primary Examiner*—Christina Bradley
(74) *Attorney, Agent, or Firm*—Arnall Golden Gregory LLP; David E. Huizenga

(57) ABSTRACT

Disclosed are compositions and methods for treating ischemia and molecules related to hibernation states. FPA molecules having the sequence set forth in SEQ ID NO: 2 can be used for as anti-infarction agents.

14 Claims, 18 Drawing Sheets

OTHER PUBLICATIONS

Cote et al. Hemostatic markers in patients at risk of cerebral ischemia. *Stroke* 31(8):1856-62 (Aug. 2000).

Cui et al. In vivo microdialysis study on changes in septal dynorphin and beta-endorphin activities in active and hibernating Columbian ground squirrels. *Brain Res* 710:271-1 (1996).

Dawson et al. Cerebrovascular hemodynamics and ischemic tolerance: lipopolysaccharide-induced resistance to focal cerebral ischemia is not due to changes in severity of the initial ischemic insult, but is associated with preservation of microvascular perfusion. *J Cereb Blood Flow Metab* 6:616-23 (1999).

Di Cera et al. The Na+ Binding Site of Thrombin. *J. Of Biol. Chem.* 270(38):22089-22092 (Sep. 1995).

Diener et al. Lubeluzole in Acute Ischemic Stroke Treatment A Double-Blind study with an 8-Hour Inclusion Window Comparing a 10-mg Daily Dos of Lubeluzole with Placebo. *Stroke* 2543-2551 (Nov. 2000).

Fallavollita et al. Stability f Hibernating Myocardium in Pigs with a Chronic Left Anterior Descending Coronary Artery Stenosis: Absence of Progressive Fibrosis in the Setting of Stable Reductions in Flow, Function and Coronary Flow Reserve. *J. of the Amer. College of Cardiology* 37(7):1989-1995 (Jun. 2001).

Fassbender et al. Changes in coagulation and fibrinolysis markers in acute ischemic stroke treated with recombinant tissue plasminogen activator. *Stroke* 30(10):2101-4 (Oct. 1999).

Ford et al. Angiotensin II reduces infarct size and has no effect on post-ischemic contractile dysfunction in isolated rat hearts *Br. J. Pharmacol.* 134(1):38-45 (2001).

Ford et al. Characterization of cardioprotection mediated by AT2 receptor antagonism after ischemia-reperfusion in isolated working rat hearts *J. Cardiovasc. Pharmacol. Ther.* 5(3):211-21 (2000).

Ford et al. Opposite effects of angiotensin AT1 and AT2 receptor antagonists on recovery of mechanical function after ischemia-reperfusion in isolated working rat hearts *Circulation* 94(12):3087-9 (1996).

Frerichs et al. Local cerebral blood flow during hibernation, a model of natural tolerance to "cerebral ischemia". *J Cereb Blood Flow Metab* 14:193-205 (1994).

Furuya et al. Cell permeable exogenous ceramide reduces infarct size in spontaneously hypertensive rats supporting in vitro studies that have implicated ceramide in induction of tolerance to ischemia. *J Cereb Blood Flow Metab* 3:226-32 (2001).

Furuya et al. Examination of Several Potential Mechanisms for the Negative Outcome in a Clinical Stroke Trial of Enlimomab, a Murine Anti-Human Intercellular Adhesion Molecule-1 Antibody: A Bedside-to-Bench Study. *Stroke* 32(11):2665-74 (Nov. 2001).

Futterman LG and Lemberg L., Hibernating myocardium, stunning, ischemic preconditioning: clinical relevance. *Am J Crit Care* 9:430-6 (2000).

Ginis et al. TNF-alpha pretreatment prevents subsequent activation of cultured brain cells with TNF-alpha and hypoxia via ceramide. *Am J Physiol*, 276:C1171-83 (1999).

Gorham et al. Hibernation induces expression of moesin in intestinal epithelial cells. *Cryobiology* 37:146-54 (1998).

Grotta J; The Combination Therapy Stroke Trial Investigators. Combination Therapy Stroke Trial: recombinant tissue-type plasminogen activator with/without lubeluzole. *Cerebrovasc Dis* 12:258-63 (2001).

Hashimi et al. Loss of myocardial protection from ischemic preconditioning following chronic exposure to R(-)-N6-(2-phenylisopropyl)adenosine is related to defect at the adenosine A1 receptor. *Mol Cell Biochem* 186:19-25 (1998).

Horton et al. Biochemical characterisation of a hibernation-specific 88 kDa protein derived from the plasma of deeply hibernating woodchucks. *Adaptations to the Cold: Tenth International Hibernation Symposium*, edited by Geiser F., Hulbert & Nicol. University of New England Press, Armidale (1996).

Horton et al. Isolation and partial characterization of an opioid-like 88 kDa hibernation-related protein. *Comp Biochem Physiol B Biochem Mol Biol* 119(4)787-805 (Apr. 1998).

Kim et al. A novel mechanism for myocardial stunning involving impaired Ca(2+) handling. *Circ Res* 26;89:831-7 (Oct. 2001).

Koinig et al. Lubeluzole inhibits accumulation of extracellular glutamate in the hippocampus during transient global cerebral ischemia. *Brain Research* 898:297-302 (2001).

Lesage et al. A novel long-term neuroprotectant, inhibits the glutamate-activated nitric oxide synthase pathway. *J Pharmacol Exp Ther*, 279:759-66 (1996).

Malkowski, M. G. et al. Crystal structure of fibrinogen-Aα peptide 1-23 (F8Y) bound to bovine thrombin explains why the mutation of Phe-8 to tyrosine strongly inhibits normal cleavage at Arg-16. *Biochem J* 326:815-822 (1997).

Martin, P. D. et al. "Bovine Thrombin Complexed with an Uncleavable analog of residues 7-19 of Fibrinogen Aα: GEmoetry of the catalytic triad and interactions of the P1', P2'. And P3' substrate residues." *Biochemistry* 35:13030-13039 (1996).

Martin, P. D. et al. The Structure of Residues 7-16 of the Aα-Chain of Human Fibrinogen Bound to Bovine Thrombin at 2.3-Å Resolution. *J Biol Chem* 267(11):7911-7920 (1992).

Maurer et al. Structural examination of the influence of phosphorylation on the binding of fibrinopeptide A to bovine thrombin. *Biochemistry* 37(17):5888-902 (Apr. 28, 1998).

Michaelis EK. Molecular biology of glutamate receptors in the central nervous system and their role in excitotoxicity, oxidative stress and aging. *Prog Neurobiol* 54(4):369-15 (1998).

Minnema et al. Activation of clotting factors XI and IX in patients with acute myocardial infarction. *Arterioscler Thromb Vasc Biol* 20(11):2489-93 (Nov. 2000).

Nejime et al. Habutobin recognizes Thr(7) in the sequence of fibrinopeptide A of rabbit fibrinogen. *Toxicon* 38(8):1029-41 (Aug. 2000).

Nelson et al. Ratio of serum urea to serum creatinine in wild black bears. *Science* 226(4676):841-2 (1984).

Noonan, Groundhog Mortality. Wildlife Control Technology. (Sep. 1-2, 2000). www.wctech.com/hbt.htm, 2000.

O'Hara et al. Gene expression in the brain across the hibernation cycle. *J Neurosci* 19:3781-90 (1999).

Oeltgen et al. Extended lung preservation with the use of hibernation trigger factors. *Ann Thorac Surg* 61(5):1488-93 (May 1996).

Ottani and Galvani Prognostic role of hemostatic markers in acute coronary syndromes patients. *Clin Chim Acta* 311(1):33-9 (Sep. 15, 2001).

Plata-Salaman et al. "Modulation of feeding by $\beta_2$-microglobulin, a marker of immune activation," *Am. J. Physio.* 268:R1513-1519(1995).

Que et al. Transient up-regulation of $\gamma$-aminobutyric acid$_A$ receptor binding by lubeluzole after neocortical specify lesion in rats. *Neurosci. Letters* 296:125-128 (2000).

Reganon et al. Elevated high molecular weight fibrinogen in plasma is predictive of coronary ischemic events after acute myocardial infarction. *Thromb Haemost* 82(5):1403-5. (Nov. 1999).

Reganon et al. Studies on the functionality of newly synthesized fibrinogen after treatment of acute myocardial infarction with streptokinase, increase in the rate of fibrinopeptide release. *Thromb Haemost* 70(6):978-83 (Dec. 20, 1993).

Rose and Di Dera, Three-dimensional Modeling of Thrombin-Fibrinogen Interaction. *J. of Biol. Chem.* 277(21):28875-18880 (May 2002).

Schipke and Birkenkamp-Demtröder, Another view of myocardial hibernation. *Int'l J. of Cardiology* 79:13-17 (2001).

Skinner et al. Higher cerebral regulation of cardiovascular and respiratory function. *Principles and Practice of Sleep Medicine*. Edited by M. H. Kryger, T. Roth, and W. C. Dement. W. B. Saunders Co., Chapter 27, pp. 276-293, 1989.

Skinner et al. Sleepstage regulation of ventricular arrhythmias in the unanesthetized pig. *Circ. Res.*, 37: 342_349, 1975.

Skinner, The regulation of cardiac vulnerability by the cerebral defense system. *J. Amer. Coll. Cardiol.* 5:88B94B (1985).

Skinner, Reduction of cardiac vulnerability during REM sleep in the pig. In: Sleep Disorders, *Basic and Clinical Research*, edited by M. Chase and E. D. Weitzman. New York: Spectrum Publications 49-63 (1983).

Skordalakes et al. Inhibition of Human α-Thrombin by a Phosphonate Tripeptide Proceeds *via* a Metastable Pentacoordinated Phosphorus Intermediate. *J. Mol. Biol.* 311:549-555 (2001).

Sonel et al. Prospective study correlating fibrinopeptide A, troponin I, myoglobin, and myosin light chain levels with early and late ischemic events in consecutive patients presenting to the emergency department with chest pain. *Circulation* 102(10):1107-13 (Sep. 5, 2000).

Srere et al. Alpha 2-Macroglobulin gene expression during hibernation in ground squirrels is independent of acute phase response. *Am J Physiol* 268:R1507-12 (1995).

Srere et al. Central role for differential gene expression in mammalian hibernation *PNAS* 89:7119-7123, 1992.

Stubbs, et al. The interaction of thrombin with fibrinogen. A structural basis for its specificity. Eur J Biochem. May 15, 1992;206(1):187-95.

Takamatsu et al. Hibernation-associated gene regulation of plasma proteins with a collagen-like domain in mammalian hibernators. *Mol Cell Biol* 13:1516-21 (1993).

Xu et al. AT(1) and AT(2) receptor expression and blockade after acute ischemia-reperfusion in isolated working rat hearts *Am. J. Physiol. Heart Circ. Physiol.* 282(4):H206-15 (2002).

Yasuma et al. Effect of Hibernation Plasma on Monocyle Endothelial Cell Interactions. Abstract. *21st International Joint Conference on Stroke*.

Zito et al. Epidemiological and genetic associations of activated factor XII concentration with factor VII activity, fibrinopeptide A concentration, and risk of coronary heart disease in men. *Circulation* 102(17):2058-62 (Oct. 24, 2000).

Armaganian et al., "Role of tissue factor-mediated coagulation in ishchemia/reperfusion-induced injiru of Langendorf-perfused rabbit hearts," Coronary Artery Disease 11(6):481-487 (2000).

Carey, H. et al. "Hibernation Induces Oxidative Stress and Activation of NF-kappaB in Ground Squirrel Intestine" *J. Comp. Physiol. B* 170:551-559 (2000).

Kondo, Noriak and Kondo, Jun "Identification of Novel Blood Proteins Specific for Mammalian Hibernation" *J. Biol. Chem.* 267(1):473-478 (Jan. 1992).

Raeburn, Christopher et al. "Ischemic Preconditioning: Fact or Fantasy?" *J. Card Surg* 17:536-542 (2002).

Rubin, Lisa et al. "Protective Role of Bradykinin in Cardiac Anaphylaxis: Coronary-Vasodilating and Antiarrhytmic Activities Mediated by Autocrine/Paracrine Mechanisms" *Circulation Research* 76(3):434-440 (1995).

Examiner's Reoprt, New Zealand Patent Application No. 535025, Aug. 8, 2008.

Eng, "Exciting, radical, suicidal: How brain cells die after stroke," Stroke, 2005, 36:189-192.

Ebaldi et al., "Use of antiocoagulants in elderly patients: practical recommendations," Clinical Interventions in Aging, 2009, 4:165-177.

Undas et al., "Antithrombotic properties of aspirrin and resistance to aspirin: beyond strictly antiplatelet actions." Blood 2007, 109:2285-2292.

Markus et al., Dual antiplately therapy with Clopidogrel and aspirin in symptomatic carotid stenosis evaluated using doppler embolic signal detection: the Clopidogrel and aspirin for reduction of enboli in symptomatic carotid stenosis (CARESS) trial, Circulation, 2005, 111:2233-2240.

Peter Lipton, "Ischemic Cell death in brain neurons," 1999, 79:1431-1568.

VanDer Werf, et al., "Management of actue myocardial infacrtion in patients presentin with ST-segment elevation," The Task Force on the Management of Actue myocardial infarction of the European Society of Cardiology, 2003.

Thourani et al., "Nonanticoagulant heparin inhibits NF-kB activation and attenuates myocardial reperfusion injury," Am. J. Physiol. Heart Circ. Physiol, 2000 48:H2084-2093.

Saliba MJ., et al. , "Effects of heparin in large does on the extent of myocardial ischemia after acute coronary occlusion in the dog," 1976, Am. J. Cardiol. 37:599-604.

Adams et al., Review article: Coagulation cascade and therapeutics update: Relevance to nephrology. Part 1: Overview of coagulation, thrombophilias and history of anticoagulants. Nephrology, 14:462-470, (2009).

Mann et al. Thrombin Formation. Chest, 124:4S-10S, (2003).

Jesty et al. Positive Feedbacks of Coagulation—Their Role in Threshold Regulation. Arterioscler Thromb Vasc Biol 25:2463-2469, (2005).

Doolittle, R. F., Fibriniogen and Fibrin. Annu. Rev. Biochem. 53, 195-229; (1984).

Hermans, J. & McDonagh, Fibrin: Structure and Interactions. J. Semin. Thromb. Hemostasis 8, 11-24; (1982).

Bettelheim FR, The Clotting of Fibrinogen. Biochim Biophys Acta 19, 121-130, 1956.

Blomback B, Vestermark A., Isolation of fibrino-peptides by chromatography. Ark Kemi 12, 173-182, 1958.

Warkentin et al. Reversing anticoagulants both old and new. Can J Anesth 49:S11-S25, (2002).

\* cited by examiner

Products of m/z 452.7 $[M+2H]^{2+}$

RPPGFSPF

Products of m/z 473.7 [M+2H+1 acetylation]$^{2+}$

**\*RPPGFSPF**

ANTI-INFARCTION MOLECULES

This application claims priority to U.S. Provisional Application Ser. No. 60/354,678 filed on Feb. 6, 2002, U.S. Provisional Application Ser. No. 60/392,133 filed on Jun. 28, 2002 and U.S. Provisional Application Ser. No. 60/429,278 filed on Nov. 25, 2002. The U.S. Ser. Nos. 60/354,678, 60/392,133 and 60/429,278 provisional applications are all herein incorporated by this reference in their entirety.

I. BACKGROUND

Many small and medium-sized mammals in north-temperate regions enter a prolonged and controlled state of dormancy during the winter months when food is less available. True hibernators, such as ground squirrels, groundhogs, and mice, prepare for hibernation by building up large amount of body fat. Some, such as the groundhog, also lay in stores of food in their burrow. When animals go into hibernation, there are changes that take place in their physiology. Heart rates decrease, metabolism changes, and their ability to be aroused changes.

Disclosed herein are methods for assessing the state of hibernation of an animal, at various times during hibernation. Also disclosed herein is that hibernating animals are more likely to survive waking events early in hibernation and late in hibernation, than during mid-hibernation. In addition, it is disclosed that plasma fractions obtained from the early state of hibernating animals, but not the mid state of hibernating animals contains molecules that affect ischemia in a rat model, and which can be used in the treatment of ischemia. Furthermore, it is shown herein that these molecules include FPA and its derivatives as well as Bradykinin and its derivatives.

II. SUMMARY

Disclosed are compositions and methods that in one respect relate to state dependent methods for identifying molecules of interest. Also disclosed are compositions and methods that in one respect relate to molecules having anti-infarction and anti-ischemic properties.

It is to be understood that both the foregoing general description and the following detailed description are exemplary and explanatory only and are not restrictive of the invention, as claimed.

III. BRIEF DESCRIPTION OF THE DRAWINGS

The accompanying drawings, which are incorporated in and constitute a part of this specification, illustrate several embodiments and together with the description, serve to explain the principles.

FIG. 1 shows the effects of arousal during early and late-hibernation on the heartbeat dynamics and mortality in adult and juvenile woodchucks. The animals were aroused in mid-December and mid-January by outstretching the limbs for 8 minutes while the animal was on its back. This stimulus in mid-January resulted in severe bradycardia and complete arousal, which was associated with death within 6 to 12 hours in 4 of 4 subjects. The stimulus in mid-December did not lead to arousal, bradycardia, or death.

FIG. 2 shows identification of state-dependent proteins in D2 and NE2 fractions, as revealed in 2-dimensional SDS gels. The upper two panels show the proteins in State #1 (NE2) and in State #2 (D2, 02) with a State #1 overlay upper right). In the overlay only a very light epicenter is shown for each State #1 spot, leaving its surrounding grays to white as clear. The enlargement at the lower left shows the comparison of the State #2 with State #1 overlay in the 32 kDa region (box), and the enlargement at the lower right shows the same comparison in the 66 kDa region (box). Those State #2 spots without an associated overlay spot are thus State #2-dependent (oblique dotted line markers). One of the effects of these state-dependent pure proteins is seen in the stroke models of FIG. 1. The pI range was 4 to 7.

FIG. 3 shows an LC/MS/MS identification of spots, of interest (circled) that are specific to either State #1 NE2, or State #2 D2 materials. The spots of interest are located on 2-dimensional BATS gels. The BATS gels are less sensitive and quantitative than the 2D SDS gels (previous figure), as only 9 state-dependent spots are found at this 4-7 pI range (left lane pair is 4, right is 7).

FIG. 4 shows that the D2 specific molecule that prevents stroke. BATS comparisons of D2 bands with those of SA (a control) and NE2 (its nearest control) indicate three D2 specific molecules (circled). The upper three slices show the infarction volumes in the MCAO model in the mouse. Only tissue with functioning mitochondria take up the red (dark) TTC (2%) stain.

FIG. 5 shows a computerized comparison of state dependent 2D gels. The D2 gel is compared to its nearest control, NE2. CSF and urine gels (hibernation) are compared to their summer controls. Each of the 3 gel-pairs employed computerized spatial-alignment of the spots. The silver grain density of each spot was normalized to its own gel to compensate for concentration differences in the fluid volumes (i.e., Total protein in each gel is presumed to be constant). The difference between each spot-pair was then calculated. Spots that contained greater than 2-fold increases in State 2 (hibernation) are shown in green. Those slight increases in State2 spot density, which are thought to be due to concentration differences not compensated by the normalization procedure, are shown in filled dark. Those spots which showed a 2 fold or greater reduction in State 2 are shown in light. Those unchanged between the two states are shown in unfilled dark outlines.

FIG. 6 shows the effect of time of injection of D2 on cerebral infarction size in the mouse of middle cerebral artery occlusion. Pre-treatment with D2 at 2-Hrs prior to the 1-Hr of middle cerebral occlusion resulted in no to minimal infarction (vertical bars –SD). Progressively longer times of injection resulted in progressively larger infarction sizes, but the effect was non-linear. Treating D2 by dialysis in 8M-urea to dislodge the proteins from the albumin carrier and with a membrane cutoff of l0kDa to remove the peptides resulted in a significantly improved effect on infarction size with injection at 1 hr.

FIG. 7 shows fingerprinting of polypeptides below 10 kDa by LC/MS/MS. Eight molecules in the peptide range are identified to be altered during early-hibernation (D2) compared to late-hibernation (NE). One of these has been identified as Fibrinopeptide A. Of the eight, two are more abundant in late-hibernation (1310 and 2011).

FIG. 13 shows the effects on the recycling rate of blood urea in the rat produced by IV injections of D2 or D01 (20 mg/kg) or an albumin control (Xeno, 20 mg/kg). Each animal was injected at time zero with 1-mg of double-labeled urea (less than 1% of total urea). The presence of single-labeled urea above the native background level can only be explained by the cleavage of the two labeled nitrogens and their recycling back to form the additional single-labeled urea. The y-axis expresses for each rat, over time, how much single-labeled urea relative to unlabeled urea (% Mole Fraction) is present above the baseline of native single-labeled urea (Excess). At 3 to 6 hours after injection the mean difference between the D2 and D01 group and the Albumin group is statistically significant (P<0.025). No change occurred in mean arterial blood pressure following any of the injections.

Figure 14:
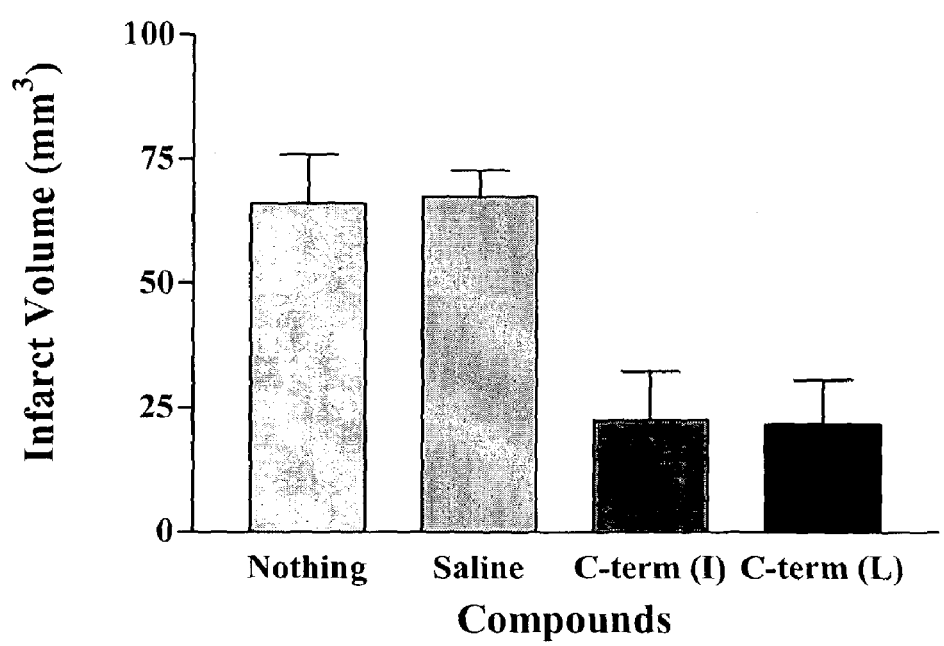
Figure 15:
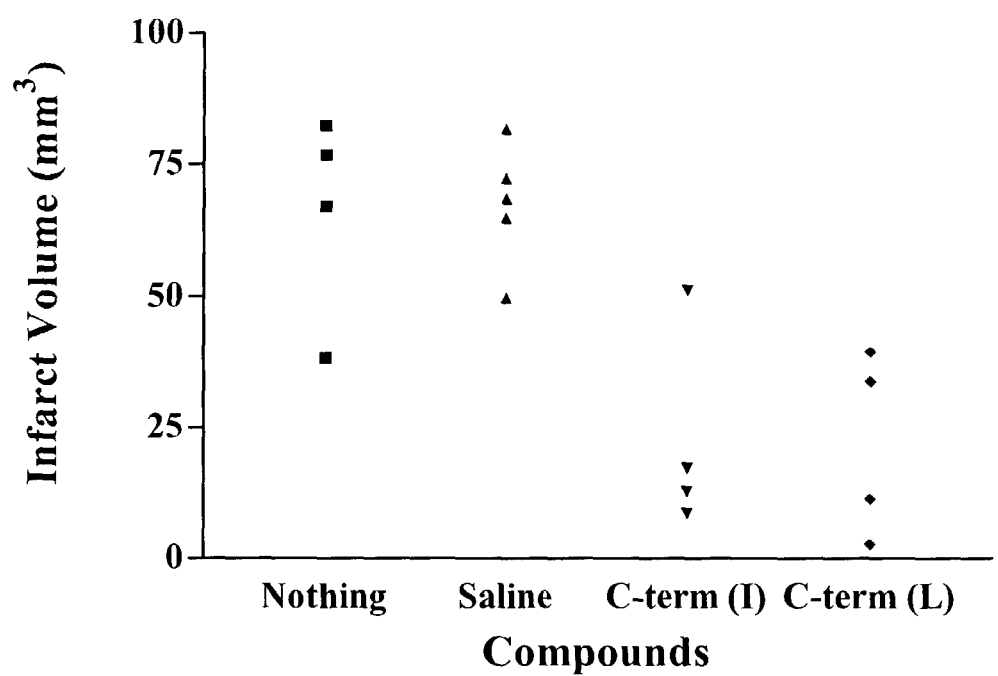

FIG. 14 shows the effect of C-terminal fragments of FPAw on infarct volumes in the mouse following transient ischemia. All mice were subjected to 1 hour of cerebral ischemia followed by 24 hours of reperfusion. Animals were injected with nothing, vehicle (saline) or C-terminal fragments of FPAw (at 10 mg/kg) intravenously at the end of ischemia. Animals were sacrificed on day 2 and processed to determine the infarct volume. p<0.02 for C-term (I) and C-term (L) compared to nothing, p<0.004 for C-term (I) compared to saline, and p<0.003 for C-term (L) compared to saline FIG. 15 shows the effect of C-terminal fragments of FPAw on infarct volumes in the mouse following transient ischemia. All mice were subjected to 1 hour of cerebral ischemia followed by 24 hours of reperfusion. Animals were injected with nothing, vehicle (saline) or C-terminal fragments of FPAw (at 10 mg/kg) intravenously at the end of ischemia. Animals were sacrificed on day 2 and processed to determine the infarct volume. Infarct volumes are listed as $mm^3$.

Figure 16:
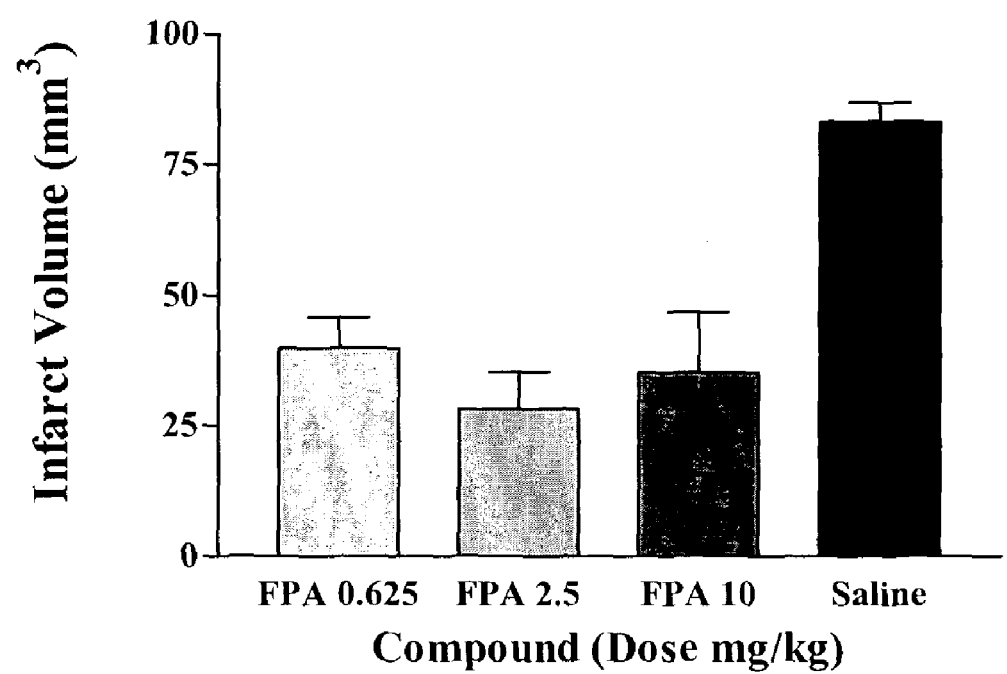

FIG. 16 shows the effect of FPA on infarct volumes in the mouse following transient ischemia. All mice were subjected to 1 hour of cerebral ischemia followed by 24 hours of reperfusion. Animals were injected with vehicle (saline) or FPA (0.625 mg/kg; 2.5 mg/kg; and 10 mg/kg) intravenously at the end of ischemia. Animals were sacrificed on day 2 and processed to determine the infarct volume. p<0.0001 for all values compared to control except for FPA 10, p<0.0047.

Figure 17:
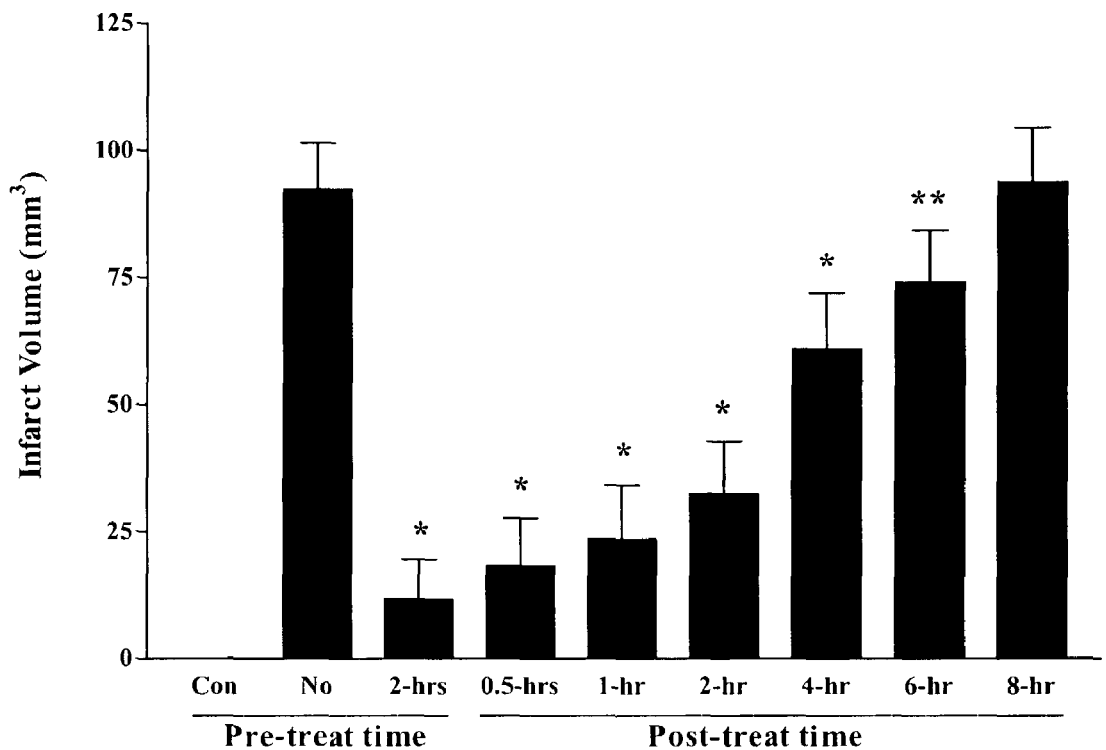

FIG. 17 shows the effect of D2 on infarct volumes in the mouse prior to and following transient ischemia. All mice were subjected to 1 hour of cerebral ischemia followed by 24 hours of reperfusion. Animals were injected with vehicle (saline) or D2 (at 5 mg/kg) intravenously prior to or at the end of ischemia. Animals were sacrificed on day 2 and processed to determine the infarct volume. Individual infarct volumes for each animal. Infarct volumes are listed as $mm^3$.

Figure 18:
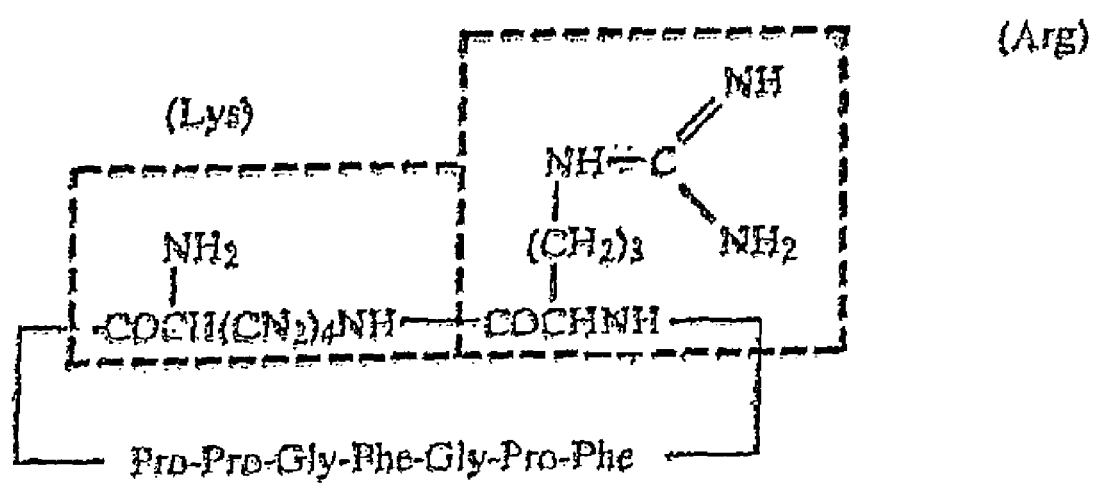

FIG. 18 shows the formula for cyclo [(N-ε-I-L-lysine, 6-glycine)-bradykinin], a cyclic bradykinin variant, where N-terminal bradykinin arginine is substituted by L-lysine and serine in position 6 of bradykinin is substituted by glycine. The cycle is closed with the peptide bond formed by the arginine carbonyl group and the ε-amino group of lysine.

IV. DETAILED DESCRIPTION

Before the present compounds, compositions, articles, devices, and/or methods are disclosed and described, it is to be understood that the compositions and methods are not limited to specific synthetic methods or specific recombinant biotechnology methods unless otherwise specified, or to particular reagents unless otherwise specified, as such may, of course, vary. It is also to be understood that the terminology used herein is for the purpose of describing particular embodiments only and is not intended to be limiting.

A. DEFINITIONS

Abbreviations: MCAO, Middle cerebral artery occlusion; TTC, triphenyltetrazolium chloride; I.V., Intravenous; FPAw, Fibrinopeptide A Woodchuck sequence; C-terminus (I), C-terminal fragment of FPA isoleucine position 4; and C-terminus (L), C-terminal fragment of FPA leucine position 4.

As used in the specification and the appended claims, the singular forms "a," "an" and "the" include plural referents unless the context clearly dictates otherwise. Thus, for example, reference to "a pharmaceutical carrier" includes mixtures of two or more such carriers, and the like.

Ranges can be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that when a value is disclosed that "less than or equal to" the value, "greater than or equal to the value" and possible ranges between values are also disclosed, as appropriately understood by the skilled artisan. For example, if the value "10" is disclosed the "less than or equal to 10" as well as "greater than or equal to 10" is also disclosed. It is also understood that the throughout the application, data is provided in a number of different formats, and that this data, represents endpoints and starting points, and ranges for any combination of the data points. For example, if a particular data point "10" and a particular data point 15 are disclosed, it is understood that greater than, greater than or equal to, less than, less than or equal to, and equal to 10 and 15 are considered disclosed as well as between 10 and 15.

Throughout this application, various publications are referenced. The disclosures of these publications in their entireties are hereby incorporated by reference into this application in order to more fully describe the state of the art. The references disclosed are also individually and specifically incorporated by reference herein for the material contained in them that is discussed in the sentence in which the reference is relied upon.

Disclosed are the components to be used to prepare the disclosed compositions as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds cannot be explicitly disclosed, each is specifically contemplated and described herein. For example, if a particular FPA is disclosed and discussed and a number of modifications that can be made to a number of molecules including the FPA are discussed, specifically contemplated is each and every combination and permutation of FPA and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the disclosed compositions. Thus, if there are a variety of additional steps that can be performed it is understood that each of these additional steps can be performed with any specific embodiment or combination of embodiments of the disclosed methods.

"Optional" or "optionally" means that the subsequently described event or circumstance can or cannot occur, and that the description includes instances where said event or circumstance occurs and instances where it does not.

"Primers" are a subset of probes which are capable of supporting some type of enzymatic manipulation and which can hybridize with a target nucleic acid such that the enzymatic manipulation can occur. A primer can be made from any combination of nucleotides or nucleotide derivatives or analogs available in the art, which do not interfere with the enzymatic manipulation.

"Probes" are molecules capable of interacting with a target nucleic acid, typically in a sequence specific manner, for example through hybridization. The hybridization of nucleic acids is well understood in the art and discussed herein. Typically a probe can be made from any combination of nucleotides or nucleotide derivatives or analogs available in the art.

B. COMPOSITIONS AND METHODS

Disclosed are compositions and methods related to ischemia, such as cardiac ischemia and cerebral ischemia. Disclosed are compositions and methods, which reduce the infarctions, which can occur due to ischemic events. There are over 600,000 new or recurrent strokes each year, with over 157,991 deaths in 1995 (1 of every 14.6 deaths). To date there are 4,000,000 stroke survivors and this number continues to grow. The origin of strokes is 80% ischemic and 20% hemorrhagic. Stroke is the third most common cause of death and the main cause of disability in the United States. The outcome and infarction size after focal cerebral ischemia is determined by both "necrotic" (paraptosis) cell death and by delayed neuronal cell loss in the borderzone of ischemia (programmed cell death or apoptosis). Recent therapies have emerged to treat ischemic stroke, however, these treatments are not sufficient.

Disclosed are state dependent methods for isolation of desired compounds. Also disclosed are methods for the state dependent isolation of compounds that have anti-infarction properties. Anti-infarction molecules have been identified in the blood of hibernating animals and have been isolated and disclosed herein.

Disclosed herein, it is understood that the high mortality of first year hibernators is connected to molecules having anti-infarction properties. There is a high mortality among first-year hibernators, up to 77% in a field study of woodchucks (Noonan, R. Groundhog Mortality. Wildlife Control Technology. (September): Jan. 2, 2000. www.wctech.com/hbt.htm, 2000). Up to 77% mortality in juveniles, 30% in adults (in the wild; mark and recapture data). The mortality rate for the adults, using mark and re-capture methods, is reported to be around 30%. The younger animals den later, awaken later, and those juveniles with lower body-weight are less likely to survive. Insufficient brown-fat storage (starvation) is often thought to be the mediating factor, but autopsies consistently show quite sufficient fat in these juvenile victims.

1. Substates of Hibernation

When mammals go into hibernation there are a number of physiological changes that must take place, both upon the onset of hibernation and as disclosed herein, constantly during hibernation as well. For example, the heart rate of hibernating animals must decrease, as well as a many other metabolic functions including cell replication. In addition, the urea cycle must be altered to prevent urea toxicity to the animal. Thus, there are relative differences between mammals in a state of hibernation vs. mammals not in a state of hibernation. Disclosed herein, there are also differences within the hibernation state of hibernating mammals. Disclosed are methods for assessing the molecular differences between states of hibernation, not just between a hibernating and non-hibernating state. For example, there are physiological differences and molecular differences between mammals that are in an early state of hibernation compared to a later one. The state (or substates) of hibernation can be characterized by physiology, endocrine secretion, or behavior, for example. An example of physiology is that of slowed heartbeats below the normal physiological range; an example of endocrine secretion is the relative elevation of Fibrinopeptide-A in the circulation; an example of behavior is complete evoked-arousal from a torporous condition with or without unexpected death.

The onset of hibernation can be defined as occurring when there is a reduction in the normal cardiovascular state of the animal. This reduction can be, for example, the point at which the heart rate of the animal remains at 80% or less its nonnal resting heart rate. In certain embodiments, the hibernation has begun when there is a statistically significant difference between the resting heart rate and the reduced heart rate, as opposed to reduction caused by sleep for example. A $p<0.05$ would be considered significant. At the onset of hibernation, typically the temperature of the animal also decreases and the animal curls up into a ball. Final arousal is characterized as the state that follows hibernation in which the animal stays aroused and does not return to late-hibernation. Final arousal can also be defined as the time at which the heart rate of a hibernating animal increases up to the normal heart rate for that animal after being in a state of hibernation. Typically, in the wild, animals begin to leave their den and forage for food at the time of final arousal.

It is understood that the onset of hibernation defines a point from which different animals can be normalized. It is disclosed that there is a difference between fractions of blood plasma taken at different times from within the hibernating state of a hibernating animal. Disclosed are substates that are obtained 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 45, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 days after the onset of hibernation. Disclosed are substates that are obtained 1, 2, 3, 4, 5, 6, 7, 8, 9, 10, 11, 12, 13, 14, 15, 16, 17, 18, 19, 20, 21, 22, 23, 24, 25, 26,27, 28, 29, 30, 31, 32, 33, 34, 35, 36, 37, 38, 39, 40, 41, 42, 43, 45, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 days before final arousal. It is understood that 1 day after the onset of hibernation can be considered a different substate of hibernation than 5 days after the onset of hibernation, which can be a different substate than 1 day before final arousal, for example. It is also understood that substates that comprise a range of days after the onset of hibernation are also disclosed. For example, a range of 1 day to 5 days after hibernation can be a different substate than the substate of 20 days to 25 days. For example, substates that contain increased levels of anti-infarction molecules are substates made up from 1-30 days, or 4-25 days or 10-20 days or 13-18 days after onset of hibernation and substates that contain decreased levels of anti-infarction molecules are substates made up from 30-60 days, or 35-55 days or 40-50 days or 43 to 48 days after the onset of hibernation. Also disclosed are substates that take place on a 14 day interval after the onset of hibernation, or on a 14 day interval from the first sample taken. For example, day 1, 14, 28, 42, 56, 70, 84, 98, and/or 112 or day 10, 24, 38, 52, 66, 80, 94, 108, and/or 122. Other disclosed substates are from hibernation onset to 1 second, 1 minute, 1 hour, 1 day, 1 week, 1 month, 2 months, 3 months, 4 months, 5 months, or 6 months after the onset of hibernation.

Early-hibernation can be defined as the time after the onset of hibernation but before mid-hibernation. Mid-hibernation can be defined as the time after early-hibernation and before late-hibernation. Late-hibernation can be defined as the time after mid-hibernation to final arousal.

Early-hibernation can be associated with the state in which when an animal is awoken from hibernation there is a decreased incidence of bradycardia, and death (typically no death). Early-hibernation is also associated with increased FPA and Bradykinin secretion (compared to the mid-hibernation). For example early-hibernation is typically a time when the cardiovascular dynamics reach a low point (e.g., heart rate is decreased to around 4 seconds per beat), and body temperature is reduced to approximately 35° C. to 40° C. Furthermore, as disclosed herein during early-hibernation there are molecules in circulation that, among other things, protect the animal from ischemia and induce urea recycling.

Mid-hibernation can be associated with the state in which when an animal is awoken from hibernation there is an increased incidence of bradycardia, and death. Mid-hibernation is also associated with decreased FPA and Bradykinin secretion (compared to the early-hibernation). Because both sub-states are temporally correlated and occur relative to each other and relative to the onset and ending of hibernation a date can also be associated with the collective term, mid-hibernation.

As shown herein, mid-hibernation is also typically associated with a hibernating animal conserving energy by reducing the number of molecules in circulation, including those that protect the animal from ischemia. There are very likely other regulatory molecules that stop being secreted, as well.

Late-hibernation can be seen as a state where there is an increase in anti-infarction molecules including FPA and Bradykinin relative to the amount of anti-infarction molecules during mid-hibernation, similar to early hibernation. It is understood that the various states of hibernation, early, mid, and late, for example, do not overlap within a given year, or hibernation cycle of a given animal, but they could overlap from a year to year basis. For example, in some years, hibernation can be very short, such that early-hibernation hibernation would be over in early December, and in other years, hibernation can be long, such that early-hibernation would end in late December. For example, early-hibernation can be seen as 15±15 days after onset; Mid as 45±15 days after onset, and Late=60±30 days after onset.

Different substates can also be defined by the number of days before the onset of hibernation. From 1 to 75 days before the onset of hibernation are disclosed. For example, appetite is typically suppressed, beginning in some animals in the wild as early as the first week in October, but generally observed in all animals in the wild in the few weeks of mid to late November before hibernation begins. This substate has not been shown to be associated with the Fibrinopeptide-A elevation or the arousal-evoked bradycardia. Similarly urea-recycling molecules are secreted early in hibernation, and are typically present from 1 to 21 days after onset, but cannot be secreted if metabolism is switched off and urea is not being formed. Thus hibernation is viewed as a collection of various physiological, chemical and behavioral sub-states that are temporally displayed as overlapping and non-overlapping sub-epochs.

In general by looking at physiological and behavioral events, that occur either spontaneously or are evoked by experimental means and take place at different times during hibernation, for example, such as arousal-evoked death, it is herein disclosed that different states, such as secretory states, can be described for plasma molecules. Once the different state is described, i.e. by time after hibernation onset, or for example, by assessing a physiological condition for each delineated state, then plasma or other types of tissue samples, such as muscle or neural tissue, can be acquired from the two different states, e.g., early-hibernation and mid-hibernation.

These tissue samples can then be compared using any technique: GC mass spec, fractionation, or gel chromatography. Differences in the molecular makeup of the tissue samples can then be assessed for various activities related to hibernation or to any other physiological characteristic. The molecule representing the differences can then be, for example, further purified, or synthetically produced, or further characterized.

Disclosed herein is the fact that hibernating animals, such as a woodchuck, undergo severe cardiovascular stress upon waking from hibernation. Hibernating animals, however, are able to handle this stress better during early and late-hibernation, for example, 1 to 30 days and 60 to 90 days after onset of hibernation, respectively, than they are during mid-hibernation, for example, 31 to 59 days after onset of hibernation. Using the techniques disclosed herein, molecules were found to be present in the early and late plasma of hibernating animals, such as woodchucks, which are capable of helping hibernating animals, such as woodchucks, as well as other animals, handle the stress of waking from a hibernating state. These molecules are present in lower quantities during mid-hibernation. Two such molecules are FPA and its derivatives and Bradykinin and its derivatives and functional variants of each.

It is also disclosed that these molecules are able to reduce infarctions when administered to animals that have undergone an arterial occlusion. These disclosed compositions thus can be administered to subjects who have undergone an event that precipitates an infarction, such as "stroke" or "heart attack."

Disclosed are methods for isolating proteins and peptides in a comparison of "state-dependent" fractions of molecules collected from hibernating animals. These small state-dependent differences in physiology are used to collect separate fractions of molecules that, when examined with proteomic methods (e.g., 2D SDS PAGE gel-electrophoresis, LC/MS/MS tandem mass spectroscopy, etc.), lead to both the isolation and identification of the relevant molecule underlying a major effect in one or another of the specific bio-assay models that can be related to hibernation physiologies and models.

Disclosed are models, wherein the model is a model of stroke, such as a model in a rodent, in which occlusion of the middle cerebral artery for one hour is followed by reflow and later examination of infarction size by using triphenly tetrazolium chloride staining of the remaining viable tissue (TTC, 1%). The variants of such stroke models include partial or permanent occlusion of any cerebral artery and all mammalian species, although rodent models are commonplace to conserve testing materials. Many compounds have been tested in this model under a variety of rationales (e.g., one or another of a variety of glutamate receptor inhibitors, tumor necrosis factor inhibitors, etc.).

Disclosed herein, hibernation is analogous to sleep in that it is comprised of subtle sub-states. For example, sleep can be divided into two states, synchronized and non-synchronized EEG states. Further investigation shows that there are considerable differences in the underlying physiologies of these two major sub-states. Disclosed herein, hibernation is an analog of desynchronized sleep itself (i.e., REM sleep), as both conditions are associated with neurosecretion, atonia, and loss of autonomic tone (both sympathetic and parasympathetic branches). This means that sub-states of this sleep sub-state exist as well. During the state of rapid eye-movement sleep (REM sleep) there is a remarkable salutary affect on ventricular ectopy and cardiac vulnerability to lethal arrhythmias in a pig-model of myocardial ischemia. The latency between the onset of REM sleep, as determined by EEG criteria, and the onset of the salutary cardiovascular effects, as determined by ECG criteria, was 20 to 30 seconds, a finding that suggested a neurohumoral mechanism of action. Further studies showed that the salutary affect on arrhythmogenesis was conveyed to the heart through the autonomic nervous system and originated from neural activity in the frontal lobes (Skinner, J. E., Reduction of cardiac vulnerability during REM sleep in the pig. In: Sleep Disorders, Basic and Clinical Research, edited by M. Chase and E. D. Weitzman. New York: Spectrum Publications, 1983, pp. 49-63; Skinner, J. E., J. Amer. Coll. Cardiol., 5:88B94B, (1985)), the part of the brain that initiates EEG synchronization and sleep (Skinner, J. E., Douglis, F. M., and Harper, R. M. Higher cerebral regulation of cardiovascular and respiratory function. In: Principles and Practice of Sleep Medicine. Edited by M. H. Kryger, T. Roth, and W. C. Dement. W. B. Saunders Co., Chapter 27, pp. 276-293, (1989)). It proved difficult to sample molecules from the interstitial space of the brain during REM, because the period is so brief. As REM is a highly neurosecretory state of the brain, accompanied by the turnoff of both branches of the autonomic nervous system and by muscle atonia, a similar brain state was searched for and found in mammalian hibernation. The latter was hypothesized to be a long-term condition that would permit the adequate sampling of molecules secreted by non-hibernating animals during REM sleep.

Disclosed herein, evoked arousal accompanied by severe bradycardia in mid-hibernation invariably led to death; and 2) evoked arousal and its attendant bradycardia, during either early- or late-hibernation, resulted in successful arousals.

Disclosed herein the relative ischemia produced by the metabolic demand created by the arousal behavior, which is not adequately supported by the circulation (inappropriate bradycardia), cannot be countered during mid-hibernation because insufficient anti-infarction molecules are present. Disclosed herein, the molecular fractions extracted from animals in early- and late-hibernation contain molecules that can regulate and allow successful arousal without death, but molecules in mid-hibernation cannot. In the rodent model of stroke it was found that only the early- and late-hibernation fractions contained an anti-infarction molecule. Differential comparisons with the mid-hibernation molecular fraction, through various proteomic techniques (2D gels, LC/MS/MS), led to the identification of the disclosed anti-infarction molecules. This state-dependent method of purification produced 9 proteins and 5 peptides that were up-regulated during early-hibernation compared to mid-hibernation.

Disclosed herein, hibernation has sub-states. Also disclosed herein, this subtle partitioning into independent sub-states is associated with different profiles of neurosecretion. It is also disclosed herein that these hibernation-related sub-states also typically occur during waking, prior to hibernation, if they relate to ischemia.

Also disclosed are hibernation sub-state-dependent profiles of neurosecretion that lead to loss of appetite. Disclosed is that a comparison of plasma fractions taken just before and after the hibernators stop eating can result in the isolation and identification of a specific molecule that suppresses appetite in the waking pre-hibernation period. Available data to support this differential comparison are shown in Table 15.

TABLE 15

Woodchuck Eating Behavior

| Date | Eating Behavior for Animals Summarized for Date of Observation |
|---|---|
| September 1 | 6 of 6 consumed most food, daily |
| October 1 | 6 of 6 consumed most food; 2 ate significantly less, but ate apple |
| November 1 | 2 of 6 consumed most food; 4 ate significantly less, but ate apple |
| November 30 | 2 of 6 ate some food; 3 ate little food; 1 ate very little food |
| December 1 | All food was removed and animals left undisturbed; within 1 week all 6 were quiet (i.e., in hibernation), as determined by 24-hr monitoring of activity. |

These observations were made on 6 woodchucks captured and studied through hibernation. Food materials provided daily were 1 small carrot, ½ apple, 1 leaf of cabbage, and water was provided ad libitum. The food consumption was noted 24-hr later; uneaten food was removed from cage before fresh food was placed in food dish.

The method of discovery of molecules in state-dependent fractions of hibernation-related samples of plasma, cerebrospinal fluid, urine or other biological groupings of molecules are disclosed for both the conditions of wakefulness and hibernation in the hibernating animals.

Disclosed are uses of the state-dependent methods to capture hibernation-related molecules. Disclosed are molecules, or partially or substantially purified fractions of molecules that contain molecules related to 1) preventing brain damage in stroke, 2) preventing myocardial damage in heart attack, and 3) recycling blood urea in kidney failure or any other condition.

Disclosed herein are FPA, and FPA-related molecules, such as molecules having identity to FPA, which have anti-infarction effects. Disclosed are anti-infarction molecules. If thrombosis occurs inadvertently in a vessel with the downstream lumen intact (i.e., not in a cut vessel), then before thrombolysis can begin to remove the obstruction, there will be inadvertent ischemia in the downstream tissues. Examples of such inadvertent clotting are those associated with bruises, low perfusion pressure, positional vessel occlusion, and so forth. The ischemic damage produced by the forming of an inadvertent clot can be offset by the free FPA-fragments or variants or derivatives that are released. If the FPA flows out of the body due to a cut or severed vessel, then ischemia is less effectively countered, but if the circulation remains intact, then the unphosphorylated FPA dumped into the circulation can serve the selective advantage of an anti-infarction function pending the resolution of the clot and the restoration of the circulation.

2. Ischemia a) Mechanisms of Moderate Neuro- and Cardio-Protection

Protective molecules for ischemia have been sought in the past based on the observation that neurons can destroy themselves by an overactive excitatory process. Glutamate and its receptors, some of which are involved in leaning and memory processes, seem to be the root cause of this over-excitation (Michaelis E K. Prog Neurobiol 1998, 54(4):369-15). L-Glutamate is the most widespread excitatory transmitter system in the vertebrate brain and in addition to its actions as a synaptic transmitter it produces long-lasting changes in neuronal metabolism and viability.

These effects are produced through the activation of two general classes of receptors, those that form ion channels, and those that are linked to G-proteins to control metabolism. The pharmacological and physiological characterization of these various forms of the receptors has led to the definition of three ion-channels and three (groups) of metabolic receptors. More than twenty-five genes are now identified for specific subunits of these receptors and another five proteins are likely to function as receptor subunits or receptor associated proteins (These sequences for these proteins can be found in Genbank and are herein incorporated by reference in their entireties). The regulation of expression of these protein subunits, their localization in neuronal and glial membranes, and their role in determining the physiological properties of glutamate receptors is a field of current investigation. Both ionotropic and metabotropic receptors are linked to multiple intracellular messengers, such as Ca2+, cyclic AMP, reactive oxygen species, and these links initiate multiple signaling cascades that determine neuronal growth, differentiation, and survival. Aarts et al., have found two small peptides with some anti-infarction activity that work through the NMDA receptor. Aarts et al., Scuence, 298:846850, (2002) which is herein incorporated by reference for material at least related to anti-infarction molecules. (Lys-Leu-Ser-Ser-Ile-Glu-Ser-Asp-Val SEQ ID NO: 104) (Tyr-Gly-Arg-Lys-Lys-Arg-Arg-Gln-Arg-Arg-Arg SEQ ID NO: 105).

These L-glutamate findings lead to the suggestion that that if one or more of the glutamate receptors or sub-cellular links is blocked, then perhaps the excitation-death that occurs with glutamate-dumping during ischemic injury can be prevented. Lubeluzole is one such molecule that does indeed block the effects of stimulation of the glutamate receptor (Lesage A S, et al., J Pharmacol Exp Ther 1996, 279:759-66). A clinical trial, however, showed that it does not prove to be medically useful in treating patients with enrollment out to 8 hours after the stroke onset (Grotta J; Cerebrovasc Dis 2001, 12:258-63). There are several other lines of evidence supporting other moderately effective anti-stroke interventions. An endothelial adhesion molecule has been proposed as a leading candidate for the cause of stroke and the necrotic cell death it engenders. The molecule TNF-alpha (tumor necrotic factor, alpha) through a second messenger, ceramide, leads to the up-regulation of ICAM-1 (intercellular adhesion molecule-1), a molecule that causes the binding of monocytes and macrophages to the endothelial lining of the small blood vessels (Ginis I, et al., Am J Physiol 1999, 276:C1171-83). This mechanism also manifests ischemic "preconditioning" in the brain (Chen Y, et al., J Cereb Blood Flow Metab 2001, 21:34-40), a phenomenon which has a lot of appeal because it leads to tissue-savings in both brain and heart models of infarction. Intervention in the TNF-ICAM-monocyte mechanism with a murine anti-human ICAM antibody (Enlimomab), however, was found in a small clinical trial to have a negative outcome (Furuya K, et al., Stroke November 2001; 32(11):2665-74).

Preconditioning was first investigated in the myocardium. A prior experience with ischemia (i.e., "preconditioning") was found to lead to a smaller infarction volume at a later time, after recovery, when an artery was then tied off. It was initially shown that the myocardial mechanism involved the inhibitory g-protein connected to the adenosine receptor (Hashimi M W, et al., Mol Cell Biochem 186:19-25). Since the early adenosine-$g_i$-cyclase hypothesis, the preconditioning phenomenon has been found to be considerably more complex.

Preconditioning has two phases (Bolli R. The late phase of preconditioning. Circ Res 2000, 87(11):972-83). Unlike the early phase of preconditioning, which lasts 2 to 3 hours and protects against myocardial infarction, but not against "stunning", there is a late phase that lasts 3 to 4 days and does protect against both infarction and stunning of cardiac tissue. This longer lasting affect can thus have greater clinical relevance. Late preconditioning is a polygenic phenomenon that requires the simultaneous activation of multiple stress-responsive genes. Chemical signals released by a sublethal ischemic stress (such as NO, reactive oxygen species, and adenosine) trigger a complex cascade of signaling events. These events include the activation of protein kinase C, Src protein tyrosine kinases, and nuclear factor kappa-B and culminates in increased synthesis of inducible NO synthase, cyclooxygenase-2, aldose reductase, Mn superoxide dismutase, and probably other cardio-protective proteins. An analogous sequence can be triggered by a variety of stimuli, such as heat stress, exercise, and cytokines. Thus, late preconditioning appears to be a universal response of the heart to stress in general. Importantly, the cardio-protective effects of late preconditioning can be reproduced pharmacologically with clinically relevant agents (e.g., NO donors, adenosine receptor agonists, endotoxin derivatives, or opioid receptor agonists).

In both the brain and the heart, however, the tissue-savings that results from either cerebral or cardiac preconditioning is moderate, with a major infarction still being manifested. This moderate amount of tissue savings, for example, is 25% to 35% (Furuya K, et al., J Cereb Blood Flow Metab 2001 3:226-32; Dawson D A, et al., J Cereb Blood Flow Metab 1999, 6:616-23; and Nawashiro H, et al., Brain Res 1997, 778(2):265-71.) for the TNF-ICAM pathway in the brain when treatment is provided pre-ischemia.

b) "Stunned" Tissue: a Mechanism for 100% Recovery of Function

A phenomenon of recovery of non-contractile function of ischemic cardiac tissue was discovered in the 1980's following revascularization surgery in patients with severe ischemic heart disease (Cooper H A, Braunwald E., Coron Artery Dis 2001 12:387-92). Myocardium that has sustained a transient sublethal injury but has the potential for complete recovery with time is referred to as "stunned" myocardium. Short-lived myocardial stunning is commonly seen after coronary artery bypass surgery.

"Hibernating" myocardium is similar to stunning, but is a chronic condition that can be due to either chronic low perfusion or repetitive stunning. For example, when oxygen demands increase in patients with angina, prolonged periods of ischemia occur, resulting in multiple episodes of stunning and this series eventually leads to hibernating myocardium. When myocytes are chronically supplied at a low perfusion rate they simply lose their ability to contract, but they do not die and follow necrotic resolution. Rather, once the circulation is restored, these cells, even after years of dysfunction, recover their contractile properties. Recovery is usually more complete in stunned tissue than in hibernating tissue, and the latter tissue usually has small islands of necrotic damage within its mass.

The relationship between stunned, hibernating, and preconditioned myocardium is not yet clearly understood (Futtermnan L G, Lemberg L., Am J Crit Care 2000 9:430-6), but like the effects of experience of ischemia in the brain, which alters both the ionic and metabolic glutamate-controlled pathways, the underlying molecular biology is likely to follow polygenic pathways. These pathways of molecular dynamics that are altered will likely depend on the particular state-dependencies that are present at the time of modification, including species differences (Kim S J, et al., Circ Res Oct. 26, 2001; 89:831-7).

c) Ischemia Models

Since the introduction of FDA-approved thrombolysis into medicine, using such tissue plasminogen activators as tPA, the models for stroke and heart attack have changed from long-term occlusion of vessels to produce the infarctions to shorter-term ones. To mimic a medically-realistic time between the onset of the occlusion and the injection of the thrombolytic and candidate drugs, the occlusion time in most animal models has been reduced from 24-hours to 1 to 2 hours (i.e., the occlusion is released to mimic thrombolysis and tissue damage is assed histologically at 24-hours).

Often in cases of cardiac models of ischemia, a control group called "pre-conditioning" is run to compare the new drug candidate to this non-drug protection. In "cardiac pre-conditioning" there is previous experience in each animal with short-term ischemia sessions that will not produce permanent tissue damage. There is evidence that this physiological protective mechanism is adenosine-receptor-related and g-protein-mediated, It is thought that the tissue-protection by this "pre-conditioning" may be related to that of "cardiac stunning" (reversal of non-contracting tissue) or "cardiac hibernation" (partial reversal of non-contracting tissue) that occurs after reestablishment of long-term ischemia, as in coronary artery bypass allographs. The difference between stunning and hibernating tissues is whether or not there is any non-reversal of tissue dysfunction.

Pre-conditioning controls typically only provide tissue savings up to 30% to 50%, which is substantially less than that expected for any new drugs that would have an impact on limiting infarction size.

It is assumed that even the short-term occlusions will produce some irreversible tissue damage. For example, a 1-hour occlusion might produce some outlying tissue in the volume of ischemia that is capable of reversal of tissue damage, but some of the core tissue will already have been rendered incapable of reversal and will ultimately necrotize.

The disclosed molecules and fractions can produce 100% reversal of infarction in some of the animals in which 1-hr occlusions are made (mouse-MCAO), including reversals in the central core, and thus the core vs. peripheral damage issue appears to be addressed. With pre-treatment by the disclosed molecule(s) and fractions after 1-hr of occlusion a tissue savings of 100% was observed at 24 hrs in all of the animals. Injection of the relevant molecule(s) show efficacy when injected out to 8-hours after the onset of the 1-hour of ischemia. A mouse requires only ½0th the amount of injection material as the rat, which makes the mouse more efficient for multiple studies.

Disclosed are methods, wherein the step of assaying comprises using the mouse MCAO model of cerebral or myocardial ischemia. Also disclosed are methods wherein the step of assaying comprises using the rat model, or any other animal model, such as mammalian models, of coronary artery occlusion for myocardial or cerbral ischemia. Also disclosed are methods utilizing animal models of new vessel angiogenesis, old vessel remodeling where collateral anastomoses open wider to fill distal ends of blocked vessels, reperfusion damage where high-levels of accumulated byproducts of ischemia enter the distal ischemic tissues and/or osmosis-induced organelle or membrane damage occurs in ischemic tissues, and wherein any other organ is made ischemic or wherein all the organs and tissues are made ischemic by whole-body ischemia induced by temporary cardiac arrest (e.g., ventricular fibrillation) or blockade of flow (e.g., clamping of aortic output). There are a variety of other models that are adjunctive to the more conventional ischemia (vessel-occlusion)/infarction (engendered-necrosis) models. For example, infarction can be engendered by trauma from a mechanical blow, coagulopathy from a snake venom, and so on. Similarly ischemia can be evoked slowly by ameroid constrictors, produced in small distal vessels by infused microspheres, and so on. Furthermore these models can be modulated by global variants such as gene-knockout (e.g., myocardial receptor deletions), bio-behavioral modifications (e.g., psycho-social stress), and so on.

C. COMPOSITIONS

Disclosed are compositions that have anti-infarction properties. Disclosed is a state-dependent method in which albumin fractions (affi-blue gel column, for example) isolated from a mid-hibernation fraction extracted, for example, 6 weeks after hibernation onset and the early-hibernation fraction extracted, for example, 2 weeks after hibernation onset showed 9 proteins and 5 peptides that were differentially expressed between the early and mid-hibernation states. The fractions were filtered (10 kDa cut-off) into protein and peptide sub-fractions and after testing in the mouse MCAO model it was shown that both produced anti-infarction effects. Two of the peptides were shown to be differentially up-regulated and three were identified by LC/MS/MS as matrix artifacts. Using proteomic "fingerprinting" and de novo sequencing, the peptides were identified as Fibrinopeptide-A (FPA) and Bradykinin. The FPA molecule was systematically tested in the mouse-MCAO model, by synthesizing various fragments of FPA. Disclosed herein, the C terminal fixed region is an active fragment of FPA, having anti-infarction property. Synthesized Bradykinin and Des-Arg-Bradykinin were also shown to have anti-infarction properties in the mouse MCAO model. Using reverse-phase columns, additional peptides have been identified (below 10 kDa cut-off, LC/MS/MS) in the D2 vs. NE2 differential fractions.

The compositions disclosed can be isolated using state dependent methods disclosed herein or they are related to molecules that can be isolated using the state dependent methods disclosed herein or they are molecules that mimic the function of molecules that can be isolated using the state dependent properties disclosed herein. Disclosed herein art methods of comparing early and mid-hibernation that resulted in the differential-state identifications of 9 proteins. Also disclosed are state-dependent methods that compare sub-states-of-hibernation and before-and-within-sub-states-of-hibernation many different molecules. These identifications were and can be achieved with molecular methods of 2D gel electrophoresis and tandem LC/MS/MS proteomic methods. The state-dependent comparisons and molecular identifications can occur with any number of other molecular technologies, such as, specifically, that of comparing gene-arrays, and, generally, that of any other comparison technology suitable for identifying the specific state-dependent molecules.

It is understood that when using molecules isolated from an animal using a state dependent method disclosed herein the molecule can be used at varying levels of purity. For example, the state dependent methods can produce plasma, which can be fractionated based on for example size or charge or hydrophobicity. One or all of these procedures, or others, can be employed to increase the specific activity of the sample. The fractions can be monitored for an activity, such as anti-infarction properties in a rat or mouse model, as disclosed herein. Raw biomaterials such as blood can first be processed into plasma. The plasma can then be purified in a variety of ways. The plasma can be purified using an affinity matrix (affi-gel blue, for example), which separates the albumin fraction from other plasma-based materials. This albumin fraction can then be purified using any number of methods, which make use of differences in pore size, tortuosity, charge, molecular weight, hydrophobicity, and/or solubility, for example.

The albumin fraction can then be fractionated based on size, by for example, using molecular sieves or membranes having cutoff molecular weights of 3.5 kD, 7 kD, 10 kD, 15 kD, 20 kD 30 kD, 50 kD, 75 kD, 100 kD, 150 kD, or 200 kD, for example.

1. Hibernating Animal Fractions

Disclosed are fractions of plasma isolated from a hibernating animal, such as a woodchuck, having anti-infarction properties, wherein the fraction is obtained from a hibernating animal, up to 1, 2, 3, 4, 5, 6, 7, 8, 9, 10, 15, 20, 25, 30, or 40 days after the onset of hibernation or 1, 2, 3, 4, 5, 6, 7, 8, 9, 10, 15, 20, 25, 30, or 40 days before final arousal from hibernation. Disclosed are fractions of plasma isolated from a hibernating animal, such as a woodchuck, having anti-infarction properties, wherein the fraction is obtained from a hibernating animal, 1-25 days, or 5-20 days, or 10 18 days or 14 days after the onset of hibernation 2 to 6 weeks, 3 to 6 weeks, 4 to 6 weeks, or 5 weeks before the end of hibernation for the animal or whole colony.

Disclosed are fractions of plasma isolated from a hibernating animal. The hibernating animal can be any hibernating animal. For example, the hibernating animal can be a mammal (e.g., ground squirrel, bear, woodchuck (ground hog), marmot, skunk, bat), insect (e.g., mosquito, yellow jacket, bee), fish (e.g., blackfish), reptile (e.g., snake, turtle), amphibian (e.g., frog), or bird (e.g., poorwills).

Figure 6:
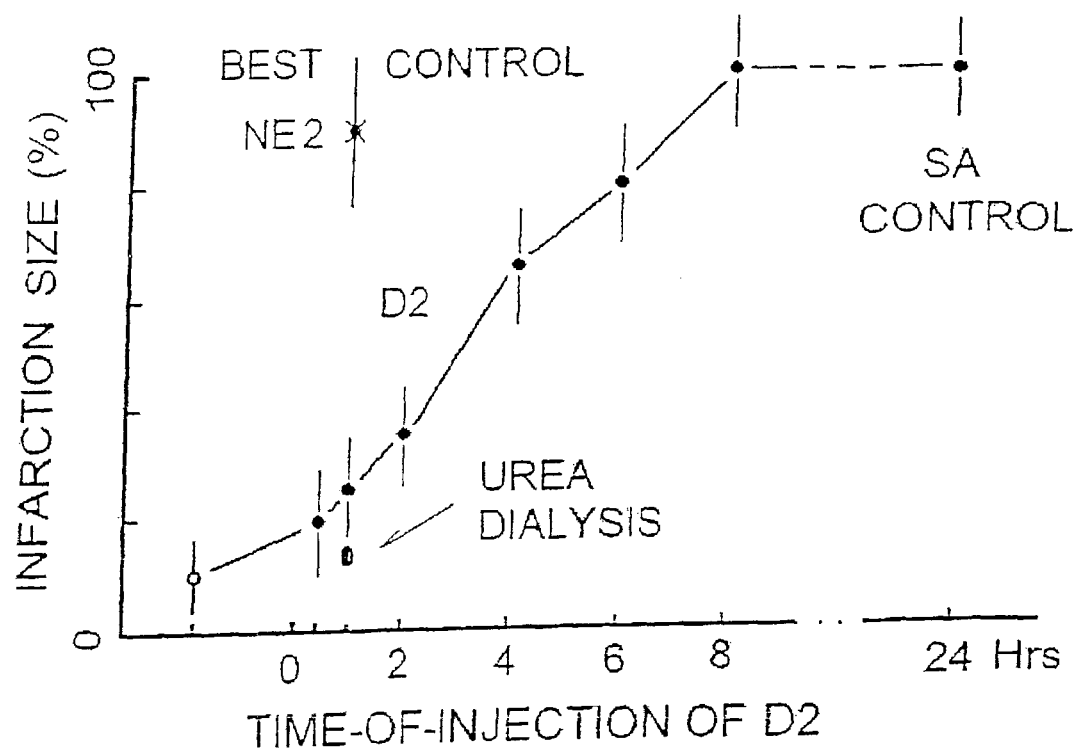
Figure 8:
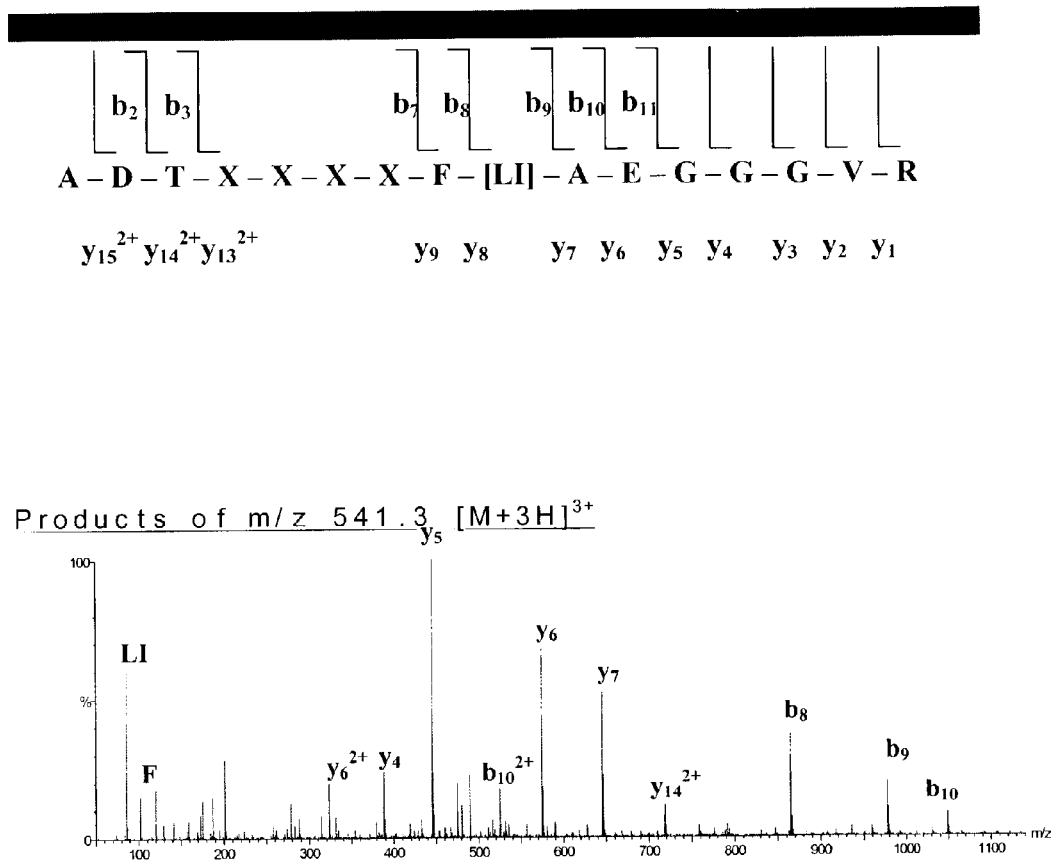
FIG. 8 shows results for a Peptide: Mass 1620.9 Da.
Figure 9:
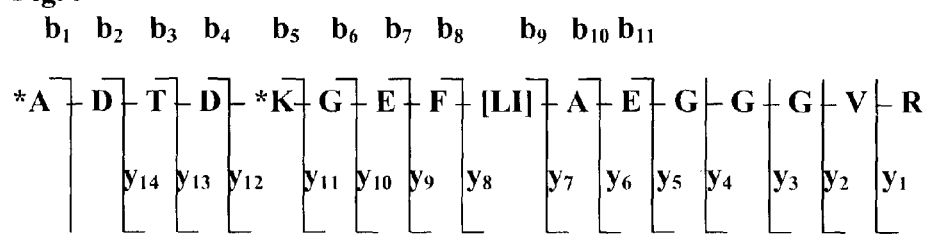
FIG. 9 shows results for a Peptide: Mass 904.4 Da.
Figure 9:
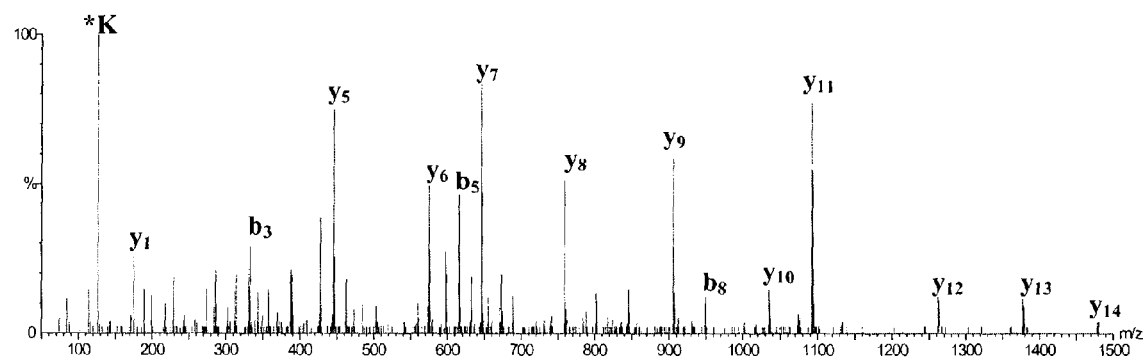

Disclosed are plasma fractions and molecules identified within those fractions that have anti-infarction effects for many hours after the onset of ischemia. For example, the results shown in FIG. 6 show positive results 6 hours after the ischemia. The dialyzed D2 fraction when injected 1-hour after the start of ischemia results in no- to minimal-infarction volume in most of the subjects. Disclosed are molecules having identity to woodchuck FPA and human FPA. (FIG. 8). Disclosed herein the relevant state-dependent molecules found in the rodent (Woodchuck, rat, mouse) work effectively in stroke-prevention in cross species such as humans. Because of its paramount importance in survival during periods of ischemia (e.g., birth ischemia, relative-ischemia in sublethal exercise, circulatory ischemia, hibernation ischemia, etc.) it is likely that this molecule was functionally conserved across mammalian species during the course of evolution.

Disclosed are fractions of a hibernating animal's plasma comprising a molecule, wherein the molecule has anti-infarction activity, and wherein the fraction is isolated by collecting an animal's blood 1, 2, 3, 4, 5, 6, 7, 8, 9, 10, 11, 12, 13, 14, 15, 16, 17, 18, 19, 20, 21, 22, 23, 24, or 25 days after the onset of hibernation.

Also disclosed are fractions, wherein the fractions are isolated by collecting the animal's blood 10, 11, 12, 13, 14, 15, 16, 17, 18, 19, or 20 days after the onset of hibernation or wherein the fraction is isolated by collecting the animal's blood 14, 15, or 16 days after the onset of hibernation and wherein the fraction is isolated by collecting the animal's blood 15 days after the onset of hibernation.

Disclosed are fractions of a hibernating animal's plasma comprising a molecule, wherein the molecule has anti-infarction activity, and wherein the fraction is isolated by collecting a first animal's blood, wherein the first animal is in early hibernation, and wherein the fraction does not comprise any blood from a second animal if the second animal is in mid hibernation.

Disclosed are fractions of a hibernating animal's plasma comprising a molecule, wherein the molecule has anti-infarction activity, and wherein the fraction is isolated by collecting an animal's blood 1, 2, 3, 4, 5, 6, 7, 8, 9, 10, 11, 12, 13, 14, 15, 16, 17, 18, 19, 20, 21, 22, 23, 24, or 25 days before the final arousal of the animal.

Also disclosed are fractions, wherein the fractions are isolated by collecting the animal's blood 10, 11, 12, 13, 14, 15, 16, 17, 18, 19, or 20 days before the final arousal of the animal, wherein the fractions are isolated by collecting an animal's blood 14, 15, or 16 days before the final arousal of the animal, and wherein the fractions are isolated by collecting an animal's blood 15 days before the final arousal of the animal.

Also disclosed are fractions of a hibernating animal's plasma comprising a molecule, wherein the molecule has anti-infarction activity, and wherein the fraction is isolated by collecting a first animal's blood, wherein the first animal is in late hibernation, and wherein the fraction does not comprise any blood from a second animal if the second animal is in mid hibernation.

Disclosed are fractions, wherein the anti-infarction activity is a cerebral anti-infarction activity and fractions wherein the anti-infarction activity is a cardiac anti-infarction activity or both.

Disclosed are fractions of a hibernating animal's plasma comprising a molecule, wherein the molecule induces urea recycling, and wherein the fraction is isolated by collecting an animal's blood 1, 2, 3, 4, 5, 6, 7, 8, 9, 10, 11, 12, 13, 14, 15, 16, 17, 18, 19, 20, 21, 22, 23, 24, or 25 days after the onset of hibernation.

Also disclosed are fractions having urea recycling activity wherein the fractions are isolated by collecting the animal's blood 10, 11, 12, 13, 14, 15, 16, 17, 18, 19, or 20 days after the onset of hibernation, wherein the fractions are isolated by collecting the animal's blood 14, 15, or 16 days after the onset of hibernation, and wherein the fractions are isolated by collecting the animal's blood 15 days after the onset of hibernation.

Disclosed are fractions of a hibernating animal's plasma comprising a molecule, wherein the molecule induces urea recycling, and wherein the fraction is isolated by collecting a first animal's blood, wherein the first animal is in early hibernation, and wherein the fraction does not comprise any blood from a second animal if the second animal is in mid hibernation.

Also disclosed are fractions of a hibernating animal's plasma comprising a molecule, wherein the molecule induces urea recycling, and wherein the fraction is isolated by collecting an animal's blood 1, 2, 3, 4, 5, 6, 7, 8, 9, 10, 11, 12, 13, 14, 15, 16, 17, 18, 19, 20, 21, 22, 23, 24, or 25 days before the final arousal of the animal.

Also disclosed are fractions, wherein the fraction is isolated by collecting the animal's blood 10, 11, 12, 13, 14, 15, 16, 17, 18, 19, or 20 days before the final arousal of the animal, wherein the fractions are isolated by collecting an animal's blood 14, 15, or 16 days before the final arousal of the animal, and wherein the fractions are isolated by collecting an animal's blood 15 days before the final arousal of the animal.

Disclosed are fractions of a hibernating animal's plasma comprising a molecule, wherein the molecule induces urea recycling, and wherein the fraction is isolated by collecting a first animal's blood, wherein the first animal is in late hibernation, and wherein the fraction does not comprise any blood from a second animal if the second animal is in mid hibernation.

2. Methods of Purifying Anti-Infarction Molecules

Also disclosed are methods of purifying a molecule having anti-infarction activity comprising 1) collecting a sample from a hibernating animal, 2) collecting a control sample from a hibernating animal, 3) comparing the sample to the control sample.

Disclosed are methods of purifying a molecule having anti-infarction activity comprising 1) collecting a sample from a hibernating animal, 2) collecting a second sample from a hibernating animal, 3) and comparing the sample to the second sample.

Disclosed are methods of purifying a molecule having anti-infarction activity comprising 1) collecting a sample from a hibernating animal, 2) collecting a second sample from a hibernating animal in a different sub-state, 3) and comparing the sample to the second sample.

Disclosed are methods of purifying a molecule having anti-infarction activity comprising 1) collecting a sample from a hibernating animal at a first time, 2) collecting a second sample from a hibernating animal at a second time, wherein the first time and second time are different, 3) and comparing the sample to the second sample.

Disclosed are methods of purifying a molecule having anti-infarction activity comprising 1) collecting a blood sample from a hibernating animal, 2) collecting a second blood sample from a hibernating animal, 3) comparing the blood sample to the second blood sample.

Also disclosed are methods, wherein the step of comparing the sample and the second sample comprises assaying gene expression in the sample and the second sample and methods wherein the step of comparing the sample and the second sample comprises assaying protein expression in the sample and the second sample.

Disclosed are methods, wherein the sample and second sample are obtained from the blood, urine, spinal fluid, or cerebral spinal fluid, tissues, organs, cells.

Disclosed are methods, wherein the animal is a mammal, such as a ground squirrel, bear, woodchuck, marmot, skunk, or bat.

Disclosed are methods, wherein the blood sample was obtained from an animal in early-hibernation or late-hibernation.

Disclosed are methods, wherein the second sample was obtained from an animal in mid-hibernation.

Disclosed are methods, wherein the sample was obtained from an animal 1-25 days after the onset of hibernation.

Disclosed are methods, wherein the second sample was obtained from an animal 26 to 60 days after the onset of hibernation.

Disclosed are methods, wherein the step of comparing comprises identifying differentially regulated molecules, wherein the differentially regulated molecules are present in different amounts in the sample as compared to the second sample.

Disclosed are methods, wherein identifying differentially regulated molecules comprises fractionating the sample and the second sample.

Also disclosed are methods, wherein the fractionating occurs by collecting molecules of 10 kDA or less.

Disclosed are methods, wherein the fractionating comprises the step of separating the molecules in the blood sample and the second sample by charge, hydrophobicity, hydrophilicity, lipophilicity tortuosity, molecular weight, protein, peptide or carbohydrate affinity chromatography, or solubility.

Disclosed are methods wherein the affinity separation comprises using affi-gel blue chromatography.

Disclosed are methods, wherein identifying comprises analyzing the samples with GC-Mass Spectroscopy, Gel Chromatography, High Performance Liquid Chromatography, or LC/MS/MS mass spectroscopy was performed using standard procedures (Liquid chromatography-tandem with mass spectrometry).

Disclosed are methods, wherein the High Performance Liquid Chromatography comprises reverse phase chromatography and methods wherein the Gel Chromatography comprises two dimensional polyacrylamide gel electrophoresis.

Disclosed are methods, wherein the method further comprises purifying the differentially regulated molecules obtaining a purified differentially regulated molecule.

Disclosed are methods, wherein the method further comprises assaying the anti-infarction activity of the purified differentially regulated molecule.

Disclosed are methods, wherein the step of assaying comprises using the mouse MCAO model of cerebral ischemia. Also disclosed are methods utilizing models of new vessel angiogenesis, remodeling, reperfusion damage, and tests for whole body ischemia.

Disclosed are methods, wherein the anti-infarction activity is a cerebral anti-infarction activity and methods wherein the anti-infarction activity is a cardiac anti-infarction activity.

3. Fibrinogen A (FPA)

a) Structure of the FPA Molecule

FPA is a fragment of soluble fibrinogen, which is released upon cleavage of fibrinogen by thrombin. The thrombin (IIa) catalyzed cleavage of soluble fibrinogen (Fbg) to form fibrin (Fbn) is the terminal proteolytic event in the coagulation cascade. These soluble Fbn monomers spontaneously polymerize to form an insoluble Fbn network which is stabilized by the factor XIIIa catalyzed crosslinking of lys and glu residues of a and g chains. This Fbn network is the major protein component of the haemostatic plug.

Plasma fibrinogen is a glycoprotein of approximately 340,000 kd, which is synthesized in the liver. It circulates in animals at a concentration of 2.6 mg/ml. It consists of a disulfide linked dimer composed of 3 pairs of disulfide linked non-identical polypeptide chains (Aa, Bb and g).

FPA is the N-terminus of the Aa chain, which contains factor XIIIa crosslinking sites and 2 phosphorylation sites. Fbg is typically fully phosphorylated after synthesis, but circulates at only 20-30% phosphorylation. The release of FPA by cleavage at R16-G17 generates Fbn I, exposing a polymerization site (17-20) on the Aa chain. These regions bind to complimentary regions on the D domain of Fbn to form protofibrils. Subsequent IIa cleavage of FPB (R14-G15) from the Bb chain exposes additional polymerization sites and promotes lateral growth of the Fbn network. Thus, typically FPA constitutes the N-terminal amino acids up to the cleavage site of thrombin, which typically occurs at the R-G cleavage site. Thus, one way of defining FPA is by the cleavage site of thrombin, and is thus a relative system. Typically there will be 11, 12, 13, 14, 15, 16, 17, 18, 19, or 20 amino acids N-terminal to the cleavage site. Thus, one way of discussing the relative positions of FPA is to discuss the position in terms of the cleavage site, such as, 3 amino acids N-terminal to the cleavage site or 7 amino acids N-terminal to the cleavage site. For example, in woodchuck FPA the sequence AEG would be 7, 6, and 5 amino acids terminal to the cleavage site respectively.

The structure of Fibrinogen fragments including the FPA having been solved and modeled with for example, thrombin. (Martin, P. D., et al., *J Biol Chem* 267 pp. 7911 (1992); Stubbs, M. T., et al., *Eur J Biochem* 206 pp. 187(1992); Martin, P. D., et al., *Biochemistry* 35 pp. 13030(1996); Malkowski, M. G., et al., *Biochem J* 326 pp. 815 (1997). These structures can be used to find structural mimics of FPA and variants that retain the function of FPA, such as anti-infarction properties. For example, the contacts of thrombin with a sub-region of FPA are known, (for example, GEFLAEGGGV). This subregion is known to have anti-infarction properties. Thus, mimics of this sub-region can be isolated by modeling with thrombin and comparing the contacts of the known sub-region thrombin coordinates with the sub-region of interest. Molecules binding thrombin in a similar way would be expected to have the same properties of human FPA and human FPA fragments, such as anti-infarction properties because of their equivalency in a known FPA assay, thrombin binding. As disclosed herein this information can also be coupled with combinatorial chemistry techniques and screening procedures to isolate molecules having the properties of FPA. For example, molecules can be bound to thrombin in some type of binding assay and then these molecules can be competed off with FPA or a fragment thereof. Molecules which are collected in this competitive binding assay will yield molecules having binding properties similar to FPA which allows for the similar functional properties, such as anti-infarction activity.

It is understood as discussed herein that there are a variety of sequences of FPA. For example, there are sequences of FPA that can be obtained from a variety of different animals. There are also sequences that can be obtained from hibernating animals. Table 1 shows an exemplary list of FPA sequences from a variety of different animals. The sequences can be compared and a percent identity as discussed herein can be obtained for any of the sequences using standard techniques. In addition a consensus sequence can be obtained using techniques discussed herein. It is understood that any comparison of these disclosed sequences that can be preformed to produce a percent identity is specifically disclosed along with the specific identity. For example, human and woodchuck differ at 4 of the 15 positions. This produces approximately a 74% identity between human and woodchuck FPA. It is also understood that specific fragments can be compared for their identity as well. For example, the fragment comprising the 10 amino acids nearest the cleavage site (GEFLAEGGGV) differ between human and woodchuck by only 1 amino acid, indicating a 90% identity between human and woodchuck for this fragment. This type of analysis can be performed for any FPA sequence.

As disclosed herein, human FPA works in a rat model. The human and rat FPA have II of 15 differences indicating an identity of 13%. It is noted however, that positions 3, 4, and 8 are highly conserved and, are also conserved in the rat. Thus, disclosed are sequences that retain a G, G, and F at positions 3, 4, and 8 N-terminal to the cleavage site respectively, but allow other variation to take place. The following are specific FPA-derivatives disclosed herein and can be tested in the mouse-MCAO model: Table 1 provides a number of FPA sequences. The sequences vary from positions 1 to 5, vary less from positions 6 to 10 and have 100% homology between positions 11 to 16.

A dosage can be determined by, for example, on the 5 mg/kg effective dose of plasma as being 1/1000$^{th}$ of 5 mg/kg, of plasma, 0.005 mg/kg of a pharmocaphore. 0.005 mg/kg des-arg-BK worked.

TABLE 1

| Sequence Variable Region | Conserved Region (N-terminal to C-terminal) | Activity % | Source q | SEQ ID NO: |
|---|---|---|---|---|
| ADTDK | GEFLAEGGGVR | | Woodchuck | 1 |
| ADSGE | GDFLAEGGGVR | | Human | 2 |
| TDTEDK | GEFLSEGGGVR | | Mouse | 3 |
| ATGTT | SEFTEAGGDIR | | Rat | 4 |
| TDPDADE | GEFLAEGGGVR | | Arabian Camel | 5 |
| TDPDADK | GEFLAEGGGVR | | Lama | 6 |
| AEVQDK | GEFLAEGGGVR | | Pig | 7 |
| TKTEE | GEFISEGGGVR | | Donkey | 8 |
| TKDE | GTFIAEGGGVR | | Kangaroo | 9 |
| EDGS | GEFLAEGGGVR | | Buffalo | 10 |
| ADTGE | GEFLAEGGGVR | | Gibbon | 11 |
| TKATE | GEFLAEGGGVR | | Tapir | 12 |
| ADDSDPVG | GEFLAEGGGVR | | Goat | 13 |
| ADGSDPAS | GEFLTEGGGVR | | Muntjak | 14 |
| ADTGD | GDFITEGGGVR | | Drill | 15 |
| TEEGE | FLHEGGGVR | | Horse | 16 |
| ADGSDPAG | GEFLAEGGGVR | | Moose | 17 |
| TDTKESD | FLAEGGGVR | | Grey Seal | 18 |
| TKTE | GSFLAEGGGVR | | Wombat | 19 |
| TNSKE | GEFIAEGGGVR | | Wolf | 20 |
| TNSKE | GEFIAEGGGVR | | Dog | 21 |
| SDPAG | GEFLAEGGGVR | | Deer | 22 |
| TETTE | GDFLAEGGGVR | | Rhino | 23 |
| EDGSDPPS | GDFLTEGGGVR | | Cow | 24 |
| ADTGE | GDFLAEGGGVR | | Macague | 25 |
| VDPGEST | FIDEGATGR | | Rabbit | 26 |
| TDGKE | GEFIAEGGGVR | | Bear | 27 |
| AQDGK | TTFEKEGGGGR | | Chicken | 28 |
| | GEFLAEGGGVR | 13.4 | Synthetic | 89 |
| | GEFLAEGGGV | 27.8 | Synthetic | 29 |
| | GEFLAEGGG | 27.2 | Synthetic | 30 |
| | GEFLAEGG | 22.9 | Synthetic | 31 |
| | GEFLAEG | 17.5 | Synthetic | 32 |
| | GEFLAE | 28.7 | Synthetic | 33 |

TABLE 1-continued

| Sequence Variable Region (N-terminal to C-terminal) | Conserved Region | Activity % | Source | SEQ ID NO: |
|---|---|---|---|---|
| GEFLA | | 27.3 | Synthetic | 34 |
| EFLAEGGGVR | | 26.2 | Synthetic | 35 |
| FLAEGGGVR | | 14.1 | Synthetic | 36 |
| LAEGGGVR | | 28.4 | Synthetic | 37 |
| AEGGGVR | | 15.6 | Synthetic | 38 |
| EGGGVR | | 19.9 | Synthetic | 39 |
| EFLAE | | 16.4 | Synthetic | 40 |
| FLAEG | | 22.2 | Synthetic | 41 |
| LAEGG | | 25.8 | Synthetic | 42 |
| AEGGG | | 36.8 | Synthetic | 43 |
| EGGGV | | 31.1 | Synthetic | 44 |
| GGGVR | | 13.9 | Synthetic | 45 |
| AEFLAEGGGVR | | 5.6 | Synthetic | 46 |
| GAFLAEGGGVR | | 18.3 | Synthetic | 47 |
| GEALAEGGGVR | | 18.7 | Synthetic | 48 |
| GEFAAEGGGVR | | 22.4 | Synthetic | 49 |
| GEFLGEGGGVR | | 15.4 | Synthetic | 50 |
| GEFLAAGGGVR | | 21.8 | | 51 |
| GEFLAEAGGVR | | 19.0 | | 52 |
| GEFLAEGAGVR | | 28.9 | | 53 |
| GEFLAEGGAVR | | 16.9 | | 54 |
| GEFLAEGGGAR | | 32.3 | | 55 |
| GEFLAEGGGVA | | 24.8 | | 56 |
| AEFLAEGGGPR | | | VP067 | 96 |
| GEFLAEGGGPR | | | VP068 | 97 |
| AEGGGPR | | | VP069 | 98 |
| GGGPR | | | VP070 | 99 |
| FEFLAEGGGVR | | | VP071 | 100 |
| AGGGVR | | | VP072 | 101 |
| FGGVR | | | VP073 | 102 |
| AGVR | | | VP074 | 103 |
| AVR | | | VP075 | |
| FGVR | | | VP076 | 104 |
| FVR | | | VP077 | |

Amino acid residues in a substrate undergoing cleavage are designated P1, P2, P3, or P4 etc. in the N-terminal direction from the cleaved bond. Cleavage occurs between P1 and P1' with P1 being composed of the amino acid arginine in the FPA molecule and P1' designating the amino acid c-terminal to the arginine in the original fibrinogen molecule.

b) FPA and Thrombosis

FPA is a by-product molecule in the coagulation reaction that results when thrombin interacts with fibrinogen to form insoluble fibrin (a blood clot) plus free FPA. Free FPA is commonly regarded to be a good marker of fibrin formation (Ottani F, Galvani M., Clin Chim Acta Sep. 15, 2001; 311(1): 33-9.). FPA is located at the N-terminal of the fibrinogen molecule which when cleaved leads to the blood clot formation. The clotting reaction occurs when thrombin docks on the FPA variable region while FPA is attached to fibrinogen. This docking occurs with the aid of the phosphorylation of serine in the 3-position (Maurer M C, et al., Biochemistry Apr. 28, 1998;37(17):5888-902.). Once FPA is cleaved, it exposes the bonds of the remaining fibrinogen to cross-link with those other exposed peptide-bonds of other fibrinogen molecules to form the long fibrin chains FPA levels can be measured and used as a marker of clinical disease states. FPA is elevated in patients with acute myocardial infarction, and increases in association with the activation of clotting factors XI and IX, which are involved in the thrombin activation of fibrinogen (Minnema M C, et al., Arterioscler Thromb Vasc Biol November 2000;20(11):2489-93) ). Factor XII leads to coagulation by assisting FPA cleavage from fibrinogen (Zito F, et al., Circulation Oct. 24, 2000;102(17):2058-62.). A pro-thrombin fragmnent (f1.2) is increased in association with both FPA and ischemic events in both the heart and the brain (Cote R, et al., Stroke August 2000;31(8):1856-62.). Urinary FPA is elevated in Emergency Room patients presenting with chest pain, and it is associated with increased risk of mortality (Sonel A, et al., Circulation Sep. 5, 2000;102(10):1107-13).

Animal research has examined FPA correlates. In rabbits, an evolutionary modification of the end of the variable-region of FPA, at the position-7 (Thr) location, prevents the action of Habutobin, a thrombin-like enzyme from a snake venom, from cleaving FPA and precipitating a lethal coagulopathy (Nejime T, et al., Toxicon August 2000;38(8):1029-41). A tissue factor (TF) acting upstream of prothrombin in the overall coagulation pathway appears to mediate the coagulation that forms in models of ischemia/reperfusion injury in the isolated rabbit heart (Annaganian L, et al., Coron Artery Dis September 2000; 11(6):481-7.).

FPA and thrombolysis have been associated (clot dissolving). The D-dimer molecule is produced as a consequence of the thrombolytic conversion of insoluble fibrin (i.e., a clot dissolving action), and evidence indicates that this molecule is increased in some acute and chronic stroke patients without significant elevation of FPA (Ince B, et al., Thromb Res Nov. 1, 1999;96(3):169-74.). Thrombolysis, however, by injection of a tissue plasminogen activator that causes plasminogen to convert to plasmin and start the onset of the fibrinolysis that forms the D-dimer, leads to a marked increase in FPA; this increase can occur during inhibition of thrombin by heparin (Fassbender K, et al., Stroke October 1999;30(10):2101-4). Somehow FPA can be increased without evoking coagulation, and somehow thrombolysis can occur without FPA levels changing, though it usually does with injection of tissue plasminogen activators (tPA's).

The elevation of FPA during thrombolysis can be related to its state of phosphorylation. High molecular weight fibrinogen (i.e., in which the position-3 Ser is phosphorylated) is pro-thrombotic, as phosphorylation aids the docking of thrombin onto this molecule, as described above, to lead to assisted cleaving of FPA (Maurer M C, et al., Biochemistry Apr. 28, 1998;37(17):5888-902). High molecular weight fibrinogen is what is most associated with additional coronary ischemic events in acute MI patients (Reganon E, et al., Thromb Haemost November 1999;82(5): 1403-5). This makes sense, as phosphorylation of fibrinogen leads to a pro-thrombotic state.

Thrombosis is antithetical to thrombolysis, yet an unexpected result occurs when both are evoked together. Fibrinogen found in circulation is 95% phosphorylated at 20- to 35-hrs after TPA-treatment, which results in patency of the occluded coronary vessel. The phosphorylated FPA fragment and HMW-fibrinogen, however, are both elevated in patients who did not show coronary patency after thrombolysis treatment (Reganon E, et al., Thromb Haemost Dec. 20, 1993;70 (6):978-83). The implication here is that successful thrombolysis somehow results in reduced phosphorylation of position-3 Ser of free FPA, both in its free state and when bound to fibrinogen. Thus there seems to be a negative feedback of thrombolysis to thrombosis that involves the phosphorylation of FPA. Un-phosphorylated free FPA would then seem to be anti-thrombotic.

4. Bradykinin a) Bradykinin Structure

Bradykinin is another D2 vs. NE2 specific up-regulated peptide. Bradykinin is a peptide that was discovered in 1909 with known effects described previously including: 1) cardiovascular effects (i.e., vasoconstriction), 2) sensory-pain perception (receptor activator), and 3) blood clotting (i.e., by activation above prothrombin pathways).

Bradykinin is a proinflammatory peptide (RPPGFSPFR) that is released from kininogen by the enzyme, kallikrein. Bradykinin is also a potent vasodilator, a contractor of a variety of different kinds of extravascular smooth muscle (e.g., bronchial), and an inducer of increased vascular permeability. It also causes pain, a cardinal sign of inflammation.

It is understood as discussed herein that there are a variety of sequences of Bradykinin. For example, there are sequences of Bradykinin that can be obtained from a variety of different animals (See Table 2 for example). There are also sequences that can be obtained from hibernating animals. Table 2 shows an exemplary list of Bradykinin sequences from a variety of different animals and synthetic sequences. The sequences can be compared and a percent identity as discussed herein can be obtained for any of the sequences using standard techniques. In addition a consensus sequence can be obtained using techniques discussed herein. It is understood that any comparison of these disclosed sequences that can be preformed to produce a percent identity is specifically disclosed along with the specific identity. For example, rainbow trout and woodchuck differ at 4 of the 10 positions. This produces approximately a 60% identity between rainbow trout and woodchuck FPA. It is also understood that specific fragments can be compared for their identity as well. For example, the fragment comprising the 10 amino acids nearest the cleavage site (rppgfspf) differ between rainbow trout and woodchuck by 2 amino acids, indicating a 80% identity between human and woodchuck for this fragment. This type of analysis can be performed for any FPA sequence.

As disclosed herein, the disclosed anti-infarction molecule, for example, the C-terminal end of woodchuck FPA work in a rat or mouse model.

Table 2 provides a number of Bradykinin molecules and variants and Table (BK). The anti-infarction properties of BK can be performed by molecules related to BK, such as B9340, and other derivatives of BK having analogs of amino acids or other chemical substituents incorporated into the molecule. The anti-infarction properties of BK can be described as set forth herein using the MCAO mouse model of infarction, for example.

TABLE 2

Bradykinin and exemplary variants
136. The sequences have identity and this identity can be determined as described herein.

| Name | Sequence | Source | SEQ ID NO: | Activity/ inhibition ATII binding assay |
|---|---|---|---|---|
| Bradykinin | Arg-Pro-Pro-Gly-Phe-Ser-Pro-Phe-Arg | Synthetic | 57 | 12 |
| Lys-(Des-Arg9, Leu8)-Bradykinin | Lys-Arg-Pro-Pro-Gly-Phe-Ser-Pro-Leu | | 58 | 98 |
| Hoe 140 | (DArg-Arg-Pro-Hyp-Gly-Thi-Ser-DTic-Oic-Arg | | 59 | 29 |
| DPhe7] Bradykinin | Arg-Pro-Pro-Gly-Phe-Ser-DPhe-Phe-Arg | | 60 | 9 |
| Des-Arg$^9$] Bradykinin | Arg-Pro-Pro-Giy-Phe-SeF-Pro-Phe | | 61 | 92 |
| [Thi5,8,DPhe7] Bradykinin | Arg-Pro-Pro-Gly-Thi-Ser-DPhe-Thi-Arg | | 62 | 53 |
| N- | N-Adamantaneacetyl-DArg-Arg-Pro- | | 63 | 61 |

TABLE 2-continued

Bradykinin and exemplary variants
136. The sequences have identity and this identity can be determined as described herein.

| Name | Sequence | Source | SEQ ID NO: | Activity/ inhibition ATII binding assay |
|---|---|---|---|---|
| Admantaneacetyl-DArg0-Hyp3, Thi5,8,DPhe7] Bradykinin | Hyp-Gly-Thi-Ser-DPhe-Thi-Arg | | | |
| N-Adamantanecarbonyl-DArg-Arg-Pro-Hyp-Gly-Thi-Ser-DPhe Thi-Arg | N-Admantanecarbonyl-DArg0-HyP3, Thi5,8, DPhe7] Bradykinin | | 64 | 63 |
| [Lys0] Bradykinin | Lys-Arg-Pro-Pro-Gly-Phe-Ser-Pro-Phe-Arg | | 65 | 29 |
| Met-Lys0] Bradykinin | Met-Lys-Arg-Pro-Pro-Gly-Phe-Ser Pro-Phe-Arg | | 66 | 38 |
| Lys0-AIa3] Bradykinin | Lys-Arg-Pro-AIa-Gly-Phe-Ser-Pro-Phe-Arg | | 67 | 18 |
| [Tyr0] Bradykinin | Tyr-Arg-Pro-Pro-Gly-Phe-Ser-Pro-Phe-Arg | | 68 | 33 |
| [Tyr8] Bradykinin | Arg-Pro-Pro-Gly-Phe-Ser-Pro-Tyr-Arg | | 69 | -1 |
| Tyr5] Bradykinin | Arg-Pro-Pro-Gly-Tyr-Ser-Pro-Phe-Arg | | 70 | 13 |
| Ile-Ser0]-Bradykinin | Il-eSer-Arg-Pro-Pro-Gly-Phe-Ser-Pro-Phe-Arg | | 71 | 29 |
| [Lys0-Hyp3] Bradykinin | Lys-Arg-Pro-Hyp-Gly-Phe-Ser-Pro Phe-Arg | | 72 | 13 |
| [(pCl)Phe5,8] Bradykinin | Arg-Pro-Pro-Gly-(pCl)Phe-Ser-Pro-(pCl)Phe-Arg | | 73 | |
| Bradykinin (1-3) | Arg-Pro-Pro | | 74 | -2 |
| Bradykinin (1-5) | Arg-Pro-Pro-Gly-Phe | | 75 | 1 |
| Bradykinin (1-6) | Arg-Pro-Pro-Gly-Phe-Ser | | 76 | -12 |
| Bradykinin (1-7) | Arg-Pro-Pro-Gly-Phe-Ser-Pro | | 77 | 55 |
| Bradykinin (2-7) | Pro-Pro-Gly-Phe-Ser-Pro | | 78 | -6 |
| Bradykinin (2-9) | Pro-Pro-Gly-Phe-Ser-Pro-Phe-Arg | | 79 | -13 |
| B9340 | DArg-Arg-Pro-Hyp-Gly-Thi-Ser-Dlgl Oic-Arg | | 80 | 35 |
| B9430 | DArg-Arg-Pro-Hyp-Gly-Igl-Ser-Dlgl-Oic-Arg | | 81 | 70 |
| | RPPGFSPFR | woodchuck | 57 | |
| | RPPGFSPFR | Human | 57 | |

TABLE 2-continued

Bradykinin and exemplary variants
136. The sequences have identity and this identity can be determined as described herein.

| Name | Sequence | Source | SEQ ID NO: | Activity/ inhibition ATII binding assay |
|------|----------|--------|------------|-----------------------------------------|
|      | ISRPPGFSPFR | human | 82 | |
|      | KRPPGWSPLR | rainbow trout | 83 | |
|      | RPPGFTPFR | red eared slider turtle | 84 | |
|      | RPPGFSPFR | common frog | 85 | |

Tic = tetra hydro isoquinoline 3' carboxylic acid
Oic = octahydro indo 2' carboxylic acid
Thi = Beta-[2-Thienyl] Alanine
Hyp = hydroxyproline The anti-infarction properties of Bradykinin can be performed by molecules related to Bradykinin having anti-infarction activities. For example, des-arg-BK has activity similar to or greater than BK itself. Des describes a side chain. For example, des-Arg9 refers to Bradykinin without the C-term Arg.

b) Functional Analogs of Bradykinin

There are a variety of Bradykinin variants, many of which are shown in Table 2. Many of these variants have nonstandard amino acid derivatives in them. For example, analogs Cereport (also known as RMP-7 or lobradamil) (Arg-Pro-Hyp-Gly-Thi-Ser-Pro-Tyr (Me)-psi(CH2NH)-Arg, SEQ ID NO: 90), lysylbradykinin (Bradykinin with a N-terminal lysine added), Bradykinin with a C-terminal lysine added, 7-Methoxycoymarin-4-acetyl [Ala7-(2,4-Dinitrophenyl) Lys9]-Bradykinin trifluoroacetate salt (MOCAc-Arg-Pro-Pro-Gly-Phe-Ser-Ala-Phe-Lys-DNP, SEQ ID NO: 91), D-Arg-[Hyp3, D-Phe7, Leu8]-Bradykinin (D-Arg-Arg-Pro-Hyp-Gly-Phe-Ser-D-Phe-Leu-Arg, SEQ ID NO: 92), D-Arg-[Hyp3, D-Phe7]-Bradykinin (D-Arg-Arg-Pro-Hydroxy-Pro-Gly-Phe-Arg, SEQ ID NO: 93), D-Arg-[Hyp3, Thi5,8, D-Phe7]-Bradykinin (D-Arg-Arg-Pro-Hydroxy-Pro-Gly-b-(2-Thienyl)Ala-Ser-D-Phe-b-(2-Thienyl)Ala-Arg, SEQ ID NO: 94), Lys-(De-Arg9, Leu8)-Bradykinin trifluoroacetate salt (des(Arg10, Leu9)-KallidinH-Lys-Arg-Pro-Pro-Gly-Phe-Ser-Pro-Leu, SEQ ID NO: 95) exist.

Cyclic analogs of Bradykinin have desirable properties such as increased stability and increased activity and increases specific activity. Cyclic analogs of Bradykinin are disclosed in U.S. Pat. No. 4,187,217, which is herein incorporated by reference for material at least related to Bradykinin variants. An example of a cyclic Bradykinin variant is shown in FIG. 18. There are also a number of Bradykinin variants that contain non-peptide bonds and non-amino acid analogs. (for example, U.S. Pat. No. 5,162,497, which is herein incorporated by reference at least for material related to Bradykinin and Bradykinin variants.)

There are also a wide variety of Bradykinin variants and molecules which function like Bradykinin, such as functional analogs of Bradykinin, which can be found in for example, the Handbook of Experimental Pharmacology, vol. XXV. Bradykinin, Kallidin and Kallikrein. Ed. E. G. Erdos. Springer-Verlag, Berlin-Heidelberg, New York, 1970, pp. 1-768, which is herein incorporated by reference at lest for material related to functional Bradykinin analogs.

5. Anti-Infarction Properties

The anti-infarction properties of FPA or molecules related to FPA (C-terminus, 11-mer, for example,) or Bradykinin or molecules related to Bradykinin, (DES-arg-Bradykinin, for example), or any other anti-infarction molecules disclosed herein can be assayed by characterizing the reduction of the infarction volume compared to a control. Using the mouse MCAO model, the amount of infarcted tissue after an ischemic event can be determined. The volume of the infarction can be assayed and the smaller the infarction volume after the ischemic event, the more potent the tested molecule is in preventing or reversing an infarction. For example, the mean infarction volume, can be determined as a percent of the total volume of tissue. The mean infarction volume for the 11-mer FPA-fragment was 18.5%, which was markedly reduced compared to 54.7% for controls (p<0.0001). The range of the infarction volumes for a number of different animals tested for the FPA-derivative was 0% to 44% compared to 34% to 71% for the controls. The mean infarction volume for BK was 33.2% and 17.0% for daBK and 18.0% for daBK combined with the C-terminus. The mean infarction volume for the BK and daBK groups combined (25.2%) was statistically significant compared to 54.7% for controls (p<0.003). The range of the infarction volumes for the more effective daBK was 9% to 27% compared to 34% to 71% for the controls.

Thus, one way to determine the anti-infarction efficacy of a given molecule is to obtain an infarction ratio of the mean infarction volume of a control, (no molecule or carrier, for example) to the mean infarction volume present when the molecule is administered. An infarction volume in this infarction ratio is itself a ratio of the amount of infarcted tissue to the total volume of tissue (a % infarcted tissue). These volumes can be determined as disclosed herein. Thus, an anti-infarction molecule, such as FPA or BK or derivatives, can be a molecule whose infarction ratio is greater than 1, or greater than or equal to 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.5, 6.0, 6.5, 7.0, 7.5, 8.0, 8.5, 9.0, 10, 11, 12, 13, 14, 15, 16, 17, 18, 20, 25, 30, 35, 40, 45, 50, 60, 65, 70, 75, 80, 85, 90, 100, 500, 1000, 2,000, 5,000, 10,000, 100,000, or more. This can be determined by looking at mean volumes or absolute volumes for a given test. Another way of determining if a molecule is an anti-infarction molecule is to simply look at the absolute amount of infarcted volume present in the MCAO mouse model after administration of the molecule. For example, disclosed are anti-infarction molecules, such as FPA, BK, or their derivatives, that produce an infarcted volume of less than or equal to 95%, 90%, 85%, 80%, 75%, 70%, 65%, 60%, 55%, 50%, 45%, 40%, 35%, 30%, 29%, 28%, 27%, 26%, 25%, 24%, 23%, 22%, 21%, 20%, 19%, 18%, 17%, 16%, 15%, 14%, 13%, 12%, 11%, 10%, 9%, 8%, 7%, 6%, 5%, 4%, 3%, 2, or 1%. This can be determined as means or as an absolute volume from a single test.

6. Compositions Identified Using State Dependencies

Disclosed herein are methods for identifying molecules that are related to certain physiological states. The disclosed methods have been identified to function when the states are very closely linked in time, physiology, or characteristics, for example. One example that has been discussed herein is the identification of molecules associated with the anti-infarction activity that can be found in hibernating animals. The method for identification involved comparing nearest neighbor hibernating fractions to identify differences, rather than comparing hibernating fractions to non-hibernating fractions. This nearest neighbor concept can be applied to a number of different physiologies. This allows the finding of within substate, substates, and nearest neighbor substates. For example, hibernation, eating behavior, sleep, hypnosis, rocking motion pregnancy, G-force, weightlessness, sex, postprandial euphoria, psychotic episodes, such as bipolar, sun-exposure, for example, the resulting euphoria, dark-light cycle, for example, for the resulting depression, exercise, hyperbaric conditions or stress-related conditions are all states that can have substates and nearest neighbor states.

There are a variety of physiologies that can be monitored, such as heart beat, blood pressure, breathing rate, EEG, or eye movements. These can be measured using any means. One means for collecting and analyzing these types of states, is through the use of a non-linear improved Point Correlation Dimension (PD2i) algorithm. For many years it was known that the measurement of heart rate variability (HRV) by a linear stochastic algorithm (the Standard Deviation, the Power Spectra, etc.) could be used to predict arrhythmic death in hospitalized cardiac patients. The predictability (i.e., the Sensitivity, Specificity or Relative Risk statistics), however, were not very good, so the algorithm was not clinically useful for an individual patient. U.S. Pat. Nos. 5,720,924 and 5,709, 214 show that the analysis of HRV by a nonlinear deterministic algorithm, the PD2i, had much better predictability than the linear stochastic analysis (which are herein incorporated by reference at least for material related to using the PD2i algorithm).

Thus, the analytic measure of the PD2i is deterministic and based on caused variation in data. It does not require stationarity and actually tracks nonstationary changes in the data; and is sensitive to chaotic as well as nonchaotic, linear data. This analytic measure is based on previous analytic measures that are collectively, the algorithms for estimating the correlation dimension, and it is insensitive to data nonstationarities. Because of this feature, the PD2i can predict clinical outcomes with high sensitivity and specificity that the other measures cannot. This predictability can be enhanced by a Noise Consideration Algorithm (U.S. patent application to Skinner, 2003). This nonlinear algorithm is thought to be successful because it is able to track changes in state that occur in time in the biological organism. Most stochastic measures require data-stationarity, which means that the generator of the data cannot change state while producing it; that is, its stochastic properties cannot change (the mean, the standard deviation, and other parameters must remain the same). However, biological data series change state constantly. By solving the problem of the data non-stationarity inherent in most, if not all, biological data, the PD2i prediction of arrhythmic death is now clinically useful. Disclosed herein, this device, a device incorporating the PD2i algorithm or analogous algorithm, can be used for detecting physiological data between states and substates. These devices can be used to identify subtle changes of state (i.e., sub-state) that occur, i.e. they can be used to identify physiological differences within a state, which define two substates. These substates can be associated with the release of a targeted molecule.

a) The "Nearest-Neighbor Sub-state Method"

The nearest neighbor substate method is characterized by the recognition that two different conditions, i.e. substates, are recognized to be contained within a previous state. For example, in the state of hibernation it is disclosed herein that there are, for example, two different substates that occur related to bradycardia, which have been used to identify molecules that protect against infarction. There is a substate during the state of hibernation where sudden awaking results in high instances of death. The nearest neighbor substate is a point in hibernation when arousal does not result in increased instances of death. A comparison of the substate, death induced, with the nearest neighbor substate, or control, where death is not induced, can provide very specific molecular comparisons, which are associated with the physiology.

Thus a "state" can be thought of as a binary condition, such as sleep vs. awake, hungry vs. satiated, sick vs. well, etc. A substate can be characterized as a condition within a state, which is identified and which further sub-divides the state. That defining physiology or behavior must separate a substate from another within the overall state to be the control. When these substates are combined with proteomics and genomics techniques to identify molecular differences physiologically relevant molecules can be identified. This approach as demonstrated herein allows for the identification of many molecular differences, and in certain instances all differences that are associated with the physiology.

b) Different Types of States

Physiological sub-states, in addition to those in which the anti-infarction molecules are present, are transiently present to support a larger overall-state, such as hibernation. For example, non-urinating pregnant hibernating bears make complex molecules in larger and larger amounts for the growing fetus, so they must have an underlying physiology to handle the build-up of blood urea and thus prevent their own uremic toxicity. Disclosed herein, physiological data show that the double-labeled urea injected into normal awake lab rats (1, 2, or 3 mg/rat) can be stimulated by IV injection of hibernation-related fractions of molecules (i.e., D2, D01 at 20 mg/kg) to form single-labeled urea (i.e., "re-cycled" urea). At 3 hrs following injection of the hibernation-related fraction of molecules the mean excess above each animal's individualized background is approximately 50% compared to control (IV, Xeno albumin, 20 mg/kg) ($p<0.025$) and becomes even more significant at 6 hrs post injection ($p<0.01$). At 6-hrs post injection the largest stimulated recycling rate was found to be in excess of a 13-fold increase in the urea-recycling rate.

7. Compositions Identified by Screening with Disclosed Compositions/Combinatorial Chemistry It is understood that the fact that FPA and Bradykinin have anti-infarction properties means that the knowledge of what FPA and Bradykinin interact with can be used to identify molecules that function like FPA and Bradykinin in the particular assay and then these can be tested in the disclosed infarction models to determine their activity. For example the binding information available for FPA and thrombin can be utilized to isolate molecules that bind thrombin like FPA and these then can be tested in the disclosed infarction models. For example, selection experiments that isolate competitive inhibitors of FPA and thrombin binding are disclosed. Thus, there are a variety of ways to make anti-infarction molecules, including molecules, which can be made by synthesizing molecules, which can be isolated by screening methods.

It is also understood that a variety of molecules can be isolated, protein variants, antibodies, functional nucleic acids, and peptide mimetics to name a few. What follows is a discussion of these and other molecules, including small molecules that can be identified as having FPA and Bradykinin like anti-infarction properties. It is understood that FPA and Bradykinin refer to all FPA and Bradykinin variants and derivatives respectively, i.e. they have some level of identity to FPA and Bradykinin. Molecules which function like FPA and/or Bradykinin but do not have an amino acid based structure are termed anti-infarction molecules, having a particular property, such as FPA activity or Bradykinin activity.

Disclosed are methods of making an anti-infarction molecule comprising synthesizing the anti-infarction molecule or a variant of the anti-infarction molecule, wherein the anti-infarction molecule can be purified by a method comprising 1) collecting a blood sample from a hibernating animal, 2) collecting a second blood sample from a hibernating animal, 3) comparing the blood sample to the second blood sample, wherein the blood sample is collected less than or equal to 25 days after the onset of hibernation, and the second blood sample is collected greater than 25 days after the onset of hibernation and wherein the anti-infarction molecule is a present in greater amounts in the blood sample than in the second blood sample.

Disclosed are methods of making an anti-infarction molecule comprising synthesizing the anti-infarction molecule or a variant of the anti-infarction molecule, wherein the anti-infarction molecule can be purified by a method comprising 1) collecting a blood sample from a hibernating animal, 2) collecting a second blood sample from a hibernating animal, 3) comparing the blood sample to the second blood sample, wherein the blood sample is collected less than or equal to 25 days before the end of hibernation, and the second blood sample is collected greater than 25 days after the onset of hibernation, but before 25 days before the end of hibernation, and wherein the anti-infarction molecule is a present in greater amounts in the blood sample than in the second blood sample.

Also disclosed are methods of identifying an anti-infarction molecule comprising administering a molecule to a mouse MCAO model, comparing the anti-infarction activity of the molecule to the anti-infarction activity of FPA in a mouse MCAO model, and selecting the molecule if the anti-infarction activity of the molecule is at least 20% of the activity of FPA.

Disclosed are methods of identifying an inhibitor of the interaction between Bradykinin and the angiotensin II receptor comprising: contacting a cell expressing the angiotensin II receptor type 2 with the putative inhibitor in the presence of Bradykinin; detecting the amount Bradykinin bound to the angiotensin II receptor type 2; wherein a reduction in Bradykinin binding to the angiotensin II receptor type 2 identifies an inhibitor.

Disclosed are methods of identifying an inhibitor of the interaction between Bradykinin and the angiotensin II receptor type 2 comprising: contacting a cell expressing the angiotensin II receptor type 2 with a putative inhibitor in the presence of Bradykinin, wherein the angiotensin II receptor type 2 comprises a fluorescence donor, wherein Bradykinin comprises a fluorescence acceptor; and measuring Fluorescence Resonance Energy Transfer (FRET), wherein a decrease in FRET as compared to FRET measurement in a cell that was not contacted with the putative inhibitor indicates the presence of an inhibitor.

Disclosed are methods of identifying an inhibitor of the interaction between Bradykinin and an angiotensin II receptor type 2 comprising: contacting a cell system with a putative inhibitor, wherein the cell system comprises an angiotensin II receptor type 2, wherein the cell system comprises Bradykinin, wherein the angiotensin II receptor type 2 comprises a fluorescence donor, and wherein the Bradykinin comprises a fluorescence acceptor; and measuring Fluorescence Resonance Energy Transfer (FRET) before contacting the cell system with the putative inhibitor and after contacting the cell system with the putative inhibitor, wherein a decrease in FRET in the cell system when the putative inhibitor is contacted with the putative inhibitor identifies an inhibitor. A cell system refers to a cell containing the necessary components for functioning and assaying as disclosed herein.

Disclosed are methods further comprising the step of testing the identified inhibitor in an in vivo model of infarction, and selecting molecules that reduce an infarction in the animal model.

Disclosed are methods, wherein the putative inhibitor is found within a library of molecules.

Disclosed are methods of screening for an anti-infarction molecule that modulates the angiotensin II receptor type 2 comprising: contacting an animal model of infarction, known to express the angiotensin II receptor, with a putative anti-infarction molecule in the absence of exogenous Bradykinin; assaying for an infarction; and correlating a absence of infarction with the presence of an anti-infarction mimetic of Bradykinin that modulates the angiotensin II receptor.

Disclosed are methods of screening for an anti-infarction molecule that modulates the angiotensin II receptor type 2 comprising: contacting an animal model of infarction, known to express the angiotensin II receptor, with a putative anti-infarction molecule in the absence of Bradykinin; detecting the absence or presence of an infarction; and correlating the absence of infarction with the presence of an anti-infarction molecule that modulates the angiotensin II receptor.

Disclosed are methods, wherein the putative anti-infarction mimetic is an angiotensin II receptor agonist or antagonist.

Disclosed are methods of identifying a putative anti-infarction molecule comprising: contacting a cell expressing the angiotensin II receptor type 2 with the putative anti-infarction molecule, in the presence of Bradykinin; detecting a reduction in binding of Bradykinin to the angiotensin II receptor type 2; and correlating the reduction in binding of Bradykinin to the angiotensin II receptor type 2 to the presence of an anti-infarction molecule.

It is understood that these methods can be used to find inhibitors of the interaction between Bradykinin and the Angiotensin II receptor type 2.

Disclosed are methods of identifying a putative anti-infarction molecule comprising: contacting a cell expressing the angiotensin II receptor type 2 functionally linked to a fluorescence donor with Bradykinin functionally linked to a fluorescence acceptor and the putative anti-infarction molecule; and measuring Fluorescence Resonance Energy Transfer (FRET), wherein a decrease in FRET as compared to FRET measurement in a cell that was not contacted with the putative anti-infarction molecule indicates the presence of an anti-infarction molecule.

It is understood that the disclosed methods can further comprise testing the isolated compounds or compositions in an animal model of, for example, ischemia. For example, the amount of infarction occurring in the presence of the isolated molecules can be measured and compared to the amount of infarction present in the absence of the molecule. Animal models, as disclosed herein, can also be used to de novo to isolate anti-infarction molecules as disclosed herein. In particular animal models can be used to competitively compare a putative anti-infarction molecule to for example Bradykinin or FPA or variant or derivative.

The disclosed methods can also be used with libraries of molecules to screen for active compositions or compounds. Typically the methods will employ a step of isolating the active molecules from the non-active molecules when a library is screened, as disclosed herein.

Disclosed are methods of treating subjects in need of reducing an infarction, comprising administering an effective amount of the molecules isolated using the disclosed methods.

It is understood that the disclosed methods can be practiced for cerebral or myocardial or other types of infarctions.

It is understood that infarctions, which are regions of necrotic tissue can arise in a variety of ways, but typically an infarction will arise from an ischemia, or a reduction of oxygen to a region of tissue. The loss of oxygen, and the subsequent reperfusion, should it occur, can cause necrotic tissue to arise. The disclosed methods are designed to reduce the effects of ischemic events, such as infarctions caused by reperfusion and/or oxygen deprivation. These types of events occur, for example, during a stroke, where there is blood vessel blockage in cerebral tissue causing ischemia or in a cardiac event, such as a heart attack, where blockage of a coronary artery leads to ischemia.

Treatment of ischemia typically involves reduction of blockage. For example, nitroglycerin treats ischemia (opens clogged coronary vessels a little more than normal and makes angina pain from the ischemia go away). Suppression of blood flow causes ischemia. The mouse-MCAO model produces ischemia and sets the stage for infarction to occur at, typically 24-hrs. It is the infarction that is prevented/treated, as the flow has been re-established at the time of the injection the disclosed compositions and the tissue is therefore no longer ischemic. Anti-infarction molecules are sometimes referred to as "neuro-protectant drugs." There are a variety of different types of molecules that can have FPA or bradykinin anti-infarction activity. Exemplary compounds are discussed herein.

a) Functional Nucleic Acids

Functional nucleic acids are nucleic acid molecules that have a specific function, such as binding a target molecule or catalyzing a specific reaction. Functional nucleic acid molecules can be divided into the following categories, which are not meant to be limiting. For example, functional nucleic acids include antisense molecules, aptamers, ribozymes, triplex forming molecules, and external guide sequences. The functional nucleic acid molecules can act as affectors, inhibitors, modulators, and stimulators of a specific activity possessed by a target molecule, or the functional nucleic acid molecules can possess a de novo activity independent of any other molecules.

Functional nucleic acid molecules can interact with any macromolecule, such as DNA, RNA, polypeptides, or carbohydrate chains. Thus, functional nucleic acids can interact with the mRNA of FPA or Bradykinin or molecules they interact with such as thrombin, or fragments thereof, or the genomic DNA of FPA or Bradykinin or molecules they interact with such as thrombin, or fragments thereof or they can interact with the polypeptide FPA or Bradykinin or molecules they interact with such as thrombin, or fragments thereof. Often functional nucleic acids are designed to interact with other nucleic acids based on sequence homology between the target molecule and the functional nucleic acid molecule. In other situations, the specific recognition between the functional nucleic acid molecule and the target molecule is not based on sequence homology between the functional nucleic acid molecule and the target molecule, but rather is based on the formation of tertiary structure that allows specific recognition to take place.

Antisense molecules are designed to interact with a target nucleic acid molecule through either canonical or non-canonical base pairing. The interaction of the antisense molecule and the target molecule is designed to promote the destruction of the target molecule through, for example, RNAseH mediated RNA-DNA hybrid degradation. Alternatively the antisense molecule is designed to interrupt a processing function that normally would take place on the target molecule, such as transcription or replication. Antisense molecules can be designed based on the sequence of the target molecule. Numerous methods for optimization of antisense efficiency by finding the most accessible regions of the target molecule exist. Exemplary methods would be in vitro selection experiments and DNA modification studies using DMS and DEPC. It is preferred that antisense molecules bind the target molecule with a dissociation constant ($k_d$) less than $10^{-6}$. It is more preferred that antisense molecules bind with a $k_d$ less than $10^{-8}$. It is also more preferred that the antisense molecules bind the target molecule with a $k_d$ less than $10^{-10}$. It is also preferred that the antisense molecules bind the target molecule with a $k_d$ less than $10^{-12}$. A representative sample of methods and techniques which aid in the design and use of antisense molecules can be found in the following non-limiting list of U.S. Pat. Nos. 5,135,917, 5,294,533, 5,627,158, 5,641,754, 5,691,317, 5,780,607, 5,786,138, 5,849,903, 5,856,103, 5,919,772, 5,955,590, 5,990,088, 5,994,320, 5,998,602, 6,005,095, 6,007,995, 6,013,522, 6,017,898, 6,018,042, 6,025,198, 6,033,910, 6,040,296, 6,046,004, 6,046,319, and 6,057,437.

Aptamers are molecules that interact with a target molecule, preferably in a specific way. Typically aptamers are small nucleic acids ranging from 15-50 bases in length that fold into defined secondary and tertiary structures, such as stem-loops or G-quartets. Aptamers can bind small molecules, such as ATP (U.S. Pat. No. 5,631,146) and theophiline (U.S. Pat. No. 5,580,737), as well as large molecules, such as reverse transcriptase (U.S. Pat. No. 5,786,462) and thrombin (U.S. Pat. No. 5,543,293). Aptamers can bind very tightly with $k_d$s from the target molecule of less than $10^{-12}$ M. It is preferred that the aptamers bind the target molecule with a $k_d$ less than $10^{-6}$. It is more preferred that the aptamers bind the target molecule with a $k_d$ less than $10^{-8}$. It is also more preferred that the aptamers bind the target molecule with a $k_d$ less than $10^{-10}$. It is also preferred that the aptamers bind the target molecule with a $k_d$ less than $10^{-12}$. Aptamers can bind the target molecule with a very high degree of specificity. For example, aptamers have been isolated that have greater than a 10000 fold difference in binding affinities between the target molecule and another molecule that differ at only a single position on the molecule (U.S. Pat. No. 5,543,293). It is preferred that the aptamer have a $k_d$ with the target molecule at least 10 fold lower than the $k_d$ with a background binding molecule. It is more preferred that the aptamer have a $k_d$ with the target molecule at least 100 fold lower than the $k_d$ with a background binding molecule. It is more preferred that the aptamer have a $k_d$ with the target molecule at least 1000 fold lower than the $k_d$ with a background binding molecule. It is preferred that the aptamer have a $k_d$ with the target molecule at least 10000 fold lower than the $k_d$ with a background binding molecule. It is preferred when doing the comparison for a polypeptide for example, that the background molecule be a different polypeptide. For example, when determining the specificity of FPA or Bradykinin or molecules they interact with such as thrombin, or fragments thereof, aptamers, the background protein could be serum albumin. Representative examples of how to make and use aptamers to bind a variety of different target molecules can be found in the following non-limiting list of U.S. Pat. Nos. 5,476,766, 5,503,978, 5,631,146, 5,731,424, 5,780,228, 5,792,613, 5,795,721, 5,846,713, 5,858,660, 5,861,254, 5,864,026, 5,869,641, 5,958,691, 6,001,988, 6,011,020, 6,013,443, 6,020,130, 6,028,186, 6,030,776, and 6,051,698.

Ribozymes are nucleic acid molecules that are capable of catalyzing a chemical reaction, either intramolecularly or intermolecularly. Ribozymes are thus catalytic nucleic acid. It is preferred that the ribozymes catalyze intermolecular reactions. There are a number of different types of ribozymes that catalyze nuclease or nucleic acid polymerase type reactions which are based on ribozymes found in natural systems, such as hammerhead ribozymes, (for example, but not limited to the following U.S. Pat. Nos. 5,334,711, 5,436,330, 5,616,466, 5,633,133, 5,646,020, 5,652,094, 5,712,384, 5,770,715, 5,856,463, 5,861,288, 5,891,683, 5,891,684, 5,985,621, 5,989,908, 5,998,193, 5,998,203, WO 9858058 by Ludwig and Sproat, WO 9858057 by Ludwig and Sproat, and WO 9718312 by Ludwig and Sproat) hairpin ribozymes (for example, but not limited to the following U.S. Pat. Nos. 5,631,115, 5,646,031, 5,683,902, 5,712,384, 5,856,188, 5,866,701, 5,869,339, and 6,022,962), and tetrahymena ribozymes (for example, but not limited to the following U.S. Pat. Nos. 5,595,873 and 5,652,107). There are also a number of ribozymes that are not found in natural systems, but which have been engineered to catalyze specific reactions de novo (for example, but not limited to the following U.S. Pat. Nos. 5,580,967, 5,688,670, 5,807,718, and 5,910,408). Preferred ribozymes cleave RNA or DNA substrates, and more preferably cleave RNA substrates. Ribozymes typically cleave nucleic acid substrates through recognition and binding of the target substrate with subsequent cleavage. This recognition is often based mostly on canonical or non-canonical base pair interactions. This property makes ribozymes particularly good candidates for target specific cleavage of nucleic acids because recognition of the target substrate is based on the target substrates sequence. Representative examples of how to make and use ribozymes to catalyze a variety of different reactions can be found in the following non-limiting list of U.S. Pat. Nos. 5,646,042, 5,693,535, 5,731,295, 5,811,300, 5,837,855, 5,869,253, 5,877,021, 5,877,022, 5,972,699, 5,972,704, 5,989,906, and 6,017,756.

Triplex forming functional nucleic acid molecules are molecules that can interact with either double-stranded or single-stranded nucleic acid. When triplex molecules interact with a target region, a structure called a triplex is formed, in which there are three strands of DNA forming a complex dependant on both Watson-Crick and Hoogsteen base-pairing. Triplex molecules are preferred because they can bind target regions with high affinity and specificity. It is preferred that the triplex forming molecules bind the target molecule with a $k_d$ less than $10^{-6}$. It is more preferred that the triplex forming molecules bind with a $k_d$ less than $10^{-8}$. It is also more preferred that the triplex forming molecules bind the target molecule with a $k_d$ less than $10^{-10}$. It is also preferred that the triplex forming molecules bind the target molecule with a $k_d$ less than $10^{-12}$. Representative examples of how to make and use triplex forming molecules to bind a variety of different target molecules can be found in the following non-limiting list of U.S. Pat. Nos. 5,176,996, 5,645,985, 5,650,316, 5,683,874, 5,693,773, 5,834,185, 5,869,246, 5,874,566, and 5,962,426.

External guide sequences (EGSs) are molecules that bind a target nucleic acid molecule forming a complex, and this complex is recognized by RNase P, which cleaves the target molecule. EGSs can be designed to specifically target a RNA molecule of choice. RNAse P aids in processing transfer RNA (tRNA) within a cell. Bacterial RNAse P can be recruited to cleave virtually any RNA sequence by using an EGS that causes the target RNA:EGS complex to mimic the natural tRNA substrate. (WO 92/03566 by Yale, and Forster and Altman, Science 238:407-409 (1990)).

Similarly, eukaryotic EGS/RNAse P-directed cleavage of RNA can be utilized to cleave desired targets within eukaryotic cells. (Yuan et al., Proc. Natl. Acad. Sci. USA 89:8006-8010 (1992); WO 93/22434 by Yale; WO 95/24489 by Yale; Yuan and Altman, EMBO J 14:159-168 (1995), and Carrara et al., Proc. Natl. Acad. Sci. (USA) 92:2627-2631 (1995)). Representative examples of how to make and use EGS molecules to facilitate cleavage of a variety of different target molecules be found in the following non-limiting list of U.S. Pat. Nos. 5,168,053, 5,624,824, 5,683,873, 5,728,521, 5,869,248, and 5,877,162.

b) Combinatorial Chemistry

The disclosed compositions can be used as targets for any combinatorial technique to identify molecules or macromolecular molecules that interact with the disclosed compositions in a desired way. The nucleic acids, peptides, and related molecules disclosed herein can be used as targets for the combinatorial approaches. Also disclosed are the compositions that are identified through combinatorial techniques or screening techniques in which the compositions disclosed in Table 1 or Table 2 or portions thereof, are used as the target in a combinatorial or screening protocol or compositions that interact with sequences in Table 1 or Table 2 or portions thereof, are used as the target in a combinatorial or screening protocol.

It is understood that when using the disclosed compositions in combinatorial techniques or screening methods, molecules, such as macromolecular molecules, will be identified that have particular desired properties such as inhibition or stimulation or the target molecule's function. The molecules identified and isolated when using the disclosed compositions, such as, the compositions disclosed in Table 1 or Table 2 or portions thereof, or compositions that interact with sequences in Table 1 or Table 2 or portions thereof, are also disclosed. Thus, the products produced using the combinatorial or screening approaches that involve the disclosed compositions, such as, the compositions disclosed in Table 1 or Table 2 or portions thereof, or compositions that interact with sequences in Table 1 or Table 2 or portions thereof, are also considered herein disclosed.

Combinatorial chemistry includes but is not limited to all methods for isolating small molecules or macromolecules that are capable of binding either a small molecule or another macromolecule, typically in an iterative process. Proteins, oligonucleotides, and sugars are examples of macromolecules. For example, oligonucleotide molecules with a given function, catalytic or ligand-binding, can be isolated from a complex mixture of random oligonucleotides in what has been referred to as "in vitro genetics" (Szostak, TIBS 19:89, 1992). One synthesizes a large pool of molecules bearing random and defined sequences and subjects that complex mixture, for example, approximately $10^{15}$ individual sequences in 100 μg of a 100 nucleotide RNA, to some selection and enrichment process. Through repeated cycles of affinity chromatography and PCR amplification of the molecules bound to the ligand on the column, Ellington and Szostak (1990) estimated that 1 in $10^{10}$ RNA molecules folded in such a way as to bind a small molecule dyes. DNA molecules with such ligand-binding behavior have been isolated as well (Ellington and Szostak, 1992; Bock et al, 1992). Techniques aimed at similar goals exist for small organic molecules, proteins, antibodies and other macromolecules known to those of skill in the art. Screening sets of molecules for a desired activity whether based on small organic libraries, oligonucleotides, or antibodies is broadly referred to as combinatorial chemistry. Combinatorial techniques are particularly suited for defining binding interactions between molecules and for isolating molecules that have a specific binding activity, often called aptamers when the macromolecules are nucleic acids.

There are a number of methods for isolating proteins, which either have de novo activity or a modified activity. For example, phage display libraries have been used to isolate numerous peptides that interact with a specific target. (See for example, U.S. Pat. Nos. 6,031,071; 5,824,520; 5,596,079; and 5,565,332 which are herein incorporated by reference at least for their material related to phage display and methods relate to combinatorial chemistry).

A preferred method for isolating proteins that have a given function is described by Roberts and Szostak (Roberts R. W. and Szostak J. W. Proc. Natl. Acad. Sci. USA, 94(23)12997-302 (1997). This combinatorial chemistry method couples the functional power of proteins and the genetic power of nucleic acids. An RNA molecule is generated in which a puramycin molecule is covalently attached to the 3'-end of the RNA molecule. An in vitro translation of this modified RNA molecule causes the correct protein, encoded by the RNA to be translated. In addition, because of the attachment of the puramycin, a peptidyl acceptor that cannot be extended, the growing peptide chain is attached to the puramycin, which is attached to the RNA. Thus, the protein molecule is attached to the genetic material that encodes it. Normal in vitro selection procedures can now be done to isolate functional peptides. Once the selection procedure for peptide function is complete traditional nucleic acid manipulation procedures are performed to amplify the nucleic acid that codes for the selected functional peptides. After amplification of the genetic material, new RNA is transcribed with puramycin at the 3'-end, new peptide is translated and another functional round of selection is performed. Thus, protein selection can be performed in an iterative manner just like nucleic acid selection techniques. The peptide, which is translated, is controlled by the sequence of the RNA attached to the puramycin. This sequence can be anything from a random sequence engineered for optimum translation (i.e. no stop codons etc.) or it can be a degenerate sequence of a known RNA molecule to look for improved or altered function of a known peptide. The conditions for nucleic acid amplification and in vitro translation are well known to those of ordinary skill in the art and are preferably performed as in Roberts and Szostak (Roberts R. W. and Szostak J. W. Proc. Natl. Acad. Sci. USA, 94(23) 12997-302 (1997)).

Another preferred method for combinatorial methods designed to isolate peptides is described in Cohen et al. (Cohen B. A., et al., Proc. Natl. Acad. Sci. USA 95(24):14272-7 (1998)). This method utilizes and modifies two-hybrid technology. Yeast two-hybrid systems are useful for the detection and analysis of protein: protein interactions. The two-hybrid system, initially described in the yeast *Saccharomyces cerevisiae*, is a powerful molecular genetic technique for identifying new regulatory molecules, specific to the protein of interest (Fields and Song, Nature 340:245-6 (1989)). Cohen et al., modified this technology so that novel interactions between synthetic or engineered peptide sequences could be identified which bind a molecule of choice. The benefit of this type of technology is that the selection is done in an intracellular environment. The method utilizes a library of peptide molecules that attached to an acidic activation domain. A peptide of choice, for example an extracellular portion of the compositions disclosed in Table 1 or Table 2 or portions thereof, or compositions that interact with sequences in Table 1 or Table 2 or portions thereof is attached to a DNA binding domain of a transcriptional activation protein, such as Gal 4. By performing the Two-hybrid technique on this type of system, molecules that bind FPA or Bradykinin or molecules they interact with such as thrombin, or fragments thereof, can be identified.

Using methodology well known to those of skill in the art, in combination with various combinatorial libraries, one can isolate and characterize those small molecules or macromolecules, which bind to or interact with the desired target. The relative binding affinity of these compounds can be compared and optimum compounds identified using competitive binding studies, which are well known to those of skill in the art.

Techniques for making combinatorial libraries and screening combinatorial libraries to isolate molecules, which bind a desired target, are well known to those of skill in the art. Representative techniques and methods can be found in but are not limited to U.S. Pat. Nos. 5,084,824, 5,288,514, 5,449,754, 5,506,337, 5,539,083, 5,545,568, 5,556,762, 5,565,324, 5,565,332, 5,573,905, 5,618,825, 5,619,680, 5,627,210, 5,646,285, 5,663,046, 5,670,326, 5,677,195, 5,683,899, 5,688,696, 5,688,997, 5,698,685, 5,712,146, 5,721,099, 5,723,598, 5,741,713, 5,792,431, 5,807,683, 5,807,754, 5,821,130, 5,831,014, 5,834,195, 5,834,318, 5,834,588, 5,840,500, 5,847,150, 5,856,107, 5,856,496, 5,859,190, 5,864,010, 5,874,443, 5,877,214, 5,880,972, 5,886,126, 5,886,127, 5,891,737, 5,916,899, 5,919,955, 5,925,527, 5,939,268, 5,942,387, 5,945,070, 5,948,696, 5,958,702, 5,958,792, 5,962,337, 5,965,719, 5,972,719, 5,976,894, 5,980,704, 5,985,356, 5,999,086, 6,001,579, 6,004,617, 6,008,321, 6,017,768, 6,025,371, 6,030,917, 6,040,193, 6,045,671, 6,045,755, 6,060,596, and 6,061,636.

Combinatorial libraries can be made from a wide array of molecules using a number of different synthetic techniques. For example, libraries containing fused 2,4-pyrimidinediones (U.S. Pat. No. 6,025,371) dihydrobenzopyrans (U.S. Pat. Nos. 6,017,768 and 5,821,130), amide alcohols (U.S. Pat. No. 5,976,894), hydroxy-amino acid amides (U.S. Pat. No. 5,972,719) carbohydrates (U.S. Pat. No. 5,965,719), 1,4-benzodiazepin-2,5-diones (U.S. Pat. No. 5,962,337), cyclics (U.S. Pat. No. 5,958,792), biaryl amino acid amnides (U.S. Pat. No. 5,948,696), thiophenes (U.S. Pat. No. 5,942,387), tricyclic Tetrahydroquinolines (U.S. Pat. No. 5,925,527), benzofurans (U.S. Pat. No. 5,919,955), isoquinolines (U.S. Pat. No. 5,916,899), hydantoin and thiohydantoin (U.S. Pat. No. 5,859,190), indoles (U.S. Pat. No. 5,856,496), imidazol-pyrido-indole and imidazol-pyrido-benzothiophenes (U.S. Pat. No. 5,856, 107) substituted 2-methylene-2,3-dihydrothiazoles (U.S. Pat. No. 5,847,150), quinolines (U.S. Pat. No. 5,840,500), PNA (U.S. Pat. No. 5,831,014), containing tags (U.S. Pat. No. 5,721,099), polyketides (U.S. Pat. No. 5,712,146), morpholino-subunits (U.S. Pat. Nos. 5,698,685 and 5,506,337), sulfamides (U.S. Pat. No. 5,618,825), and benzodiazepines (U.S. Pat. No. 5,288,514).

Screening molecules similar to thrombin for inhibition of FPA binding is a method of isolating desired compounds.

As used herein combinatorial methods and libraries included traditional screening methods and libraries as well as methods and libraries used in iterative processes.

c) Computer Assisted Drug Design

The disclosed compositions can be used as targets for any molecular modeling technique to identify either the structure of the disclosed compositions or to identify potential or actual molecules, such as small molecules, which interact in a desired way with the disclosed compositions. The nucleic acids, peptides, and related molecules disclosed herein can be used as targets in any molecular modeling program or approach.

It is understood that when using the disclosed compositions in modeling techniques, molecules, such as macromolecular molecules, will be identified that have particular desired properties such as inhibition or stimulation or the target molecule's function. The molecules identified and isolated when using the disclosed compositions, such as, the compositions disclosed in Table 1 or Table 2 or portions thereof, or compositions that interact with sequences in Table 1 or Table 2 or portions thereof, are also disclosed. Thus, the products produced using the molecular modeling approaches that involve the disclosed compositions, such as, the compositions disclosed in Table 1 or Table 2 or portions thereof, or compositions that interact with sequences in Table 1 or Table 2 or portions thereof, are also considered herein disclosed.

Thus, one way to isolate molecules that bind a molecule of choice is through rational design. This is achieved through structural information and computer modeling. Computer modeling technology allows visualization of the three-dimensional atomic structure of a selected molecule and the rational design of new compounds that will interact with the molecule. The three-dimensional construct typically depends on data from x-ray crystallographic analyses or NMR imaging of the selected molecule. The molecular dynamics require force field data. The computer graphics systems enable prediction of how a new compound will link to the target molecule and allow experimental manipulation of the structures of the compound and target molecule to perfect binding specificity. Prediction of what the molecule-compound interaction will be when small changes are made in one or both requires molecular mechanics software and computationally intensive computers, usually coupled with user-friendly, menu-driven interfaces between the molecular design program and the user.

Examples of molecular modeling systems are the CHARMm and QUANTA programs, Polygen Corporation, Waltham, Mass. CHARMm performs the energy minimization and molecular dynamics functions. QUANTA performs the construction, graphic modeling and analysis of molecular structure. QUANTA allows interactive construction, modification, visualization, and analysis of the behavior of molecules with each other.

A number of articles review computer modeling of drugs interactive with specific proteins, such as Rotivinen, et al., 1988 *Acta Pharmaceutica Fennica* 97, 159-166; Ripka, *New Scientist* 54-57 (Jun. 16, 1988); McKinaly and Rossmann, 1989 *Annu. Rev. Pharmacol. Toxiciol.* 29, 111-122; Perry and Davies, *QSAR: Quantitative Structure-Activity Relationships in Drug Design* pp. 189-193 (Alan R. Liss, Inc. 1989); Lewis and Dean, 1989 *Proc. R. Soc. Lond.* 236, 125-140 and 141-162; and, with respect to a model enzyme for nucleic acid components, Askew, et al., 1989 *J. Am. Chem. Soc.* 111, 1082-1090. Other computer programs that screen and graphically depict chemicals are available from companies such as BioDesign, Inc., Pasadena, Calif., Allelix, Inc, Mississauga, Ontario, Canada, and Hypercube, Inc., Cambridge, Ontario. Although these are primarily designed for application to drugs specific to particular proteins, they can be adapted to design of molecules specifically interacting with specific regions of DNA or RNA, once that region is identified.

Although described above with reference to design and generation of compounds, which could alter binding, one could also screen libraries of known compounds, including natural products or synthetic chemicals, and biologically active materials, including proteins, for compounds, which alter substrate binding or enzymatic activity.

d) Antibodies (1) Antibodies Generally

The term "antibodies" is used herein in a broad sense and includes both polyclonal and monoclonal antibodies. In addition to intact immunoglobulin molecules, also included in the term "antibodies" are fragments or polymers of those immunoglobulin molecules, and human or humanized versions of immunoglobulin molecules or fragments thereof, as long as they are chosen for their ability to mimic FPA or Bradykinin or fragments thereof, such that, for example, anti-infarction properties of FPA, Bradykinin, or fragments thereof, disclosed herein. The antibodies can be tested for their desired activity using the in vitro assays described herein, or by analogous methods, after which their in vivo therapeutic and/ or prophylactic activities are tested according to known clinical testing methods. Also disclosed are functional equivalents of antibodies.

The term "monoclonal antibody" as used herein refers to an antibody obtained from a substantially homogeneous population of antibodies, i.e., the individual antibodies within the population are identical except for possible naturally occurring mutations that can be present in a small subset of the antibody molecules. The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, as long as they exhibit the desired antagonistic activity (See, U.S. Pat. No. 4,816,567 and Morrison et al., *Proc. Natl. Acad. Sci. USA*, 81:6851-6855 (1984)).

The disclosed monoclonal antibodies can be made using any procedure, which produces monoclonal antibodies. For example, monoclonal antibodies can be prepared using hybridoma methods, such as those described by Kohler and Milstein, *Nature,* 256:495 (1975). In a hybridoma method, a mouse or other appropriate host animal is typically immunized with an immunizing agent to elicit lymphocytes that produce or are capable of producing antibodies that will specifically bind to the immunizing agent.

The monoclonal antibodies can also be made by recombinant DNA methods, such as those described in U.S. Pat. No. 4,816,567 (Cabilly et al.). DNA encoding the disclosed monoclonal antibodies can be readily isolated and sequenced using conventional procedures (e.g., by using oligonucleotide probes that are capable of binding specifically to genes encoding the heavy and light chains of murine antibodies). Libraries of antibodies or active antibody fragments can also be generated and screened using phage display techniques, e.g., as described in U.S. Pat. No. 5,804,440 to Burton et al. and U.S. Pat. No. 6,096,441 to Barbas et al.

In vitro methods are also suitable for preparing monovalent antibodies. Digestion of antibodies to produce fragments thereof, particularly, Fab fragments, can be accomplished using routine techniques known in the art. For instance, digestion can be performed using papain. Examples of papain digestion are described in WO 94/29348 published Dec. 22, 1994 and U.S. Pat. No. 4,342,566. Papain digestion of antibodies typically produces two identical antigen binding fragments, called Fab fragments, each with a single antigen binding site, and a residual Fc fragment. Pepsin treatment yields a fragment that has two antigen combining sites and is still capable of cross-linking antigen.

The fragments, whether attached to other sequences or not, can also include insertions, deletions, substitutions, or other selected modifications of particular regions or specific amino acids residues, provided the activity of the antibody or antibody fragment is not significantly altered or impaired compared to the non-modified antibody or antibody fragment. These modifications can provide for some additional property, such as to remove/add amino acids capable of disulfide bonding, to increase its bio-longevity, to alter its secretory characteristics, etc. In any case, the antibody or antibody fragment must possess a bioactive property, such as specific binding to its cognate antigen. Functional or active regions of the antibody or antibody fragment can be identified by mutagenesis of a specific region of the protein, followed by expression and testing of the expressed polypeptide. Such methods are readily apparent to a skilled practitioner in the art and can include site-specific mutagenesis of the nucleic acid encoding the antibody or antibody fragment. (Zoller, M. J. *Curr. Opin. Biotechnol.* 3:348-354, 1992).

As used herein, the term "antibody" or "antibodies" can also refer to a human antibody and/or a humanized antibody. Many non-human antibodies (e.g., those derived from mice, rats, or rabbits) are naturally antigenic in humans, and thus can give rise to undesirable immune responses when administered to humans. Therefore, the use of human or humanized antibodies in the methods serves to lessen the chance that an antibody administered to a human will evoke an undesirable immune response.

(2) Human Antibodies

The human antibodies can be prepared using any technique. Examples of techniques for human monoclonal antibody production include those described by Cole et al. (*Monoclonal Antibodies and Cancer Therapy*, Alan R. Liss, p. 77, 1985) and by Boemer et al. (*J. Immunol.,* 147(1):86-95, 1991). Human antibodies (and fragments thereof) can also be produced using phage display libraries (Hoogenboom et al., *J. Mol. Biol.,* 227:381, 1991; Marks et al., *J. Mol. Biol.,* 222:581, 1991).

The human antibodies can also be obtained from transgenic animals. For example, transgenic, mutant mice that are capable of producing a full repertoire of human antibodies, in response to immunization, have been described (see, e.g., Jakobovits et al., *Proc. Natl. Acad. Sci. USA,* 90:2551-255 (1993); Jakobovits et al., *Nature,* 362:255-258 (1993); Bruggermatm et al., *Year in Immunol.,* 7:33 (1993)). Specifically, the homozygous deletion of the antibody heavy chain joining region (J(H)) gene in these chimeric and germ-line mutant mice results in complete inhibition of endogenous antibody production, and the successful transfer of the human germ-line antibody gene array into such germ-line mutant mice results in the production of human antibodies upon antigen challenge.

(3) Humanized Antibodies

Antibody humanization techniques generally involve the use of recombinant DNA technology to manipulate the DNA sequence encoding one or more polypeptide chains of an antibody molecule. Accordingly, a humanized form of a non-human antibody (or a fragment thereof) is a chimeric antibody or antibody chain (or a fragment thereof, such as an Fv, Fab, Fab', or other antigen-binding portion of an antibody) which contains a portion of an antigen binding site from a non-human (donor) antibody integrated into the framework of a human (recipient) antibody.

To generate a humanized antibody, residues from one or more complementarity determining regions (CDRs) of a recipient (human) antibody molecule are replaced by residues from one or more CDRs of a donor (non-human) antibody molecule that is known to have desired antigen binding characteristics (e.g., a certain level of specificity and affinity for the target antigen). In some instances, Fv framework (FR) residues of the human antibody are replaced by corresponding non-human residues. Humanized antibodies can also contain residues, which are found neither in the recipient antibody nor in the imported CDR or framework sequences. Generally, a humanized antibody has one or more amino acid residues introduced into it from a source, which is non-human. In practice, humanized antibodies are typically human antibodies in which some CDR residues and possibly some FR residues are substituted by residues from analogous sites in rodent antibodies. Humanized antibodies generally contain at least a portion of an antibody constant region (Fc), typically that of a human antibody (Jones et al., *Nature,* 321:522-525 (1986), Reichmann et al., *Nature,* 332:323-327 (1988), and Presta, *Curr. Opin. Struct. Biol.,* 2:593-596 (1992)).

Methods for humanizing non-human antibodies are well known in the art. For example, humanized antibodies can be generated according to the methods of Winter and co-workers (Jones et al., *Nature,* 321:522-525 (1986), Riechmann et al., *Nature,* 332:323-327 (1988), Verhoeyen et al., *Science,* 239:1534-1536 (1988)), by substituting rodent CDRs or CDR sequences for the corresponding sequences of a human antibody. Methods that can be used to produce humanized antibodies are also described in U.S. Pat. No. 4,816,567 (Cabilly et al.), U.S. Pat. No. 5,565,332 (Hoogenboom et al.), U.S. Pat. No. 5,721,367 (Kay et al.), U.S. Pat. No. 5,837,243 (Deo et al.), U.S. Pat. No. 5,939,598 (Kucherlapati et al.), U.S. Pat. No. 6,130,364 (Jakobovits et al.), and U.S. Pat. No. 6,180,377 (Morgan et al.).

(4) Administration of Antibodies

Administration of the antibodies can be done as disclosed herein. Nucleic acid approaches for antibody delivery also exist. The broadly acting anti FPA or Bradykinin mimicking antibodies and antibody fragments can also be administered to patients or subjects as a nucleic acid preparation (e.g., DNA or RNA) that encodes the antibody or antibody fragment, such that the patient's or subject's own cells take up the nucleic acid and produce and secrete the encoded antibody or antibody fragment. The delivery of the nucleic acid can be by any means, as disclosed herein, for example.

8. Receptors

Disclosed herein the molecules, FPA, and BK, as well as variants of these, are shown to have anti-infarction properties after ischemic events, for example in the cerebrum and the heart. It is understood that these molecules mediate these effects through molecular interactions. Disclosed are methods and compositions which use FPA and BK, as well as their variants, to isolate and determine the molecular interactions and signal transduction pathways that are responsible for the anti-infarction effect that these molecules have. These molecules can, for example, be used to screen receptors and other known molecules to look for interactions that take place, as well as used in screening assays to identify novel receptors and molecules that they interact with.

For example, FPA was used in a screen of 150 receptors to determine which receptors FPA could interact with. One way of assessing FPA interactions is to look at the amount that FPA can modulate a given receptor relative to its natural ligand. Disclosed in tables 13 and 14 are ligand-receptor binding studies that are, for example, modulated by more than 20% (inhibition or excitation) by the human form of Fibrinopeptide-A (FPA-h).

TABLE 13

| FPAh 10 μM Inhibited | |
|---|---|
| Bradykinin B1 | 24% |
| Cholecystokinin | 33% |
| Estrogen ERa | 33% |
| Inositol Triphosphate IP3 | 33% |
| Potassium Channel [Ka] | 25% |
| Thyrotropin Releasing Hormone | 23% |

TABLE 14

| FPAh 10 μM Stimulated | |
|---|---|
| Vascular endothelial growth factor | 22% |
| Glutamate AMPA | 30% |
| Serotonin 5-HT 2a | 21% | a) Bradykinin Receptors

Bradykinin was also used to screen the same 150 receptors discussed above and as discussed in the Examples. This assay was used to determine whether any of the receptors in a panel of receptors was bound by Bradykinin. This assay indicated that Bradykinin bound the Angiotensin receptor type 2 (AT2). Bradykinin inhibited the binding of ATII binding at the AT2 receptor. A panel of Bradykinin variants and derivatives was used to identify the important binding regions of Bradykinin.

(1) The Angiotensin Pathway

The AT2 receptor is part of the Renin-angiotensin II pathway. Angiotensin II plays important roles in the regulation of fluid and sodium and is involved in the Renin cascade. Angiotensinogen is converted into Angiotensin I via the enzyme Renin. There are enzymes called Angiotensin converting enzymes (ACE), which convert Angiotensin I to Angiotensin II. Angiotensin II binds Angiotensin II type 1 receptors (AT1) and causes vasoconstriction and Aldosterone secretion among other things, such as controlling the secretion of vasopressin and ACTH. Molecules, which block the AT1/ATII interaction, are used as therapeutics to treat a variety of cardiac conditions including hypertension. For example, Losartan (Cozaar®) (25-100 mg daily dose), Valsartan (Diovan®) (80-160 mg daily dose), Irbesartan (Avapro®) (75-300 mg daily dose), Candesartan (Atacand®) (4-16 mg daily dose), are members of this class of compounds, i.e. AT1 blockers.

AT 1 blockers have similar effects as ACE inhibitors, in that they decrease the effect of AT 1 stimulation by ATII. However, ACE inhibitors also decrease Bradykinin break$_d$ own and this action could be involved in some of the beneficial and adverse effects of that class of drugs. Therefore, a potential for differential clinical effects exists for these two classes of drugs.

Angiotensin I/hypertensin I is a decapeptide having the sequence DRV YIH PFH L (SEQ ID NO: 86). ACE hydrolyzes the C-terminal dipeptide (His, Leu) producing ATII having the sequence DRV YIH PF(SEQ ID NO: 87). Angiotensin III which has the N-terminal Asp, removed from ATII (RVY IHP F, SEQ ID NO: 88) is less potent than Angiotensin II. Angiotensin III induces the release of aldosterone and it inhibits degradation of enkephalins and potentiates analgesic activity of Met-enkephalin.

Angiotensin II, interacts with two types of G-protein coupled membrane receptors, AT1 (type 1) and AT2 (type 2). AT1 has three major isoforms (rat AT1A 359 aa; AT1B/AT III, 359 aa; and AT1C, 177 aa, which can be found on Genbank, along with any other isoforms). Structure analysis indicates that the rat AT1 receptors contain seven transmembrane domains, while the N-terminus is extracellular and the C-terminus is intracellular. The binding of ATII with AT1 receptors activates a phosphatidylinositol-calcium cascade. AT1 receptors are expressed at least in the liver, kidney, aorta, lung, uterus, ovary, spleen, heart, adrenal and vascular smooth muscle. The AT2 gene (chromosome x) encodes 363 aa protein (SEQ ID NO: 89, Accession NP_000677, angiotensin II receptor, type 2; angiotensin receptor 2 [Homo sapiens]).

SEQ ID NO: 89

1 gnstlatt sknitsglhf glvnisgime stlncsqkps dkhldaipil yyiifvigfl 61 nivvvtlfc cqkgpkkvss iyifnlavad llllatlplw atyysyrydw lfgpvmckvf 121 gsfltlnmfa siffitcmsv dryqsviypf lsqrrnpwqa syivplvwcm aclsslptfy 181 frdvrtieyl gvnacimafp pekyaqwsag ialmknilgf iiplifiatc yfgirkhllk 241 tnsygknrit rdqvlkmaaa vvlafiicwl pthvltflda lawmgvinsc eviavidlal 301 pfaillgftn scvnpflycf vgnrfqqklr svfrvpitwl qgkresmscr kssslremet 361 fvs It is highly expressed in myometrium with lower levels in adrenal.

Stimulation of the AT1 and AT2 receptors has differing effects. For example, the AT1 receptors increase vasoconstriction and the AT2 receptors increase vasodilation. Also, the AT2 receptors are thought to increase NO, which can be cardioprotective. Gene knockout studies in mice of the AT2 receptor have indicated that loss of the AT2 receptor causes cardiac recupture after myocardial infarction. (Ichihara S. et al., Circulation October 2002 106:2244-9). AT1 and AT2 appear to be up-regulated during myocardial infarction. The AT$_2$ receptor is involved in a renal vasodilator cascade. This cascade includes the production of Bradykinin, nitric oxide, and cyclic GMP. This role can counter act the action and activity of the AT1 receptor. Both AT1 and AT2 are thought to be involved in apoptosis, as blocking of AT1 and AT2 ATII interactions prevents apoptosis, but stimulating AT2 causes apoptosis. Ono H. and Ishimitsu, Nippon Rinsho, October 2002, 60:1987.

(2) ATII2 Antagonists and Agonists

Disclosed are angiotensin II type 2 receptor antagonists and agonists. For example, PD123177 and PD 123319 (Timmennans P B, et al., Pharmacol Rev June 1993;45(2):205-51, Angiotensin II receptors and angiotensin II receptor antagonists, (Incorporated by reference at least for material related to AT1 and AT2 antagonists and agonists and their structures), and CPG42112A [Nicotinyl-Tyr-Lys (2-Arg)-His-Pro-Ile-OH], function as AT2 receptor antagonists. ATII type 2 receptor antibodies can function as agonists and antagonists as well.

Angiotensin receptor agonists and antagonists are discussed for example, in Wilmington, Del. 19880. Angiotensin II receptor subtypes: selective antagonists and functional correlates, European Heart Journal. 15 Suppl D:79-87, 1994; Wilmington, Del. 19880-0400. New perspectives in angiotensin system control, Journal of Human Hypertension. 7 Suppl 2:S19-31, 1993; and Dinh, D. T., et al., Angiotensin receptors: distribution, signaling and function, Clinical Science (2001) 100, (481-492) (Printed in Great Britain, which are herein incorporated by reference at least for material related to manipulation of the angiotensin pathway and the structure of AT2 and AT1 antagonists and agonists).

A variety of antagonists and their effects on infarction have been discussed in Xu et al. ("AT(1) and AT(2) receptor expression and blockade after acute ischemia-reperfusion in isolated working rat hearts" *Am. J. Physiol. Heart Circ. Physiol.* 282(4):H206-15 (2002)); Ford et al. ("Angiotensin II reduces infarct size and has no effect on post-ischemic contractile dysfunction in isolated rat hearts" *Br. J. Pharmacol.* 134(1): 38-45 (2001)); Ford et al. ("Characterization of cardioprotection mediated by AT2 receptor antagonism after ischemia-reperfusion in isolated working rat hearts" *J. Cardiovasc. Pharmacol. Ther.* 5(3): 211-21 (2000)); and Ford et al. ("Opposite effects of angiotensin AT1 and AT2 receptor antagonists on recovery of mechanical function after ischemia-reperfusion in isolated working rat hearts" *Circulation* 94(12): 3087-9 (1996)) are all incorporated herein in their entireties by this reference as material related to the modulation of angiotension II type 2 receptor. It is understood that the material contained in these references can be utilized by applicants to support claims to subject matter that do not include the material contained in these references.

9. Aspects Applicable to All Appropriate Compositions a) Sequence Similarities

It is understood that as discussed herein the use of the terms homology and identity mean the same thing as similarity. Thus, for example, if the use of the word homology is used between two non-natural sequences it is understood that this is not necessarily indicating an evolutionary relationship between these two sequences, but rather is looking at the similarity or relatedness between their nucleic acid sequences. Many of the methods for determining homology between two evolutionarily related molecules are routinely applied to any two or more nucleic acids or proteins for the purpose of measuring sequence similarity regardless of whether they are evolutionarily related or not.

In general, it is understood that one way to define any known variants and derivatives or those that might arise, of the disclosed genes and proteins herein, is through defining the variants and derivatives in terms of homology to specific known sequences. This identity of particular sequences disclosed herein is also discussed elsewhere herein. In general, variants of genes and proteins herein disclosed typically have at least, about 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99 percent homology to the stated sequence or the native sequence. Those of skill in the art readily understand how to determine the homology of two proteins or nucleic acids, such as genes. For example, the homology can be calculated after aligning the two sequences so that the homology is at its highest level.

Another way of calculating homology can be performed by published algorithms. Optimal alignment of sequences for comparison can be conducted by the local homology algorithm of Smith and Waterman Adv. Appl. Math. 2: 482 (1981), by the homology alignment algorithm of Needleman and Wunsch, J. MoL Biol. 48: 443 (1970), by the search for similarity method of Pearson and Lipman, Proc. Natl. Acad. Sci. U.S.A. 85: 2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by inspection.

The same types of homology can be obtained for nucleic acids by for example the algorithms disclosed in Zuker, M. *Science* 244:48-52, 1989, Jaeger et al. *Proc. Natl. Acad. Sci. USA* 86:7706-7710, 1989, Jaeger et al. *Methods Enzymol.* 183:281-306, 1989 which are herein incorporated by reference for at least material related to nucleic acid alignment. It is understood that any of the methods typically can be used and that in certain instances the results of these various methods can differ, but the skilled artisan understands if identity is found with at least one of these methods, the sequences would be said to have the stated identity, and be disclosed herein.

For example, as used herein, a sequence recited as having a particular percent homology to another sequence refers to sequences that have the recited homology as calculated by any one or more of the calculation methods described above. For example, a first sequence has 80 percent homology, as defined herein, to a second sequence if the first sequence is calculated to have 80 percent homology to the second sequence using the Zuker calculation method even if the first sequence does not have 80 percent homology to the second sequence as calculated by any of the other calculation methods. As another example, a first sequence has 80 percent homology, as defined herein, to a second sequence if the first sequence is calculated to have 80 percent homology to the second sequence using both the Zuker calculation method and the Pearson and Lipman calculation method even if the first sequence does not have 80 percent homology to the second sequence as calculated by the Smith and Waterman calculation method, the Needleman and Wunsch calculation method, the Jaeger calculation methods, or any of the other calculation methods. As yet another example, a first sequence has 80 percent homology, as defined herein, to a second sequence if the first sequence is calculated to have 80 percent homology to the second sequence using each of calculation methods (although, in practice, the different calculation methods will often result in different calculated homology percentages).

b) Hybridization/Selective Hybridization

The term hybridization typically means a sequence driven interaction between at least two nucleic acid molecules, such as a primer or a probe and a gene. Sequence driven interaction means an interaction that occurs between two nucleotides or nucleotide analogs or nucleotide derivatives in a nucleotide specific manner. For example, G interacting with C or A interacting with T are sequence driven interactions. Typically sequence driven interactions occur on the Watson-Crick face or Hoogsteen face of the nucleotide. The hybridization of two nucleic acids is affected by a number of conditions and parameters known to those of skill in the art. For example, the salt concentrations, pH, and temperature of the reaction all affect whether two nucleic acid molecules will hybridize.

Parameters for selective hybridization between two nucleic acid molecules are well known to those of skill in the art. For example, in some embodiments selective hybridization conditions can be defined as stringent hybridization conditions. For example, stringency of hybridization is controlled by both temperature and salt concentration of either or both of the hybridization and washing steps. For example, the conditions of hybridization to achieve selective hybridization can involve hybridization in high ionic strength solution (6×SSC or 6×SSPE) at a temperature that is about 12-25° C. below the Tm (the melting temperature at which half of the molecules dissociate from their hybridization partners) followed by washing at a combination of temperature and salt concentration chosen so that the washing temperature is about 5° C. to 20° C. below the Tm. The temperature and salt conditions are readily determined empirically in preliminary experiments in which samples of reference DNA immobilized on filters are hybridized to a labeled nucleic acid of interest and then washed under conditions of different stringencies. Hybridization temperatures are typically higher for DNA-RNA and RNA-RNA hybridizations. The conditions can be used as described above to achieve stringency, or as is known in the art. (Sambrook et al., Molecular Cloning: A Laboratory Manual, 2nd Ed., Cold Spring Harbor Laboratory, Cold Spring Harbor, N.Y., 1989; Kunkel et al. Methods Enzymol. 1987:154:367, 1987 which is herein incorporated by reference for material at least related to hybridization of nucleic acids). A preferable stringent hybridization condition for a DNA:DNA hybridization can be at about 68° C. (in aqueous solution) in 6×SSC or 6×SSPE followed by washing at 68° C. Stringency of hybridization and washing, if desired, can be reduced accordingly as the degree of complementarity desired is decreased, and further, depending upon the G-C or A-T richness of any area wherein variability is searched for. Likewise, stringency of hybridization and washing, if desired, can be increased accordingly as homology desired is increased, and further, depending upon the G-C or A-T richness of any area wherein high homology is desired, all as known in the art.

Another way to define selective hybridization is by looking at the amount (percentage) of one of the nucleic acids bound to the other nucleic acid. For example, in some embodiments selective hybridization conditions would be when at least about, 60, 65, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 percent of the limiting nucleic acid is bound to the non-limiting nucleic acid. Typically, the non-limiting primer is in for example, 10 or 100 or 1000 fold excess. This type of assay can be performed at under conditions where both the limiting and non-limiting primer are for example, 10 fold or 100 fold or 1000 fold below their $k_d$, or where only one of the nucleic acid molecules is 10 fold or 100 fold or 1000 fold or where one or both nucleic acid molecules are above their $k_d$.

Another way to define selective hybridization is by looking at the percentage of primer that gets enzymatically manipulated under conditions where hybridization is required to promote the desired enzymatic manipulation. For example, in some embodiments selective hybridization conditions would be when at least about, 60, 65, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 percent of the primer is enzymatically manipulated under conditions which promote the enzymatic manipulation, for example if the enzymatic manipulation is DNA extension, then selective hybridization conditions would be when at least about 60, 65, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 percent of the primer molecules are extended. Preferred conditions also include those suggested by the manufacturer or indicated in the art as being appropriate for the enzyme performing the manipulation.

Just as with homology, it is understood that there are a variety of methods herein disclosed for determining the level of hybridization between two nucleic acid molecules. It is understood that these methods and conditions can provide different percentages of hybridization between two nucleic acid molecules, but unless otherwise indicated meeting the parameters of any of the methods would be sufficient. For example if 80% hybridization was required and as long as hybridization occurs within the required parameters in any one of these methods it is considered disclosed herein.

It is understood that those of skill in the art understand that if a composition or method meets any one of these criteria for determining hybridization either collectively or singly it is a composition or method that is disclosed herein.

c) Nucleic Acids

There are a variety of molecules disclosed herein that are nucleic acid based, including for example the nucleic acids that encode, for example FPA, Bradykinin, or fragment thereof, as well as various functional nucleic acids. The disclosed nucleic acids are made up of for example, nucleotides, nucleotide analogs, or nucleotide substitutes. Non-limiting examples of these and other molecules are discussed herein. It is understood that for example, when a vector is expressed in a cell, that the expressed mRNA will typically be made up of A, C, G, and U. Likewise, it is understood that if, for example, an antisense molecule is introduced into a cell or cell environment through for example exogenous delivery, it is advantageous that the antisense molecule be made up of nucleotide analogs that reduce the degradation of the antisense molecule in the cellular environment.

(1) Nucleotides and Related Molecules

A nucleotide is a molecule that contains a base moiety, a sugar moiety and a phosphate moiety. Nucleotides can be linked together through their phosphate moieties and sugar moieties creating an internucleoside linkage. The base moiety of a nucleotide can be adenin-9-yl (A), cytosin-1-yl (C), guanin-9-yl (G), uracil-1-yl (U), and thymin-1-yl (T). The sugar moiety of a nucleotide is a ribose or a deoxyribose. The phosphate moiety of a nucleotide is pentavalent phosphate. A non-limiting example of a nucleotide would be 3'-AMP (3'-adenosine monophosphate) or 5'-GMP (5'-guanosine monophosphate).

A nucleotide analog is a nucleotide that contains some type of modification to either the base, sugar, or phosphate moieties. Modifications to nucleotides are well known in the art and would include for example, 5-methylcytosine (5-me-C), 5-hydroxymethyl cytosine, xanthine, hypoxanthine, and 2-aminoadenine as well as modifications at the sugar or phosphate moieties.

Nucleotide substitutes are molecules having similar functional properties to nucleotides, but which do not contain a phosphate moiety, such as peptide nucleic acid (PNA). Nucleotide substitutes are molecules that will recognize nucleic acids in a Watson-Crick or Hoogsteen manner, but which are linked together through a moiety other than a phosphate moiety. Nucleotide substitutes are able to conform to a double helix type structure when interacting with the appropriate target nucleic acid.

It is also possible to link other types of molecules (conjugates) to nucleotides or nucleotide analogs to enhance for example, cellular uptake. Conjugates can be chemically linked to the nucleotide or nucleotide analogs. Such conjugates include but are not limited to lipid moieties such as a cholesterol moiety. (Letsinger et al., Proc. Natl. Acad. Sci. USA, 1989,86, 6553-6556), A Watson-Crick interaction is at least one interaction with the Watson-Crick face of a nucleotide, nucleotide analog, or nucleotide substitute. The Watson-Crick face of a nucleotide, nucleotide analog, or nucleotide substitute includes the C2, N1, and C6 positions of a purine based nucleotide, nucleotide analog, or nucleotide substitute and the C2, N3, C4 positions of a pyrimidine based nucleotide, nucleotide analog, or nucleotide substitute.

A Hoogsteen interaction is the interaction that takes place on the Hoogsteen face of a nucleotide or nucleotide analog, which is exposed in the major groove of duplex DNA. The Hoogsteen face includes the N7 position and reactive groups (NH2 or O) at the C6 position of purine nucleotides.

(2) Sequences

There are a variety of sequences related to the genes of FPA, Bradykinin, or fragment thereof, which can be found at Genbank, at for example, http://www.pubmed.gov and these sequences and others are herein incorporated by reference in their entireties as well as for individual subsequences contained therein.

One particular sequence set forth in Table 1 for human FPA is used herein, as an example, to exemplify the disclosed compositions and methods. It is understood that the description related to this sequence is applicable to any sequence related to FPA or any sequence disclosed herein, unless specifically indicated otherwise. Those of skill in the art understand how to resolve sequence discrepancies and differences and to adjust the compositions and methods relating to a particular sequence to other related sequences (i.e. sequences of FPA or Bradykinin). Primers and/or probes can be designed for any FPA or Bradykinin sequence given the information disclosed herein and known in the art.

(3) Primers and Probes

Disclosed are compositions including primers and probes, which are capable of interacting with the FPA, Bradykinin, or fragment thereof, as disclosed herein. In certain embodiments the primers are used to support DNA amplification reactions. Typically the primers will be capable of being extended in a sequence specific manner. Extension of a primer in a sequence specific manner includes any methods wherein the sequence and/or composition of the nucleic acid molecule to which the primer is hybridized or otherwise associated directs or influences the composition or sequence of the product produced by the extension of the primer. Extension of the primer in a sequence specific manner therefore includes, but is not limited to, PCR, DNA sequencing, DNA extension, DNA polymerization, RNA transcription, or reverse transcription. Techniques and conditions that amplify the primer in a sequence specific manner are preferred. In certain embodiments the primers are used for the DNA amplification reactions, such as PCR or direct sequencing. It is understood that in certain embodiments the primers can also be extended using non-enzymatic techniques, where for example, the nucleotides or oligonucleotides used to extend the primer are modified such that they will chemically react to extend the primer in a sequence specific manner. Typically the disclosed primers hybridize with the FPA nucleic acid, Bradykinin nucleic acid, and/or fragments thereof, or they hybridize with the complement of the FPA nucleic acid, Bradykinin nucleic acid and/or fragments thereof.

d) Delivery of the Compositions to Cells (1) Nucleic Acid Delivery

There are a number of compositions and methods which can be used to deliver nucleic acids to cells, either in vitro or in vivo. These methods and compositions can largely be broken down into two classes: viral based delivery systems and non-viral based delivery systems. For example, the nucleic acids can be delivered through a number of direct delivery systems such as, electroporation, lipofection, calcium phosphate precipitation, plasmids, viral vectors, viral nucleic acids, phage nucleic acids, phages, cosmids, or via transfer of genetic material in cells or carriers such as cationic liposomes. Appropriate means for transfection, including viral vectors, chemical transfectants, or physico-mechanical methods such as electroporation and direct diffusion of DNA, are described by, for example, Wolff, J. A., et al., Science, 247, 1465-1468, (1990); and Wolff, J. A. Nature, 352, 815-818, (1991) Such methods are well known in the art and readily adaptable for use with the compositions and methods described herein. In certain cases, the methods will be modified to specifically function with large DNA molecules. Further, these methods can be used to target certain diseases and cell populations by using the targeting characteristics of the carrier.

In the methods described herein, which include the administration and uptake of exogenous DNA into the cells of a subject (i.e., gene transduction or transfection), the nucleic acids can be in the form of naked DNA or RNA, or the nucleic acids can be in a vector for delivering the nucleic acids to the cells, whereby the encoding DNA or DNA or fragment is under the transcriptional regulation of a promoter, as would be well understood by one of ordinary skill in the art as well as enhancers. The vector can be a commercially available preparation, such as an adenovirus vector (Quantum Biotechnologies, Inc. (Laval, Quebec, Canada).

As one example, vector delivery can be via a viral system, such as a retroviral vector system, which can package a recombinant retroviral genome (see e.g., Pastan et al., *Proc. Natl. Acad. Sci. U.S.A.* 85:4486, 1988; Miller et al., *Mol. Cell. Biol.* 6:2895, 1986). The recombinant retrovirus can then be used to infect and thereby deliver to the infected cells nucleic acid encoding a broadly neutralizing antibody (or active fragment thereof). The exact method of introducing the altered nucleic acid into mammalian cells is, of course, not limited to the use of retroviral vectors. Other techniques are widely available for this procedure including the use of adenoviral vectors (Mitani et al., *Hum. Gene Ther.* 5:941-948, 1994), adeno-associated viral (AAV) vectors (Goodman et al., *Blood* 84:1492-1500, 1994), lentiviral vectors (Naidini et al., *Science* 272:263-267, 1996), pseudotyped retroviral vectors (Agrawal et al., *Exper. Hematol.* 24:738-747, 1996). Physical transduction techniques can also be used, such as liposome delivery and receptor-mediated and other endocytosis mechanisms (see, for example, Schwartzenberger et al., *Blood* 87:472-478, 1996). The disclosed compositions can be used in conjunction with any of these or other commonly used gene transfer methods.

As one example, if the antibody-encoding nucleic acid or some other nucleic acid encoding a mimic of FPA or Bradykinin or fragment thereof, or encoding a particular variant of the FPA or Bradykinin or fragment thereof, to be used in the disclosed methods, is delivered to the cells of a subject in an adenovirus vector, the dosage for administration of adenovirus to humans can range from about $10^7$ to $10^9$ plaque forming units (pfu) per injection but can be as high as $10^{12}$ pfu per injection (Crystal, *Hum. Gene Ther.* 8:985-1001, 1997; Alvarez and Curiel, *Hum. Gene Ther.* 8:597-613, 1997). A subject can receive a single injection, or, if additional injections are necessary, they can be repeated at six month intervals (or other appropriate time intervals, as determined by the skilled practitioner) for an indefinite period and/or until the efficacy of the treatment has been established.

Parenteral administration of the nucleic acid or vector, if used, is generally characterized by injection. Injectables can be prepared in conventional forms, either as liquid solutions or suspensions, solid forms suitable for solution of suspension in liquid prior to injection, or as emulsions. A more recently revised approach for parenteral administration involves use of a slow release or sustained release system such that a constant dosage is maintained. See, e.g., U.S. Pat. No. 3,610,795, which is incorporated by reference herein. For additional discussion of suitable formulations and various routes of administration of therapeutic compounds, see, e.g., *Remington: The Science and Practice of Pharmacy* (19th ed.) ed. A. R. Gennaro, Mack Publishing Company, Easton, Pa. 1995.

Nucleic acids that are delivered to cells, which are to be integrated into the host cell genome, typically contain integration sequences. These sequences are often viral related sequences, particularly when viral based systems are used. These viral integration systems can also be incorporated into nucleic acids which are to be delivered using a non-nucleic acid based system of deliver, such as a liposome, so that the nucleic acid contained in the delivery system can become integrated into the host genome.

Other general techniques for integration into the host genome include, for example, systems designed to promote homologous recombination with the host genome. These systems typically rely on sequence flanking the nucleic acid to be expressed that has enough homology with a target sequence within the host cell genome that recombination between the vector nucleic acid and the target nucleic acid takes place, causing the delivered nucleic acid to be integrated into the host genome. These systems and the methods necessary to promote homologous recombination are known to those of skill in the art.

(2) Non-Nucleic Acid Based Systems

The disclosed compositions can be delivered to the target cells in a variety of ways. For example, the compositions can be delivered through electroporation, or through lipofection, or through calcium phosphate precipitation. The delivery mechanism chosen will depend in part on the type of cell targeted and whether the delivery is occurring for example in vivo or in vitro.

Thus, the compositions can comprise, in addition to the disclosed compositions or vectors for example, lipids such as liposomes, such as cationic liposomes (e.g., DOTMA, DOPE, DC-cholesterol) or anionic liposomes. Liposomes can further comprise proteins to facilitate targeting a particular cell, if desired. Administration of a composition comprising a compound and a cationic liposome can be administered to the blood afferent to a target organ or inhaled into the respiratory tract to target cells of the respiratory tract. Regarding liposomes, see, e.g., Brigham et al. *Am. J. Resp. Cell. Mol. Biol.* 1:95-100 (1989); Felgner et al. *Proc. Natl. Acad. Sci USA* 84:7413-7417 (1987); U.S. Pat. No. 4,897,355. Furthermore, the compound can be administered as a component of a microcapsule that can be targeted to specific cell types, such as macrophages, or where the diffusion of the compound or delivery of the compound from the microcapsule is designed for a specific rate or dosage.

In the methods described above which include the administration and uptake of exogenous DNA into the cells of a subject (i.e., gene transduction or transfection), delivery of the compositions to cells can be via a variety of mechanisms. As one example, delivery can be via a liposome, using commercially available liposome preparations such as LIPOFECTIN, LIPOFECTAMINE (GIBCO-BRL, Inc., Gaithersburg, Md.), SUPERFECT (Qiagen, Inc. Hilden, Germany) and TRANSFECTAM (Promega Biotec, Inc., Madison, Wis.), as well as other liposomes developed according to procedures standard in the art. In addition, the nucleic acid or vector can be delivered in vivo by electroporation, the technology for which is available from Genetronics, Inc. (San Diego, Calif.) as well as by means of a SONOPORATION machine (ImaRx Pharmaceutical Corp., Tucson, Ariz.).

The materials can be in solution, suspension (for example, incorporated into microparticles, liposomes, or cells). These can be targeted to a particular cell type via antibodies, receptors, or receptor ligands. The following references are examples of the use of this technology to target specific proteins to tumor tissue (Senter, et al., *Bioconjugate Chem.*, 2:447-451, (1991); Bagshawe, K. D., *Br. J. Cancer*, 60:275-281, (1989); Bagshawe, et al., *Br. J. Cancer*, 58:700-703, (1988); Senter, et al., *Bioconjugate Chem.*, 4:3-9, (1993); Battelli, et al., *Cancer Immunol. Immunother.*, 35:421-425, (1992); Pietersz and McKenzie, *Immunolog. Reviews*, 129: 57-80, (1992); and Roffler, et al., *Biochem. Pharmacol*, 42:2062-2065, (1991)). These techniques can be used for a variety of other specific cell types. Vehicles such as "stealth" and other antibody conjugated liposomes (including lipid mediated drug targeting to colonic carcinoma), receptor mediated targeting of DNA through cell specific ligands, lymphocyte directed tumor targeting, and highly specific therapeutic retroviral targeting of murine glioma cells in vivo. The following references are examples of the use of this technology to target specific proteins to tumor tissue (Hughes et al., *Cancer Research*, 49:6214-6220, (1989); and Litzinger and Huang, *Biochemica et Biophysica Acta*, 1104:179-187, (1992)). In general, receptors are involved in pathways of endocytosis, either constitutive or ligand induced. These receptors cluster in clathrin-coated pits, enter the cell via clathrin-coated vesicles, pass through an acidified endosome in which the receptors are sorted, and then either recycle to the cell surface, become stored intracellularly, or are degraded in lysosomes. The internalization pathways serve a variety of functions, such as nutrient uptake, removal of activated proteins, clearance of macromolecules, opportunistic entry of viruses and toxins, dissociation and degradation of ligand, and receptor-level regulation. Many receptors follow more than one intracellular pathway, depending on the cell type, receptor concentration, type of ligand, ligand valency, and ligand concentration. Molecular and cellular mechanisms of receptor-mediated endocytosis have been reviewed (Brown and Greene, *DNA and Cell Biology* 10:6, 399-409 (1991)).

(3) In Vivo/Ex Vivo

As described above, the compositions can be administered in a pharmaceutically acceptable carrier and can be delivered to the subjects cells in vivo and/or ex vivo by a variety of mechanisms well known in the art (e.g., uptake of naked DNA, liposome fusion, intramuscular injection of DNA via a gene gun, endocytosis and the like).

If ex vivo methods are employed, cells or tissues can be removed and maintained outside the body according to standard protocols well known in the art. The compositions can be introduced into the cells via any gene transfer mechanism, such as, for example, calcium phosphate mediated gene delivery, electroporation, microinjection or proteoliposomes. The transduced cells can then be infused (e.g., in a pharmaceutically acceptable carrier) or homotopically transplanted back into the subject per standard methods for the cell or tissue type. Standard methods are known for transplantation or infusion of various cells into a subject.

e) Expression Systems

The nucleic acids that are delivered to cells typically contain expression controlling systems. For example, the inserted genes in viral and retroviral systems usually contain promoters, and/or enhancers to help control the expression of the desired gene product. A promoter is generally a sequence or sequences of DNA that function when in a relatively fixed location in regard to the transcription start site. A promoter contains core elements required for basic interaction of RNA polymerase and transcription factors, and can contain upstream elements and response elements.

(1) Viral Promoters and Enhancers

Preferred promoters controlling transcription from vectors in mammalian host cells can be obtained from various sources, for example, the genomes of viruses such as: polyoma, Simian Virus 40 (SV40), adenovirus, retroviruses, hepatitis-B virus and most preferably cytomegalovirus, or from heterologous mammalian promoters, e.g. beta actin promoter. The early and late promoters of the SV40 virus are conveniently obtained as an SV40 restriction fragment which also contains the SV40 viral origin of replication (Fiers et al., Nature, 273: 113 (1978)). The immediate early promoter of the human cytomegalovirus is conveniently obtained as a HindIII E restriction fragment (Greenway, P. J. et al., Gene 18: 355-360 (1982)). Of course, promoters from the host cell or related species also are useful herein.

Enhancer generally refers to a sequence of DNA that functions at no fixed distance from the transcription start site and can be either 5' (Laimins, L. et al., Proc. Natl. Acad. Sci. 78: 993 (1981)) or 3' (Lusky, M. L., et al., Mol. Cell Bio. 3: 1108 (1983)) to the transcription unit. Furthermore, enhancers can be within an intron (Banerji, J. L. et al., Cell 33: 729 (1983)) as well as within the coding sequence itself (Osborne, T. F., et al., Mol. Cell Bio. 4: 1293 (1984)). They are usually between 10 and 300 bp in length, and they function in cis. Enhancers function to increase transcription from nearby promoters. Enhancers also often contain response elements that mediate the regulation of transcription. Promoters can also contain response elements that mediate the regulation of transcription. Enhancers often determine the regulation of expression of a gene. While many enhancer sequences are now known from mammalian genes (globin, elastase, albumin, fetoprotein and insulin), typically one will use an enhancer from a eukaryotic cell virus for general expression. Preferred examples are the SV40 enhancer on the late side of the replication origin (bp 100-270), the cytomegalovirus early promoter enhancer, the polyoma enhancer on the late side of the replication origin, and adenovirus enhancers.

The promoter and/or enhancer can be specifically activated either by light or specific chemical events, which trigger their function. Systems can be regulated by reagents such as tetracycline and dexamethasone. There are also ways to enhance viral vector gene expression by exposure to irradiation, such as gamma irradiation, or alkylating chemotherapy drugs.

In certain embodiments the promoter and/or enhancer region can act as a constitutive promoter and/or enhancer to maximize expression of the region of the transcription unit to be transcribed. In certain constructs the promoter and/or enhancer region be active in all eukaryotic cell types, even if it is only expressed in a particular type of cell at a particular time. A preferred promoter of this type is the CMV promoter (650 bases). Other preferred promoters are SV40 promoters, cytomegalovirus (full length promoter), and retroviral vector LTF.

It has been shown that all specific regulatory elements can be cloned and used to construct expression vectors that are selectively expressed in specific cell types such as melanoma cells. The glial fibrillary acetic protein (GFAP) promoter has been used to selectively express genes in cells of glial origin.

Expression vectors used in eukaryotic host cells (yeast, fungi, insect, plant, animal, human or nucleated cells) can also contain sequences necessary for the termination of transcription, which can affect MRNA expression. These regions are transcribed as polyadenylated segments in the untranslated portion of the mRNA encoding tissue factor protein. The 3' untranslated regions also include transcription termination sites. It is preferred that the transcription unit also contains a polyadenylation region. One benefit of this region is that it increases the likelihood that the transcribed unit will be processed and transported like mRNA. The identification and use of polyadenylation signals in expression constructs is well established. It is preferred that homologous polyadenylation signals be used in the transgene constructs. In certain transcription units, the polyadenylation region is derived from the SV40 early polyadenylation signal and consists of about 400 bases. It is also preferred that the transcribed units contain other standard sequences alone or in combination with the above sequences improve expression from, or stability of, the construct.

(2) Markers

The viral vectors can include nucleic acid sequence encoding a marker product. This marker product is used to determine if the gene has been delivered to the cell and once delivered is being expressed. Preferred marker genes are the E. Coli lacZ gene, which encodes β-galactosidase, and green fluorescent protein.

In some embodiments the marker can be a selectable marker. Examples of suitable selectable markers for mammalian cells are dihydrofolate reductase (DHFR), thymidine kinase, neomycin, neomycin analog G418, hydromycin, and puramycin. When such selectable markers are successfully transferred into a mammalian host cell, the transformed mammalian host cell can survive if placed under selective pressure. There are two widely used distinct categories of selective regimes. The first category is based on a cell's metabolism and the use of a mutant cell line, which lacks the ability to grow independent of a supplemented media. Two examples are: CHO DHFR-cells and mouse LTK-cells. These cells lack the ability to grow without the addition of such nutrients as thymidine or hypoxanthine. Because these cells lack certain genes necessary for a complete nucleotide synthesis pathway, they cannot survive unless the missing nucleotides are provided in a supplemented media. An alternative to supplementing the media is to introduce an intact DHFR or TK gene into cells lacking the respective genes, thus altering their growth requirements. Individual cells which were not transformed with the DHFR or TK gene will not be capable of survival in non-supplemented media.

The second category is dominant selection which refers to a selection scheme used in any cell type and does not require the use of a mutant cell line. These schemes typically use a drug to arrest growth of a host cell. Those cells, which have a novel gene, would express a protein conveying drug resistance and would survive the selection. Examples of such dominant selection use the drugs neomycin, (Southern P. and Berg, P., J. Molec. Appl. Genet. 1: 327 (1982)), mycophenolic acid, (Mulligan, R. C. and Berg, P. Science 209: 1422 (1980)) or hygromycin, (Sugden, B. et al., Mol. Cell. Biol. 5: 410-413 (1985)). The three examples employ bacterial genes under eukaryotic control to convey resistance to the appropriate drug G418 or neomycin (geneticin), xgpt (mycophenolic acid) or hygromycin, respectively. Others include the neomycin analog G418 and puramycin.

f) Peptides (1) Protein Variants

As discussed herein there are numerous variants of the FPA, Bradykinin, and/or fragments thereof that are known and herein contemplated. In addition, to the known functional FPA, Bradykinin, and/or fragments thereof, species homologs, there are derivatives of the FPA, Bradykinin, and/or fragments thereof, which also function in the disclosed methods and compositions. Protein variants and derivatives are well understood to those of skill in the art and in can involve amino acid sequence modifications. For example, amino acid sequence modifications typically fall into one or more of three classes: substitutional, insertional or deletional variants. Insertions include amino and/or carboxyl terminal fusions as well as intrasequence insertions of single or multiple amino acid residues. Insertions ordinarily will be smaller insertions than those of amino or carboxyl terminal fusions, for example, on the order of one to four residues. Immunogenic fusion protein derivatives, such as those described in the examples, are made by fusing a polypeptide sufficiently large to confer immunogenicity to the target sequence by cross-linking in vitro or by recombinant cell culture transformed with DNA encoding the fusion. Deletions are characterized by the removal of one or more amino acid residues from the protein sequence. Typically, no more than about from 2 to 6 residues are deleted at any one site within the protein molecule. These variants ordinarily are prepared by site specific mutagenesis of nucleotides in the DNA encoding the protein, thereby producing DNA encoding the variant, and thereafter expressing the DNA in recombinant cell culture. Techniques for making substitution mutations at predetermined sites in DNA having a known sequence are well known, for example M13 primer mutagenesis and PCR mutagenesis. Amino acid substitutions are typically of single residues, but can occur at a number of different locations at once; insertions usually will be on the order of about from 1 to 10 amino acid residues; and deletions will range about from 1 to 30 residues. Deletions or insertions preferably are made in adjacent pairs, i.e. a deletion of 2 residues or insertion of 2 residues. Substitutions, deletions, insertions or any combination thereof can be combined to arrive at a final construct. The mutations must not place the sequence out of reading frame and preferably will not create complementary regions that could produce secondary mRNA structure. Substitutional variants are those in which at least one residue has been removed and a different residue inserted in its place. Such substitutions generally are made in accordance with the following Tables 1 and 2 and are referred to as conservative substitutions.

TABLE 4

Amino Acid Abbreviations

| Amino Acid | Abbreviations |
| --- | --- |
| alanine | AlaA |
| allosoleucine | AIle |
| arginine | ArgR |
| asparagine | AsnN |
| aspartic acid | AspD |
| cysteine | CysC |
| glutamic acid | GluE |
| glutamine | GlnQ |
| glycine | GlyG |
| histidine | HisH |
| isoleucine | IleI |
| leucine | LeuL |
| lysine | LysK |
| phenylalanine | PheF |
| proline | ProP |

TABLE 4-continued

Amino Acid Abbreviations

| Amino Acid | Abbreviations |
| --- | --- |
| pyroglutamic acidp | Glu |
| serine | SerS |
| threonine | ThrT |
| tyrosine | TyrY |
| tryptophan | TrpW |
| valine | ValV |

TABLE 5

Amino Acid Substitutions
Original Residue Exemplary Conservative Substitutions,
others are known in the art.

| | |
| --- | --- |
| Ala | ser |
| Arg | lys, gln |
| Asn | gln; his |
| Asp | glu |
| Cys | ser |
| Gln | asn, lys |
| Glu | asp |
| Gly | pro |
| His | asn; gln |
| Ile | leu; val |
| Leu | ile; val |
| Lys | arg; gln; |
| Met | Leu; ile |
| Phe | met; leu; tyr |
| Ser | thr |
| Thr | ser |
| Trp | tyr |
| Tyr | trp; phe |
| Val | ile; leu |

Substantial changes in function or immunological identity are made by selecting substitutions that are less conservative than those in Table 5, i.e., selecting residues that differ more significantly in their effect on maintaining (a) the structure of the polypeptide backbone in the area of the substitution, for example as a sheet or helical conformation, (b) the charge or hydrophobicity of the molecule at the target site or (c) the bulk of the side chain. The substitutions which in general are expected to produce the greatest changes in the protein properties will be those in which (a) a hydrophilic residue, e.g. seryl or threonyl, is substituted for (or by) a hydrophobic residue, e.g. leucyl, isoleucyl, phenylalanyl, valyl or alanyl; (b) a cysteine or proline is substituted for (or by) any other residue; (c) a residue having an electropositive side chain, e.g., lysyl, arginyl, or histidyl, is substituted for (or by) an electronegative residue, e.g., glutamyl or aspartyl; or (d) a residue having a bulky side chain, e.g., phenylalanine, is substituted for (or by) one not having a side chain, e.g., glycine, in this case, (e) by increasing the number of sites for sulfation and/or glycosylation.

For example, the replacement of one amino acid residue with another that is biologically and/or chemically similar is known to those skilled in the art as a conservative substitution. For example, a conservative substitution would be replacing one hydrophobic residue for another, or one polar residue for another. The substitutions include combinations such as, for example, Gly, Ala; Val, Ile, Leu; Asp, Glu; Asn, Gln; Ser, Thr; Lys, Arg; and Phe, Tyr. Such conservatively substituted variations of each explicitly disclosed sequence are included within the mosaic polypeptides provided herein.

Substitutional or deletional mutagenesis can be employed to insert sites for N-glycosylation (Asn-X-Thr/Ser) or O-glycosylation (Ser or Thr). Deletions of cysteine or other labile residues also can be desirable. Deletions or substitutions of potential proteolysis sites, e.g. Arg, is accomplished for example by deleting one of the basic residues or substituting one by glutaminyl or histidyl residues.

Certain post-translational derivatizations are the result of the action of recombinant host cells on the expressed polypeptide. Glutaminyl and asparaginyl residues are frequently post-translationally deamidated to the corresponding glutamyl and asparyl residues. Alternatively, these residues are deamidated under mildly acidic conditions. Other post-translational modifications include hydroxylation of proline and lysine, phosphorylation of hydroxyl groups of seryl or threonyl residues, methylation of the o-amino groups of lysine, arginine, and histidine side chains (T. E. Creighton, Proteins: Structure and Molecular Properties, W. H. Freeman & Co., San Francisco pp 79-86 [1983]), acetylation of the N-terminal amine and, in some instances, amidation of the C-terminal carboxyl.

It is understood that one way to define the variants and derivatives of the disclosed proteins herein is through defining the variants and derivatives in terms of homology/identity to specific known sequences. Specifically disclosed are variants of these and other proteins herein disclosed which have at least, 70% or 75% or 80% or 85% or 90% or 95% homology to the stated sequence. Those of skill in the art readily understand how to determine the homology of two proteins. For example, the homology can be calculated after aligning the two sequences so that the homology is at its highest level.

Another way of calculating homology can be performed by published algorithms. Optimal alignment of sequences for comparison can be conducted by the local homology algorithm of Smith and Waterman Adv. Appl. Math. 2: 482 (1981), by the homology alignment algorithm of Needleman and Wunsch, J. MoL Biol. 48: 443 (1970), by the search for similarity method of Pearson and Lipman, Proc. Natl. Acad. Sci. U.S.A. 85: 2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by inspection.

The same types of homology can be obtained for nucleic acids by for example the algorithms disclosed in Zuker, M. Science 244:48-52, 1989, Jaeger et al. Proc. Natl. Acad. Sci. USA 86:7706-7710, 1989, Jaeger et al. Methods Enzymol. 183:281-306, 1989 which are herein incorporated by reference for at least material related to nucleic acid alignment.

It is understood that the description of conservative mutations and homology can be combined together in any combination, such as embodiments that have at least 70% homology to a particular sequence wherein the variants are conservative mutations.

As this specification discusses various proteins and protein sequences it is understood that the nucleic acids that can encode those protein sequences are also disclosed. This would include all degenerate sequences related to a specific protein sequence, i.e. all nucleic acids having a sequence that encodes one particular protein sequence as well as all nucleic acids, including degenerate nucleic acids, encoding the disclosed variants and derivatives of the protein sequences. Thus, while each particular nucleic acid sequence can not be written out herein, it is understood that each and every sequence is in fact disclosed and described herein through the disclosed protein sequence. It is also understood that while no amino acid sequence indicates what particular DNA sequence encodes that protein within an organism, where particular variants of a disclosed protein are disclosed herein, the known nucleic acid sequence that encodes that protein in the particular organism from which that protein arises is also known and herein disclosed and described.

It is understood that there are numerous amino acid and peptide analogs, which can be incorporated into the disclosed compositions. For example, there are numerous D amino acids or amino acids which have a different functional substituent then the amino acids shown in Table 1 and Table 2. The opposite stereo isomers of naturally occurring peptides are disclosed, as well as the stereo isomers of peptide analogs. These amino acids can readily be incorporated into polypeptide chains by charging tRNA molecules with the amino acid of choice and engineering genetic constructs that utilize, for example, amber codons, to insert the analog amino acid into a peptide chain in a site specific way (Thorson et al., Methods in Molec. Biol. 77:43-73 (1991), Zoller, Current Opinion in Biotechnology, 3:348-354 (1992); Ibba, Biotechnology & Genetic Engineering Reviews 13:197-216 (1995), Cahill et al., TIBS, 14(10):400-403 (1989); Benner, TIB Tech, 12:158-163 (1994); Ibba and Hennecke, Bio/technology, 12:678-682 (1994) all of which are herein incorporated by reference at least for material related to amino acid analogs).

Molecules can be produced that resemble peptides, but which are not connected via a natural peptide linkage. For example, linkages for amino acids or amino acid analogs can include $CH_2NH$—, —$CH_2S$—, —$CH_2$—$CH_2$—, —CH=CH— (cis and trans), —$COCH_2$—, —CH(OH) $CH_2$—, and —$CHH_2SO$—(These and others can be found in Spatola, A. F. in Chemistry and Biochemistry of Amino Acids, Peptides, and Proteins, B. Weinstein, eds., Marcel Dekker, New York, p. 267 (1983); Spatola, A. F., Vega Data (March 1983), Vol. 1, Issue 3, Peptide Backbone Modifications (general review); Morley, Trends Pharm Sci (1980) pp. 463-468; Hudson, D. et al., Int J Pept Prot Res 14:177-185 (1979) (—$CH_2NH$—, $CH_2CH_2$—); Spatola et al. Life Sci 38:1243-1249 (1986) (—CH $H_2$—S); Hann J. Chem. Soc Perkin Trans. I 307-314 (1982) (—CH—CH—, cis and trans); Almquist et al. J. Med. Chem. 23:1392-1398 (1980) (—$COCH_2$—); Jennings-White et al. Tetrahedron Lett 23:2533 (1982) (—$COCH_2$—); Szelke et al. European Appln, EP 45665 CA (1982): 97:39405 (1982) (—CH(OH)$CH_2$—); Holladay et al. Tetrahedron. Lett 24:4401-4404 (1983) (—C (OH)$CH_2$—); and Hruby Life Sci 31:189-199 (1982) (—$CH_2$—S—); each of which is incorporated herein by reference. A particularly preferred non-peptide linkage is —$CH_2NH$—. It is understood that peptide analogs can have more than one atom between the bond atoms, such as b-alanine, g-aminobutyric acid, and the like.

Amino acid analogs and analogs and peptide analogs often have enhanced or desirable properties, such as, more economical production, greater chemical stability, enhanced pharmacological properties (half-life, absorption, potency, efficacy, etc.), altered specificity (e.g., a broad-spectrum of biological activities), reduced antigenicity, and others.

D-amino acids can be used to generate more stable peptides, because D amino acids are not recognized by peptidases and such. Systematic substitution of one or more amino acids of a consensus sequence with a D-amino acid of the same type (e.g., D-lysine in place of L-lysine) can be used to generate more stable peptides. Cysteine residues can be used to cyclize or attach two or more peptides together. This can be beneficial to constrain peptides into particular conformations. (Rizo and Gierasch Ann. Rev. Biochem. 61:387 (1992), incorporated herein by reference).

g) Pharmaceutical Carriers/Delivery of Pharmaceutical Products

As described above, the compositions can also be administered in vivo in a pharmaceutically acceptable carrier. By "pharmaceutically acceptable" is meant a material that is not biologically or otherwise undesirable, i.e., the material can be administered to a subject, along with the nucleic acid or vector, without causing any undesirable biological effects or interacting in a deleterious manner with any of the other components of the pharmaceutical composition in which it is contained. The carrier would naturally be selected to minimize any degradation of the active ingredient and to minimize any adverse side effects in the subject, as would be well known to one of skill in the art.

The compositions can be administered orally, parenterally (e.g., intravenously), by intramuscular injection, by intraperitoneal injection, transdermally, extracorporeally, topically or the like, including topical intranasal administration or administration by inhalant. As used herein, "topical intranasal administration" means delivery of the compositions into the nose and nasal passages through one or both of the nares and can comprise delivery by a spraying mechanism or droplet mechanism, or through aerosolization of the nucleic acid or vector. Administration of the compositions by inhalant can be through the nose or mouth via delivery by a spraying or droplet mechanism. Delivery can also be directly to any area of the respiratory system (e.g., lungs) via intubation. The exact amount of the compositions required will vary from subject to subject, depending on the species, age, weight and general condition of the subject, the severity of the allergic disorder being treated, the particular nucleic acid or vector used, its mode of administration and the like. Thus, it is not possible to specify an exact amount for every composition. However, an appropriate amount can be determined by one of ordinary skill in the art using only routine experimentation given the teachings herein.

Parenteral administration of the composition, if used, is generally characterized by injection. Injectables can be prepared in conventional forms, either as liquid solutions or suspensions, solid forms suitable for solution of suspension in liquid prior to injection, or as emulsions. A more recently revised approach for parenteral administration involves use of a slow release or sustained release system such that a constant dosage is maintained. See, e.g., U.S. Pat. No. 3,610,795, which is incorporated by reference herein.

The materials can be in solution, suspension (for example, incorporated into microparticles, liposomes, or cells). These can be targeted to a particular cell type via antibodies, receptors, or receptor ligands. The following references are examples of the use of this technology to target specific proteins to tumor tissue (Senter, et al., *Bioconjugate Chem.*, 2:447-451, (1991); Bagshawe, K. D., *Br. J. Cancer*, 60:275-281, (1989); Bagshawe, et al., *Br. J. Cancer*, 58:700-703, (1988); Senter, et al., *Bioconjugate Chem.*, 4:3-9, (1993); Battelli, et al., *Cancer Immunol. Immunother.*, 35:421-425, (1992); Pietersz and McKenzie, *Immunolog. Reviews*, 129:57-80, (1992); and Roffler, et al., *Biochem. Pharmacol*, 42:2062-2065, (1991)). Vehicles such as "stealth" and other antibody conjugated liposomes (including lipid mediated drug targeting to colonic carcinoma), receptor mediated targeting of DNA through cell specific ligands, lymphocyte directed tumor targeting, and highly specific therapeutic retroviral targeting of murine glioma cells in vivo. The following references are examples of the use of this technology to target specific proteins to tumor tissue (Hughes et al., *Cancer Research*, 49:6214-6220, (1989); and Litzinger and Huang, *Biochemica et Biophysica Acta*, 1104:179-187, (1992)). In general, receptors are involved in pathways of endocytosis, either constitutive or ligand induced. These receptors cluster in clathrin-coated pits, enter the cell via clathrin-coated vesicles, pass through an acidified endosome in which the receptors are sorted, and then either recycle to the cell surface, become stored intracellularly, or are degraded in lysosomes. The internalization pathways serve a variety of functions, such as nutrient uptake, removal of activated proteins, clearance of macromolecules, opportunistic entry of viruses and toxins, dissociation and degradation of ligand, and receptor-level regulation. Many receptors follow more than one intracellular pathway, depending on the cell type, receptor concentration, type of ligand, ligand valency, and ligand concentration. Molecular and cellular mechanisms of receptor-mediated endocytosis have been reviewed (Brown and Greene, *DNA and Cell Biology* 10:6, 399-409 (1991)).

(1) Pharmaceutically Acceptable Carriers

The compositions, including antibodies, can be used therapeutically in combination with a pharmaceutically acceptable carrier.

Suitable carriers and their formulations are described in *Remington: The Science and Practice of Pharmacy* (19th ed.) ed. A. R. Geimaro, Mack Publishing Company, Easton, Pa. 1995. Typically, an appropriate amount of a pharmaceutically-acceptable salt is used in the formulation to render the formulation isotonic. Examples of the pharmaceutically-acceptable carrier include, but are not limited to, saline, Ringer's solution and dextrose solution. The pH of the solution is preferably from about 5 to about 8, and more preferably from about 7 to about 7.5. Further carriers include sustained release preparations such as semipermeable matrices of solid hydrophobic polymers containing the antibody, which matrices are in the form of shaped articles, e.g., films, liposomes or microparticles. It will be apparent to those persons skilled in the art that certain carriers can be more preferable depending upon, for instance, the route of administration and concentration of composition being administered.

Pharmaceutical carriers are known to those skilled in the art. These most typically would be standard carriers for administration of drugs to humans, including solutions such as sterile water, saline, and buffered solutions at physiological pH. The compositions can be administered intramuscularly or subcutaneously. Other compounds will be administered according to standard procedures used by those skilled in the art.

Pharmaceutical compositions can include carriers, thickeners, diluents, buffers, preservatives, surface active agents and the like in addition to the molecule of choice. Pharmaceutical compositions can also include one or more active ingredients such as antimicrobial agents, antiinflammatory agents, anesthetics, and the like.

The pharmaceutical composition can be administered in a number of ways depending on whether local or systemic treatment is desired, and on the area to be treated. Administration can be topically (including ophthalmically, vaginally, rectally, intranasally), orally, by inhalation, or parenterally, for example by intravenous drip, subcutaneous, intraperitoneal or intramuscular injection. The disclosed antibodies can be administered intravenously, intraperitoneally, intramuscularly, subcutaneously, intracavity, or transdermally.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives can also be present such as, for example, antimicrobials, antioxidants, chelating agents, and inert gases and the like.

Formulations for topical administration can include ointments, lotions, creams, gels, drops, suppositories, sprays, liquids and powders. Conventional pharmaceutical carriers, aqueous, powder or oily bases, thickeners and the like can be necessary or desirable.

Compositions for oral administration include powders or granules, suspensions or solutions in water or non-aqueous media, capsules, sachets, or tablets. Thickeners, flavorings, diluents, emulsifiers, dispersing aids or binders can be desirable., Some of the compositions can potentially be administered as a pharmaceutically acceptable acid- or base-addition salt, formed by reaction with inorganic acids such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base such as sodium hydroxide, ammonium hydroxide, potassium hydroxide, and organic bases such as mono-, di-, trialkyl and aryl amines and substituted ethanolamines.

(2) Therapeutic Uses

Effective dosages and schedules for administering the compositions can be determined empirically, and making such determinations is within the skill in the art. The dosage ranges for the administration of the compositions are those large enough to produce the desired effect in which the symptoms are effected. The dosage should not be so large as to cause adverse side effects, such as unwanted cross-reactions, anaphylactic reactions, and the like. Generally, the dosage will vary with the age, condition, sex and extent of the disease in the patient, route of administration, or whether other drugs are included in the regimen, and can be determined by one of skill in the art. The dosage can be adjusted by the individual physician in the event of any counterindications. Dosage can vary, and can be administered in one or more dose administrations daily, for one or several days. Guidance can be found in the literature for appropriate dosages for given classes of pharmaceutical products. For example, guidance in selecting appropriate doses for antibodies can be found in the literature on therapeutic uses of antibodies, e.g., Handbook of Monoclonal Antibodies, Ferrone et al., eds., Noges Publications, Park Ridge, N.J., (1985) ch. 22 and pp. 303-357; Smith et al., Antibodies in Human Diagnosis and Therapy, Haber et al., eds., Raven Press, New York (1977) pp. 365-389. A typical daily dosage of the antibody used alone might range from about 1 µg/kg to up to 100 mg/kg of body weight or more per day, depending on the factors mentioned above.

Following administration of a disclosed composition, such as an antibody or other molecule, such as a fragment of FPA, Bradykinin, or fragment thereof, for forming or mimicking an interaction between FPA, Bradykinin, or fragment thereof, for example, and their cognate receptor, the efficacy of the therapeutic molecule can be assessed in various ways well known to the skilled practitioner. For instance, one of ordinary skill in the art will understand that a composition, such as an antibody or fragment, disclosed herein, is efficacious in forming or mimicking FPA, Bradykinin, or fragment thereof, receptor interaction in a subject by observing, for example, that the composition reduces the amount of infarction seen in any of the models disclosed herein. The anti-infarction activity can be measured using assays as disclosed herein. Any change in activity is disclosed, but a 5%, 10%, 15%, 20%, 25%, 30%, 35%, 40%, 45%, 50%, 55%, 60%, 65%, 70%, 75%, 80%, 90%, or a 95% reduction in infarction relative to controls are disclosed.

Other molecules that interact with the receptors of FPA and Bradykinin which inhibit interactions with FPA, Bradykinin, and/or fragments thereof, which do not have a specific pharmaceutical function, but which can be used for tracking changes within cellular chromosomes or for the delivery of diagnostic tools for example can be delivered in ways similar to those described for the pharmaceutical products.

The disclosed compositions and methods can also be used for example as tools to isolate and test new drug candidates for a variety of ischemia, stroke, and coronary related diseases.

h) Chips and Micro Arrays

Disclosed are chips where at least one address is the sequences or part of the sequences set forth in any of the nucleic acid sequences disclosed herein. Also disclosed are chips where at least one address is the sequences or portion of sequences set forth in any of the peptide sequences disclosed herein.

Also disclosed are chips where at least one address is a variant of the sequences or part of the sequences set forth in any of the nucleic acid sequences disclosed herein. Also disclosed are chips where at least one address is a variant of the sequences or portion of sequences set forth in any of the peptide sequences disclosed herein.

i) Computer Readable Mediums

It is understood that the disclosed nucleic acids and proteins can be represented as a sequence consisting of the nucleotides of amino acids. There are a variety of ways to display these sequences, for example the nucleotide guanosine can be represented by G or g. Likewise the amino acid valine can be represented by Val or V. Those of skill in the art understand how to display and express any nucleic acid or protein sequence in any of the variety of ways that exist, each of which is considered herein disclosed. Specifically contemplated herein is the display of these sequences on computer readable mediums, such as, commercially available floppy disks, tapes, chips, hard drives, compact disks, and video disks, or other computer readable mediums. Also disclosed are the binary code representations of the disclosed sequences. Those of skill in the art understand what computer readable mediums are. Thus, computer readable mediums on which the nucleic acids or protein sequences are recorded, stored, or saved, are disclosed.

Disclosed are computer readable mediums comprising the sequences and information regarding the sequences set forth herein.

j) Kits

Disclosed herein are kits that are drawn to reagents that can be used in practicing the methods disclosed herein. The kits can include any reagent or combination of reagent discussed herein or that would be understood to be required or beneficial in the practice of the disclosed methods. For example, the kits could include primers to perform the amplification reactions discussed in certain embodiments of the methods, as well as the buffers and enzymes required to use the primers as intended.

D. METHODS OF MAKING THE COMPOSITIONS

The compositions disclosed herein and the compositions necessary to perform the disclosed methods can be made using any method known to those of skill in the art for that particular reagent or compound unless otherwise specifically noted.

1. Nucleic Acid Synthesis

For example, the nucleic acids, such as, the oligonucleotides to be used as primers can be made using standard chemical synthesis methods or can be produced using enzymatic methods or any other known method. Such methods can range from standard enzymatic digestion followed by nucleotide fragment isolation (see for example, Sambrook et al., *Molecular Cloning: A Laboratory Manual,* 2nd Edition (Cold Spring Harbor Laboratory Press, Cold Spring Harbor, N.Y., 1989) Chapters 5, 6) to purely synthetic methods, for example, by the cyanoethyl phosphoramidite method using a Milligen or Beckman System 1 Plus DNA synthesizer (for example, Model 8700 automated synthesizer of Milligen-Biosearch, Burlington, Mass. or ABI Model 380B). Synthetic methods useful for making oligonucleotides are also described by Ikuta et al., *Ann. Rev. Biochem.* 53:323-356 (1984), (phosphotriester and phosphite-triester methods), and Narang et al., *Methods Enzymol.,* 65:610-620 (1980), (phosphotriester method). Protein nucleic acid molecules can be made using known methods such as those described by Nielsen et al., *Bioconjug. Chem.* 5:3-7 (1994).

2. Peptide Synthesis

One method of producing the disclosed proteins is to link two or more peptides or polypeptides together by protein chemistry techniques. For example, peptides or polypeptides can be chemically synthesized using currently available laboratory equipment using either Fmoc (9-fluorenylmethyloxy-carbonyl) or Boc (tert-butyloxycarbonoyl) chemistry. (Applied Biosystems, Inc., Foster City, Calif.). One skilled in the art can readily appreciate that a peptide or polypeptide corresponding to the disclosed proteins, for example, can be synthesized by standard chemical reactions. For example, a peptide or polypeptide can be synthesized and not cleaved from its synthesis resin whereas the other fragment of a peptide or protein can be synthesized and subsequently cleaved from the resin, thereby exposing a terminal group, which is functionally blocked on the other fragment. By peptide condensation reactions, these two fragments can be covalently joined via a peptide bond at their carboxyl and amino termini, respectively, to form an antibody, or fragment thereof. (Grant G A (1992) Synthetic Peptides: A User Guide. W. H. Freeman and Co., N.Y. (1992); Bodansky M and Trost B., Ed. (1993) Principles of Peptide Synthesis. Springer-Verlag Inc., N.Y. (which is herein incorporated by reference at least for material related to peptide synthesis). Alternatively, the peptide or polypeptide is independently synthesized in vivo as described herein. Once isolated, these independent peptides or polypeptides can be linked to form a peptide or fragment thereof via similar peptide condensation reactions.

For example, enzymatic ligation of cloned or synthetic peptide segments allow relatively short peptide fragments to be joined to produce larger peptide fragments, polypeptides or whole protein domains (Abrahmsen L et al., Biochemistry, 30:4151 (1991)). Alternatively, native chemical ligation of synthetic peptides can be utilized to synthetically construct large peptides or polypeptides from shorter peptide fragments. This method consists of a two step chemical reaction (Dawson et al. Synthesis of Proteins by Native Chemical Ligation. Science, 266:776-779 (1994)). The first step is the chemoselective reaction of an unprotected synthetic peptide—thioester with another unprotected peptide segment containing an amino-terminal Cys residue to give a thioester-linked intermediate as the initial covalent product. Without a change in the reaction conditions, this intermediate undergoes spontaneous, rapid intramolecular reaction to form a native peptide bond at the ligation site (Baggiolini M et al. (1992) FEBS Lett. 307:97-101; Clark-Lewis I et al., J. Biol. Chem., 269:16075 (1994); Clark-Lewis I et al., Biochemistry, 30:3128 (1991); Rajarathnam K et al., Biochemistry 33:6623-30 (1994)).

Alternatively, unprotected peptide segments are chemically linked where the bond formed between the peptide segments as a result of the chemical ligation is an unnatural (non-peptide) bond (Schnolzer, M et al. Science, 256:221 (1992)). This technique has been used to synthesize analogs of protein domains as well as large amounts of relatively pure proteins with full biological activity (deLisle Milton R C et al., Techniques in Protein Chemistry IV. Academic Press, New York, pp. 257-267 (1992)).

3. Process for Making the Compositions

Disclosed are processes for making the compositions as well as making the intermediates leading to the compositions. For example, disclosed are proteins related to FPA or Bradykinin, such as those set forth in Tables 1 and 2 respectively. There are a variety of methods that can be used for making these compositions, such as synthetic chemical methods and standard molecular biology methods. It is understood that the methods of making these and the other disclosed compositions are specifically disclosed.

Disclosed are nucleic acid molecules produced by the process comprising linking in an operative way a nucleic acid molecule comprising a sequence that hybridizes under stringent hybridization conditions to a sequence encoding the sequences in Tables 1 and 2 and a sequence controlling the expression of the nucleic acid.

Disclosed are nucleic acid molecules produced by the process comprising linking in an operative way a nucleic acid molecule comprising a sequence encoding a peptide set forth in the sequences in Tables 1 and 2 and a sequence controlling an expression of the nucleic acid molecule.

Disclosed are nucleic acid molecules produced by the process comprising linking in an operative way a nucleic acid molecule comprising a sequence encoding a peptide having 80% identity to a peptide set forth in the sequences in Tables 1 and 2 and a sequence controlling an expression of the nucleic acid molecule.

Disclosed are nucleic acids produced by the process comprising linking in an operative way a nucleic acid molecule comprising a sequence encoding a peptide having 80% identity to a peptide set forth in the sequences in Tables 1 and 2, wherein any change from the sequences in Tables 1 and 2 are conservative changes and a sequence controlling an expression of the nucleic acid molecule.

Disclosed are cells produced by the process of transforming the cell with any of the disclosed nucleic acids. Disclosed are cells produced by the process of transforming the cell with any of the non-naturally occurring disclosed nucleic acids.

Disclosed are any of the disclosed peptides produced by the process of expressing any of the from a nucleic acid encoding them disclosed nucleic acids. Disclosed are any of the non-naturally occurring disclosed peptides produced by the process of expressing any of the disclosed nucleic acids. Disclosed are any of the disclosed peptides produced by the process of expressing any of the non-naturally disclosed nucleic acids.

Disclosed are animals produced by the process of transfecting a cell within the animal with any of the nucleic acid molecules disclosed herein or any of the disclosed peptides. Disclosed are animals produced by the process of transfecting a cell within the animal any of the nucleic acid molecules disclosed herein, wherein the animal is a mammal. Also disclosed are animals produced by the process of transfecting a cell within the animal any of the nucleic acid molecules disclosed herein, wherein the mammal is mouse, rat, rabbit, cow, sheep, pig, or primate.

Also disclosed are animals produced by the process of adding to the animal any of the cells disclosed herein.

E. METHODS OF USING THE COMPOSITIONS

1. Methods of Using the Compositions as Research Tools

The disclosed compositions can be used in a variety of ways as research tools. For example, the disclosed compositions and methods can be used in models of infarction in the study of ischemia as well as reagents for the isolation of molecules that affect infarction.

The compositions can be used for example as targets in combinatorial chemistry protocols or other screening protocols to isolate molecules that possess desired functional properties related to infarction.

The disclosed compositions can be used as discussed herein as either reagents in micro arrays or as reagents to probe or analyze existing microarrays. The compositions can also be used in any known method of screening assays, related to chip/micro arrays. The compositions can also be used in any known way of using the computer readable embodiments of the disclosed compositions, for example, to study relatedness or to perform molecular modeling analysis related to the disclosed compositions.

2. Methods of Modulating the Effects of Ischemia and Treating Infarctions

Disclosed are methods for modulating the effects of stroke and coronary disease and attack, or any other disease where ischemia is causing the production of necrotic tissue. For example, one of the characteristics of a stroke or of a heart attack caused by vasculature occlusion, or of any other state characterized by loss or decrease of blood flow to a particular tissue is the onset of an infarction, or damaged or dead tissue. The infarction is caused by an ischemic event, a loss of oxygen because of the loss of blood flow to the tissue. An ischemic event is any event where oxygen delivery is reduced to a tissue or cell. The disclosed compositions can be used in methods to reduce the infarction caused by an ischemia. The disclosed methods comprise the administration of one or more of the disclosed compositions to a subject in need. A subject in need is anyone who could undergo, is undergoing, or has undergone an ischemic event. It is understood that the disclosed compositions re capable of 100% tissue recovery in a mouse model of ischemia, as disclosed herein.

In certain embodiments the compositions can be administered during the ischemic event or within 0.2 hour, 0.4 hour, 0.6 hour, 0.8 hour, 1 hour, 1.5 hours, 2 hours, 2.5 hours, 3 hours, 3.5 hours, 4 hours, 4.5 hours, 5 hours, 6 hours, 7 hours, 8 hours, 9 hours, 10 hours, 12 hours 15 hours, 20, or more hours after the ischemic event. When the tissue is true "stunned" tissue and not "hibernating" tissue, then savings can occur more than 20 hours, and in fact could function up to years after the ischemic event. The main difference between the two types of non-functional tissue is that stunned tissues typically recover completely and hibernating tissue typically has islands of necrosis that remain within it. Also stunned tissue can be non-functional for years, as in slowly closing coronary arteries in heart disease, which are operated and then show return of function when opened.

The compositions can be given at any concentration that is effective to reduce the effects of an ischemia. For example, the compositions can be given at an equivalent of at least 0.0001, 0.001, 0.01, 0.05, 0.1, 1, 2, 3, 4, 5, 6, 7, 8, 9, 10, 11, 12, 13, 14, 15, 20, 25, 30, 35, 40, 45, 50, 60, 70, 80, 90, or 100 mg/kg. For example, allometric scaling can be used to take doses used in, for example, a mouse model, to arrive at equivalent doses in a human, or other animal. For example, the total body surface area can be used to get species equivalents. For example, a 10 mg/kg dose in a mouse represents 30 mg/m2 of total body surface area. That dose in humans, i.e. a 30 mg/m2 dose in a human, is equivalent to 0.76 mg/kg for a 70 kg person.

Another way of referring to the dose is to look at the concentrations in the blood. For example, a 0.76 mg/kg dose in a human would amount to approximately 7.6 mg/liter (70 kg×0.76 mg/kg=53.2 mg a 53.2 mg/7 liters=7.6 µg/liter=7.6 µg/ml). Thus disclosed are plasma levels of FPA or its derivatives or Bradykinin or its derivatives or any other active molecules as disclosed herein, after administration, that are at least 0.001 µg/ml, 0.01 µg/ml, 0.1 µg/ml, 1.0 µg/ml, 10 µg/ml 100 µg/ml, or 1000 µg/ml, for example. These calculations were assumed a seven liter blood volume, but they can be changed for differing blood volumes using the techniques disclosed herein.

Dosing can also be adjusted by analyzing the pharmacophordynamics and the pharmacophore kinetics, which adjust, for example, not only for the activity of the active material, but also adjust for the rate at which for example, the active material is metabolized within the subject.

It is understood that he disclosed compositions can be used in combination with each other, as well as in combination with other known therapies for the treatment or prevention of the effects of ischemia. For example, human tPA can be applied in certain circumstances to reduces a clot. The disclosed compositions can be administered in combination with tPA. Another example would be Plavix™ and the compositions making up Plavix™. Plavix™ is an antiplatelet medication that helps keep platelets in the blood from sticking together to form clots. Plavix™ can help protect patients from having another heart attack or stroke.

Disclosed are methods of reducing an infarction in a subject comprising administering FPA to the subject.

Disclosed are methods, wherein the FPA comprises a structure having at least 20% or 70%, or any other percentage as disclosed herein, identity to SEQ ID NO: 2. Also disclosed are methods wherein amino acids 8, 12, and 13 of SEQ ID NO: 2 are not varied and methods, wherein any variation at amino acids 7, 9, and 15 of SEQ ID NO: 2 are conservative substitutions.

Disclosed are methods, wherein the FPA comprises amino acids having at least 40% or 70%, or any other percentage as disclosed herein, identity to amino acids 6-16 of SEQ ID NO: 2, and methods wherein amino acids 8, 12, and 13 are not varied, as well as methods wherein any variation at amino acids 7, 9, and 15 are conservative substitutions.

Disclosed are methods, wherein the FPA reduces the amount of infarction present in a mouse MCAO model. Also disclosed are methods, wherein the infarction is reduced by at least 20%, 40%, 60%, 80%, or any percent between 20% and 100% as disclosed herein.

Disclosed are methods, wherein an infarction ratio in a mouse MCAO model is greater than or equal to 1.1, 1.5, or 2, or any other ratio as disclosed herein.

Also disclosed are methods wherein the ratio is determined using mean infarcted volumes. Disclosed are methods, wherein the mean infarction volume in a mouse MCAO model is less than or equal to 90%, 70%, 50%, or 30% or any percentage between 20% and 100% as disclosed herein.

Disclosed are methods of reducing an infarction in a subject comprising administering a composition, wherein the composition comprises a peptide sequence set forth in SEQ ID NO: 34, SEQ ID NO: 40, SEQ ID NO: 41, SEQ ID NO: 42, SEQ ID NO: 43, SEQ ID NO: 44, SEQ ID NO: 45, SEQ ID NOs: 96-103, AVR, or FVR to the subject, or any of the other functional FPA sequence disclosed herein.

Disclosed are methods, wherein the FPA has the sequence set forth in SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, or SEQ ID NO: 52, SEQ ID NO: 53, SEQ ID NO: 54, SEQ ID NO: 55, SEQ ID NO: 56, SEQ ID NO: 89, or SEQ ID NOs: 96-103, AVR, or FVR, or any of the other functional FPA sequence disclosed herein.

Disclosed are methods, wherein the FPA has the sequence set forth in SEQ ID NO: 46, SEQ ID NO: 45, SEQ ID NO: 36, SEQ ID NO: 50, SEQ ID NO: 38, SEQ ID NO: 40, or SEQ ID NO: 54, SEQ ID NO: 32, SEQ ID NO: 47, SEQ ID NO: 48, SEQ ID NO: 52, or SEQ ID NO: 39 or any of the other functional FPA sequence disclosed herein.

Disclosed are methods, wherein the infarction is a cerebral infarction and methods wherein the infarction is a cardiac infarction. Also disclosed are methods wherein the infarction is any type of infarction.

Disclosed are methods of reducing an infarction in a subject comprising administering Bradykinin to the subject.

Disclosed are methods, wherein the Bradykinin comprises a structure having 60% or 80% or any other percentage as disclosed herein, identity to SEQ ID NO: 57. Also disclosed are methods wherein any variation away from SEQ ID NO: 57 are conservative substitutions.

Disclosed are methods, wherein the Bradykinin does not have a basic amino acid at the C-terminal end, and methods wherein the basic amino acid is Arg, Lys, or His.

Disclosed are methods, wherein the Bradykinin comprises a basic amino acid at the N-terminal end and methods wherein the basic amino acid is Arg, Lys, or His.

Disclosed are methods, wherein the Bradykinin has the sequence set forth in SEQ ID NO: 57, SEQ ID NO: 58, SEQ ID NO: 59, SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, SEQ ID NO: 70, SEQ ID NO: 71, SEQ ID NO: 72, SEQ ID NO: 73, SEQ ID NO: 75, SEQ ID NO: 77, SEQ ID NO: 80, SEQ ID NO: 81, SEQ ID NO: 82, SEQ ID NO: 83, SEQ ID NO: 84, or SEQ ID NO: 85 or any other functional Bradykinin sequence disclosed herein.

Disclosed are methods, wherein the Bradykinin has the sequence set forth in SEQ ID NO: 58, SEQ ID NO: 61, SEQ ID NO: 62, SEQ ID NO: 63, SEQ ID NO: 64, SEQ ID NO: 77, or SEQ ID NO: 81. Also disclosed are methods wherein the Bradykinin has the sequence set forth in SEQ ID NO: 58 or SEQ ID NO: 61 or any other functional Bradykinin sequence disclosed herein.

Also disclosed are methods of reducing an infarction in a subject in need of reducing an infarction, comprising administering an effective amount of an angiotensin II receptor antagonist in a pharmaceutically acceptable form to the subject.

Disclosed are methods of reducing an infarction in a subject, wherein the angiotensin II receptor type 2 antagonist is Bradykinin.

Disclosed are methods of treating a subject in need of reducing an infarction comprising administering an effective amount of a Bradykinin in a pharmaceutically acceptable form to the subject, wherein Bradykinin modulates the angiotensin II receptor, thus reducing the infarction.

F. EXAMPLES

The following examples are put forth so as to provide those of ordinary skill in the art with a complete disclosure and description of how the compounds, compositions, articles, devices and/or methods claimed herein are made and evaluated, and are intended to be purely exemplary and are not intended to limit the scope unless specified. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

1. Example 1

Active Fractions and Molecules

Disclosed is a purified fraction of molecules (albumin fraction, Affi-gel-blue) extracted from the plasma of hibernating woodchucks (VPF). Specific sub-fractions, D1 and D2 were collected during early-hibernation of the woodchucks (mid-December, 6 weeks into hibernation) at the Delaware Water Gap Science Institute. The plasma samples from individual animals were pooled. D1 and D2 were identical, except they were made during different batch-purification runs. A simple control fraction was extracted from summer active woodchucks during July (SA). The batch materials were lyophilized and stored at −70° C.

A "nearest" control fraction was similarly prepared after collection of the plasma during late-hibernation at the North Eastern Wildlife facility (VPF-C1). The NE plasma was collected at two different times and not pooled. NE1 was collected in mid-December and NE2 was collected in mid-January.

Bioassay models that work with intravenous (IV) injection of materials, as opposed to intracerebral (IC) injection, were sought initially to eliminate the complication of having to get medicinal doses of protein and/or peptide molecules across the "blood-brain barrier." The D1/D2, NE1, NE2, and SA materials were thus tested for their IV affects on blood-pressure in 15 Spontaneously Hypertensive Rats (SHR) and for appetite suppression in 25 obese Zucker rats. Additional toxicity effects were assessed by observation of the gross anatomy and weights of the individual internal organs. No effect, such as toxicity, was observed at IV doses (50-mg/kg) known from pilot data to be maximally effective in stimulating the re-cycling of blood urea (5 mg/kg). Doses of up at least 800 mg/kg of D1 and D2 do not appear to be toxic. In two additional SHR animals, large doses of D2 (800-mg/kg) were injected, in two parts, separated by 30 min. Again no affects were observed on blood pressure, appetite, organ toxicity, or mortality within 24-hrs.

The D2, NE2, and SA materials were subsequently tested for their affects on tissue-savings in a mouse model of middle cerebral artery occlusion (MCAO). In this model the mouse is operated under chloral hydrate anesthesia and the middle cerebral artery is totally occluded for one hour. The occlusion is then reversed and cerebral blood flow is re-established and confirmed by Doppler-laser measurements. 24-hrs after the initiation of MCAO, the animal is observed for motor behavior and brain infarction size (TTC stain, 2%). D2-injections (tail-vein, 4-mg/kg) in 21 mice at one-hr after the start of a one-hr MCAO showed remarkable tissue savings at 24-hrs in three separate replication experiments (p<0.01, t-test). In contrast, NE2-injections showed no tissue-savings when compared to similar doses of SA (NS, t-test). In 6 of the 21 D2-animals there was 90-100% savings (i.e., minimal to no detectable infarction at 4-mg/kg) and for the D2 group as a whole the tissue savings were 63% (Table 7).

In a Dose-response Study, a 5-mg/kg IV-dose of D2 was found to be optimal in the MCAO model (12 mice). A subsequent Time-of-Injection Study revealed that pretreatment with D2 (5-mg/kg, IV) injected 2-hrs before the cerebral ischemia (MCAO) resulted in 100% tissue savings in all subjects (6 mice). The same result occurred when injection was as 0.5-hrs after the start of MCAO. Statistically significant reductions in infarction volume at 24-hrs were found for injections at 2, 4, and 6 hrs after the start of MCAO, but not after 8 hrs (Table 7. This indicates prophylactic as well as post-ischemia treatments (six hours post MACO) are beneficial.

In a Dialysis Study the D2 material was dialyzed against water, sodium chloride (2M), and urea (8M), for 24-hrs, using molecular sieve membranes passing molecules of 3.5, 7, or 10 kDa (i.e., passing peptides out of D2 into the large volumes of dialysis fluid). Each of the retained fractions with molecules above the membrane cut-offs were found to be effective in tissue savings in the MCAO model. The retained molecules dialyzed against urea, however, were even more effective in that now most of the animals (9 mice) showed no- or minimal-infarction volumes (shown below, FIG. 6). This dialysis experiment is consistent with a protein being dislodged from its carrier or an inhibitor peptide being removed, either of which then results in the more consistent tissue savings when D2 is injected at 1-hr after the beginning of the MCAO.

Behavioral studies confirmed the lack of infarction, or its small size, in the D2-injected mice. A free-field exercise was given to each mouse 24-hrs after recovery from the 1-hr of ischemia. Normal mice will jump upon a small box in the field; each animal with prior ischemia was judged in its ability to jump on top of it. In addition, limb flexion was noted, as well as coerced movements (circling behavior). The animals with 90% to 100% savings showed no motor deficits. The controls with cerebral infarctions all showed hemiplegia.

Initially 2D-gel electrophoresis (SDS-PAGE) was performed comparing SA and D2 fractions to further purify the active component. Approximately 40 proteins, mostly in the 32-kDa range, were identified with this differential method. There were approximately 20 hibernation-specific and 20 up-regulated proteins with spot densities greater than 2-fold that of the SA controls. BATS gels made by cutting the SA and D2 gels into strips of similar pI and then running them side-by-side for the SDS molecular weight separations was another method used to identify the state-dependent 2D proteins. Once a BATS or conventional 2D spot was determined to be of interest, it was then identified using tandem mass-spectroscopy (LC/MS/MS) and bioinformatics "fingerprinting" to determine the sequence.

Figure 2:
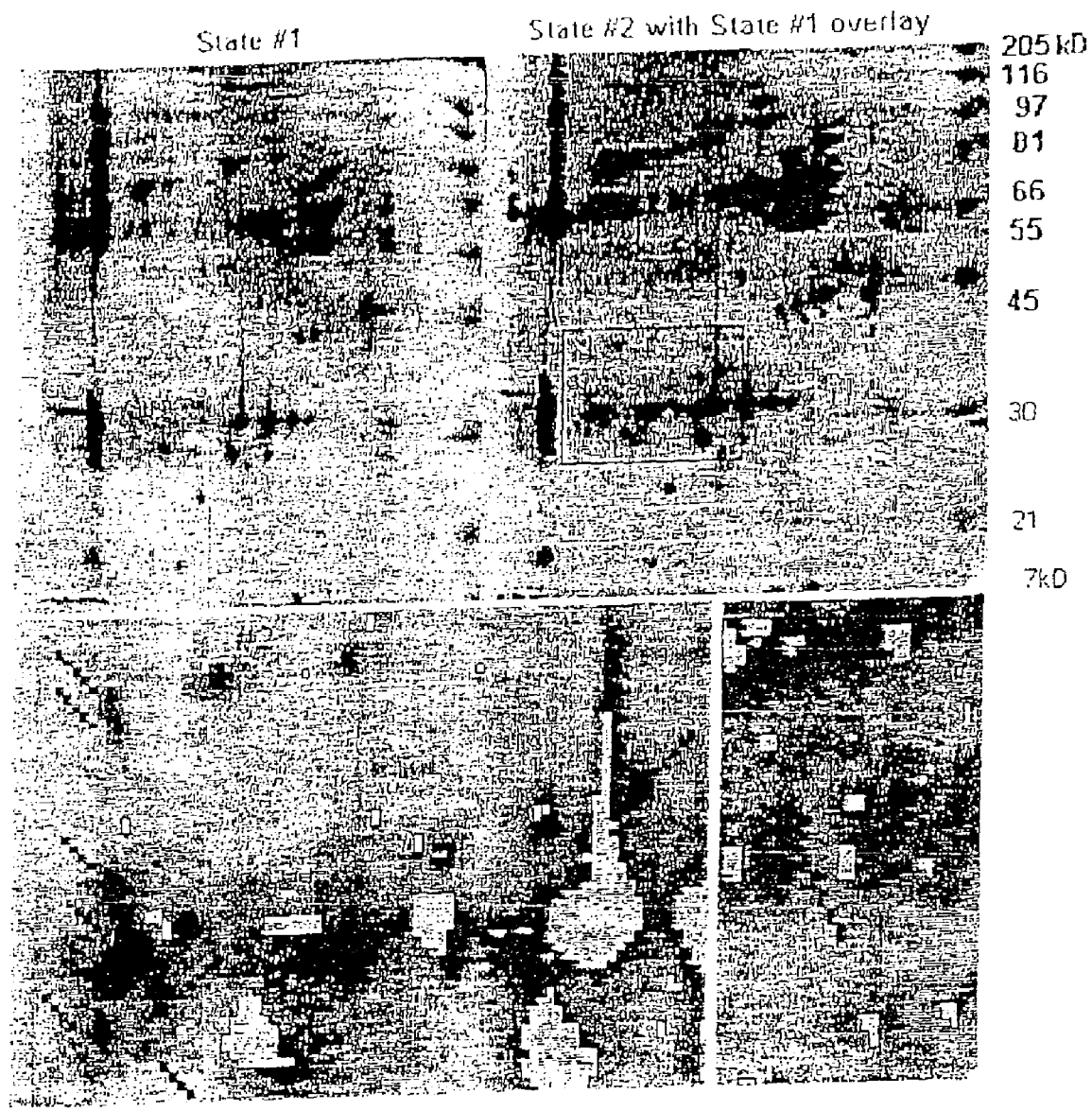
Figure 3:
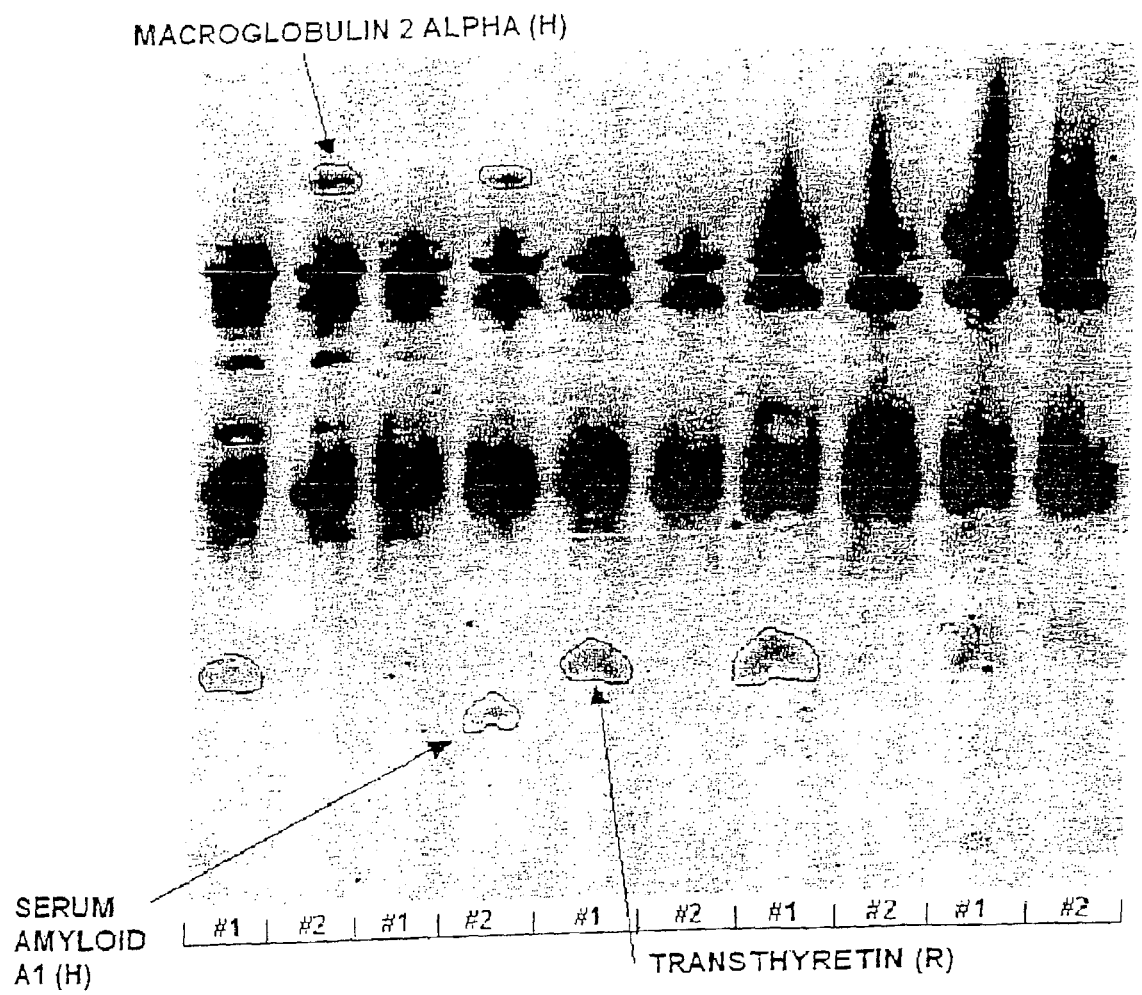
Figure 5:
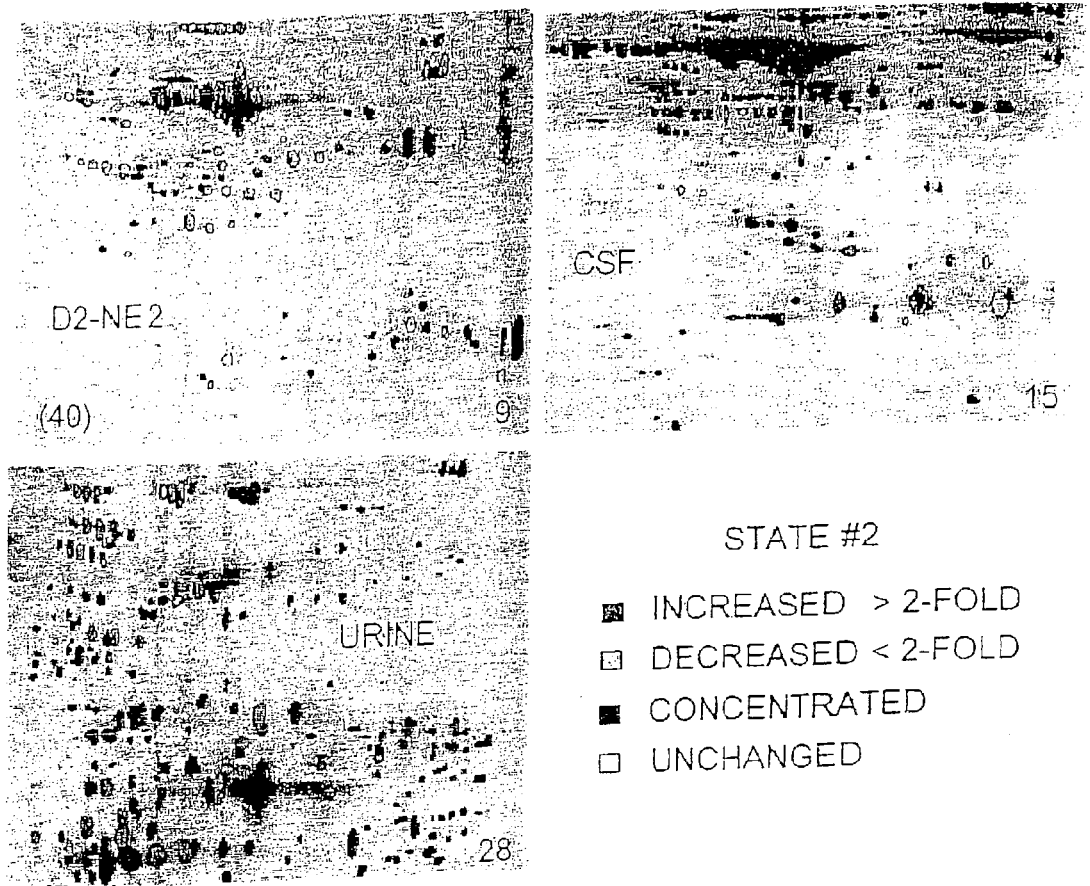

Using the NE2 vs. D2 differential comparison, quantitative 2D gels were made in which the software aligns the differential spots, measures their densities quantitatively, and then marks those that show 2-fold or greater differentials. In this manner only 9 pure protein spots were indicated as being up regulated and/or hibernation-specific (FIGS. 2, 3, 5). Some of these spots were also found in CSF differentials, further isolating the ones of interest. These spots can be treated as described herein to further purify and identify active components.

LC/MS/MS was performed on peptide-fractions of D2 and NE2, using centrifugal filtering of molecules below 10 kDa. One of these differential molecules was identified by conventional fingerprinting, but at least 5 others could not be so easily identified. This peptide fraction is of little interest, however, as it does not contain the active ingredient for the stroke-prevention and it is not one of nine proteins observed in the D2 vs. NE2 differential 2D gels.

It is concluded that a protein molecule(s) in the D2 fraction, but not NE2, or SA, produces an affect on ischemic cerebral tissue in mice that prevents or minimizes stroke after 1-hr of MCAO. The D2-molecule(s) produces no overt signs of toxic effects in rats at greater than 10-times the effective center dose observed in mice. The relevant molecule, after significant cerebral ischemia, can lead to remarkable tissue-savings in the stroke model when injected up to 6-hours after the MCAO. The pure molecular form is actually visualized as one of the 9 proteins seen in FIGS. 3, 5.

a) Methods (1) Hibernaculum

The hibernaculum at North Eastern Wildlife is a 1,000 sq ft temperature-regulated facility housing approximately 100 woodchucks. Animals are individually housed in their own wire cages containing a straw nest. Each animal is checked every 3 to 4 days, under red-light conditions, to determine the stage of hibernation. All blood samples taken during hibernation are via intracardiac punctures using hibernation as the anesthetic.

The hibernaculum at the Delaware Water Gap Science Institute is a 500 sq ft temperature-regulated facility housing up to 20 woodchucks. Animals are individually housed in a sound-attenuated, two-compartment, ¾-inch, pressed-wood cage with a wire bottom in the eating chamber. The sleeping chamber has a nest of straw. The larger hibernaculum is kept completely dark. The animals are monitored by a listening device and are not checked by up-close observation, except at 6 weeks after the start of hibernation initiation.

(2) Animal Species

Woodchucks are the source of the hibernation plasma. The lab rat was used for toxicity studies, as these are the most commonly used subjects. Spontaneously hypertensive rats (SHR) and obese rats (Zucker) were used for the hypertension and appetite studies and for the assessment of toxicity. The C57 mouse was the subject for the middle cerebral artery occlusion studies, as these are most commonly used in the stroke model.

(3) Plasma Collections (Mid-December and Mid-January)

Woodchucks were either sampled for 10 ml of blood by intracardiac puncture, or exanguinated through intracardiac puncture or bleeding into the thoracic cavity after removal of the heart (i.e., hemolyzed plasma). Collections were made at two times, mid-December (6 weeks into hibernation) and mid-January (10 weeks into hibernation). Hibernation was initiated on November 1 by placing the animals in the hibernaculum and providing only water. The temperature of the North Eastern Wildlife facility was constant at 35° C. and that of the Delaware Water Gap Science Institute oscillated daily between 35° C. to 35° C. After collection, the blood was centrifuged in the cold (NEW) or placed on ice for later room-temperature separations (DWGSI). After separation (5 g for 10 min), the decanted plasma was frozen for storage.

(4) Preparation of Molecular Fractions for Testing

D1/D2 were prepared from DWGSI plasma collected by means of intracardiac puncture in mid-December; D2hemo was made from hemolyzed blood collected by aortic bleeding into the thoracic cavity. After Affi-gel purification, the material was lyophilized and administered in milligram amounts (Mettler scale) dissolved in saline. The dosage was 50-mg/kg (toxicity studies in rats) and 5-mg/kg (infarction studies in mice). All injections were in tail veins and administered as bolus volumes of 0.1 ml (mice) and 0.5 ml (rats).

NE1, NE2 were prepared from NEW plasma collected by means of intracardiac puncture in mid-December (NE1) and mid-January (NE2). The lyophilized materials injected were weighed and dissolved as above. The dosage and injection was the same as for D1 and D2.

SA was prepared the same way as D2, except the plasma was collected during the summer, in August, from awake and active woodchucks sedated with ketamine (25 mg/kg).

CSF was taken from a dorsal puncture of the dura at the foremen magnum. The winter extractions were from anesthetized woodchucks and the summer extractions were from ketamine-anesthetized woodchucks (35 mg/kg). The clear fluid was injected in the mice tail-veins as a 100-microliter volume. Intracerebral injections were into the lateral ventricle (100 microliter volume) through an exposed dura with the overlying bone removed (20 mm-sq area).

Urine was collected in summer and winter animals, and was used in the 2D PAGE (two-dimensional polyacrylamide gel electrophoresis) gels and 2D BATS (2-dimensional Band Analysis of Two-D Separations) identifications only.

(5) Molecular Sieving of D2

D2 material (30 mg) was dissolved in 600 microliters of urea, NaCl, or water at 50 mg/ml. The dissolved material was sealed inside 10- or 3.5-Kd cut-off "snakeskin" dialysis tubing. The sealed tube was then placed in 100 ml of the appropriate buffer (same as used to dissolve) and allowed to dialyze for 18 hrs at 2-6° C. The dialysis buffer was then exchanged for fresh buffer and then once again 3 hrs later. The buffer-dialyzed material was then dialyzed exhaustively against pure water for 24-hrs. The final dialyzed material was then lyophilized by conventional means (vacuum, water-trap, etc.). The tail-vein injection was a dosage of 5 mg/kg in a 0.1 ml volume.

(6) Measurement of RR-Intervals

The ECG was recorded by low-noise amplifiers (UFI 2280 20,000 gain, 0.1 to 1000 Hz) connected to low-noise electrodes (Vermed A10005) that were pasted and taped to the bare palms of the limbs. The ECG was digitized at 1000-Hz (National Instruments) and written to disk (Compaq computer). The R-wave was identified by the first zero crossing of an upward (positive polarity) trace that had a dV/dt greater than 10 integers but less than 15 (adjusted visually). The number of data points between successive R-waves was the measure of the RR interval (msec). Visual confirmation of RR intervals was hand check by display on the computer screen in 10% of the data. Artifacts due to EMG activity were easily identified by outlier statistics.

(7) Model of Middle Cerebral Artery Occlusion (Mouse)

The C57 mouse (Charles River) was operated under chloral hydrate anesthesia (IP). An incision was made in the neck in proximity to the right internal carotid artery. A polyethylene occluder whose diameter is known to be just larger than the diameter of the middle cerebral artery at its bifurcation with the internal carotid was inserted from a position in the cervical region at the branch of the internal and external carotid arteries. The IV materials were injected while the occluder was in place at both the 30-minutes or after 60-minutes injection times. All injections were through a 36-ga hypodermic needle inserted into the tail vein. The occluder was removed in all cases after 1-hr of ischemia. The return of cerebral blood flow though the previously ischemic cortical field was verified by laser-Doppler flow measurement of the exposed cortical surface. The cervical and cranial wounds were then closed and the animal recovered in a warm quiet environment (1-2 hr). After complete recovery the animal was returned to its individual home cage.

(8) Assessment of Cerebral Infarction by Behavior and by TTC Staining

Twenty-four hours after recovery from surgery the animal is examined for motor behavior. The extension or flexion of the limbs contralateral to the ischemic hemisphere was compared to the ipsilateral limbs as controls. The animal was placed in a free-field environment containing a box approximately 2 inches high. Normal mice will jump on top of the box within a few minutes. Any abnormalities in jumping behavior were noted. If the animal does not move spontaneously, it is coerced by gentle prodding from behind. The animal is then decapitated and the cranial bone removed. The dura is cut with micro scissors and the whole brain removed. It is then placed in a metal mold used for rapid brain sectioning with razor blades. The 2 mm brain sections are then placed in a 2% solution of triphenyltetrazolieum chloride and incubated at room temperature for 10 minutes. The sections are then photographed by a video camera and written to disk on a PC. Software from NIMH is then used to determine the area of infarction for each brain slice. The infarction volume is normalized relative to the contralateral side to control for the effects of cerebral edema. The calibrated result is a measure of infarction volume expressed in cubic mm.

(9) Toxicity (Gross Organs, Arterial Blood Pressure, Eating Behavior)

The SHR (Charles River) were operated under barbiturate anesthesia (35 mg/kg). A polyethylene catheter was placed in the abdominal aorta (Weeks method, 25). The incision was closed and the animal allowed to recover for 24-hrs. Tail-vein injections of test material were made during continuous blood-pressure monitoring. Eating behavior was observed daily in Zucker rats (Charles River) by weight gain. Animals were injected with test material in the tail vein and weighed daily for 3 weeks. They were fed and watered ad libitum. After the completion of the blood pressure or eating behavior study, the animals were sacrificed and the internal organs removed, inspected for abnormalities, and weighed.

(10) Surgery

Rats (Sprague Dawly) of both sexes of approximately 350 to 450 gms were anesthetized by sodium pentobarbital and placed on a small animal ventilator (Harvard Apparatus) coupled through a tracheal cannula (PE 200 polyethylene tubing). Demand ventilation was monitored. A left thoracotomy was made to expose the heart. The forced ventilation was then set at the same rate and volume as during the previous period of monitoring. A 4-0 surgical silk with a 26-ga taper point half-circle needle was inserted through the field of muscle containing the LAD. The level was at approximately 1/3 of the distance from the atrium to the apex. The ends of the 4-0 suture were firmly drawn together, tied once, and secured through the use of a quick-release clamp. After 45 minutes of complete LAD occlusion, as verified by the dark blue color of the left ventricular field, the suture was released and the tissue at the site of the previous ligation was massaged to assure the complete release of the intra-ligature pressure. An immediate return of arterial blood was noted, and if reperfusion fibrillation occurred, defibrillation was preformed by a cold cotton tissue swab gently rubbed over the surface of the heart. All test materials (D2 and NE2) were injected in the jugular catheter immediately after release of the ligature. Once the fibrillation was converted to a normal sinus rhythm, the animal remained anesthetized by supplemental barbiturate injections for 3 hrs.

At the end of the 3-hrs, the suture around the LAD was re-tied and a Unisperse Blue dye was injected into the left atrium to fill all of the normally-perfused coronary arteries. The heart was extracted, washed in saline, and sliced into 2-mm thick sections through the use of a mold and 6 razor blades. Photographs were taken of both sides of the sliced sections (Cam-on digital camera, 2.1 megapixels each). The sliced sections were then placed in an incubator bath containing 1% triphenyl tetrazolium chloride at 38-degrees C. After 30 min of incubation in TTC, the slices were photographed for a second time.

(11) Analysis of Infarction Size

The blue dye showed the normal zone (NZ), as observed in the first series of photographs. The area of risk is what remains in the photographs that lies outside the NZ. The dye diffuses out of the tissue during incubation in the TTC and is less intense in the second series of photographs, so the NZ must be determined in the first series. In the second series, each surface of the 7 pieces of sliced tissue is examined for TTC stain (recovered tissue in the area of risk, TTC) and infarcted tissue in the area of risk (INF). Each slice has the two surfaces measures averaged and from these measures the volumetric measure of % infarction size is made for each subject (TTC/TTC+INF). The areas of interest in the digital photographs were measured in pixels by Photoshop software and independently confirmed by ImageJ software (freeware from NIH).

(12) Sample Preparation for Mass Spectrometry Analysis

Purification of small molecular weight peptides from albumin fractions: 539 µg of each albumin fraction (D2 and NE2) was added to 25 mM Tris buffer to a total volume of 200 µl and passed through a 3 kd MW Amicon filtration device. The flow through from each sample was saved as the 3 kd peptide fraction of albumin.

(13) Preparation of Unlabeled Peptides for MALDI Analysis

One µl of each peptide fraction was diluted 25 or 50 fold and processed through a C18 'Zip-tip' to clean away any MALDI interfering substances. Purified peptides were eluted in MALDI matrix and spotted onto a MALDI target for subsequent analysis.

(14) LC/MS/MS 50 ul of 0.1% Fornic Acid was added to 50 ul of the ICAT solution and placed in a Speed Vac. The volume was reduced to 10 ul and this was injected on a 75 uM NanoHPLC column flowing at 200 nl/min. The peptides were eluted using either a 40 min or 70 min gradient directly into a Micromass QTOF2 electrospray mass spectrometer.

(15) De Novo Sequence Analysis

The following ions were sequenced: m/z 809, 904, 1010, 1012, 1621 and 1662. The ions m/z 809 and 1010 are matrix ions from the MALDI ionization process, m/z 1012 is the third isotope of m/z 1010. Analysis of m/z 1662 proved inconclusive, analysis of m/z 904 and 1621 is described herein 539 µg of each albumin fraction (D2 and NE#2) was added to 25 mM Tris buffer to a total volume of 200 µl and passed through a 3 kd MW Amicon filtration device (Any molecular weight based filtration device can be used). The flow through from each sample was saved as the 3 kd peptide fraction of albumin. This material was loaded onto a reverse phase column for LC/MS/MS analysis. Gradient flow was delivered from a MicroTech Scientific Ultra-Plus II binary LC pump and split down to 200 nL/min. An applied potential of 1800 V at the head of the column permitted electrospray ionization of the eluent, which was subsequently introduced to a Q-Tof2 tandem mass spectrometer. Peptide ions observed above a specified threshold during gradient elution automatically triggered the instrument to select the desired m/z in the first mass analyzer and perform low energy collision induced dissociation (CID), with analysis of resultant product ions in the second mass analyzer. Product ion data was manually interpreted.

(16) Preparation of the Animals

Rats were operated and implanted with jugular catheters for IV injections, and with subclavian arterial catheters for measurement of mean arterial pressure. After at least 5 days of recovery from surgery the animals were given Neomycin (100 mg capsule in 500 ml drinking water) for 3 days to reduce gut bacteria (i.e., organisms which could possibly recycle some urea). On the day of the blood sampling, the arterial catheter was attached to a Statham strain-gage (calibrated) for measuring blood-pressure. The jugular catheter was attached to a small injection syringe containing 1 mg of double-labeled urea dissolved in 0.5 ml of saline. A baseline blood sample was drawn (0.5 ml) through the jugular catheter and then the labeled urea was injected. Then at 15 min, 1 hr, 2 hr, 3 hr, and 6 hr additional blood samples were withdrawn (0.5 ml each). The samples were kept on ice until the plasma was separated. The latter was obtained by spinning at 3 times gravity for 10 minutes and then pipetting. The approximately 0.3-ml samples of plasma were then individually labeled and frozen and stored until shipment to Metabolic Solutions Inc. for analysis.

(17) $^{15}N_2$-Urea and $^{15}N_1$-Urea Summary

For stable isotope labeled urea analysis, plasma samples were first deproteinized using acetonitrile. After centrifugation, the urea was cyclized to 2-hyrodypyrimidine and treated with BSFTA. The resulting TMS derivative was converted to the heptafluorobutyl derivative in accordance with the method of Nelson and Ruo (Nelson J E, Ruo T I. Assay of stable isotope labeled urea in biological fluids by selected ion monitoring. Clin Chim Acta. Jun. 30, 1988;175(1):59-65.). A Hewlett-Packard 5890 gas chromatograph coupled to a 5989A mass spectrometer was autotuned in Positive Chemical Ionization (PCI) mode according to the manufacturer's specifications. A standard curve containing unlabeled, $^{15}N_2$-Urea (Cambridge Isotope Laboratory) and $^{15}N_1$-Urea (CDN Isotopes) was prepared and analyzed. Ions representing natural or "unlabeled" urea (m/z=293), $^{15}N_1$-Urea (m/z=294) and $^{15}N_2$-urea (m/z=295) were monitored. Total area counts were compared to the standard curve and used to calculate the mole fractions on the final report.

(18) Urea Concentration Summary

For the determination of urea concentration (mmol/L) in plasma, a spectrophotometric analysis of a color reaction between urea and diacetyl monoxime was used. This is based on the method of Crocker (Crocker C L. Rapid determination of urea nitrogen in serum or plasma without deproteinization. Am J Med Technol. September-October 1967;33(5):361-5) and is available in a kit provided by Sigma Diagnostics (Sigma Procedure No. 535). A concentration curve was prepared and analyzed. The concentration of both the controls and the samples was determined directly from the calibration curve. Finally, the result was converted from blood urea nitrogen (mg/dl) to urea concentration (mmol/L).

(19) Statistics

The usual parametric statistics were used that require random variation, unbiased sampling, and unit normal distributions of samples. Student's t-test between independent samples was used for all comparisons. Beta power for the ranges of sample variation observed in the present data were greater than 90% for n greater than 8.

b) Results (1) Spontaneous and Evoked Hibernation-Related Deaths

Table 6 shows the behavioral staging of hibernation and the occurrence of spontaneous and arousal-evoked deaths, each of which were observed independently in two studies using separate hibernation facilities. Table 6 indicates the deaths that were related to, 1) the animal being in deep hibernation (D) or 2) awake during the last observation period (d). Study 1 was performed at a large commercial facility (North Eastern Wildlife) and the animals were observed, with minor disturbance every 3 to 4 days, from November through February. Study 2 was performed in a small quiet hibernaculum (Delaware Water Gap Science Institute) and the animals were completely undisturbed and monitored only by an intercom system. At approximately 6 weeks into hibernation 9 animals in Study 1 were disturbed on December 21, as indicated by the minus signs. Similarly all animals in Study 2 were disturbed on December 18. The same disturbance in 4 of the same Study-2 animals occurred again on January 12, and resulted in evoked arousal and subsequent death within 12 hours (D). In all cases the disturbance was an approximately 10-min procedure in which the animal was stretched out on its back (blood sampling, ECG recording).

In Study 1 there were 16 adults of 3.2 to 5.9 kilograms in body weight and 6 juveniles of less than 3.2 kilograms. The juveniles had an incisor width less than 2 mm. Five of six juveniles died spontaneously (83%) during the hibernation period of November 1 to February 20, whereas only 7 of 16 adults (44%) died during this period. These counts do not include the animals used for the D2, NE1, and NE2 plasma extractions or for the evoked deaths in Study (all enclosed).

In mid-December, each of 9 subjects in Study 1 (2 juveniles, 7 adults) was aroused by stretching out its limbs while it was on its back; blood samples were also taken. Three woodchucks were not in hibernation, but 5 adults and 1 juvenile were in deep hibernation. The arousal procedure did not result in any deaths within 24 hrs and in all 6 hibernators the hibernation continued. There were 9 cases of spontaneous arousal to full wakefulness (indicated by underlining) before December 26 and 7 cases after this date, and in none was the normal spontaneous transition to wakefulness associated with mortality.

In Study 2, each animal was initially observed with ECG electrodes taped to the palms of its limbs. The subjects were 4 adult and 4 juvenile woodchucks all in deep hibernation in mid-December (December 21). The 4 juveniles and 4 adults were aroused by outstretching the limbs while the animal was on its back (Table 6). In no case did arousal to full wakefulness result, but there were ECG signs of partial arousal in all cases, as demonstrated in FIG. 1 (Arousal). That is, the RR-intervals began to decrease systematically during the 8-min arousal period, but they returned to their previous levels within 2 hrs. None of these animals died.

In mid-January, 2 juveniles and 2 adults (Study 2) were aroused by the same procedure. In all 4 subjects the RR-intervals shortened during and following the arousal procedure, and episodes of severe bradycardia were observed within 2 hrs. Each animal subsequently aroused to full wakefulness, became ambulatory, and then died within a period of 6 to 12 hrs (D).

Figure 1:
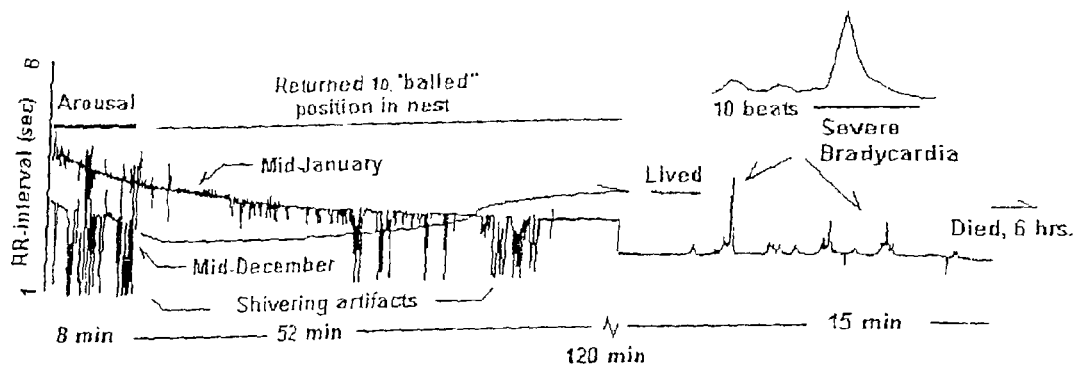

FIG. 1 shows examples of the severe bradycardia in the cardiac data. The RR-intervals contained considerable EMG artifacts at times ("shivering"), but smooth systematic reductions of the RR-intervals appeared and were confined by observation of successive QRS complexes. In the mid-January trace in FIG. 1, after the arousal, the animal was returned to its straw nest and settled in its "balled" position for 52 minutes. The electrodes were left attached and the animal was recorded 2 hrs later, after it had become ambulatory, but was not yet sufficiently mobile to move out of its nest. A type of "shivering" was manifested as muscular contractions slower than in common shivering and this was apparent all subjects. The animals were not monitored between 2 and 6 hours after the beginning of arousal to allow them the opportunity to return to the hibernating condition.

Within 6 to 12 hrs after the beginning of the arousal procedure, each of the 4 mid-January subjects was found dead outside its nest compartment. In 3 cases the animal was found dead in the eating compartment, and in one case the animal had scaled a 1-foot wall to escape its opened home cage.

TABLE 6

Hibernation Mortality

| NA | NW | N 17 | N 21 | N 24 | N 27 | N 30 | D 5 | D 8 | D 11 | D 15 | D 18 | D 21 | D 26 | J 2 | J 5 | J 9 | J 12 | J 16 | J 19 | J 25 | J 29 | F 2 | F 14 |
|---|---|---|---|---|---|---|---|---|---|---|---|---|---|---|---|---|---|---|---|---|---|---|---|
| \multicolumn{24}{c}{Study 1: Monitored for hibernation stage} |

| NA | NW | N17 | N21 | N24 | N27 | N30 | D5 | D8 | D11 | D15 | D18 | D21 | D26 | J2 | J5 | J9 | J12 | J16 | J19 | J25 | J29 | F2 | F14 |
|---|---|---|---|---|---|---|---|---|---|---|---|---|---|---|---|---|---|---|---|---|---|---|---|
| J | 3.6 | 5 | 5 | 5 | 5 | 5 | 5 | 5 | 5 | 5 | 5 | 5 | d | | | | | | | | | | |
| J | 3.1 | 5 | 5 | 5 | 5 | 5 | 4 | 3 | 2 | 3 | 4 | 3 | 3 | 5 | 5 | 5 | d | | | | | | |
| J | 2.7 | 5 | 5 | 5 | 3 | 4 | 3 | 3 | 2 | 2 | 4 | 3 | 3 | 2 | 2 | 2 | 2 | 2 | 2 | 4 | 5 | 3 | |
| J | 3.2 | 5 | 5 | 5 | 5 | 5 | 5 | 5 | 5 | 5 | 5 | 5 | 4 | d | | | | | | | | | |
| J | 3.1 | 5 | 5 | 5 | 5 | 5 | 5 | 5 | 5 | 5 | −5 | 5 | 5 | 3 | 3 | 2 | 2 | 2 | 2 | 2 | D | | |
| J | 3.1 | 5 | 5 | 5 | 5 | 5 | 5 | 5 | 5 | 5 | 5 | 5 | 4 | d | | | | | | | | | |
| A | 3.4 | 5 | 5 | 5 | 5 | 5 | 5 | 5 | 2 | 3 | 5 | 5 | 3 | 2 | 2 | 2 | 2 | 1 | 3 | 5 | 3 | | |
| A | 4.1 | 5 | 5 | 5 | 5 | 5 | 5 | 5 | 5 | 5 | 5 | 5 | 2 | 2 | 2 | D | | | | | | | |
| A | 4.5 | 5 | 5 | 5 | 3 | 3 | 4 | 5 | 5 | 5 | 5 | 5 | 5 | 5 | 5 | 5 | 5 | 5 | d | | | | |
| A | 5.3 | 5 | 5 | 5 | 5 | 5 | 5 | 5 | 2 | 2 | 2 | 3 | 2 | 4 | 4 | 3 | 3 | 3 | 3 | 3 | 5 | | |
| A | 4.9 | 5 | 5 | 5 | 3 | 4 | 5 | 5 | 2 | 3 | 5 | 5 | 5 | 5 | 5 | 3 | 3 | 1 | 2 | 2 | 3 | | |
| A | 4.4 | 5 | 5 | 4 | 5 | 4 | 3 | 3 | 3 | 3 | −3 | 2 | 2 | 3 | 5 | 5 | 3 | 3 | 2 | 3 | 5 | 3 | |
| A | 3.8 | 5 | 5 | 5 | 5 | 5 | 4 | d | | | | | | | | | | | | | | | | |
| A | 4.6 | 5 | 5 | 5 | 2 | 3 | 3 | 5 | 5 | 5 | −5 | 5 | 5 | d | | | | | | | | | |
| A | 5.9 | 5 | 5 | 5 | 5 | 5 | 5 | 5 | 5 | 5 | −5 | 5 | 5 | 5 | 5 | 5 | 5 | 5 | 5 | 5 | d | | |
| A | 4.2 | 5 | 5 | 5 | 5 | 5 | 4 | 3 | 5 | 3 | −3 | D | | | | | | | | | | | |
| A | 3.2 | 5 | 5 | 5 | 5 | 2 | 2 | 2 | 2 | 5 | 3 | −2 | 2 | 2 | 2 | 1 | 2 | 2 | D | | | | |
| A | 4.8 | 5 | 5 | 5 | 5 | 5 | 5 | 5 | 5 | 5 | −3 | D | | | | | | | | | | | |
| A | 3.3 | 5 | 5 | 5 | 5 | 5 | 5 | 5 | 5 | 5 | 5 | 5 | 3 | 2 | 3 | 2 | 2 | 2 | 2 | 3 | 3 | | |
| A | 3.8 | 5 | 5 | 5 | 5 | 5 | 5 | 5 | 5 | 5 | 4 | 3 | 3 | 5 | 3 | 3 | 2 | 2 | 2 | 3 | 3 | | |
| A | 4.6 | 5 | 5 | 5 | 5 | 3 | 4 | 5 | 5 | 5 | 5 | 4 | 3 | 3 | 3 | 3 | 3 | 3 | 2 | 2 | 2 | | |
| A | 4.3 | 5 | 5 | 5 | 4 | 3 | 3 | 5 | 2 | 2 | 4 | 3 | 5 | 5 | 5 | 5 | 3 | 2 | 2 | 2 | 2 | | |
| A | 4.6 | 5 | 5 | 5 | 4 | 5 | 4 | 2 | 2 | 1 | *2 | NE1 | | | | | | | | | | | |
| A | 4.3 | 5 | 5 | 4 | 3 | 5 | 4 | 3 | 2 | 2 | *2 | | | | | | | | | | | | |
| A | 3.6 | 5 | 5 | 5 | 5 | 5 | 5 | 5 | 5 | 3 | 2 | *2 | | | | | | | | | | | |

TABLE 6-continued

Hibernation Mortality

| N A | N W | N 17 | N 21 | N 24 | N 27 | N 30 | D 5 | D 8 | D 11 | D 15 | D 18 | D 21 | D 26 | J 2 | J 5 | J 9 | J 12 | J 16 | J 19 | J 25 | J 29 | F 2 | F 14 |
|---|---|---|---|---|---|---|---|---|---|---|---|---|---|---|---|---|---|---|---|---|---|---|---|
| A | 2.7 | 5 | 5 | 5 | 4 | 4 | 3 | 3 | 3 | 3 | 3 | *2 | | | | | | | | | | | |
| A | 4.4 | 5 | 5 | 5 | 5 | 5 | 5 | 5 | 5 | 5 | 2 | −2 | 2 | 3 | 5 | 5 | 5 | 3 | 3 | *2 | NE2 | | |
| A | 5.4 | 5 | 5 | 5 | 5 | 5 | 5 | 5 | 5 | 5 | 5 | 5 | 5 | 5 | 5 | 5 | 3 | 3 | 2 | *2 | | | |
| A | 4.6 | 5 | 5 | 5 | 5 | 5 | 5 | 5 | 5 | 5 | 3 | 2 | 2 | 2 | 2 | 2 | 2 | 2 | 2 | 1 | *1 | | |
| A | 4.6 | 5 | 5 | 5 | 5 | 5 | 5 | 5 | 5 | 5 | 3 | 2 | 2 | 2 | 2 | 2 | 2 | 2 | 2 | 1 | *1 | | |
| J | 2.8 | 5 | 5 | 5 | 5 | 5 | 5 | 3 | 2 | 2 | 2 | 3 | 3 | 2 | 2 | 2 | 2 | 3 | 3 | *2 | | | |
| Study 2: Undisturbed, except for ECG recording | | | | | | | | | | | | | | | | | | | | | | | |
| A | 4.5 | 5 | 5 | . | . | . | . | . | . | −1 | *1 | D1, D2 | | | | | | | | | | | |
| A | 3.6 | 5 | 5 | . | . | . | . | . | . | −1 | *1 | | | | | | | | | | | | |
| J | 2.9 | 5 | 5 | . | . | . | . | . | . | −1 | *1 | | | | | | | | | | | | |
| J | 2.8 | 5 | 5 | . | . | . | . | . | . | −1 | *1 | | | | | | | | | | | | |
| A | 3.8 | 5 | 5 | . | . | . | . | . | . | −1 | 1 | . | . | . | . | −1 | D | | | | | | |
| A | 3.5 | 5 | 5 | . | . | . | . | . | . | −1 | 1 | . | . | . | . | −1 | D | | | | | | |
| J | 2.4 | 5 | 5 | . | . | . | . | . | . | −1 | 1 | . | . | . | . | −1 | D | | | | | | |
| J | 2.1 | 5 | 5 | . | . | . | . | . | . | −1 | 1 | . | . | . | . | −1 | D | | | | | | |

TABLE 6
Age (A): J = juvenile (1-year),
A = adult.
Weight (W, in kilograms, Nov 1).
Stage of Hibernation (at dates shown at top):
5 = awake,
4 = torporus,
3 = hibernating, but reacts to touch by uncurling from "ball position,"
2 = hibernating, but slowly reacts to touch by partial uncurling,
1 = deeply hibernating, not reactive to touch.
Deaths (boxed): D = spontaneous death following documented hibernation within previous 3 days;
d = spontaneous death following documented wakefulness within previous 3 days,
D = evoked death within 6 to 12 hours following evoked arousal.
Evoked Arousal: −n = animal is stretched out from "ball position," while in the stage indicated.
Spontaneous Arousal: Stage 5 of each arousal is underlined.
Plasma Samples (boxed):
* = plasma samples taken during hibernation stage indicated; abbreviated pooled sample names at right.

(2) D2, but not NE2, Prevents Stroke

The effects of tail-vein injections of 5 mg/kg of the molecular fractions D2 and its nearest control NE2 were measured. These results indicated that protein/peptide fraction, (D2) can prevent cell death and loss of motor function in a mouse model of stroke C57 mice received an occlusion of the middle cerebral artery via an occluder inserted into the internal carotid artery near its bifurcation with the external branch. After 1-hour of occlusion, D2 or its nearest control NE2 was injected IV (4 mg/kg, tail vein). The occluder was then removed and the animal allowed to recover. Re-establishment of normal blood flow was confirmed by laser-Doppler measurement. Twenty-four hours later the animals were observed behaviorally for motor deficits and then sacrificed. Each brain was quickly removed, cut into 2-mm sections and incubated in triphenyltetrazolium chloride (TTC, 2%). The TTC molecules bind to normally functioning mitochondria and turn viable neurons into darkly stained red tissue. Sections were taken from an animal that received the D2 injection 1-hr after the start of ischemia. The animal subsequently showed normal behavior and no motor deficits. Sections were also taken from an animal that received the NE injection 1-hr after the start of ischemia. All injections were delivered 1-hr after the beginning of MCAO. These results illustrate that an early-hibernation molecule(s) has tissue-savings affects in the mouse MCAO model. Such molecule(s) is not present during later hibernation (NE2) and its lack is associated with the high incidence of spontaneous and evoked mortality.

The quantified measurements of the infarction volumes (cubic millimeters) are tabulated in Table 7 for each of 3 replication experiments with D2 and its controls (NE2, SA). In a fourth D2 experiment, tail-vein injections occurred at 30-min after the start of middle cerebral occlusion, with the occluder still in place. Stained slices from members of some of these subgroups, as well as from animals injected with cerebrospinal fluid, were collected, and a material that also produced significant tissue savings. The replication experiments (R1-R3) in the standard mouse model of cerebral ischemia used tail-vein injections of D2 and NE2 state-dependent molecular fractions. Each pair of sections was from a single animal with the greatest amount of tissue savings in that group. The paired numbers at the right of each label indicate the number of animals in each group showing 100% savings versus those with less savings. The mean savings for the three D2 replication experiments is 77% compared to the NE2 control that defines 0% savings (p<0.001). The model used 1-Hr occlusion of the middle cerebral artery (chloral hydrate anesthesia) followed by restoration of flow and tail vein injection of material. Infarction size was determined using triphenyltetrazolium chloride (2%) staining and computerized volumetric software. The injections were 10 mg/kg (D2, NE2) IV in tail-vein and 100 μl (CSF. IV) and 2.5 μl (CSF. IC).

The marked savings of the infarction volumes were confirmed by normal open-field behavior, including jumping on top of a small box placed in the field. All partial savings of infarction volumes were associated with only partial recovery of motor behaviors (limb weakness and inaccuracy in jumping). All controls showed the usual behavioral hemiplegia associated with coerced circling behavior and the general absence of spontaneous behavior in the open field.

The dose-response for infarction volume (i.e., savings) is shown in Table 7. Note the inverted U-shaped curve for the larger dosage. The most effective dose is 5 mg/kg as this is associated with the smallest infarction volume.

Considerably larger doses were studied in adult rats (n=25), without any apparent toxicity. Doses of 50 mg/kg administered by tail-vein injection had no significant affect on gross anatomy of the organs or of organ weight, arterial blood pressure, temperature or eating behavior. The latter was studied over a 3-week period with daily injections. Massive doses, up to 800 mg/kg, were tolerated in two additional SHR rats without affects on either blood pressure or death within 24-hrs.

The NE2, SA and CD fraction of molecules were all statistically not different from one another. Combining them all together as controls (n=16) and comparing them to the D2 group (n=21) resulted in a highly statistically significant difference (p<0.001, t-test) that has high beta power (beta>0.90) tubes, with filter cut-offs of 10- and 3.5-kDa, and then dialyzing this material against 8-M urea, 2-M NaCl, or water to wash away the peptides, over a 24-hr period and in the cold (4° C.), did not eliminate the active molecule. Rather urea-treatment seemed to increase the activity of the active molecule in D2. Dialysis might increase potency by washing away any possible peptide inhibitor or by dislodging the active ingredient from its carrier protein (albumin). The result was that one or more molecules above 10-kDa in mass are the one or ones that carry the active ingredient, as these are retained in the dialyzed D2 material that is then tested in the MCAO-mouse model and found to be effective.

TABLE 7

Cerebral Infarction Volume ($mm^3$) in Mouse MCAO Model

Various Fractions Injected after 1.0 hrs

| D2 | D2hemo | NE2 | SA | HCF icv | HCF-iv | |
|---|---|---|---|---|---|---|
| 23.12 | 37.88 | 55.92 | 74.68 | 41.56 | 34.92 | |
| 32.41 | 28.36 | 69.41 | 95.41 | 27.21 | 21.61 | |
| 88.24 | 88.52 | 78.48 | 79.88 | 46.32 | | |
| 59.52 | 77.81 | 100.04 | 91.16 | 43.24 | | |
| 83.21 | 55.96 | 82.31 | 89.48 | | | |
| 0 | 8.32 | 62.77 | 89.58 | | | |
| 66.81 | 37.61 | 75.11 | 74.62 | | | |
| 78.32 | 7.24 | | | | | |
| 53.95 | 42.71 | 74.86286 | 84.97 | 39.58 | 28.26 | Mean |
| 0.019173 | 0.003136076 | 0.287991 | | 0.00001 | 0.00008 | P-value |

D2-fraction injected after 0.5-hr

| mouse-1 | mouse-2 | mouse-3 | mouse-4 | mouse-5 | mouse-6 | mouse-7 | mouse-8 | mouse-9 | mouse-10 | |
|---|---|---|---|---|---|---|---|---|---|---|
| 4.49 | 33.62 | 106.57 | 11.62 | 0.00 | 4.22 | 70.93 | 0.00 | 8.45 | 29.35 | 26.93 Mean |
| | | | | | | | | | | 0.000774 P-value |

Dose-Response, D2-fraction, injection at 1-hr

| SA 5 mg/kg | D2 1 mg/kg | D2 5 mg/kg | D2 10 mg/kg | D2 20 mg/kg | |
|---|---|---|---|---|---|
| 89.58 | 18.52 | 10.52 | 15.88 | 47.17 | |
| 74.62 | 24.38 | 3.65 | 14.92 | 48.01 | |
| 82.11 | 21.45 | 7.09 | 15.41 | 47.59 | Mean |

(3) Molecular Sieve and Dialysis Treatments of D2: Increase in Potency

As shown in Table 8 below (Molecular Sieve Experiments), placing the D2 material inside closed membrane

TABLE 8

Molecular-Sieve Filtration (10- and 3.5- kDa) and Dialysis (Urea, Salt, Water) of D2: Effects (4 mg/kg) on Infarction Volume ($mm^3$) in the MCAO Mouse-Model (3 per group)

| D2-Treatment | Mouse 1 | Mouse 2 | Mouse 3 | Mean | Std | p-value |
|---|---|---|---|---|---|---|
| Urea 10 kD | 25.10 | 00.00 | 5.15 | 10.08 | 13.25 | 0.0026 |
| Urea 3.5 kD | 02.50 | 32.34 | 11.63 | 15.49 | 15.29 | 0.0053 |
| NaCl 10 kD | 32.18 | 29.87 | 47.75 | 36.60 | 09.73 | 0.0101 |
| NaCl 3.5 kD | 42.41 | 10.68 | 34.33 | 29.14 | 16.49 | 0.0163 |
| H2O 10 kD | 27.79 | 33.21 | 71.66 | 44.22 | 23.92 | 0.1229 |
| H2O 3.5 kD | 37.25 | 20.73 | 46.81 | 34.93 | 13.19 | 0.0156 |
| D2 (untreated) | 38.71 | 32.85 | 16.22 | 29.26 | 11.67 | 0.0075 |
| NE2-Control | 82.31 | 62.77 | 75.11 | 73.40 | 09.88 | |

(4) 2D Gels and Fingerprint Identifications

FIG. 2 (upper) shows 2, two-dimensional, SDS-PAGE gels in which the SA (State #1, NE) and D2 (State #2, D2) materials are visualized as spots of pure proteins of specific pI (x-axis) and mass (y-axis). Many of the small spots in State #1 are gray, without a black density at its epicenter. So a single black pixel was placed by computer visualization in the epicenter of each so that a black-with-clear overlay could be made and superimposed on the State #2 gel. In magnified boxes of the State #2 with State #1 overlay, a small, gray, State-#2 spot with a State #1 single pixel nearby indicates both spots (i.e., proteins) are present in both states. Those State #2 gray spots without a nearby State #1 single pixel are therefore specific to State #2. In the magnified boxes (lower) the oblique markers indicate several of the State-#2-specific proteins. In a count of all State-#2-specific spots over the entire 2D gel 20 were found. Another 20 spots (approximately) were quite up-regulated in State #2, as evidenced by at least a 2-fold greater density to the comassie-blue stain (i.e., light gray to dark black epicenters).

Once a spot of interest is identified, then it is subjected to liquid-chromatography combined with tandem mass-spectroscopy (LC/MS/MS). First the spot on the gel is excised and the protein eluted. Then the pure molecules are injected into a mass-spectroscopy beam and their mass measured. While in the beam they are bombarded by a second beam that breaks up the molecules at predetermined amino-acid bonds. This latter beam of fragments produces an output that is as specific to the molecule as a fingerprint is to a person. Once this molecular "fingerprint" is made it is then searched in all of the large databases where its "fingerprint" might be deposited, along with its structure. If the spot of interest is already a known protein, it is easily identified.

FIG. 3 shows the location of these identified differential spots on a BATS gel, which is like a 2D gel, except that after the pI gradient is made, it is cut into strips that are placed alternately next to strips made from the other state. Then the mass gradient is run for all of the alternating pairs of strips. Note that not as many State #2 spots are identified on the BATS gel as on the larger higher-resolution 2D-SDS gels. That is, only 9 state-dependent spots (blue circles) were found, at pI of 4 to 7, on the BATS gel compared the 20 found on the higher resolution 2D gel shown in FIG. 2. The three proteins identified are found to be structured in the databases (Macroglobulin 2 alpha, Serum amyloid A1, and Transthyretin, which is summer-specific).

Figure 4:
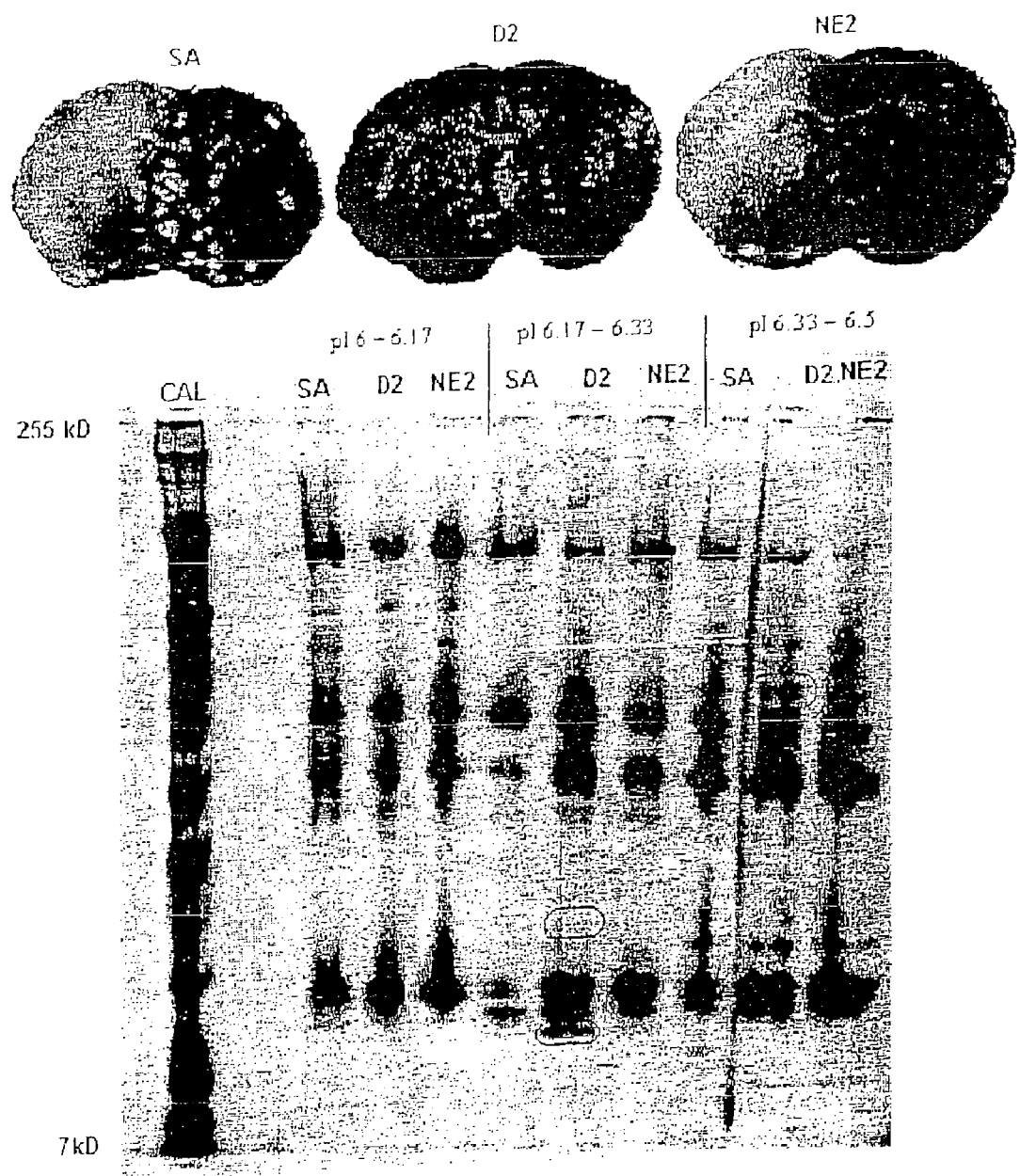

FIG. 4 shows a BATS gel with spots of interest (circled) that were for the pI 6 to 6.5 range. This smaller pI range showed the majority of the differential spots also seen in FIG. 3 for the 4 to 7 range. NE2, as the best control, shows protein bands not found in SA.

FIG. 5 shows the best and highest-resolution gels with the best and nearest controls. The result is that the fewest state-dependent spots are thus identified of which one underlies the tissue-savings effect in the MCAO model (D2-NE2). The CSF and urine panels of the figure compared winter hibernating materials with their respective summer controls. D2 was compared to its nearest neighbor, NE2. In these two 2D-gels, each pair of corresponding spots, was chosen for quantitative comparison by computer software (Genomic Solutions, Inc.) in which the computer calculates the coordinates of the corresponding spot epicenters by the use of a smoothly changed spatial gradient in one 2D gel that keeps changing until it maximizes alignment of all spots. The spots were first spatially aligned and then the gray-scale density for each spot was normalized to its whole gel; this normalization was made to compensate for concentration differences between the equal sample-volumes used to make the gels; this method presumes equal protein content for each gel. Then the relative difference in protein abundance between the two states was determined for each spot from its normalized gray-scale densities.

Instead of the 40 state-dependent increases found for D2 vs. SA only 9 were found for D2 vs. NE (FIG. 5, upper left panel, dark spots, FIG. 3). Additionally in this latter comparison there were 4 spots found which showed greater than 2-fold reductions during State #2 (hibernation, yellow spots). CSF (hibernation vs. non-hibernation) showed even greater numbers of up-regulated proteins (green spots), some of which were due to concentration differences not compensated by the normalization (blue spots). Urine showed an even larger number of up-regulated proteins and their metabolic fragments.

(5) Time of Injection Determines Infarction Size

FIG. 6 illustrates that pretreatment with D2 (5 mg/kg) can almost completely prevent cerebral infarction in the mouse model of MCAO. The vertical bars indicate +/−standard deviations around the mean. It is clear that injection at 30 min to 2 hrs after the start of the 1-hr of MCAO can also have a major affect on reducing infarction volume ($p<0.001$), especially after D2 treatment with 8M urea (UREA DIALYSIS). Also a 20% mean reduction in infarction size can still occur with injections out to 6 hrs after the beginning of the MCAO ($P<0.05$).

(6) Peptides in D2

Figure 7:
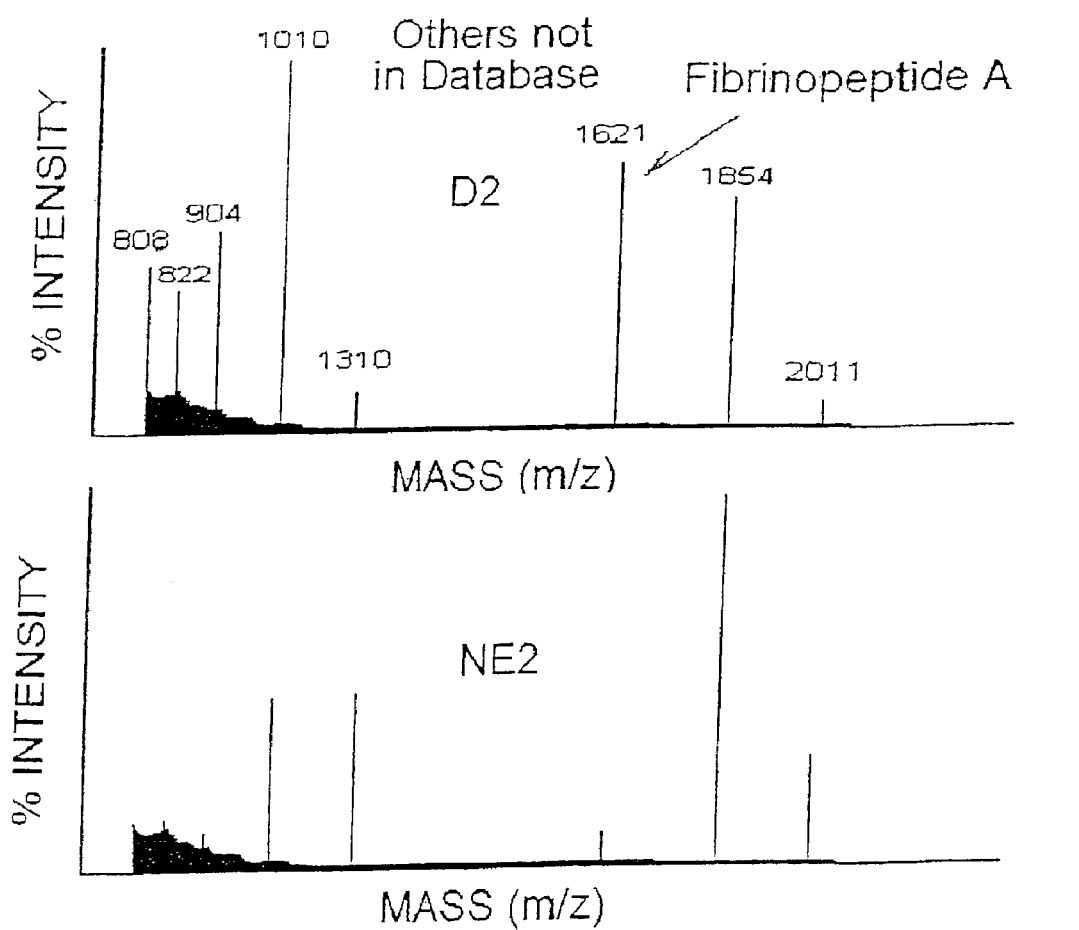

FIG. 7 shows the LC/MS/MS results for D2 and NE2 when each material is filtered by centrifugal movement through a 10-kDa membrane. One of these D2-abundant peptides was identified by molecular fingerprinting and bioinformatics to be Fibrinopeptide A. Since there were so few peptides in the differential D2 vs. NE2 comparison with this method, another differential approach was sought.

The so called ICAT approach to identifying state-dependent peptides uses differential state-dependent labeling of cysteine by two different isotopes of deuterium (deuterium-2 and deuterium-8). It was found, however, that there were not enough cysteine-labeled molecules in the D2 peptide fraction, that is, below the 10 kDa cutoff, to make this method practical.

(7) The Data

It would appear that the majority of hibernation-related deaths occur late in hibernation, beginning on or after December 26th, and extending into late January (Table 6). These clustered mortalities follow periods of hibernation (5 D) or wakefulness (7 d). Evoked deaths that immediately follow evoked arousal occur in mid-January (4 D), but these do not occur in mid-December. Neither spontaneous nor evoked arousal in mid-December results in such numbers of death as those in mid-January.

The spontaneous and evoked deaths in January appear to be associated with the loss of one or more molecules circulating in the blood that are present and protective when arousal occurs in early to mid December. This circulating December-molecule (D2 fraction) appears to involve a mechanism for protection against ischemic injury (Table 7) and this protection is not present during January (NE2 fraction).

The protection against ischemic injury must have evolved to prevent tissue damage to the brain and heart during the initiation and recovery from hibernation. An example of such injury occurs when the ambulatory behavior associated with wakefulness is not adequately supported by the circulation (FIG. 1). This physiological jeopardy is observed in all cases of evoked arousal in mid-January, but not in mid-December.

The clustering of spontaneous deaths after December 26th (i.e., to the right of the centered vertical line in Table 6) is one in which 50% of the animals that die do so within a 3 week period following this date. The overall spontaneous mortality rate up to mid-February is 55% (12 of 22 animals). The incidence of spontaneous deaths is higher for the juvenile woodchucks (83%, 5 of 6) than the adults (50%, 8 of 16).

The spontaneous arousals during mid-December (Study 1, underlined, 9 cases) are not accompanied by imminent death, a finding which suggests that the ischemia-protective molecule is present in abundance, and this hypothesis is confirmed by the injection of the December plasma fraction of molecules, D2, in the mouse-model of stroke (Table 7). The injection of the mid-January plasma fraction, NE2, has no affect in the stroke model, and it is this absence of the protective molecule that is associated with the high mortality rate during this cluster-death period (Table 7).

Evoked arousal during the mid-December period (all on December 21 in Study 1, and all on December 15 in Study 2) does not result in any deaths. Rather the hibernating animals, for which ECG data suggests they are at least partially aroused (FIG. 1, mid-December), all successfully return to hibernating (FIG. 1, Lived). Note that the two deaths on December 26 in Study 1 occurred 5 days after the evoked arousal and are therefore not associated with this stimulus. Evoked arousal during the "cluster-death" period in mid January, in contrast, resulted in ambulatory behavior and severe bradycardia with the subsequent death of 100% of these animals.

Why deaths do not always occur in January during spontaneous arousal (Table 6, underlined) can be explained by either, 1) a better match between metabolic demand (ambulatory behavior) and circulatory support in these surviving animals, or 2) a second active secretion of the ischemia-protective molecule that accompanies the spontaneous arousal, but not the evoked arousal. The first possibility is not likely, as all of the animals experiencing evoked arousal in January (Study 2) died within 12 hours, without any evidence of the development of supportive physiology. The second possibility, however, as interpreted from the observation of the protective effects of the molecule(s) present in early-hibernation and not late-hibernation, would seem to be the more likely. That is, the secretion of the ischemia-protective molecule(s) is transient at the onset of hibernation and a high level does not last throughout hibernation on into January; therefore the molecule must be secreted a second time, as part of the natural arousal process. The spontaneous arousals in January that result in death can, like the evoked arousals, be so rapid that insufficient secretion of the protective molecules occurs, that is, as required for survival.

The protective molecule appears to be a protein whose mass is above 10 kDa and therefore is not washed out during the dialysis to remove the peptides (Table 8). All of the differential up-regulated and/or state-specific molecules that are candidates for the anti-stroke effect are seen in FIG. 5. 4 identified molecules are Macroglobulin 2 Alpha, Serum Amyloid A1, Transthyretin, and Fibrinopeptide A, (FIGS. 3 and 7).

The specific anti-stroke molecule can be one of the 9 dark spots identified in FIG. 5 (D2-NE2), which uses the "nearest" control. Since the effective molecule is also found in the CSF, a fraction of molecules, which has neuroprotective effects of it own (FIG. 6, Table 7), the comparison of the two upper panels in FIG. 5 can therefore lead to even fewer spots of interest. The large green spot to the left of the large albumin spot is the single precisely overlapping spot indicated by the two upper panels. Another to the lower left of this one can be an overlapping spot.

Examination of several molecular cuts of the D2 material using the MCAO-bioassay to track which sub-fractions have efficacy, can be performed and is another way of isolating molecules having desired properties.

This same anti-stroke molecule is also likely to have anti-heart attack efficacy, as it would appear to be the molecule that also prevents ischemic death in the recovery from hibernation when cardiovascular causes, such as those demonstrated in FIG. 1, are present. There is no reason to believe that this anti-ischemia molecule is specific for the brain, when it is collected from the blood.

(8) LC/MS/MS Identification of Fibrinopeptide A in the D2 and NE2 Peptide Fractions (3 kDa Cutoff)

FIG. 7 shows the spectra for both the D2-filtered material (3 kDa. cut-off) and the NE2-filtered material (3 kDa. cut-off). In either case the D2 or NE2 flow-through was analyzed by LC tandem mass-spectroscopy (LC/MS/MS). The following ions were sequenced: m/z 809, 904, 1010, 1012, 1621 and 1662. The ions m/z 809 and 1010 are matrix ions from the MALDI ionization process, m/z 1012 is the third isotope of m/z 1010. Analysis of m/z 1662 proved inconclusive, analysis of m/z 904 and 1621 is described herein. It is clear that Fibrinopeptide A is ion represented by m/z 1621 and Bradykinin is the peak represented by m/z 904. Other spikes were identified as fragments of the matrix that holds the source material (asterisks). Six peptides were more abundant in the NE2 mid-hibernation fraction (minus sign).

(9) Unique Structure of Woodchuck FPA

Table 9 shows the sequence of woodchuck FPA.

TABLE 9

The sequence of woodchuck Fibrinopeptide-A (FPA-w) determined by LC/MS/MS in combination with tripsination fragments.

| ADTDK | GEFLAEGGGV | Woodchuck* |
|-------|------------|------------|

*The position-9 amino acid, L, may actually be an I, as both amino acids are approximately the same molecular weight and this mass was not adequately resolved in the fragment masses. The mouse has L in this position, as does the majority of the other species shown in Table 1, above. Thus fragments with both L or an I at the $9^{th}$ position are disclosed.

Following extensive analysis of product ion data the partial peptide sequence indicated was proposed. Note leucine/isoleucine are isomeric and cannot be distinguished by low energy CID. A second 15 µL aliquot of the D2 sample was derivatized (N-acetylation) by the addition of 1 µL neat acetic anhydride. Note N-acetylation derivatizes primary amine groups N-terminus and lysine side chain). The reaction was left to proceed for 5 min and the resultant solution was analyzed by LC/MS/MS as described above.

The indicated full peptide sequence was elucidated following consideration of both sets of product ion data. The presence of a lysine at position 5 greatly affected the fragmentation pattern in the underivatized sample. Conversion to a less basic side-chain following N-acetylation allowed more complete fragmentation to occur upon re-analysis of the modified peptide. Searches of the public database with the deduced sequence indicated that this peptide Fibrinopeptide A.

Figure 10:
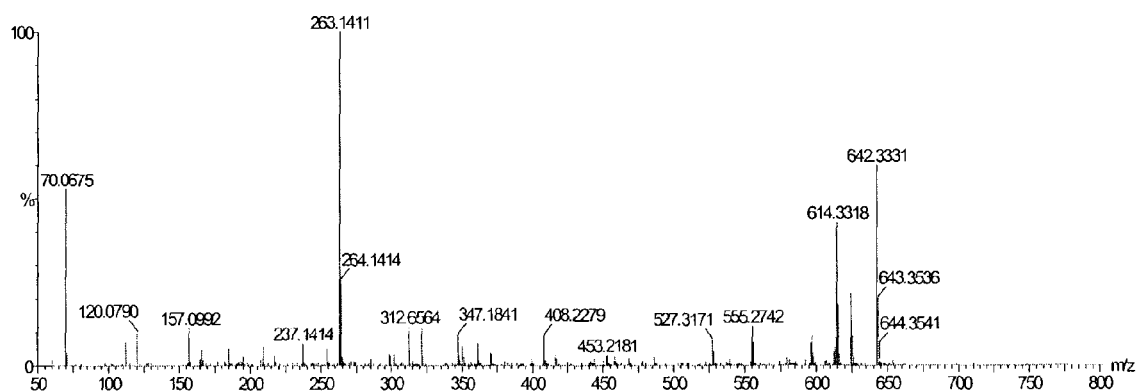
FIG. 10 shows results for a Peptide: Mass 904.4 Da—RP-PGFSPF (SEQ ID NO:61).
Figure 11:
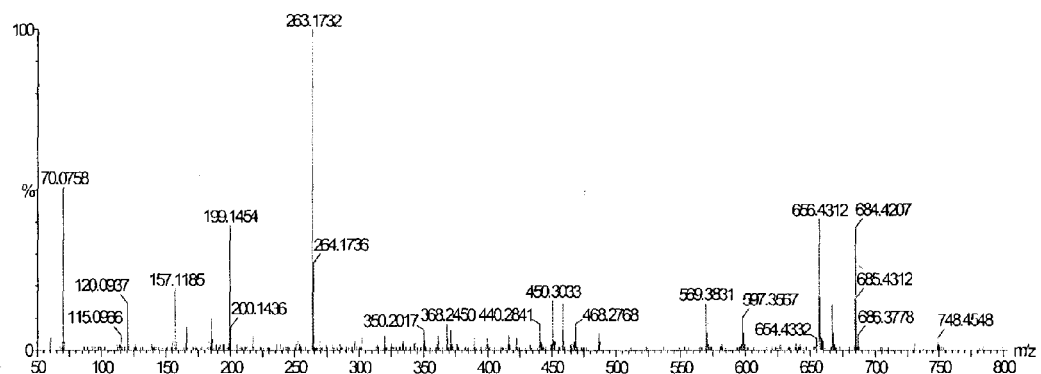
FIG. 11 shows results for a Peptide: Mass 904.4 Da—*RP-PGFSPF (SEQ ID NO:61).

The sequence of the molecule represented by the m/z 904 peak was determined to be des-arg$^1$ Bradykinin (See FIGS. 10-11).

(10) Unique Function of Human FPA (FPA-h) Tested in the Mouse-MCAO Model

Figure 12:
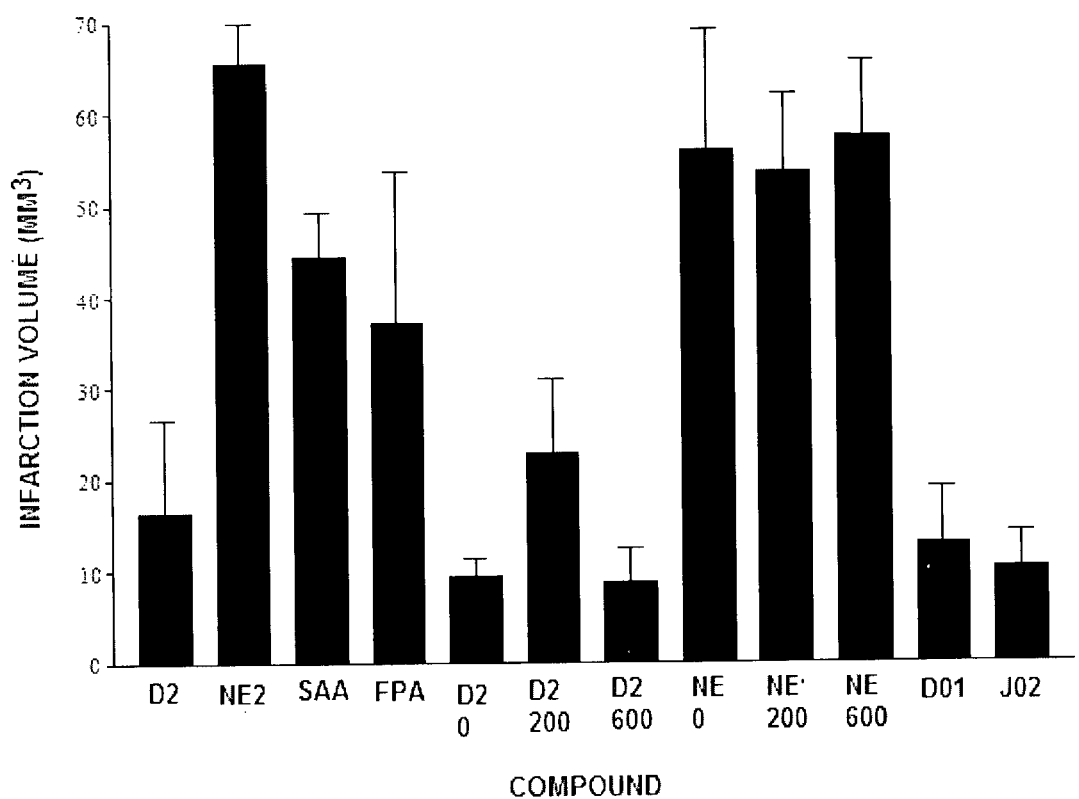
FIG. 12 shows means and standard deviations of FPA-h and other molecular-fraction treatment groups.

Table 9 below shows the results of testing of FPA-h in the mouse-model of stroke. Statistical significance is found between the mean infarction volumes for FPA-h and NE2 (p<0.01). Each cell represents one mouse. The same data are shown in FIG. 12 with the means and standard deviations.

These results show statistically significant differences of D2 peptides vs. NE2 peptides in producing a marked reduction in infarction size (P<0.01). They also demonstrate that one of these peptides, FPA-h, at 10 µg/kg (i.e., $\frac{1}{1000}^{th}$ the dose of D2) is able to produce a statistically significant reduction in infarction size in the mouse-MCAO model.

TABLE 9

| D2 | NE2 | SAA | FPA-h | D2-0 | D2-200 | D2-600 | NE2-0 | NE-200 | NE-600 | Dec D01 | Jan J02 |
|---|---|---|---|---|---|---|---|---|---|---|---|
| 14.94 | 57.92 | 50.66 | 20.76 | 9.10 | 43.50 | 3.80 | 76.40 | 78.40 | 41.40 | 35.96 | 22.98 |
| 34.54 | 60.64 | 47.84 | 53.72 | 13.80 | 7.60 | 4.60 | 50.66 | 41.70 | 69.40 | 3.70 | 13.80 |
| 0.00 | 64.80 | 34.76 | | 10.60 | 28.30 | 7.20 | 75.60 | 45.20 | 61.30 | 27.80 | 6.80 |
| | 78.42 | | | 4.20 | 11.50 | 19.60 | 20.50 | 48.60 | | 0.00 | 7.90 |
| | | | | | | | | | | 9.70 | 0.00 |
| | | | | | | | | | | 0.00 | |

Table 9. Effects of hibernation-related fractions of molecules and synthesized human Fibrinopeptide-A (FPA-h) on infarction size (mm$^3$) in the mouse-MCAO model. D2=early-hibernation albumin fraction; NE=NE2 mid-hibernation; SAA=serum amyloid A; D2-0, D2-200, D2-600, NE2-0, NE2-200, NE2-600=concentration of NaCl used to elute material from an anion exchange column. All animals were treated with a dose of 10 μg/ml for all test materials administered.

TABLE 10

| Infarc Slice 1 | Ipsilat 1 | Contra 1 | Infarc Slice 2 | Ipsilat 2 | Contra 2 | Infarc Slice 3 | Ipsilat 3 | Contra 3 | Infarct Slice 4 | Ipsi 4 | Contra 4 |
|---|---|---|---|---|---|---|---|---|---|---|---|
| 0 | 5.16 | 4.99 | 0 | 8.77 | 8.63 | 0 | 10.25 | 10.26 | 0 | 10.94 | 10.13 |
| 0 | 5.52 | 5.42 | 0 | 8.83 | 8.77 | 0 | 10.45 | 9.79 | 0 | 9.29 | 9.01 |
| 0 | 4.98 | 4.98 | 0 | 8.89 | 8.54 | 0 | 10.2 | 9.84 | 0 | 10.16 | 9.44 |
| 0.46 | 6.51 | 5.57 | 0.98 | 9.19 | 8.53 | 0.45 | 10.24 | 10.87 | 0 | 9.67 | 10.12 |
| 0 | 6.52 | NO Sy | 0 | 8.75 | 9.07 | 0.75 | 10.08 | 9.63 | 0 | 8.87 | 9.7 |
| 0 | 5.78 | NO Sy | 0 | 8.92 | 8.68 | 0 | 10.28 | 9.72 | 0 | 9.67 | 9.69 |
| 1.11 | 6.96 | NO Sy | 1.88 | 10.3 | 8.89 | 0.64 | 10.82 | 10.31 | 0.35 | 10.2 | 9.83 |
| 0.34 | 5.1 | 5.18 | 0.45 | 8.87 | 9.21 | 0.76 | 10.82 | 10.19 | 0.43 | 10.56 | 10.24 |
| 0 | 5.13 | 4.79 | 0.04 | 8.47 | 8.51 | 1.32 | 10.74 | 9.43 | 4.66 | 11.25 | 9.34 |
| 1.77 | 6.89 | 6.03 | 2.12 | 10.23 | 9.51 | 2.51 | 11.76 | 10.88 | 2.15 | 10.49 | 9.32 |
| 2.12 | 6.43 | 5.71 | 3.29 | 10.15 | 9.14 | 2.17 | 11.32 | 9.94 | 3.37 | 10.78 | 10.38 |
| 1.71 | 6.47 | 6.96 | 3.13 | 9.77 | 9.3 | 3.11 | 10.99 | 10.32 | 0.39 | 11.1 | 10.16 |
| 1.58 | 7.14 | NO Sy | 2.26 | 10.49 | 9.2 | 2.29 | 11.49 | 10.81 | 2.58 | 10.81 | 10.72 |
| 0 | 5.29 | 5.07 | 0 | 8.8 | 8.63 | 2.26 | 10.69 | 10.15 | 5.53 | 11.28 | 9.44 |
| 2.33 | 5.36 | 4.03 | 5.39 | 9.25 | 7.48 | 7.51 | 10.4 | 8.39 | 7.24 | 10.48 | 8.88 |
| 2.54 | 5.09 | NO Sy | 5.79 | 10.14 | 8.28 | 5.24 | 11.21 | 8.84 | 0 | 9.47 | 9.19 |
| 5.34 | 5.92 | 4.13 | 7.8 | 10.18 | 8.45 | 4.83 | 11.29 | 9.62 | 0.31 | 10.83 | 9.22 |
| 2.8 | 4.44 | 5.15 | 6.43 | 9.98 | 8.79 | 6.31 | 10.83 | 9.63 | 3.92 | 11.86 | 9.63 |
| 3.04 | 6.28 | 4.69 | 5.15 | 8.91 | 7.91 | 5.3 | 10.09 | 9 | 5.29 | 9.59 | 9.02 |
| 3.5 | 6.35 | 5.65 | 5.04 | 9.5 | 8.98 | 6.61 | 10.48 | 9.25 | 6.04 | 9.54 | 9.14 |
| 2.7 | 4.89 | 4.8 | 4.41 | 9.36 | 7.59 | 4.51 | 9.93 | 9.33 | 5.04 | 9.91 | 8.71 |
| 2.84 | 5.75 | 5.17 | 4.02 | 9.22 | 8.06 | 5.42 | 10.47 | 8.79 | 7.12 | 10.27 | 8.49 |
| 4.09 | 6.81 | 5.14 | 5.87 | 10.47 | 7.98 | 6.64 | 10.27 | 9.66 | 5.02 | 9 | 9.1 |

Table 10 shows the raw data for FPH-h injections (IV) in mouse-MCAO model. Each row shows for each mouse the infarction area (mm-sq) in each of four adjacent 2-mm slices (rostral to caudal) and the related areas of the ipsilateral and contralateral hemispheres (mm-sq). The 5 subjects shown in the bottom panel had summer albumin fraction injected as a control (SA). The dosages and total infarction volumes for each animal are shown in Table 11.

TABLE 11

| Molecule(s) (IV) | IV Dose (ug/a) | Group # Identifier | Ipsilateral Volume/2 | % Infarction Volume |
|---|---|---|---|---|
| FPA | 62.5 | 2 | 43.17 | 0 |
| FPA | 250 | 2 | 41.51 | 0 |
| FPA | 250 | 4 | 41.81 | 0 |

TABLE 11-continued

| Molecule(s) (IV) | IV Dose (ug/a) | Group # Identifier | Ipsilateral Volume/2 | % Infarction Volume |
|---|---|---|---|---|
| FPA | 62.5 | 3 | 43.71 | 4.9 |
| FPA | 250 | 6 | 41.92 | 1.8 |
| FPA | 250 | 7 | 42.38 | 0 |

TABLE 11-continued

| Molecule(s) (IV) | IV Dose (ug/a) | Group # Identifier | Ipsilateral Volume/2 | % Infarction Volume |
|---|---|---|---|---|
| FPAtyr | 62.5 | 3 | 46.86 | 10 |
| FPAtyr | 62.5 | 5 | 43.18 | 5.5 |
| FPA | 250 | 8 | 43.78 | 19.1 |
| FPA | 15.625 | 4 | 48.06 | 21.9 |
| FPA | 15.625 | 5 | 47.29 | 28.9 |
| FPA | 62.5 | 1 | 47.12 | 19.9 |
| FPA | 62.5 | 4 | 48.91 | 22.1 |
| FPA | 62.5 | 5 | 44.35 | 23.8 |
| FPA | 250 | 1 | 43.41 | 62.8 |
| FPA | 250 | 3 | 43.19 | 34.4 |
| FPA | 250 | 5 | 46.61 | 45.3 |
| FPAtyr | 62.5 | 6 | 45.26 | 50.4 |
| SA | 400000 | 1 | 42.05 | 53.6 |

TABLE 11-continued

| Molecule(s) (IV) | IV Dose (ug/a) | Group # Identifier | Ipsilateral Volume/2 | % Infarction Volume |
|---|---|---|---|---|
| SA | 400000 | 2 | 43.82 | 59.2 |
| SA | 400000 | 3 | 42.03 | 48.8 |
| SA | 400000 | 4 | 43.72 | 55.8 |
| SA | 400000 | 5 | 44.46 | 58.9 |

Table 11 shows the effect of FPA-h injections (IV) on % infarction volume in Mouse-MCAO Model. Each row is related to the same animal as in Table 7 and shows: the molecules injected (FPA=FPA-h, the human sequence), dosage in micrograms/animal, within dosage-group identification number (#), half of the ipsilateral hemisphere volume (num-cubed) and the % infarction volume of the ipsilateral hemisphere. The lower panel shows the controls (summer albumin fraction, SA). The t-test of the mean difference in the % infarction volume between the upper and lower panels has an associated alpha level of $p \leq 0.00005$.

The first sub-strings of FPA tested were the separated C-terminus and N-terminus. FPA and its peptide fragments were synthesized, and were tested in the mouse-MCAO model. The human form of FPA (FPA-h), but not the woodchuck form (FPA-w) is effective as an anti-infarction molecule as shown in Tables 10-12. The N-terminus of FPA-w is not effective. The C-terminus, however, is effective. Furthermore, the effectiveness of the C-terminus is potentiated by co-administration of the other upregulated D2 vs. NE2 peptide, bradykinin.

TABLE 12

Effects in the mouse-MCAO model (% infarction in ipsilateral hemisphere) of IV-Injection (250 μg/mouse of FPA-h, or its molar equivalent) of synthesized woodchuck Fibrinopeptide A (FPA-w, with either I or L in the $9^{th}$ position) or its phosphorylated form in the 3rd position (Ph FPA-w), or its sub-string fragments (N-terminis or C-terminis), or Bradykinin (Des-Arg-BK, adBK; Bradykinin, BK), or adBK combined with the (C-terminis. Group means are in bold.

| FPA(I)-w | FPA(L)-w | Ph FPA-w | | N-term | C-term(I) |
|---|---|---|---|---|---|
| 21 | 49 | 25 | | 60 | 44 |
| 46 | 53 | 24 | | 65 | 1 |
| 34 | 48 | 52 | | 64 | 8 |
| 58 | 43 | 70 | | 69 | 10 |
| | | 47 | | | |
| | | | Group | | |
| 39.7 | 48.2 | 43.6 | < Means > | 64.5 | 15.7 |

| C-term(L) | daBK | BK | daBK + C-term | saline | nothing |
|---|---|---|---|---|---|
| 15 | 17 | 23 | 7 | 71 | 34 |
| 36 | 9 | 16 | 19 | 54 | 48 |
| 34 | 27 | 27 | 18 | 60 | 70 |
| 0 | 15 | 67 | 28 | 61 | 53 |
| 42 | | | | | |
| 21.2 | 17 | 33.2 | 18 | 57.6 | 51.2 |

Combined Groups*:

| Controls | FPA-w | BK | C-term-w | FPA-h |
|---|---|---|---|---|
| 34 | 49 | 17 | 44 | |
| 48 | 53 | 9 | 1 | |
| 70 | 48 | 27 | 8 | |
| 53 | 43 | 15 | 10 | |
| 71 | 21 | 23 | 15 | |
| 54 | 46 | 16 | 36 | |
| 60 | 34 | 27 | 34 | |

TABLE 12-continued

Effects in the mouse-MCAO model (% infarction in ipsilateral hemisphere) of IV-Injection (250 μg/mouse of FPA-h, or its molar equivalent) of synthesized woodchuck Fibrinopeptide A (FPA-w, with either I or L in the $9^{th}$ position) or its phosphorylated form in the 3rd position (Ph FPA-w), or its sub-string fragments (N-terminis or C-terminis), or Bradykinin (Des-Arg-BK, adBK; Bradykinin, BK), or adBK combined with the (C-terminis. Group means are in bold.

| 61 | 58 | 67 | 0 | |
|---|---|---|---|---|
| 42 | | | | |
| 54.7 | 44 | 25.2 | 18.5 | 19.4 |
| | 0.0842 | 0.00300 | 0.00010 | 0.00003 |
| | 0.0421 | | | |

*FPA-w (I,L) combined and compared to the combined controls was not statistically significant if a legitimate one-tailed t-test was employed (p < 0.0421).
In contrast the C-terminis of FPA-w (C-term-w) was highly statistically significant (p < 0.00010).
The BK groups were also highly significantly, individually or combined (p < 0.00300).
The FPA-h group from the previous table (FPA-h) was the most highly significant group of all (p < 0.00003).
The combination of daBK with the C-term fragment did not appear statistically better.

(11) Another D2 vs. NE2 Up-Regulated Peptide, Bradykinin

Bradykinin affects infarction size and can act to potentiate the FPA infarction effect. Data in 8 saline control mice show a mean % infarction size of 52%; data from 8 additional mice treated with the C-terminis of FPA-w showed a mean % infarction size of 35% (P<0.5). Infarction size was further reduced in 8 other mice to 19% when 11-mer was accompanied by Bradykinin (P<0.05, Table 12).

(12) Urea Recycling

Figure 13:
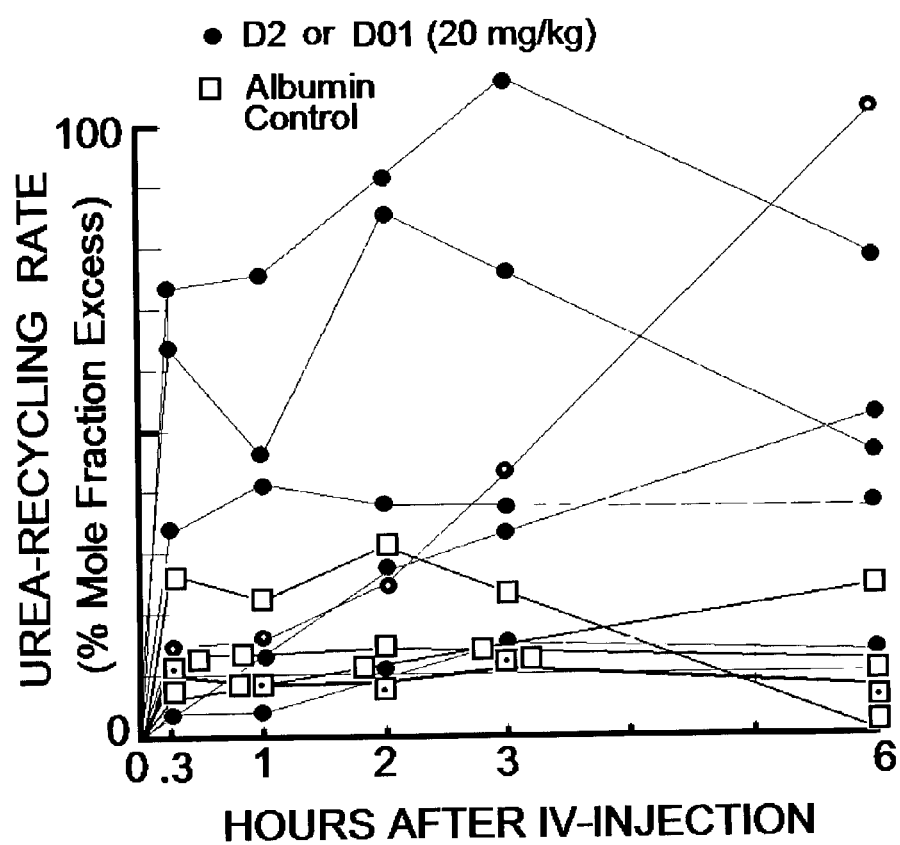

The rationale is that pregnant and hibernating polar bears must be making proteins, yet they do not suffer toxicity. Therefore a urea-recycling mechanism is hypothesized. Data in the rat suggests the urea-recycling occurs in a non-hibernating species (lab rat), and the rate is stimulated up to 13-fold when the albumin extracted from the plasma of a hibernating woodchuck is administered IV (10 mg/kg). These results are replicated (FIG. 13). According to the label D2 or D01 was used and no differences in anti-infarction efficacy or in urea-recycling efficacy is found between these two fractions.

The affect of D2, or its equivalent hibernation-related material D01, on the stimulation of the recycling of blood urea in the rat is demonstrated in FIG. 13. The medical indication here is uremic toxicity, an untoward medical condition that occurs in kidney failure and recovery from anesthesia. FIG. 13 shows the effect of the hibernation-related albumin fractions (D2, D01 at 20 mg/kg) compared to a control group injected with pure albumin (Xeno albumin, 20 mg/kg).

The data clearly show (P<0.025) that the hibernation-related albumin fractions stimulate the production of single-labeled urea above the baseline of occurrence of natural single-labeled urea (i.e., some N15 occurs in nature). This can only be explained by the cleavage of the double-labeled urea nitrogens and their re-incorporation into single-labeled urea. As time goes on after the original injection (1 mg) of double-labeled urea, some of it is excreted. This also occurs for some of the single-labeled material. The double-labeled pool by 6 hours is only $\frac{1}{6}^{th}$ (average across all subjects) that at the time of injection. Thus the recycling rate is actually 9-fold higher at 6 hours than that indicated in FIG. 13 by the 5- to 6-fold increase above the controls.

2. Example FPA Data

Fibrinopeptide A was tested for efficacy in the middle cerebral artery occlusion (MCAO) model in the mouse. In this study, two preparations of the carboxyl-terminal portion of fibrinopeptide A were tested in the MCAO model. One variant contained an isoleucine at position four while the other variant contained a leucine at position four. Intravenous (i.v.) injection of fibrinopeptide A variants, including FPA C-terminus 11-mer were started at 1 hour after the initiation of MCAO. Brains were excised and stained with triphenyltetrazolium chloride (TTC) and examined for infarct volume by image analysis. These compounds were compared to no injection and injection of saline into control animals. Injection of the C-terminal fragments of FPA demonstrated a protective effect at a dose of 10 mg/kg showing protection or greater than 66%. Overall, the C-terminal portion of FPA-10 mg/kg was effective at limiting the extent of MCAO in the brain following induction of ischemia/reperfusion in the mouse.

Also provided is a concentration series for FPA. Fibrinopeptide A was tested for efficacy in the middle cerebral artery occlusion (MCAO) model in the mouse. Intravenous (i.v.) injection of VTI compound (fibrinopeptide A, FPA) was started at 1 hour after the initiation of MCAO. Brains were excised and stained with triphenyltetrazolium chloride (TTC) and examined for infarct volume by image analysis. Injection of FPA demonstrated variable effects with a dose of 2.5 mg/kg showing the greatest protection (greater than 60%). FPA at 0.625 mg/kg and 10 mg/kg demonstrated a greater than 50% protection to the brain. All doses showed a reduction of infarct volume in the mouse brain. Overall, FPA-2.5 mg/kg was the most effective at limiting the extent of MCAO in the brain following induction of ischemia/reperfusion in the mouse.

a) Methods and Materials (1) Study Design

The mouse model of stroke, middle cerebral artery occlusion (MCAO). Mice were subjected to 1 hour MCAO followed by 24 hours of reperfusion. The C-terminal fragments of FPA were injected at the end of ischemia (10 mg/kg), and on the second day mice were sacrificed and examined for infarct volume by TTC staining. FPA was injected at the end of ischemia (0.625, 2.5 or 10 mg/kg), and on the second day mice were sacrificed and examined for infarct volume by TTC staining. These sections were compared to control and saline injected animals.

(2) In Vivo Methods

Male C57BL/6 (Jackson Laboratory) mice weighing approximately 25 grams each were given free access to food and water before and during the experiment. Animals were acclimated for 1 week prior to experimentation. The animals were injected with the compositions at 200 μl/mouse at the indicated doses. Mice were injected intravenously 1 hour after the initiation of ischemia.

(3) Induction of Ischemia

Each mouse was subjected to one hour of cerebral ischemia followed by 24 hours of reperfusion. At the end of the ischemic period, animals were injected with the composition at the indicated doses and at 24 hours examined for infarct volume. The left common carotid artery (CCA) was exposed through a midline incision in the neck. The superior thyroid and occipital arteries were electrocoagulated and divided. A microsurgical clip was placed around the origin of the internal carotid artery (ICA). The distal end of the ECA was ligated with 6-0 silk and transected. A 6-0 silk is tied loosely around the ECA stump. The clip is removed and the fire-polished tip of a 5-0 nylon suture (poly-L-lysine coated) was gently inserted into the ECA stump. The loop of the 6-0 silk was tightened around the stump and the nylon suture was advanced approximately 11 mm (adjusted for body weight) into and through the internal carotid artery (ICA) after removal of the aneurysm clip, until it rested in the anterior cerebral artery (ACA), thereby occluding the anterior communicating and middle cerebral arteries. The animal was returned to home cage after removal from anesthesia. After the nylon suture had been in place for 1 hour, the animal was re-anesthetized, and the suture was removed and the incision closed.

(4) Infarct Volume Determination

For infarct volume determination, the animals were anesthetized with an intraperitoneal injection of sodium pentobarbital (50 mg/kg). The brains were removed, sectioned into 4 2-mm sections through the infarcted region and placed in 2% triphenyltetrazolium chloride (TTC) for 30 minutes at 24 hours. After, the sections were placed in 4% paraformaldehyde over night. The infarct area in each section was determined with a computer-assisted image analysis system, consisting of a Power Macintosh computer equipped with a Quick Capture frame grabber card, Hitachi CCD camera mounted on a camera stand. NIH Image Analysis Software, v. 1.55 was used. The images were captured and the total area of infarct was determined over the sections. A single operator blinded to treatment status performed all measurements. Summing the infarct volumes of the sections calculated the total infarct volume.

(5) Statistical Analysis

The results are expressed as the mean±standard deviation (SD). The significance of difference in the infarct volume data was analyzed using a t-test.

(6) Treatment Groups.

All groups were subjected to MCAO. Animals (17 animals) were subjected to injection FPA derivatives and 23 animals were subjected to injection for the concentration study. following MCAO. Groups: 1) Nothing, 2) Saline, 3) C-terminal portion of woodchuck FPA (I) at 10 mg/kg, 4) C-terminal portion of woodchuck FPA (L) at 10 mg/kg, 5) FPA at 0.625 mg/kg, 6) FPA at 2.5 mg/kg, 7) FPA at 10 mg/kg.

b) Results (1) Ischemia in Mice

The relative severity of ischemia in these studies was assessed. Data from mice with ischemic injury that were intraperitoneally the compositions at the indicated doses.

(a) Infarct Area

Compared with no injection and with vehicle(saline)-injected group, the infarct area in the brains was significantly decreased with the C-terminal FPAw treated animals. C-terminal (I) FPAw (10 mg/kg) showed a 66% reduction in infarct volume. C-terminal (L) FPAw at 10 mg/kg showed a similar change in the decrease in infarct volume 67% (Table 16). Infarct volumes are plotted in FIGS. 14 and 15. The percent decrease in infarct volume present in the brains is presented in Table 16.

TABLE 16

Percent decrease in infarct in the brain.

| Compound | Percent reduction in Infarct volume |
|---|---|
| Nothing | — |
| Vehicle | — |
| C-terminus (I) of FPAw 10 mg/kg | 66% |
| C-terminus (L) of FPAw 10 mg/kg | 67% |

The data used to produce FIG. 15 is shown in Table 15.

TABLE 17

| Nothing | Saline | C-term (I) | C-term (L) |
|---|---|---|---|
| 38.250 | 81.730 | 51.330 | 11.360 |
| 67.200 | 64.910 | 8.630 | 33.790 |
| 82.370 | 72.370 | 12.810 | 39.420 |
| 76.820 | 68.550 | 17.250 | 2.670 |
|  | 49.680 |  |  |

The statistical data for the results is shown in Table 18. Infarct volumes are listed as $mm^3$.

TABLE 18

Statistical Analysis of the infarct volumes.

|  | Nothing | Saline | C-term (I) | C-term (L) |
|---|---|---|---|---|
| Number of values | 4 | 5 | 4 | 4 |
| Minimum | 38.25 | 49.68 | 8.630 | 2.670 |
| 25% Percentile |  |  |  |  |
| Median | 72.01 | 68.55 | 15.03 | 22.58 |
| 75% Percentile |  |  |  |  |
| Maximum | 82.37 | 81.73 | 51.33 | 39.42 |
| Mean | 66.16 | 67.45 | 22.51 | 21.81 |
| Std. Deviation | 19.63 | 11.74 | 19.54 | 17.60 |
| Std. Error | 9.817 | 5.251 | 9.768 | 8.800 |
| Lower 95% CI | 34.92 | 52.87 | −8.582 | −6.194 |
| Upper 95% CI | 97.40 | 82.03 | 53.59 | 49.81 |

There were 7 deaths in this study. Most of the deaths occurred in the saline and no treatment groups. There was one death in each of the treatment groups.

Compared with the vehicle-injected groups, the infarct area in the brains was significantly decreased with the FPA treated animals. FPA (2.5 mg/kg) showed a much larger reduction in infarct volume than other doses. FPA at 0.625 mg/kg and 10 mg/kg showed a similar change in the decrease in infarct volume however, not as large as with FPA at 2.5 (Table 19). Infarct volumes are plotted in FIG. 16. The percent decrease in infarct volume present in the brains is presented in Table 19. As shown in the table, FPA at 2.5 mg/kg showed a 66% decrease in infarct volume compared to vehicle.

TABLE 19

Percent decrease in infarct in the brain.

| Compound | Percent reduction in Infarct volume |
|---|---|
| Vehicle | — |
| FPA 0.625 mg/kg | 52% |

TABLE 19-continued

Percent decrease in infarct in the brain.

| Compound | Percent reduction in Infarct volume |
|---|---|
| FPA 2.5 mg/kg | 66% |
| FPA 10 mg/kg | 57% |

Percent decreases are compared to the vehicle control animals.

TABLE 20

Individual infarct volumes for each animal. Infarct volumes are listed as $mm^3$.

| FPA 0.625 | FPA 2.5 | FPA 10 | Saline |
|---|---|---|---|
| 42.350 | 34.850 | 91.580 | 92.340 |
| 50.620 | 5.180 | 5.220 | 76.450 |
| 52.180 | 7.290 | 47.610 | 88.120 |
| 23.510 | 25.560 | 10.390 | 69.530 |
| 41.490 | 24.870 | 37.650 | 90.410 |
| 65.190 | 41.730 | 71.030 | 82.430 |
| 14.230 | 58.310 | 11.940 |  |
| 29.710 | 6.770 |  |  |

The statistics for FIG. 16 are shown in Table 21.

TABLE 21

Statistical Analysis of the infarct volumes.

|  | FPA 0.625 | FPA 2.5 | FPA 10 | Saline |
|---|---|---|---|---|
| Number of values | 8 | 7 | 8 | 6 |
| Minimum | 14.23 | 5.180 | 5.220 | 69.53 |
| 25% Percentile | 26.61 | 16.08 | 8.580 | 72.99 |
| Median | 41.92 | 25.56 | 24.80 | 85.28 |
| 75% Percentile | 51.40 | 50.02 | 59.32 | 91.38 |
| Maximum | 65.19 | 58.31 | 91.58 | 92.34 |
| Mean | 39.91 | 28.26 | 35.27 | 83.21 |
| Std. Deviation | 16.67 | 18.79 | 32.70 | 8.863 |
| Std. Error | 5.894 | 7.103 | 11.56 | 3.618 |
| Lower 95% CI | 25.97 | 10.87 | 7.934 | 73.91 |
| Upper 95% CI | 53.85 | 45.64 | 62.61 | 92.51 |

There were 8 deaths in the study related to the concentration ranges. Most of the deaths occurred in the 0.625 mg/kg group (6 of 8), whereas 2 of 8 in the 2.5 mg/kg group died. None in the 10 mg/kg died. It is unclear as to why there were losses in the 0.625 mg/kg group.

3. Example Bradykinin Receptor Data a) Procedure:

This assay measures binding of [$^{125}$I]CGP-42112A to human angiotensin $AT_2$ receptors. HeLa cells stably transfected with a plasmid encoding the human angiotensin $AT_2$ receptor were used to prepare membranes in modified Tris HCl pH 7.4 by standard techniques. A 0.5 µg aliquot of membranes was incubated with 0.025 nM [$^{125}$I]CGP-42112A for 3 hours at 37° C. Non-specific binding was estimated in the presence of 10 µM. [Sar$^1$,Ile$^8$]Angiotensin II (Membrane protein may change from lot to lot, the concentration used will be adjusted if necessary.). Membranes were filtered and washed 3 times and the filters were assayed for radioactivity (counted) to determine [$^{125}$I]CGP-42112A specifically bound. Compounds were screened at 10 μM. The ATII binding studies were performed essentially like that disclosed in Whitebread, S. E. et al., Radioligand CGP42112A: a novel high affinity and high selective ligand for the characterization of angiotensin $AT_2$ receptors. Biochem. Biophys. Res. Comm. 181:1365-1371, 1991 (which is herein incorporated by reference at least for material related to ATII receptor characterization.)

b) Results:

The results indicate that the Kd of ATII for CGP-42112A was 0.012 nM, with a Bmax: of 2,900 fmol/mg protein. The Specific Binding was 90%. This is the highest binding molecule used in competition with the tested molecules.

Table 21 shows the reference data that can be used to compare different levels of binding to the ATII receptor.

TABLE 21

| Compound | $IC_{50}$ (nM) | Ki (nM) | nH |
|---|---|---|---|
| Angiotensin II (human) | 0.16 | 0.052 | 1.1 |
| [Sar$^1$, Ile$^8$] Angiotensin II | 0.085 | 0.028 | 1.0 |
| CGP-42112A | 0.024 | 0.0078 | 1.1 |
| *Saralasin | 0.28 | 0.091 | 0.9 |

*Indicates standard reference agent used.

CGP-42112A=nicotinic acid-Tyr-(N-benzoylcarbonyl-Arg)Lys-His-Pro-Ile-OH

Table 22 and Table 2 show the results obtained in the ATII receptor binding assay for a number of Bradykinin analogs. The results are shown in % inhibition of binding of ATII at the ATII receptor. Table 22 shows the various Bradykinin variants in rank order based on their ability to inhibit. For example, SEQ ID NO: 58 inhibited 98% of the ATII from binding the ATII receptor. Bradykinin (SEQ ID NO: 57) on the other hand inhibited 12% of the ATII from binding at the ATII receptor, which is less than the most active compounds. SEQ ID NO: 58 differs from SEQ ID NO: 12 in that SEQ ID NO: 58 has an additional Lys at the N terminal end of the peptide and substitutes the C terminal Phe-Arg of Bradykinin (SEQ ID NO: 58) with a Leu.

Consistent with the indications of SEQ ID NO: 58 and Bradykinin, (SEQ ID NO: 57), SEQ ID NO: 77, which simply is the first 7 N-terminal amino acids of Bradykinin (SEQ ID NO 57), which means the C-terminal Phe-Arg are removed from Bradykinin, inhibits the ATII/ATII receptor binding by 55%. These results indicate that a basic charge is at the C-terminal end of Bradykinin (SEQ ID NO: 57), reducing the ability for Bradykinin to compete with ATII for binding at the ATII receptor. Also, addition of a basic charge at the N-terminal end of Bradykinin is associated with an increase in competitive ability with ATII binding of the ATII receptor. (SEQ ID NO: 58, 98%, SEQ ID NO: 61, 92%). SEQ ID NOs: 62, 63, and 64 have a C-term ARG yet show inhibition perhaps due the damping of the negative charge, likely due to the unique structure of these peptides caused by the adamantane derivatives.

Table 22. Compared with the vehicle-injected group, the infarct area in the brains of the BK variants is show in Table 22. The BK variants shown in Table 22 are presented in their order of activity. SEQ ID NOs: 58, 61, and 77 were significant to less than a 0.05 p value. The p-values were derived by grouping all saline treated animals shown in Table 28 and comparing to experimental animals shown in Table 23 using a 1-tailed t-test. Any p-value found to be less than 0.05 was deemed to be statistically significant.

TABLE 22

| Name | % Inhibition ATII receptor | Sequence | Chemical name | SEQ ID NO. | % Ischemic Injury | P Value |
|---|---|---|---|---|---|---|
| VP041 | 98 | Lys-Arg-Pro-Pro-Gly-Phe-Ser-Pro-Leu | Lys-(Des-Arg9, Leu8)-Bradykinin | 58 | 12.9 | 0.0071 |
| VP044 | 92 | Arg-Pro-Pro-Gly-Phe-Ser-Pro-Phe | [Des-Arg$^9$] Bradykinin | 61 | 13.2 | 0.0025 |
| VP060 | 55 | Arg-Pro-Pro-Gly-Phe-Ser-Pro | Bradykinin (1-7) | 77 | 18.1 | 0.0263 |
| VP045 | 53 | Arg-Pro-Pro-Gly-Thi-Ser-DPhe-Thi-Arg | [Thi5,8,DPhe7] Bradykinin | 62 | 25.7 | 0.4483 |
| VP046 | 61 | N-Adamantaneacetyl-DArg-Arg-Pro-Hyp-Gly-Thi-Ser-DPhe-Thi-Arg | N-Admantaneacetyl-DArg0-Hyp3, Thi5,8,DPhe7] Bradykinin | 63 | 31.8 | 0.7653 |
| VP064 | 70 | DArg-Arg-Pro-Hyp-Gly-Igl-Ser-DIgl-Oic-Arg | B9430 | 81 | 34.2 | 0.5935 |
| VP047 | 63 | N-Adamantanecarbonyl-DArg-Arg-Pro-Hyp-Gly-Thi-Ser-DPhe-Thi-Arg | N-Admantanecarbonyl-DArg0-Hyp3, Thi5,8, DPhe7] Bradykinin | 64 | 35.2 | 0.3779 |
| | | Arg-Pro-Pro-Gly-Phe-Ser-Pro-Phe-Arg | Bradykinin | 57 | | |

TABLE 22-continued

| Name | % Inhibition ATII receptor | Sequence | Chemical name | SEQ ID NO. | % Ischemic Injury | P Value |
|---|---|---|---|---|---|---|
| VP049 | 38 | Met-Lys-Arg-Pro-Pro-Gly-Phe-Ser-Pro-Phe-Arg | Met-Lys0] Bradykinin | 66 | | |
| VP063 | 35 | DArg-Arg-Pro-Hyp-Gly-Thi-Ser-DIgl-Oic-Arg | B9340 | 80 | | |
| VP051 | 33 | Tyr-Arg-Pro-Pro-Gly-Phe-Ser-Pro-Phe-Arg | [Tyr0] Bradykinin | 68 | | |
| VP042 | 29 | DArg-Arg-Pro-Hyp-Gly-Thi-Ser-D-Tic-Oic-Arg | Hoe 140 | 59 | | |
| VP048 | 29 | Lys-Arg-Pro-Pro-Gly-Phe-Ser-Pro-Phe-Arg | [Lys0] Bradykinin | 65 | | |
| VP054 | 29 | Ile-Ser-Arg-Pro-Pro-Gly-Phe-Ser-Pro-Phe-Arg | Ile-Ser0]-Bradykinin | 71 | | |
| VP050 | 18 | Lys-Arg-Pro-Ala-Gly-Phe-Ser-Pro-Phe-Arg | Lys0-Ala3] Bradykinin | 67 | | |
| VP053 | 13 | Arg-Pro-Pro-Gly-Tyr-Ser-Pro-Phe-Arg | Tyr5] Bradykinin | 70 | | |
| VP055 | 13 | Lys-Arg-Pro-Hyp-Gly-Phe-Ser-Pro-Phe-Arg | [Lys0-Hyp3] Bradykinin | 72 | | |
| VP040 | 12 | Arg-Pro-Pro-Gly-Phe-Ser-Pro-Phe-Arg | Bradykinin | 57 | | |
| VP043 | 9 | Arg-Pro-Pro-Gly-Phe-Ser-DPhe-Phe-Arg | [DPhe7] Bradykinin | 60 | | |
| VP058 | 1 | Arg-Pro-Pro-Gly-Phe | Bradykinin (1-5) | 75 | | |
| VP052 | -1 | Arg-Pro-Pro-Gly-Phe-Ser-Pro-Tyr-Arg | [Tyr8] Bradykinin | 69 | | |
| VP057 | -2 | Arg-Pro-Pro | Bradykinin (1-3) | 74 | | |
| VP061 | -6 | Pro-Pro-Gly-Phe-Ser-Pro | Bradykinin (2-7) | 78 | | |
| VP059 | -12 | Arg-Pro-Pro-Gly-Phe-Ser | Bradykinin (1-6) | 76 | | |
| VP062 | -13 | Pro-Pro-Gly-Phe-Ser-Pro-Phe-Arg | Bradykinin (2-9) | 79 | | |

A number of the Bradykinin variants were tested in the MCAO mouse model as disclosed in the examples herein. The results of these experiments are disclosed in Table 22. The Bradykinin variants with the tightest binding to the AT2 receptor were also the most effective at preventing ischemic injury.

The data used to generate the data presented in Table 22 are shown in Table 23. The numbers designating the columns refer to the animals used in a particular experiment for the designated variant. For example, in certain experiments there were 9 parallel animals undergoing occlusion and subsequent FPA variant injection. The infarct area in each section was determined with a computer-assisted image analysis system, consisting of a Power Macintosh computer equipped with a Quick Capture frame grabber card, Hitachi CCD camera mounted on a camera stand. NIH Image Analysis Software, v. 1.55 was used. The images were captured and the total area of infarct was determined over the sections. A single operator blinded to treatment status performed all measurements. Summing the infarct volumes of the sections calculated the total infarct volume. The results are expressed as the mean±standard deviation (SD).

2, 4, 6, or 8 hr after the start of reperfusion), and on the second day mice were sacrificed and examined for infarct volume by TTC staining. Mice were given a single bolus intravenous injection of D2 at a final dose of 5 mg/kg.

TABLE 23

| Animal # | | 1 | 2 | 3 | 4 | 5 | Total | Mean | SD |
|---|---|---|---|---|---|---|---|---|---|
| VP041 | total damage area | 7.1 | 20.4 | 5.3 | 0.0 | | 32.9 | 8.2 | 8.7 |
| | total area | 64.2 | 64.8 | 63.2 | 61.6 | | 253.8 | 63.5 | 1.4 |
| | ischemia injury % | 11.1 | 31.5 | 8.4 | 0.0 | | | 12.9 | 13.4 |
| VP044/010 | total damage area | 12.3 | 4.7 | 11.4 | 11.6 | 3.5 | 43.5 | 8.7 | 4.2 |
| | total area | 63.1 | 63.8 | 72.1 | 67.3 | 64.43 | 30.6 | 66.1 | 3.7 |
| | ischemia injury % | 19.5 | 7.3 | 15.9 | 17.2 | 5.5 | | 13.2 | 5.3 |
| VP045 | total damage area | 21.3 | 4.5 | 23.1 | 20.3 | | 69.2 | 17.3 | 8.6 |
| | total area | 68.1 | 63.3 | 71.3 | 66.3 | | 269.0 | 67.2 | 3.3 |
| | ischemia injury % | 31.2 | 7.2 | 32.4 | 30.6 | | | 25.7 | 12.1 |
| | | | | | died | | | | |
| VP046 | total damage area | 11.8 | 30.1 | 19.9 | 22.7 | | 84.6 | 21.1 | 7.6 |
| | total area | 66.7 | 66.4 | 66.3 | 66.7 | | 266.1 | 66.5 | 0.2 |
| | ischemia injury % | 17.7 | 45.3 | 30.1 | 34.0 | | | 31.8 | 13.8 |
| | | | | | died | | | | |
| VP047 | total damage area | 27.5 | 23.5 | 20.9 | 19.9 | | 91.8 | 23.0 | 3.4 |
| | total area | 67.7 | 63.7 | 64.0 | 65.4 | | 260.7 | 65.5 | 1.8 |
| | ischemia injury % | 40.6 | 37.0 | 32.6 | 30.5 | | | 35.2 | 4.0 |
| VP060 | total damage area | 12.4 | 14.8 | 6.6 | 14.6 | 18.7 | 67.1 | 13.4 | 4.4 |
| | total area | 72.1 | 78.5 | 69.8 | 73.5 | 76.8 | 370.6 | 74.1 | 3.5 |
| | ischemia injury % | 17.2 | 18.9 | 9.4 | 19.8 | 24.3 | | 18.1 | 4.8 |
| VP0641 | total damage area | 11.7 | 34.6 | 14.6 | 32.9 | | 93.8 | 23.4 | 12.0 |
| | total area | 64.9 | 72.8 | 62.7 | 74.1 | | 274.6 | 68.6 | 5.7 |
| | ischemia injury % | 18.0 | 47.5 | 23.2 | 44.4 | | | 34.2 | 14.8 |
| | | | died | died | died | | | | |

4. Example 4 Time Course of D2 Fraction

Hibernating woodchuck fraction, D2 was tested for efficacy in the middle cerebral artery occlusion (MCAO) model in the mouse. Intravenous (i.v.) injection of D2 was started 2 hours prior to or at various times up to 8 hours after the end of MCAO. Brains were excised and stained with triphenyltetrazolium chloride (TTC) and examined for infarct volume by image analysis. Injection of D2 demonstrated significant protection of the brain prior to cerebral ischemia and reperfusion injury. In addition, D2 showed significant protection from ischemia and reperfusion injury when injected up to 6 hours following ischemic injury. D2 was administered at 5 mg/kg in a single bolus intravenous injection. Overall, D2 was effective at limiting the extent of MCAO in the brain when treated up to 6 hours following induction of ischemia/reperfusion in the mouse.

a) Materials and Methods (1) Study Design

The mouse model of stroke, middle cerebral artery occlusion (MCAO). Mice were subjected to 1 hour MCAO followed by 24 hours of reperfusion. D2 was injected at 2 hours prior to the ischemic injury or at the end of ischemia (0.5, 1, (2) In Vivo Methods Male C57BL/6 (Jackson Laboratory) mice weighing approximately 25 grams each were given free access to food and water before and during the experiment. Animals were acclimated for 1 week prior to experimentation. The animals were injected with VTI fraction (D2) at 200 μl/mouse at a dose of 5 mg/kg. Mice were injected intravenously at the indicated times prior to or after the termination of ischemia.

(3) Induction of Ischemia

Each mouse was subjected to one hour of cerebral ischemia followed by 24 hours of reperfusion. Prior to or at the end of the ischemic period (indicated times), animals were injected with D2 at 5 mg/kg and at 24 hours examined for infarct volume. The left common carotid artery (CCA) was exposed through a midline incision in the neck. The superior thyroid and occipital arteries were electrocoagulated and divided. A microsurgical clip was placed around the origin of the internal carotid artery (ICA). The distal end of the ECA was ligated with 6-0 silk and transected. A 6-0 silk is tied loosely around the ECA stump. The clip is removed and the fire-polished tip of a 5-0 nylon suture (poly-L-lysine coated) was gently inserted into the ECA stump. The loop of the 6-0 silk was tightened around the stump and the nylon suture was advanced approximately 11 mm (adjusted for body weight) into and through the internal carotid artery (ICA) after removal of the aneurysm clip, until it rested in the anterior cerebral artery (ACA), thereby occluding the anterior communicating and middle cerebral arteries. The animal was returned to home cage after removal from anesthesia. After the nylon suture had been in place for 1 hour, the animal was re-anesthetized, and the suture was removed and the incision closed.

(4) Infarct Volume Determination

For infarct volume determination, the animals were anesthetized with an intraperitoneal injection of sodium pentobarbital (50 mg/kg). The brains were removed, sectioned into 4 2-mm sections through the infarcted region and placed in 2% triphenyltetrazolium chloride (TTC) for 30 minutes at 24 hours after reperfusion. After, the sections were placed in 4% paraformaldehyde over night. The infarct area in each section was determined with a computer-assisted image analysis system, consisting of a Power Macintosh computer equipped with a Quick Capture frame grabber card, Hitachi CCD camera mounted on a camera stand. NIH Image Analysis Software, v. 1.55 was used. The images were captured and the total area of infarct was determined over the sections. A single operator blinded to treatment status performed all measurements. Summing the infarct volumes of the sections calculated the total infarct volume.

(5) Statistical Analysis

The results are expressed as the mean±standard deviation (SEM). The significance of difference in the infarct volume data was analyzed using a t-test. All animals were included in the study.

(6) Treatment Groups

All groups were subjected to MCAO. Animals (27 animals) were subjected to injection FPA following MCAO. The Groups are as follows. Group 1, Control mice, no ischemia/reperfusion injury; Group 2, Control mice, 1 hour of ischemia and 24 hours of reperfusion vehicle injected at 1 hour following ischemia; Group 3, 1 hour of ischemia and 24 hour of reperfusion, D2 administered 2 hour prior to injury; Group 4, 1 hour of ischemia and 24 hour of reperfusion, D2 administered 0.5 hour after injury; Group 5, 1 hour of ischemia and 24 hour of reperfusion, D2 administered 1 hour after injury; Group 6, 1 hour of ischemia and 24 hour of reperfusion, D2 administered 2 hour after injury; Group 7, 1 hour of ischemia and 24 hour of reperfusion, D2 administered 4 hour after injury; Group 8, 1 hour of ischemia and 24 hour of reperfusion, D2 administered 6 hour after injury; and Group 9, 1 hour of ischemia and 24 hour of reperfusion, D2 administered 8 hour after injury.

b) Results (1) Ischemia in Mice

The relative severity of ischemia in these studies was assessed. Data from mice with ischemic injury that were intraperitoneally injected D2 fraction at a dose of 5 mg/kg. There were zero deaths in this study.

(a) Infarct Area

Compared with the vehicle-injected group, the infarct area in the brains was significantly decreased with the D2 treated animals. D2 (2 hour prior to ischemia) showed the greatest reduction in infarct volume than other times. D2 at 0.5 and 1 hour following reperfusion showed a similar change in the decrease in infarct volume however, not as large as with D2 at 2 hours prior to ischemia (Table 24). Infarct volumes are plotted in FIG. 17. The percent decrease in infarct volume present in the brains is presented in Table 24 As shown in Table 24, D2 at 2 hours prior to ischemia showed an 88% decrease in infarct volume compared to vehicle.

TABLE 24

Percent decrease in infarct in the brain.

| Compound | Percent reduction in Infarct volume |
|---|---|
| Control | — |
| Control, ischemic | 0% |
| D2 at 2 h pre-ischemic | 88% |
| D2 at 0.5 h post-ischemic | 80% |
| D2 at 1 h post-ischemic | 75% |
| D2 at 2 h post-ischemic | 65% |
| D2 at 4 h post-ischemic | 34% |
| D2 at 6 h post-ischemic | 20% |
| D2 at 8 h post-ischemic | 0% |

Percent decreases are compared to the vehicle control animals.

In addition, at the earlier time points there was significant protection from the detrimental effects of the ischemia and reperfusion injury.

(b) Data by Animal

TABLE 25

| Animal number | 1 | 2 | 3 | Mean | SD |
|---|---|---|---|---|---|
| Con | 0.0 | 0.0 | 0.0 | 0.000 | 0.000 |
| No | 87.960 | 79.550 | 109.780 | 92.430 | 9.008308 |
| Pre-treat 2-hrs | 0.000 | 8.360 | 26.780 | 11.71333 | 7.910452 |
| Post-treat 0.5-hrs | 12.4300 | 5.9200 | 36.5100 | 18.28667 | 9.303447 |
| Post-treat 1-hr | 23.860 | 4.900 | 41.690 | 23.48333 | 10.62203 |
| Post-treat 2-hr | 35.780 | 12.940 | 48.560 | 32.42667 | 10.41841 |
| Post-treat 4-hr | 58.4300 | 42.7900 | 81.2600 | 60.82667 | 11.1698 |
| Post-treat 6-hr | 74.900 | 55.870 | 91.220 | 73.99667 | 10.21466 |
| Post-treat 8-hr | 90.42 | 113.860 | 76.950 | 93.74332 | 10.78379 |

5. Example 5 FPA Variants

A series of FPA variants were tested for their efficacy in the middle cerebral artery occlusion (MCAO) model in the mouse. These variants included deletion mutants from both the C- and N-terminal as well as mutants which had an alanine residue substitute for one amino acid at a time starting from the N-term and continuing through the entire sequence to the C-terminal residue. Intravenous (i.v.) injection of FPA variant was started, 1 hour after MCAO. Brains were excised and stained with triphenyltetrazolium chloride (TTC) and examined for infarct volume by image analysis. Injection of FPA demonstrated significant protection of the brain prior to cerebral ischemia and reperfusion injury. The FPA variants were administered in a single bolus intravenous injection.

a) Materials and Methods (1) Study Design

The mouse model of stroke, middle cerebral artery occlusion (MCAO). Mice were subjected to 1 hour MCAO followed by 24 hours of reperfusion. FPA variants were injected at 1 hour after the start of reperfusion, and on the second day mice were sacrificed and examined for infarct volume by TTC staining. Mice were given a single bolus intravenous injection of FPA variant at a final equivalent dose to the parent peptide (wood chuck C-terminal FPA) of 10 mg/kg.

(2) In Vivo Methods

Male C57BL/6 (Jackson Laboratory) mice weighing approximately 25 grams each were given free access to food and water before and during the experiment. Animals were acclimated for 1 week prior to experimentation. The animals were injected with FPA variants at 200 μl/mouse at an equivalent dose of 10 mg/kg. Mice were injected intravenously at the indicated times prior to or after the termination of ischemia.

(3) Induction of Ischemia

Each mouse was subjected to one hour of cerebral ischemia followed by 24 hours of reperfusion. Prior to or at the end of the ischemic period (indicated times), animals were injected with FPA variant at an equivalent dose of 10 mg/kg and at 24 hours examined for infarct volume. The left common carotid artery (CCA) was exposed through a midline incision in the neck. The superior thyroid and occipital arteries were electrocoagulated and divided. A microsurgical clip was placed around the origin of the internal carotid artery (ICA). The distal end of the ECA was ligated with 6-0 silk and transected. A 6-0 silk is tied loosely around the ECA stump. The clip is removed and the fire-polished tip of a 5-0 nylon suture (poly-L-lysine coated) was gently inserted into the ECA stump. The loop of the 6-0 silk was tightened around the stump and the nylon suture was advanced approximately 11 mm (adjusted for body weight) into and through the internal carotid artery (ICA) after removal of the aneurysm clip, until it rested in the anterior cerebral artery (ACA), thereby occluding the anterior communicating and middle cerebral arteries. The animal was returned to home cage after removal from anesthesia. After the nylon suture had been in place for 1 hour, the animal was re-anesthetized, and the suture was removed and the incision closed.

(4) Infarct Volume Determination

For infarct volume determination, the animals were anesthetized with an intraperitoneal injection of sodium pentobarbital (50 mg/kg). The brains were removed, sectioned into 4 2-mm sections through the infarcted region and placed in 2% triphenyltetrazolium chloride (TTC) for 30 minutes at 24 hours after reperfusion. After, the sections were placed in 4% paraformaldehyde over night. The infarct area in each section was determined with a computer-assisted image analysis system, consisting of a Power Macintosh computer equipped with a Quick Capture frame grabber card, Hitachi CCD camera mounted on a camera stand. NIH Image Analysis Software, v. 1.55 was used. The images were captured and the total area of infarct was determined over the sections. A single operator blinded to treatment status performed all measurements. Summing the infarct volumes of the sections calculated the total infarct volume.

(5) Statistical Analysis

The results are expressed as the mean±standard deviation (SEM). The significance of difference in the infarct volume data was analyzed using a t-test. All animals were included in the study.

b) Results (1) Ischemia in Mice

The relative severity of ischemia in these studies was assessed. Data from mice with ischemic injury that were intraperitoneally injected FPA variant at a dose equivalent to a dose 10 mg/kg of full length C-term WC FPA. There were 30 deaths in this study. The doses used are shown in Table 29. Table 30 shows a comparison of human and woodchuck FPA sequences.

TABLE 29

| Molecule | MW | Factor | mg/kg |
|---|---|---|---|
| VP012 | 935 | 1.64 | 16.4 |
| VP013 | 835.9 | 1.84 | 18.4 |
| VP014 | 778.8 | 1.97 | 19.7 |
| VP015 | 721.8 | 2.13 | 21.3 |
| VP016 | 664.7 | 2.31 | 23.1 |
| VP017 | 535.6 | 2.87 | 28.7 |
| VP018 | 1034.1 | 1.49 | 14.9 |
| VP019 | 905 | 1.70 | 17.0 |
| VP020 | 757.8 | 2.03 | 20.3 |
| VP021 | 644.7 | 2.38 | 23.8 |
| VP022 | 573.6 | 2.68 | 26.8 |
| VP023 | 607.7 | 2.53 | 25.3 |
| VP024 | 535.6 | 2.87 | 28.7 |
| VP025 | 445.5 | 3.45 | 34.5 |
| VP026 | 389.4 | 3.95 | 39.5 |
| VP027 | 417.4 | 3.68 | 36.8 |
| VP028 | 444.5 | 3.46 | 34.6 |
| VP029 | 1105.2 | 1.39 | 13.9 |
| VP030 | 1033.2 | 1.49 | 14.9 |
| VP031 | 1015.1 | 1.51 | 15.1 |
| VP032 | 1049.1 | 1.46 | 14.6 |
| VP033 | 1077.2 | 1.43 | 14.3 |
| VP034 | 1033 | 1.49 | 14.9 |
| VP035 | 1105.2 | 1.39 | 13.9 |
| VP036 | 1105.2 | 1.39 | 13.9 |
| VP037 | 1105.2 | 1.39 | 13.9 |
| VP038 | 1063.1 | 1.45 | 14.5 |
| VP039 | 1006.1 | 1.53 | 15.3 |

Parent compound is VP-001 MW=1536.8. This compound was tested at a dose of 10 mg/kg.

Test compounds VP-012-VP039 at an equivalent dose according to MW.

| Peptide | N-Term Fragment | | | | | | | | C-Term Fragment | | | | | | |
|---|---|---|---|---|---|---|---|---|---|---|---|---|---|---|---|
| Position | 1 | 2 | 3 | 4 | 5 | 6 | 7 | 8 | 9 | 10 | 11 | 12 | 13 | 14 | 15 | 16 |
| Human FPA | | | | | | | | | | | | | | | | |
| SEQ ID NO:2 | Ala | Asp | Ser | Gly | Glu | Gly | Asp | Phe | Leu | Ala | Glu | Gly | Gly | Gly | Val | Arg |
| WC FPA | | | | | | | | | | | | | | | | |
| SEQ ID NO:1 | Ala | Asp | Thr | Asp | Lys | Gly | Glu | Phe | Leu | Ala | Glu | Gly | Gly | Gly | Val | Arg |

(a) Infarct Area

Compared with the vehicle-injected group, the infarct area in the brains of the FPA variants is show in Table 26. The FPA variants shown in Table 26 are presented in their order of activity. SEQ ID NOs: 46, 45, 35, 50, 38, 40, 54, 32, 47, and 48 were significant to less than a 0.05 p value. The p-values were derived by grouping all saline treated animals shown in Table 28 and comparing to experimental animals shown in Table 27 using a 1-tailed t-test. Any p-value found to be less than 0.05 was deemed to be statistically significant.

TABLE 26

| Amino Acid Sequence | Mutation or Deletion | % Ischemic Injury | P-value | Compound-SEQ ID # | NO | Comment |
|---|---|---|---|---|---|---|
| Ala-Glu-Phe-Leu-Ala-Glu-Gly-Gly-Gly-Val-Arg | Ala Scan Position 6 | 5.6 | <0.0001 | VP029 | 46 | Ala greater hydrophobicity than Gly on C-term |
| Gly-Gly-Gly-Val-Arg | C-term 5-MER (12-16) | 13.9 | 0.0083 | VP028 | 45 | A 5mer active peptide |
| Phe-Leu-Ala-Glu-Gly-Gly-Gly-Val-Arg | C-term deletion Gly, Glu (8-16) | 14.1 | 0.0048 | VP019 | 36 | C-term negative charge removal |
| Gly-Glu-Phe-Leu-Gly-Glu-Gly-Gly-Gly-Val-Arg | Gly Scan Position 10 | 15.4 | 0.0101 | VP033 | 50 | Very similar to parent peptide |
| Ala-Glu-Gly-Gly-Gly-Val-Arg | C-term deletion Gly, Glu, Phe, Leu (10-16) | 15.6 | 0.0044 | VP021 | 38 | Contains 5mer active peptide as VP028 |
| Glu-Phe-Leu-Ala-Glu | C-term 5-MER (7-11) | 16.4 | 0.0147 | VP023 | 40 | |
| Gly-Glu-Phe-Leu-Ala-Glu-Gly-Gly-Ala-Val-Arg | Ala Scan Position 14 | 16.9 | 0.0101 | VP037 | 54 | Ala more hydrophobic and larger than Gly at this position |
| Gly-Glu-Phe-Leu-Ala-Glu-Gly | N-term deletion Gly, Gly, Val, Arg (6-12) | 17.5 | 0.0233 | VP015 | 32 | |
| Gly-Ala-Phe-Leu-Ala-Glu-Gly-Gly-Gly-Val-Arg | Ala Scan Position 7 | 18.3 | 0.0154 | VP030 | 47 | Loss of proximal N-term acidic charge |
| Gly-Glu-Ala-Leu-Ala-Glu-Gly-Gly-Gly-Val-Arg | Ala Scan Position 8 | 18.7 | 0.0485 | VP031 | 48 | Ala less hydrophobic and smaller than Phe in this position |
| Gly-Glu-Phe-Leu-Ala-Glu-Ala-Gly- | Ala Scan Position | 19.0 | 0.0732 | VP035 | 52 | Ala more hydrophobic and |

TABLE 26-continued

| Amino Acid Sequence | Mutation or Deletion | % Ischemic Injury | P-value | Compound-SEQ ID # | NO | Comment |
|---|---|---|---|---|---|---|
| Gly-Val-Arg | 12 | | | | | larger than Gly at this position |
| Glu-Gly-Gly-Gly-Val-Arg | C-term deletion Gly, Glu, Phe, Leu, Ala (11-16) | 19.9 | 0.0667 | VP022 | 39 | Contains 5mer active peptide as VP028 |
| Gly-Glu-Phe-Leu-Ala-Ala-Gly-Gly-Gly-Val-Arg | Ala Scan Position 11 | 21.8 | 0.1482 | VP034 | 51 | Loss if internal acidic change |
| Phe-Leu-Ala-Glu-Gly | C-term 5-MER | 22.2 | 0.2183 | VP024 | 41 | Does not contain minimum active peptide |
| Gly-Glu-Phe-Ala-Ala-Glu-Gly-Gly-Gly-Val-Arg | Ala Scan Position 9 | 22.4 | 0.1002 | VP032 | 49 | Ala less hydrophobic than Leu in this position |
| Gly-Glu-Phe-Leu-Ala-Glu-Gly-Gly | N-term deletion Gly, Val, Arg (6-13) | 22.9 | 0.1098 | VP014 | 31 | Deletion of C-term hydrophobic essential element |
| Gly-Glu-Phe-Leu-Ala-Glu-Gly-Gly-Gly-Val-Ala | Ala Scan Position 16 | 24.8 | 0.1707 | VP039 | 56 | Loss of N-term basic charge |
| Leu-Ala-Glu-Gly-Gly | C-term 5-MER | 25.8 | 0.4764 | VP025 | 42 | Does not contain minimum active peptide |
| Glu-Phe-Leu-Ala-Glu-Gly-Gly-Gly-Val-Arg | C-term deletion Gly (7-16) | 26.2 | 0.5248 | VP018 | 35 | Loss of C-term hydrophobic residue |
| Gly-Glu-Phe-Leu-Ala-Glu-Gly-Gly-Gly | N-term deletion Val, Arg (6-14) | 27.2 | 0.6441 | VP013 | 30 | Loss of N-term basic charge |
| Gly-Glu-Phe-Leu-Ala | N-term deletion Glu, Gly, Gly, Gly, Val, Arg (6-10) | 27.3 | 0.6395 | VP017 | 34 | Loss of N-term basic charge |
| Gly-Glu-Phe-Leu-Ala-Glu-Gly-Gly-Gly-Val | N-term deletion Arg (6-15) | 27.8 | 0.5080 | VP012 | 29 | Loss of N-term basic charge |
| Leu-Ala-Glu-Gly- | C-term | 28.4 | 0.7229 | VP020 | 37 | Loss of C-term |

TABLE 26-continued

| Amino Acid Sequence | Mutation or Deletion | % Ischemic Injury | P-value | Compound-# | SEQ ID NO | Comment |
|---|---|---|---|---|---|---|
| Gly-Gly-Val-Arg | deletion Gly, Glu, Phe (9-16) | | | | | hydrophobic residue |
| Gly-Glu-Phe-Leu-Ala-Glu | N-term deletion Gly, Gly, Gly, Val, Arg (6-11) | 28.7 | 0.8376 | VP016 | 33 | Loss of N-term basic charge |
| Gly-Glu-Phe-Leu-Ala-Glu-Gly-Ala-Gly-Val-Arg | Ala Scan Position 13 | 28.9 | 0.8329 | VP036 | 53 | Ala more hydrophobic and larger than Gly at this position |
| Glu-Gly-Gly-Gly-Val | C-term 5-MER | 31.1 | 0.8641 | VP027 | 44 | |
| Gly-Glu-Phe-Leu-Ala-Glu-Gly-Gly-Gly-Ala-Arg | Ala Scan Position 15 | 32.3 | 0.7000 | VP038 | 55 | Structural change |
| Ala-Glu-Gly-Gly-Gly | C-term 5-MER | 36.8 | 0.1948 | VP026 | 43 | |
| | | | <0.0001 | | | |
| Gly-Glu-Phe-Leu-Ala-Glu-Gly-Gly-Gly-Val-Arg | Parent Peptide | 13.4 | | VP007 | 89 | |
| Saline Control | No treatment | 30.5 | | | | |

The data used to generate the data presented in Table 26 are shown in Table 27. The numbers designating the columns refer to the animals used in a particular experiment for the designated variant. For example, in certain experiments there were 9 parallel animals undergoing occlusion and subsequent FPA variant injection. The infarct area in each section was determined with a computer-assisted image analysis system, consisting of a Power Macintosh computer equipped with a Quick Capture frame grabber card, Hitachi CCD camera mounted on a camera stand. NIH Image Analysis Software, v. 1.55 was used. The images were captured and the total area of infarct was determined over the sections. A single operator blinded to treatment status performed all measurements. Summing the infarct volumes of the sections calculated the total infarct volume. The results are expressed as the mean±standard deviation (SD).

TABLE 27

| Animal # | | 1 | 2 | 3 | 4 | 5 | 6 | 7 | 8 | 9 | Total | Mean | SD |
|---|---|---|---|---|---|---|---|---|---|---|---|---|---|
| VP001 | total damage area | 1.5 | 26.9 | 16.7 | 26.5 | 12.6 | 24.8 | 2.8 | 3.3 | 4.5 | 119.5 | 13.3 | 10.8 |
| | total area | 67.2 | 67.5 | 69.2 | 71.0 | 65.6 | 68.1 | 67.6 | 68.8 | 72.0 | 616.8 | 68.5 | 2.0 |
| | ischemia injury % | 2.3 | 39.9 | 24.1 | 37.3 | 19.2 | 36.4 | 4.1 | 4.8 | 6.2 | | 19.4 | 15.7 |
| VP001 | total damage area | 23.4 | 20.6 | 5.2 | 11.3 | 7.3 | 12.1 | 8.2 | 7.1 | | 95.4 | 11.9 | 6.7 |
| | total area | 73.0 | 71.9 | 69.4 | 65.7 | 68.4 | 66.8 | 69.3 | 73.5 | | 557.9 | 69.7 | 3.2 |
| | ischemia injury % | 32.1 | 28.6 | 7.5 | 17.2 | 10.7 | 18.2 | 11.9 | 9.7 | | | 17.1 | 11.2 |

TABLE 27-continued

| Animal # | | 1 | 2 | 3 | 4 | 5 | 6 | 7 | 8 | 9 | Total | Mean | SD |
|---|---|---|---|---|---|---|---|---|---|---|---|---|---|
| VP007 | total damage area | 0.0 | 0.0 | 15.8 | 14.4 | 2.6 | 0.0 | 28.0 | 12.1 | | 72.9 | 9.1 | 10.2 |
| | total area | 59.5 | 60.8 | 67.6 | 71.9 | 63.5 | 66.0 | 67.8 | 66.3 | | 523.4 | 65.4 | 4.0 |
| | ischemia injury % | 0.0 | 0.0 | 23.4 | 20.0 | 4.1 | 0.0 | 41.3 | 18.2 | | | 13.4 | 15.0 |
| | | | | died | | | | | | | | | |
| VP007 | total damage area | 59.5 | 60.8 | 106.9 | 106.3 | 70.2 | | | | | 74.5 | 14.9 | 9.5 |
| | total area | 119.0 | 121.6 | 197.9 | 198.3 | 137.8 | | | | | 335.6 | 67.1 | 1.3 |
| | ischemia injury % | 54.0 | 47.1 | 7.1 | 16.2 | 15.2 | | | | | | 22.2 | 14.0 |
| VP007 | total damage area | 10.8 | 17.8 | 11.5 | 14.3 | 18.1 | | | | | 72.4 | 14.5 | 3.4 |
| | total area | 63.7 | 63.4 | 62.3 | 67.5 | 62.3 | | | | | 319.2 | 63.8 | 2.2 |
| | ischemia injury % | 16.9 | 28.0 | 18.4 | 21.2 | 29.0 | | | | | | 22.7 | 5.5 |
| VP007 | total damage area | 0.0 | 0.0 | 0.0 | 0.0 | 0.0 | 0.0 | 0.0 | 4.1 | 10.5 | 14.5 | 1.6 | 3.6 |
| | total area | 71.5 | 70.7 | 70.8 | 71.2 | 69.1 | 69.0 | 68.1 | 70.3 | 68.5 | 629.3 | 69.9 | 1.2 |
| | ischemia injury % | 0.0 | 0.0 | 0.0 | 0.0 | 0.0 | 0.0 | 0.0 | 5.8 | 15.3 | | 2.3 | 5.2 |
| VP012 | total damage area | 22.1 | 33.9 | 0.0 | 19.4 | 13.1 | | | | | 88.5 | 17.7 | 12.4 |
| | total area | 67.0 | 79.2 | 71.5 | 64.2 | 80.2 | 362.0 | 72.4 | 7.1 | 9.8 | 362.0 | 72.4 | 7.1 |
| | ischemia injury % | 33.0 | 42.8 | 0.0 | 30.2 | 16.3 | | 24.5 | 16.6 | 68.0 | | 24.5 | 16.6 |
| | | | | died | | | | | | | | | |
| VP012 | total damage area | 15.0 | 22.4 | 22.1 | | | | | | | 59.4 | 19.8 | 4.2 |
| | total area | 64.2 | 62.4 | 64.8 | | | | | | | 191.4 | 63.8 | 1.3 |
| | ischemia injury % | 23.3 | 35.8 | 34.0 | | | | | | | | 31.0 | 6.8 |
| VP013 | total damage area | 27.0 | 6.8 | 16.9 | 24.6 | | | | | | 75.3 | 18.8 | 9.1 |
| | total area | 72.6 | 69.7 | 66.1 | 67.9 | | | | | | 276.3 | 69.1 | 2.8 |
| | ischemia injury % | 37.2 | 9.8 | 25.5 | 36.1 | | | | | | | 27.2 | 12.7 |
| | | died | | died | | | | | | | | | |
| VP014 | total damage area | 16.7 | 14.9 | 5.6 | 16.0 | | | | | | 53.2 | 13.3 | 5.2 |
| | total area | 68.8 | 66.3 | 63.0 | 67.3 | | | | | | 265.3 | 66.3 | 2.4 |
| | ischemia injury % | 24.2 | 22.4 | 8.9 | 23.8 | | | | | | | 20.0 | 7.3 |
| VP014 | total damage area | 19.2 | 22.7 | 19.3 | 4.3 | 26.1 | | | | | 91.5 | 18.3 | 8.3 |
| | total area | 69.2 | 75.8 | 67.2 | 71.9 | 69.6 | | | | | 353.7 | 70.7 | 3.3 |
| | ischemia injury % | 27.7 | 29.9 | 28.7 | 5.9 | 37.5 | | | | | | 25.9 | 11.8 |
| VP015 | total damage area | 6.0 | 15.7 | 17.3 | 11.7 | 12.0 | | | | | 62.6 | 12.5 | 4.4 |
| | total area | 72.9 | 73.2 | 69.3 | 70.2 | 71.0 | | | | | 356.6 | 71.3 | 1.7 |
| | ischemia injury % | 8.2 | 21.4 | 24.9 | 16.7 | 16.8 | | | | | | 17.6 | 7.2 |
| VP016 | total damage area | 12.8 | 28.0 | 14.4 | 27.6 | | | | | | 82.8 | 20.7 | 8.3 |
| | total area | 73.2 | 73.2 | 75.0 | 69.1 | | | | | | 290.5 | 72.6 | 2.5 |
| | ischemia injury % | 17.4 | 38.3 | 19.2 | 40.0 | | | | | | | 28.7 | 12.1 |
| | | died | died | died | | | | | | | | | |
| VP017 | total damage area | 32.5 | 18.7 | 11.7 | 15.3 | | | | | | 78.2 | 19.5 | 9.1 |
| | total area | 73.9 | 70.2 | 70.2 | 72.3 | | | | | | 286.6 | 71.6 | 1.8 |
| | ischemia injury % | 44.0 | 26.6 | 16.7 | 21.2 | | | | | | | 27.3 | 12.0 |
| | | died | | | | | | | | | | | |
| VP018 | total damage area | 10.1 | 17.7 | 16.1 | 27.1 | | | | | | 71.0 | 17.7 | 7.1 |
| | total area | 58.7 | 67.8 | 67.7 | 72.1 | | | | | | 266.3 | 66.6 | 5.6 |
| | ischemia injury % | 17.1 | 26.2 | 23.8 | 37.6 | | | | | | | 26.2 | 8.5 |
| | | | | died | died | | | | | | | | |
| VP019 | total damage area | 12.4 | 4.9 | 11.8 | 12.2 | 5.2 | | | | | 46.3 | 9.3 | 3.9 |
| | total area | 62.4 | 62.5 | 64.3 | 64.8 | 74.5 | | | | | 328.5 | 65.7 | 5.0 |
| | ischemia injury % | 19.8 | 7.8 | 18.3 | 18.8 | 6.9 | | | | | | 14.1 | 5.6 |
| | | died | | died | | | | | | | | | |

TABLE 27-continued

| Animal # | | 1 | 2 | 3 | 4 | 5 | 6 | 7 | 8 | 9 | Total | Mean | SD |
|---|---|---|---|---|---|---|---|---|---|---|---|---|---|
| VP020 | total damage area | 28.4 | 3.8 | 7.4 | 23.1 | 23.4 | 13.5 | 29.3 | | | 128.8 | 18.4 | 10.2 |
| | total area | 65.8 | 64.0 | 63.7 | 61.6 | 63.7 | 63.5 | 70.3 | | | 452.7 | 64.7 | 2.8 |
| | ischemia injury % | 43.1 | 5.9 | 11.5 | 37.4 | 36.7 | 21.2 | 41.7 | | | | 28.4 | 15.2 |
| | | died | | | died | died | | | | | | | |
| VP021 | total damage area | 13.0 | 8.3 | 8.4 | 17.0 | 6.8 | 13.7 | | | | 67.1 | 11.2 | 4.0 |
| | total area | 72.3 | 72.8 | 70.4 | 71.8 | 70.3 | 72.4 | | | | 430.1 | 71.7 | 1.1 |
| | ischemia injury % | 17.9 | 11.4 | 11.9 | 23.7 | 9.6 | 18.9 | | | | | 15.6 | 5.5 |
| | | died | | | | | | | | | | | |
| VP022 | total damage area | 12.4 | 5.5 | 15.6 | 12.2 | 26.7 | | | | | 72.4 | 14.5 | 7.8 |
| | total area | 68.4 | 74.1 | 75.5 | 71.0 | 74.5 | | | | | 363.5 | 72.7 | 2.9 |
| | ischemia injury % | 18.2 | 7.4 | 20.6 | 17.2 | 35.8 | | | | | | 19.9 | 5.8 |
| | | | | | | died | | | | | | | |
| VP023 | total damage area | 0.0 | 8.2 | 13.0 | 7.0 | 32.6 | | | | | 60.8 | 12.2 | 12.3 |
| | total area | 73.8 | 69.6 | 75.5 | 70.8 | 81.9 | | | | | 371.5 | 74.3 | 4.9 |
| | ischemia injury % | 0.0 | 11.8 | 17.2 | 9.9 | 39.8 | | | | | | 16.4 | 7.2 |
| | | | | | died | | | | | | | | |
| VP024 | total damage area | 6.2 | 29.8 | 19.9 | 6.9 | | | | | | 62.8 | 15.7 | 11.3 |
| | total area | 68.7 | 71.2 | 70.6 | 70.2 | | | | | | 280.7 | 70.2 | 1.1 |
| | ischemia injury % | 9.0 | 41.9 | 28.2 | 9.8 | | | | | | | 22.2 | 15.8 |
| | | | died | died | | | | | | | | | |
| VP025 | total damage area | 8.6 | 20.6 | 18.8 | 24.6 | | | | | | 72.5 | 18.1 | 6.8 |
| | total area | 68.8 | 71.6 | 69.5 | 71.0 | | | | | | 280.9 | 70.2 | 1.3 |
| | ischemia injury % | 12.5 | 28.7 | 27.0 | 34.6 | | | | | | | 25.8 | 9.4 |
| VP026 | total damage area | 25.4 | 21.7 | 17.4 | 27.5 | 26.0 | | | | | 118.0 | 23.6 | 4.1 |
| | total area | 62.7 | 65.2 | 64.3 | 61.1 | 67.2 | | | | | 320.5 | 64.1 | 2.4 |
| | ischemia injury % | 40.5 | 33.3 | 27.0 | 45.1 | 38.7 | | | | | | 36.8 | 7.9 |
| | | | | | | died | | | | | | | |
| VP027 | total damage area | 19.2 | 11.4 | 31.3 | 24.9 | 16.4 | | | | | 103.3 | 20.7 | 7.7 |
| | total area | 65.9 | 65.0 | 68.4 | 68.7 | 63.9 | | | | | 331.9 | 66.4 | 2.1 |
| | ischemia injury % | 29.2 | 17.6 | 45.7 | 36.3 | 25.7 | | | | | | 31.1 | 11.9 |
| | | died | | died | died | | | | | | | | |
| VP028 | total damage area | 1.7 | 12.2 | 9.5 | 14.3 | | | | | | 37.7 | 9.4 | 55 |
| | total area | 63.9 | 69.2 | 67.5 | 70.7 | | | | | | 271.3 | 67.8 | 2.9 |
| | ischemia injury % | 2.7 | 17.6 | 14.1 | 20.2 | | | | | | | 13.9 | 7.8 |
| VP029 | total damage area | 3.2 | 6.1 | 5.5 | 1.7 | 1.4 | | | | | 18.0 | 3.6 | 2.2 |
| | total area | 66.1 | 67.7 | 64.7 | 60.6 | 60.1 | | | | | 319.1 | 63.8 | 3.4 |
| | ischemia injury % | 4.9 | 9.1 | 8.6 | 2.8 | 2.3 | | | | | | 5.6 | 3.0 |
| VP030 | total damage area | 2.3 | 13.7 | 3.2 | 19.0 | 13.5 | 24.7 | 7.0 | | | 83.3 | 11.9 | 8.3 |
| | total area | 61.1 | 67.4 | 61.3 | 66.8 | 65.8 | 65.8 | 66.0 | | | 454.2 | 64.9 | 2.6 |
| | ischemia injury % | 3.7 | 20.3 | 5.2 | 28.4 | 20.5 | 37.5 | 10.6 | | | | 18.3 | 12.0 |
| VP031 | total damage area | 13.2 | 17.2 | 3.3 | 27.1 | 5.6 | | | | | 66.3 | 13.3 | 9.6 |
| | total area | 71.3 | 71.9 | 72.0 | 70.2 | 68.2 | | | | | 353.5 | 70.7 | 1.6 |
| | ischemia injury % | 18.5 | 23.9 | 4.5 | 38.6 | 8.2 | | | | | | 18.7 | 13.5 |
| | | | | | died | | | | | | | | |
| VP032 | total damage area | 5.6 | 14.0 | 18.9 | 6.8 | | | | | | 45.3 | 11.3 | 6.3 |
| | total area | 63.3 | 67.6 | 67.6 | 60.5 | | | | | | 259.0 | 64.8 | 3.5 |
| | ischemia injury % | 8.8 | 20.8 | 28.0 | 11.2 | | | | | | | 17.5 | 8.8 |

TABLE 27-continued

| Animal # | | 1 | 2 | 3 | 4 | 5 | 6 | 7 | 8 | 9 | Total | Mean | SD |
|---|---|---|---|---|---|---|---|---|---|---|---|---|---|
| VP032 | total damage area | 28.1 | 14.0 | 2.5 | 31.4 | | | | | | 76.0 | 19.0 | 13.4 |
| | total area | 70.2 | 69.2 | 66.3 | 70.3 | | | | | | 276.0 | 69.0 | 1.9 |
| | ischemia injury % | 40.0 | 20.3 | 3.7 | 44.7 | | | | | | | 27.2 | 18.9 |
| VP033 | total damage area | 2.5 | 17.8 | 2.0 | 20.9 | 7.1 | | | | | 50.3 | 10.1 | 8.8 |
| | total area | 65.4 | 67.8 | 64.9 | 67.5 | 60.1 | | | | | 325.6 | 65.1 | 3.1 |
| | ischemia injury % | 3.9 | 26.2 | 3.0 | 31.0 | 11.8 | | | | | | 15.4 | 14.7 |
| VP034 | total damage area | 29.5 | 16.6 | 14.3 | 2.8 | 15.1 | | | | | 78.1 | 15.6 | 9.5 |
| | total area | 72.8 | 69.7 | 69.0 | 75.2 | 73.2 | | | | | 359.9 | 72.0 | 2.6 |
| | ischemia injury % | 40.5 | 23.8 | 20.7 | 3.7 | 20.6 | | | | | | 21.8 | 13.1 |
| | died | | | | | | | | | | | | |
| VP035 | total damage area | 19.2 | 14.5 | 2.0 | 13.2 | | | | | | 48.9 | 12.2 | 7.3 |
| | total area | 66.7 | 63.0 | 65.5 | 62.9 | | | | | | 258.1 | 64.5 | 1.9 |
| | ischemia injury % | 28.8 | 23.0 | 3.0 | 21.0 | | | | | | | 19.0 | 11.1 |
| VP036 | total damage area | 20.8 | 15.5 | 16.8 | 12.5 | 27.0 | | | | | 92.5 | 18.5 | 5.6 |
| | total area | 63.6 | 59.8 | 67.1 | 64.5 | 65.3 | | | | | 320.3 | 64.1 | 2.7 |
| | ischemia injury % | 32.7 | 25.8 | 25.0 | 19.4 | 41.3 | | | | | | 28.9 | 5.4 |
| | died | | | | | died | | | | | | | |
| VP037 | total damage area | 6.0 | 6.7 | 21.1 | 16.5 | 14.3 | 3.9 | | | | 68.4 | 11.4 | 6.9 |
| | total area | 63.1 | 67.9 | 68.7 | 70.0 | 69.1 | 65.2 | | | | 404.1 | 67.4 | 2.7 |
| | ischemia injury % | 9.5 | 9.8 | 30.7 | 23.6 | 20.6 | 6.0 | | | | | 16.9 | 10.5 |
| VP038 | total damage area | 32.1 | 29.5 | 21.3 | 11.7 | | | | | | 94.6 | 23.7 | 9.2 |
| | total area | 76.5 | 73.4 | 71.6 | 67.7 | | | | | | 289.2 | 72.3 | 3.7 |
| | ischemia injury % | 41.9 | 40.2 | 29.8 | 17.3 | | | | | | | 32.3 | 11.4 |
| | died | died | | | | | | | | | | | |
| VP039 | total damage area | 10.8 | 17.8 | 11.5 | 14.3 | 18.1 | | | | | 72.4 | 14.5 | 3.4 |
| | total area | 63.7 | 63.4 | 62.3 | 67.5 | 62.3 | | | | | 319.2 | 63.8 | 2.2 |
| | ischemia injury % | 16.9 | 28.0 | 18.4 | 21.2 | 29.0 | | | | | | 22.7 | 4.9 |
| VP039 | total damage area | 20.6 | 18.3 | 17.8 | 20.2 | | | | | | 76.9 | 19.2 | 1.4 |
| | total are a | 75.4 | 70.8 | 68.6 | 72.1 | | | | | | 286.9 | 71.7 | 2.8 |
| | ischemia injury % | 27.3 | 25.9 | 25.9 | 28.1 | | | | | | | 26.8 | 1.1 |

Table 28. Saline Treated Control Animals. 42 animals were used as the control group. The controls were over a time period, which corresponded with the time period in which the treatment groups were tested. Over all the saline treated group showed a mean ischemic injury percent of 30.5 with a standard deviation of 3.27. This group was used to generate the p-values shown in Tables 22 and 26.

| Animal # | 1 | 2 | 3 | 4 | 5 | 6 | 7 | Total | Mean | SD | CV |
|---|---|---|---|---|---|---|---|---|---|---|---|
| total damage area | 4.27 | 18.66 | 20.3 | 32.3 | | | | 75.59 | 18.90 | 11.51 | 60.89 |
| total area | 60.73 | 66.32 | 67.19 | 69.73 | | | | 263.97 | 65.99 | 3.79 | 5.75 |
| ischemia injury % | 7.03 | 28.14 | 30.21 | 46.41 | | | | | 28.64 | 16.16 | 56.43 |
| total damage area | 13.72 | 20.11 | 29.90 | | | | | 63.73 | 21.24 | 8.15 | 38.36 |
| total area | 69.38 | 63.53 | 65.45 | | | | | 198.36 | 66.12 | 2.98 | 4.51 |
| ischemia injury % | 19.78 | 31.65 | 45.68 | | | | | | 32.13 | 12.97 | 40.37 |
| total damage area | 15.51 | 20.43 | 31.30 | 29.30 | 0.00 | | | 96.54 | 24.14 | 7.44 | 30.83 |
| total area | 70.38 | 66.39 | 70.15 | 66.39 | 68.50 | | | 273.31 | 68.33 | 2.24 | 3.28 |
| ischemia injury % | 22.04 | 30.77 | 44.62 | 44.13 | 0.00 | | | | 35.32 | 10.97 | 31.07 |

-continued

| Animal # | 1 | 2 | 3 | 4 | 5 | 6 | 7 | Total | Mean | SD | CV |
|---|---|---|---|---|---|---|---|---|---|---|---|
| total damage area | 6.31 | 24.09 | 27.49 | 30.65 | 24.44 | | | 112.98 | 22.60 | 9.48 | 41.97 |
| total area | 60.24 | 70.36 | 67.33 | 69.67 | 65.64 | | | 333.24 | 66.65 | 4.05 | 6.07 |
| ischemia injury % | 10.47 | 34.24 | 40.83 | 43.99 | 37.23 | | | | 33.90 | 15.16 | 44.72 |
| total damage area | 7.29 | 22.28 | 21.31 | 18.77 | 18.18 | 10.99 | 29.37 | 128.19 | 18.31 | 7.33 | 40.02 |
| total area | 57.30 | 63.10 | 61.66 | 66.36 | 67.65 | 67.82 | 69.02 | 452.91 | 64.70 | 4.21 | 6.51 |
| ischemia injury % | 12.72 | 35.31 | 34.56 | 28.29 | 26.87 | 16.20 | 42.55 | | 28.30 | 10.48 | 37.03 |
| total damage area | 7.29 | 22.28 | 21.31 | 18.77 | 18.18 | | | 87.83 | 17.57 | 5.99 | 34.12 |
| total area | 57.30 | 63.10 | 61.66 | 66.36 | 67.65 | | | 316.07 | 63.21 | 4.09 | 6.47 |
| ischemia injury % | 12.72 | 35.31 | 34.56 | 28.29 | 26.87 | | | | 27.79 | 10.48 | 37.72 |
| total damage area | 1.42 | 18.51 | 31.80 | 15.05 | 20.78 | | | 87.56 | 17.51 | 10.96 | 62.61 |
| total area | 67.80 | 69.25 | 71.23 | 67.19 | 69.73 | | | 345.20 | 69.04 | 1.60 | 2.32 |
| ischemia injury % | 2.09 | 26.73 | 44.64 | 22.40 | 29.80 | | | | 25.13 | 15.36 | 61.10 |
| total damage area | 13.72 | 20.11 | 29.90 | | | | | 63.73 | 21.24 | 8.15 | 39.36 |
| total area | 69.38 | 63.53 | 65.45 | | | | | 198.36 | 66.12 | 2.98 | 4.51 |
| ischemia injury % | 19.78 | 31.65 | 45.68 | | | | | | 32.37 | 12.97 | 40.06 |
| total damage area | 17.61 | 15.23 | 24.40 | 15.11 | 31.12 | | | 103.47 | 20.69 | 6.95 | 33.56 |
| total area | 65.48 | 66.91 | 66.73 | 65.94 | 68.56 | | | 333.62 | 66.72 | 1.18 | 1.77 |
| ischemia injury % | 26.89 | 22.76 | 36.57 | 22.91 | 45.39 | | | | 30.91 | 9.85 | 31.87 |
| | | | | | | | | | 30.50 | 3.27 | 10.73 |

What is claimed is:

1. A method of reducing an infarction in a subject in need thereof comprising administering Fibrinopeptide A (FPA) to the subject after or during an ischemic event, wherein the FPA comprises SEQ ID NO:2.

2. The method of claim 1, wherein the FPA reduces the amount of infarction present in a mouse Middle cerebral artery occlusion (MCAO) model.

3. The method of claim 2, wherein the infarction is reduced by at least 20%.

4. The method of claim 2, wherein the infarction is reduced by at least 40%.

5. The method of claim 2, wherein the infarction is reduced by at least 60%.

6. The method of claim 2, wherein the infarction is reduced by at least 80%.

7. The method of claim 1, wherein the infarction ratio of the FPA in a mouse MCAO model is at least 1.1.

8. The method of claim 1, wherein the infarction ratio of the FPA in a mouse MCAO model is greater or equal than 1.5.

9. The method of claim 1, wherein the infarction ratio of the FPA in a mouse MCAO model is greater or equal than 2.

10. The method of claim 9, wherein the ratio is determined using mean infarcted volumes.

11. The method of claim 10, wherein the mean infarcted volume in a mouse MCAO model is less than or equal to 90%.

12. The method of claim 10, wherein the mean infarcted volume in a mouse MCAO model is less than or equal to 70%.

13. The method of claim 10, wherein the mean infarcted volume in a mouse MCAO model is less than or equal to 50%.

14. The method of claim 1, wherein the FPA reduces the subject's reperfusion injury.

* * * * *

SEQUENCE LISTING

<160> NUMBER OF SEQ ID NOS: 104

<210> SEQ ID NO 1
<211> LENGTH: 16
<212> TYPE: PRT
<213> ORGANISM: Artificial Sequence
<220> FEATURE:
<223> OTHER INFORMATION: Description of Artificial Sequence:/Note =
      Synthetic Construct

<400> SEQUENCE: 1

Ala Asp Thr Asp Lys Gly Glu Phe Leu Ala Glu Gly Gly Gly Val Arg
 1               5                  10                  15

<210> SEQ ID NO 2
<211> LENGTH: 16
<212> TYPE: PRT
<213> ORGANISM: Artificial Sequence
<220> FEATURE:
<223> OTHER INFORMATION: Description of Artificial Sequence:/Note =
      Synthetic Construct

<400> SEQUENCE: 2

Ala Asp Ser Gly Glu Gly Asp Phe Leu Ala Glu Gly Gly Gly Val Arg
 1               5                  10                  15

<210> SEQ ID NO 3
<211> LENGTH: 17
<212> TYPE: PRT
<213> ORGANISM: Artificial Sequence
<220> FEATURE:
<223> OTHER INFORMATION: Description of Artificial Sequence:/Note =
      Synthetic Construct

```
<400> SEQUENCE: 3

Thr Asp Thr Glu Asp Lys Gly Glu Phe Leu Ser Glu Gly Gly Gly Val
 1               5                  10                  15

Arg

<210> SEQ ID NO 4
<211> LENGTH: 16
<212> TYPE: PRT
<213> ORGANISM: Artificial Sequence
<220> FEATURE:
<223> OTHER INFORMATION: Description of Artificial Sequence:/Note =
      Synthetic Construct

<400> SEQUENCE: 4

Ala Thr Gly Thr Thr Ser Glu Phe Ile Glu Ala Gly Gly Asp Ile Arg
 1               5                  10                  15

<210> SEQ ID NO 5
<211> LENGTH: 18
<212> TYPE: PRT
<213> ORGANISM: Artificial Sequence
<220> FEATURE:
<223> OTHER INFORMATION: Description of Artificial Sequence:/Note =
      Synthetic Construct

<400> SEQUENCE: 5

Thr Asp Pro Asp Ala Asp Glu Gly Glu Phe Leu Ala Glu Gly Gly Gly
 1               5                  10                  15

Val Arg

<210> SEQ ID NO 6
<211> LENGTH: 18
<212> TYPE: PRT
<213> ORGANISM: Artificial Sequence
<220> FEATURE:
<223> OTHER INFORMATION: Description of Artificial Sequence:/Note =
      Synthetic Construct

<400> SEQUENCE: 6

Thr Asp Pro Asp Ala Asp Lys Gly Glu Phe Leu Ala Glu Gly Gly Gly
 1               5                  10                  15

Val Arg

<210> SEQ ID NO 7
<211> LENGTH: 17
<212> TYPE: PRT
<213> ORGANISM: Artificial Sequence
<220> FEATURE:
<223> OTHER INFORMATION: Description of Artificial Sequence:/Note =
      Synthetic Construct

<400> SEQUENCE: 7

Ala Glu Val Gln Asp Lys Gly Glu Phe Leu Ala Glu Gly Gly Gly Val
 1               5                  10                  15

Arg

<210> SEQ ID NO 8
<211> LENGTH: 16
<212> TYPE: PRT
<213> ORGANISM: Artificial Sequence
<220> FEATURE:
<223> OTHER INFORMATION: Description of Artificial Sequence:/Note =
      Synthetic Construct
```

-continued

```
<400> SEQUENCE: 8

Thr Lys Thr Glu Glu Gly Glu Phe Ile Ser Glu Gly Gly Gly Val Arg
1               5                   10                  15

<210> SEQ ID NO 9
<211> LENGTH: 15
<212> TYPE: PRT
<213> ORGANISM: Artificial Sequence
<220> FEATURE:
<223> OTHER INFORMATION: Description of Artificial Sequence:/Note =
      Synthetic Construct

<400> SEQUENCE: 9

Thr Lys Asp Glu Gly Thr Phe Ile Ala Glu Gly Gly Gly Val Arg
1               5                   10                  15

<210> SEQ ID NO 10
<211> LENGTH: 15
<212> TYPE: PRT
<213> ORGANISM: Artificial Sequence
<220> FEATURE:
<223> OTHER INFORMATION: Description of Artificial Sequence:/Note =
      Synthetic Construct

<400> SEQUENCE: 10

Glu Asp Gly Ser Gly Glu Phe Leu Ala Glu Gly Gly Gly Val Arg
1               5                   10                  15

<210> SEQ ID NO 11
<211> LENGTH: 16
<212> TYPE: PRT
<213> ORGANISM: Artificial Sequence
<220> FEATURE:
<223> OTHER INFORMATION: Description of Artificial Sequence:/Note =
      Synthetic Construct

<400> SEQUENCE: 11

Ala Asp Thr Gly Glu Gly Glu Phe Leu Ala Glu Gly Gly Gly Val Arg
1               5                   10                  15

<210> SEQ ID NO 12
<211> LENGTH: 16
<212> TYPE: PRT
<213> ORGANISM: Artificial Sequence
<220> FEATURE:
<223> OTHER INFORMATION: Description of Artificial Sequence:/Note =
      Synthetic Construct

<400> SEQUENCE: 12

Thr Lys Ala Thr Glu Gly Glu Phe Leu Ala Glu Gly Gly Gly Val Arg
1               5                   10                  15

<210> SEQ ID NO 13
<211> LENGTH: 19
<212> TYPE: PRT
<213> ORGANISM: Artificial Sequence
<220> FEATURE:
<223> OTHER INFORMATION: Description of Artificial Sequence:/Note =
      Synthetic Construct

<400> SEQUENCE: 13

Ala Asp Asp Ser Asp Pro Val Gly Gly Glu Phe Leu Ala Glu Gly Gly
1               5                   10                  15

Gly Val Arg

<210> SEQ ID NO 14
```

```
<211> LENGTH: 19
<212> TYPE: PRT
<213> ORGANISM: Artificial Sequence
<220> FEATURE:
<223> OTHER INFORMATION: Description of Artificial Sequence:/Note =
      Synthetic Construct

<400> SEQUENCE: 14

Ala Asp Gly Ser Asp Pro Ala Ser Gly Glu Phe Leu Thr Glu Gly Gly
 1               5                  10                  15

Gly Val Arg

<210> SEQ ID NO 15
<211> LENGTH: 16
<212> TYPE: PRT
<213> ORGANISM: Artificial Sequence
<220> FEATURE:
<223> OTHER INFORMATION: Description of Artificial Sequence:/Note =
      Synthetic Construct

<400> SEQUENCE: 15

Ala Asp Thr Gly Asp Gly Asp Phe Ile Thr Glu Gly Gly Gly Val Arg
 1               5                  10                  15

<210> SEQ ID NO 16
<211> LENGTH: 14
<212> TYPE: PRT
<213> ORGANISM: Artificial Sequence
<220> FEATURE:
<223> OTHER INFORMATION: Description of Artificial Sequence:/Note =
      Synthetic Construct

<400> SEQUENCE: 16

Thr Glu Glu Gly Glu Phe Leu His Glu Gly Gly Gly Val Arg
 1               5                  10

<210> SEQ ID NO 17
<211> LENGTH: 19
<212> TYPE: PRT
<213> ORGANISM: Artificial Sequence
<220> FEATURE:
<223> OTHER INFORMATION: Description of Artificial Sequence:/Note =
      Synthetic Construct

<400> SEQUENCE: 17

Ala Asp Gly Ser Asp Pro Ala Gly Gly Glu Phe Leu Ala Glu Gly Gly
 1               5                  10                  15

Gly Val Arg

<210> SEQ ID NO 18
<211> LENGTH: 16
<212> TYPE: PRT
<213> ORGANISM: Artificial Sequence
<220> FEATURE:
<223> OTHER INFORMATION: Description of Artificial Sequence:/Note =
      Synthetic Construct

<400> SEQUENCE: 18

Thr Asp Thr Lys Glu Ser Asp Phe Leu Ala Glu Gly Gly Gly Val Arg
 1               5                  10                  15

<210> SEQ ID NO 19
<211> LENGTH: 15
<212> TYPE: PRT
<213> ORGANISM: Artificial Sequence
<220> FEATURE:
<223> OTHER INFORMATION: Description of Artificial Sequence:/Note =
```

Synthetic Construct

<400> SEQUENCE: 19

Thr Lys Thr Glu Gly Ser Phe Leu Ala Glu Gly Gly Gly Val Arg
1               5                   10                  15

<210> SEQ ID NO 20
<211> LENGTH: 16
<212> TYPE: PRT
<213> ORGANISM: Artificial Sequence
<220> FEATURE:
<223> OTHER INFORMATION: Description of Artificial Sequence:/Note =
      Synthetic Construct

<400> SEQUENCE: 20

Thr Asn Ser Lys Glu Gly Glu Phe Ile Ala Glu Gly Gly Gly Val Arg
1               5                   10                  15

<210> SEQ ID NO 21
<211> LENGTH: 16
<212> TYPE: PRT
<213> ORGANISM: Artificial Sequence
<220> FEATURE:
<223> OTHER INFORMATION: Description of Artificial Sequence:/Note =
      Synthetic Construct

<400> SEQUENCE: 21

Thr Asn Ser Lys Glu Gly Glu Phe Ile Ala Glu Gly Gly Gly Val Arg
1               5                   10                  15

<210> SEQ ID NO 22
<211> LENGTH: 16
<212> TYPE: PRT
<213> ORGANISM: Artificial Sequence
<220> FEATURE:
<223> OTHER INFORMATION: Description of Artificial Sequence:/Note =
      Synthetic Construct

<400> SEQUENCE: 22

Ser Asp Pro Ala Gly Gly Glu Phe Leu Ala Glu Gly Gly Gly Val Arg
1               5                   10                  15

<210> SEQ ID NO 23
<211> LENGTH: 16
<212> TYPE: PRT
<213> ORGANISM: Artificial Sequence
<220> FEATURE:
<223> OTHER INFORMATION: Description of Artificial Sequence:/Note =
      Synthetic Construct

<400> SEQUENCE: 23

Thr Glu Thr Thr Glu Gly Asp Phe Ile Ala Glu Gly Gly Gly Val Arg
1               5                   10                  15

<210> SEQ ID NO 24
<211> LENGTH: 19
<212> TYPE: PRT
<213> ORGANISM: Artificial Sequence
<220> FEATURE:
<223> OTHER INFORMATION: Description of Artificial Sequence:/Note =
      Synthetic Construct

<400> SEQUENCE: 24

Glu Asp Gly Ser Asp Pro Pro Ser Gly Asp Phe Leu Thr Glu Gly Gly
1               5                   10                  15

Gly Val Arg

<210> SEQ ID NO 25
<211> LENGTH: 16
<212> TYPE: PRT
<213> ORGANISM: Artificial Sequence
<220> FEATURE:
<223> OTHER INFORMATION: Description of Artificial Sequence:/Note =
     Synthetic Construct

<400> SEQUENCE: 25

Ala Asp Thr Gly Glu Gly Asp Phe Leu Ala Glu Gly Gly Gly Val Arg
1               5                   10                  15

<210> SEQ ID NO 26
<211> LENGTH: 16
<212> TYPE: PRT
<213> ORGANISM: Artificial Sequence
<220> FEATURE:
<223> OTHER INFORMATION: Description of Artificial Sequence:/Note =
     Synthetic Construct

<400> SEQUENCE: 26

Val Asp Pro Gly Glu Ser Thr Phe Ile Asp Glu Gly Ala Thr Gly Arg
1               5                   10                  15

<210> SEQ ID NO 27
<211> LENGTH: 16
<212> TYPE: PRT
<213> ORGANISM: Artificial Sequence
<220> FEATURE:
<223> OTHER INFORMATION: Description of Artificial Sequence:/Note =
     Synthetic Construct

<400> SEQUENCE: 27

Thr Asp Gly Lys Glu Gly Glu Phe Ile Ala Glu Gly Gly Gly Val Arg
1               5                   10                  15

<210> SEQ ID NO 28
<211> LENGTH: 16
<212> TYPE: PRT
<213> ORGANISM: Artificial Sequence
<220> FEATURE:
<223> OTHER INFORMATION: Description of Artificial Sequence:/Note =
     Synthetic Construct

<400> SEQUENCE: 28

Ala Gln Asp Gly Lys Thr Thr Phe Glu Lys Glu Gly Gly Gly Gly Arg
1               5                   10                  15

<210> SEQ ID NO 29
<211> LENGTH: 10
<212> TYPE: PRT
<213> ORGANISM: Artificial Sequence
<220> FEATURE:
<223> OTHER INFORMATION: Description of Artificial Sequence:/Note =
     Synthetic Construct

<400> SEQUENCE: 29

Gly Glu Phe Leu Ala Glu Gly Gly Gly Val
1               5                   10

<210> SEQ ID NO 30
<211> LENGTH: 9
<212> TYPE: PRT
<213> ORGANISM: Artificial Sequence
<220> FEATURE:
<223> OTHER INFORMATION: Description of Artificial Sequence:/Note =
     Synthetic Construct

```
<400> SEQUENCE: 30

Gly Glu Phe Leu Ala Glu Gly Gly Gly
 1               5

<210> SEQ ID NO 31
<211> LENGTH: 8
<212> TYPE: PRT
<213> ORGANISM: Artificial Sequence
<220> FEATURE:
<223> OTHER INFORMATION: Description of Artificial Sequence:/Note =
      Synthetic Construct

<400> SEQUENCE: 31

Gly Glu Phe Leu Ala Glu Gly Gly
 1               5

<210> SEQ ID NO 32
<211> LENGTH: 7
<212> TYPE: PRT
<213> ORGANISM: Artificial Sequence
<220> FEATURE:
<223> OTHER INFORMATION: Description of Artificial Sequence:/Note =
      Synthetic Construct

<400> SEQUENCE: 32

Gly Glu Phe Leu Ala Glu Gly
 1               5

<210> SEQ ID NO 33
<211> LENGTH: 6
<212> TYPE: PRT
<213> ORGANISM: Artificial Sequence
<220> FEATURE:
<223> OTHER INFORMATION: Description of Artificial Sequence:/Note =
      Synthetic Construct

<400> SEQUENCE: 33

Gly Glu Phe Leu Ala Glu
 1               5

<210> SEQ ID NO 34
<211> LENGTH: 5
<212> TYPE: PRT
<213> ORGANISM: Artificial Sequence
<220> FEATURE:
<223> OTHER INFORMATION: Description of Artificial Sequence:/Note =
      Synthetic Construct

<400> SEQUENCE: 34

Gly Glu Phe Leu Ala
 1               5

<210> SEQ ID NO 35
<211> LENGTH: 10
<212> TYPE: PRT
<213> ORGANISM: Artificial Sequence
<220> FEATURE:
<223> OTHER INFORMATION: Description of Artificial Sequence:/Note =
      Synthetic Construct

<400> SEQUENCE: 35

Glu Phe Leu Ala Glu Gly Gly Gly Val Arg
 1               5                  10

<210> SEQ ID NO 36
<211> LENGTH: 9
<212> TYPE: PRT
```

```
<213> ORGANISM: Artificial Sequence
<220> FEATURE:
<223> OTHER INFORMATION: Description of Artificial Sequence:/Note =
      Synthetic Construct

<400> SEQUENCE: 36

Phe Leu Ala Glu Gly Gly Gly Val Arg
1               5

<210> SEQ ID NO 37
<211> LENGTH: 8
<212> TYPE: PRT
<213> ORGANISM: Artificial Sequence
<220> FEATURE:
<223> OTHER INFORMATION: Description of Artificial Sequence:/Note =
      Synthetic Construct

<400> SEQUENCE: 37

Leu Ala Glu Gly Gly Gly Val Arg
1               5

<210> SEQ ID NO 38
<211> LENGTH: 7
<212> TYPE: PRT
<213> ORGANISM: Artificial Sequence
<220> FEATURE:
<223> OTHER INFORMATION: Description of Artificial Sequence:/Note =
      Synthetic Construct

<400> SEQUENCE: 38

Ala Glu Gly Gly Gly Val Arg
1               5

<210> SEQ ID NO 39
<211> LENGTH: 6
<212> TYPE: PRT
<213> ORGANISM: Artificial Sequence
<220> FEATURE:
<223> OTHER INFORMATION: Description of Artificial Sequence:/Note =
      Synthetic Construct

<400> SEQUENCE: 39

Glu Gly Gly Gly Val Arg
1               5

<210> SEQ ID NO 40
<211> LENGTH: 5
<212> TYPE: PRT
<213> ORGANISM: Artificial Sequence
<220> FEATURE:
<223> OTHER INFORMATION: Description of Artificial Sequence:/Note =
      Synthetic Construct

<400> SEQUENCE: 40

Glu Phe Leu Ala Glu
1               5

<210> SEQ ID NO 41
<211> LENGTH: 5
<212> TYPE: PRT
<213> ORGANISM: Artificial Sequence
<220> FEATURE:
<223> OTHER INFORMATION: Description of Artificial Sequence:/Note =
      Synthetic Construct

<400> SEQUENCE: 41

Phe Leu Ala Glu Gly
1               5
```

<210> SEQ ID NO 42
<211> LENGTH: 5
<212> TYPE: PRT
<213> ORGANISM: Artificial Sequence
<220> FEATURE:
<223> OTHER INFORMATION: Description of Artificial Sequence:/Note =
      Synthetic Construct

<400> SEQUENCE: 42

Leu Ala Glu Gly Gly
 1               5

<210> SEQ ID NO 43
<211> LENGTH: 5
<212> TYPE: PRT
<213> ORGANISM: Artificial Sequence
<220> FEATURE:
<223> OTHER INFORMATION: Description of Artificial Sequence:/Note =
      Synthetic Construct

<400> SEQUENCE: 43

Ala Glu Gly Gly Gly
 1               5

<210> SEQ ID NO 44
<211> LENGTH: 5
<212> TYPE: PRT
<213> ORGANISM: Artificial Sequence
<220> FEATURE:
<223> OTHER INFORMATION: Description of Artificial Sequence:/Note =
      Synthetic Construct

<400> SEQUENCE: 44

Glu Gly Gly Gly Val
 1               5

<210> SEQ ID NO 45
<211> LENGTH: 5
<212> TYPE: PRT
<213> ORGANISM: Artificial Sequence
<220> FEATURE:
<223> OTHER INFORMATION: Description of Artificial Sequence:/Note =
      Synthetic Construct

<400> SEQUENCE: 45

Gly Gly Gly Val Arg
 1               5

<210> SEQ ID NO 46
<211> LENGTH: 11
<212> TYPE: PRT
<213> ORGANISM: Artificial Sequence
<220> FEATURE:
<223> OTHER INFORMATION: Description of Artificial Sequence:/Note =
      Synthetic Construct

<400> SEQUENCE: 46

Ala Glu Phe Leu Ala Glu Gly Gly Gly Val Arg
 1               5                  10

<210> SEQ ID NO 47
<211> LENGTH: 11
<212> TYPE: PRT
<213> ORGANISM: Artificial Sequence
<220> FEATURE:
<223> OTHER INFORMATION: Description of Artificial Sequence:/Note =
      Synthetic Construct

```
<400> SEQUENCE: 47

Gly Ala Phe Leu Ala Glu Gly Gly Gly Val Arg
1               5                   10

<210> SEQ ID NO 48
<211> LENGTH: 11
<212> TYPE: PRT
<213> ORGANISM: Artificial Sequence
<220> FEATURE:
<223> OTHER INFORMATION: Description of Artificial Sequence:/Note =
      Synthetic Construct

<400> SEQUENCE: 48

Gly Glu Ala Leu Ala Glu Gly Gly Gly Val Arg
1               5                   10

<210> SEQ ID NO 49
<211> LENGTH: 11
<212> TYPE: PRT
<213> ORGANISM: Artificial Sequence
<220> FEATURE:
<223> OTHER INFORMATION: Description of Artificial Sequence:/Note =
      Synthetic Construct

<400> SEQUENCE: 49

Gly Glu Phe Ala Ala Glu Gly Gly Gly Val Arg
1               5                   10

<210> SEQ ID NO 50
<211> LENGTH: 11
<212> TYPE: PRT
<213> ORGANISM: Artificial Sequence
<220> FEATURE:
<223> OTHER INFORMATION: Description of Artificial Sequence:/Note =
      Synthetic Construct

<400> SEQUENCE: 50

Gly Glu Phe Leu Gly Glu Gly Gly Gly Val Arg
1               5                   10

<210> SEQ ID NO 51
<211> LENGTH: 11
<212> TYPE: PRT
<213> ORGANISM: Artificial Sequence
<220> FEATURE:
<223> OTHER INFORMATION: Description of Artificial Sequence:/Note =
      Synthetic Construct

<400> SEQUENCE: 51

Gly Glu Phe Leu Ala Ala Gly Gly Gly Val Arg
1               5                   10

<210> SEQ ID NO 52
<211> LENGTH: 11
<212> TYPE: PRT
<213> ORGANISM: Artificial Sequence
<220> FEATURE:
<223> OTHER INFORMATION: Description of Artificial Sequence:/Note =
      Synthetic Construct

<400> SEQUENCE: 52

Gly Glu Phe Leu Ala Glu Ala Gly Gly Val Arg
1               5                   10

<210> SEQ ID NO 53
<211> LENGTH: 11
```

```
<212> TYPE: PRT
<213> ORGANISM: Artificial Sequence
<220> FEATURE:
<223> OTHER INFORMATION: Description of Artificial Sequence:/Note =
      Synthetic Construct

<400> SEQUENCE: 53

Gly Glu Phe Leu Ala Glu Gly Ala Gly Val Arg
1               5                   10

<210> SEQ ID NO 54
<211> LENGTH: 11
<212> TYPE: PRT
<213> ORGANISM: Artificial Sequence
<220> FEATURE:
<223> OTHER INFORMATION: Description of Artificial Sequence:/Note =
      Synthetic Construct

<400> SEQUENCE: 54

Gly Glu Phe Leu Ala Glu Gly Gly Ala Val Arg
1               5                   10

<210> SEQ ID NO 55
<211> LENGTH: 11
<212> TYPE: PRT
<213> ORGANISM: Artificial Sequence
<220> FEATURE:
<223> OTHER INFORMATION: Description of Artificial Sequence:/Note =
      Synthetic Construct

<400> SEQUENCE: 55

Gly Glu Phe Leu Ala Glu Gly Gly Gly Ala Arg
1               5                   10

<210> SEQ ID NO 56
<211> LENGTH: 16
<212> TYPE: PRT
<213> ORGANISM: Artificial Sequence
<220> FEATURE:
<223> OTHER INFORMATION: Description of Artificial Sequence:/Note =
      Synthetic Construct

<400> SEQUENCE: 56

Ala Asp Thr Asp Lys Gly Glu Phe Leu Ala Glu Gly Gly Gly Val Arg
1               5                   10                  15

<210> SEQ ID NO 57
<211> LENGTH: 9
<212> TYPE: PRT
<213> ORGANISM: Artificial Sequence
<220> FEATURE:
<223> OTHER INFORMATION: Description of Artificial Sequence:/Note =
      Synthetic Construct

<400> SEQUENCE: 57

Arg Pro Pro Gly Phe Ser Pro Phe Arg
1               5

<210> SEQ ID NO 58
<211> LENGTH: 9
<212> TYPE: PRT
<213> ORGANISM: Artificial Sequence
<220> FEATURE:
<223> OTHER INFORMATION: Description of Artificial Sequence:/Note =
      Synthetic Construct

<400> SEQUENCE: 58

Lys Arg Pro Pro Gly Phe Ser Pro Leu
```

```
<210> SEQ ID NO 59
<211> LENGTH: 10
<212> TYPE: PRT
<213> ORGANISM: Artificial Sequence
<220> FEATURE:
<223> OTHER INFORMATION: Description of Artificial Sequence:/Note =
      Synthetic Construct
<220> FEATURE:
<221> NAME/KEY: VARIANT
<222> LOCATION: 1
<223> OTHER INFORMATION: Xaa = D Isomer of arginine
<220> FEATURE:
<221> NAME/KEY: VARIANT
<222> LOCATION: 4
<223> OTHER INFORMATION: Xaa = Hydroxyproline
<220> FEATURE:
<221> NAME/KEY: VARIANT
<222> LOCATION: 6
<223> OTHER INFORMATION: Xaa = Beta[2-Thienyl] Alanine
<220> FEATURE:
<221> NAME/KEY: VARIANT
<222> LOCATION: 8
<223> OTHER INFORMATION: Xaa = Tetra hydro isoquinoline 3' carboxylic
      acid
<220> FEATURE:
<221> NAME/KEY: VARIANT
<222> LOCATION: 9
<223> OTHER INFORMATION: Xaa = Octahydro indo 2' carboxylic acid

<400> SEQUENCE: 59

Xaa Arg Pro Xaa Gly Xaa Ser Xaa Xaa Arg
 1               5                  10

<210> SEQ ID NO 60
<211> LENGTH: 9
<212> TYPE: PRT
<213> ORGANISM: Artificial Sequence
<220> FEATURE:
<223> OTHER INFORMATION: Description of Artificial Sequence:/Note =
      Synthetic Construct
<220> FEATURE:
<221> NAME/KEY: VARIANT
<222> LOCATION: 7
<223> OTHER INFORMATION: Xaa = D Isomer of phenylalanine

<400> SEQUENCE: 60

Arg Pro Pro Gly Phe Ser Xaa Phe Arg
 1               5

<210> SEQ ID NO 61
<211> LENGTH: 8
<212> TYPE: PRT
<213> ORGANISM: Artificial Sequence
<220> FEATURE:
<223> OTHER INFORMATION: Description of Artificial Sequence:/Note =
      Synthetic Construct

<400> SEQUENCE: 61

Arg Pro Pro Gly Phe Ser Pro Phe
 1               5

<210> SEQ ID NO 62
<211> LENGTH: 9
<212> TYPE: PRT
<213> ORGANISM: Artificial Sequence
<220> FEATURE:
<223> OTHER INFORMATION: Description of Artificial Sequence:/Note =
      Synthetic Construct
<220> FEATURE:
<221> NAME/KEY: VARIANT
```

```
<222> LOCATION: 5
<223> OTHER INFORMATION: Xaa = Beta-[2-Thienyl] Alanine
<220> FEATURE:
<221> NAME/KEY: VARIANT
<222> LOCATION: 7
<223> OTHER INFORMATION: Xaa = D Isomer of phenylalanine
<220> FEATURE:
<221> NAME/KEY: VARIANT
<222> LOCATION: 8
<223> OTHER INFORMATION: Xaa = Beta-[2-Thienyl]Alanine

<400> SEQUENCE: 62

Arg Pro Pro Gly Xaa Ser Xaa Xaa Arg
 1               5

<210> SEQ ID NO 63
<211> LENGTH: 11
<212> TYPE: PRT
<213> ORGANISM: Artificial Sequence
<220> FEATURE:
<223> OTHER INFORMATION: Description of Artificial Sequence:/Note =
      Synthetic Construct
<220> FEATURE:
<221> NAME/KEY: VARIANT
<222> LOCATION: 1
<223> OTHER INFORMATION: Xaa = N-Adamantaneacetyl
<220> FEATURE:
<221> NAME/KEY: VARIANT
<222> LOCATION: 2
<223> OTHER INFORMATION: Xaa = D Isomer of arginine
<220> FEATURE:
<221> NAME/KEY: VARIANT
<222> LOCATION: 5
<223> OTHER INFORMATION: Xaa = Hydroxyproline
<220> FEATURE:
<221> NAME/KEY: VARIANT
<222> LOCATION: 7
<223> OTHER INFORMATION: Xaa = Beta-[Thienyl] Alanine
<220> FEATURE:
<221> NAME/KEY: VARIANT
<222> LOCATION: 9
<223> OTHER INFORMATION: Xaa = D Isomer of phenylalanine
<220> FEATURE:
<221> NAME/KEY: VARIANT
<222> LOCATION: 10
<223> OTHER INFORMATION: Xaa = Beta-[2-Thienyl] Alanine

<400> SEQUENCE: 63

Xaa Xaa Arg Pro Xaa Gly Xaa Ser Xaa Xaa Arg
 1               5                  10

<210> SEQ ID NO 64
<211> LENGTH: 11
<212> TYPE: PRT
<213> ORGANISM: Artificial Sequence
<220> FEATURE:
<223> OTHER INFORMATION: Description of Artificial Sequence:/Note =
      Synthetic Construct
<220> FEATURE:
<221> NAME/KEY: VARIANT
<222> LOCATION: 1
<223> OTHER INFORMATION: Xaa = N-Admantanecarbonyl
<220> FEATURE:
<221> NAME/KEY: VARIANT
<222> LOCATION: 2
<223> OTHER INFORMATION: Xaa = D Isomer of arginine
<220> FEATURE:
<221> NAME/KEY: VARIANT
<222> LOCATION: 5
<223> OTHER INFORMATION: Xaa = Hydroxproline
<220> FEATURE:
<221> NAME/KEY: VARIANT
<222> LOCATION: 7
<223> OTHER INFORMATION: Xaa = Tetra hydro isoquinoline 3' carboxylic
      acid
```

```
<220> FEATURE:
<221> NAME/KEY: VARIANT
<222> LOCATION: 9
<223> OTHER INFORMATION: Xaa = D Isomer of phenylalanine
<220> FEATURE:
<221> NAME/KEY: VARIANT
<222> LOCATION: 10
<223> OTHER INFORMATION: Xaa = Tetra hydro isoquinoline 3' carboxylic
      acid

<400> SEQUENCE: 64

Xaa Xaa Arg Pro Xaa Gly Xaa Ser Xaa Xaa Arg
1               5                   10

<210> SEQ ID NO 65
<211> LENGTH: 10
<212> TYPE: PRT
<213> ORGANISM: Artificial Sequence
<220> FEATURE:
<223> OTHER INFORMATION: Description of Artificial Sequence:/Note =
      Synthetic Construct

<400> SEQUENCE: 65

Lys Arg Pro Pro Gly Phe Ser Pro Phe Arg
1               5                   10

<210> SEQ ID NO 66
<211> LENGTH: 11
<212> TYPE: PRT
<213> ORGANISM: Artificial Sequence
<220> FEATURE:
<223> OTHER INFORMATION: Description of Artificial Sequence:/Note =
      Synthetic Construct

<400> SEQUENCE: 66

Met Lys Arg Pro Pro Gly Phe Ser Pro Phe Arg
1               5                   10

<210> SEQ ID NO 67
<211> LENGTH: 10
<212> TYPE: PRT
<213> ORGANISM: Artificial Sequence
<220> FEATURE:
<223> OTHER INFORMATION: Description of Artificial Sequence:/Note =
      Synthetic Construct

<400> SEQUENCE: 67

Lys Arg Pro Ala Gly Phe Ser Pro Phe Arg
1               5                   10

<210> SEQ ID NO 68
<211> LENGTH: 10
<212> TYPE: PRT
<213> ORGANISM: Artificial Sequence
<220> FEATURE:
<223> OTHER INFORMATION: Description of Artificial Sequence:/Note =
      Synthetic Construct

<400> SEQUENCE: 68

Tyr Arg Pro Pro Gly Phe Ser Pro Phe Arg
1               5                   10

<210> SEQ ID NO 69
<211> LENGTH: 9
<212> TYPE: PRT
<213> ORGANISM: Artificial Sequence
<220> FEATURE:
<223> OTHER INFORMATION: Description of Artificial Sequence:/Note =
      Synthetic Construct
```

```
<400> SEQUENCE: 69

Arg Pro Pro Gly Phe Ser Pro Tyr Arg
 1               5

<210> SEQ ID NO 70
<211> LENGTH: 9
<212> TYPE: PRT
<213> ORGANISM: Artificial Sequence
<220> FEATURE:
<223> OTHER INFORMATION: Description of Artificial Sequence:/Note =
      Synthetic Construct

<400> SEQUENCE: 70

Arg Pro Pro Gly Tyr Ser Pro Phe Arg
 1               5

<210> SEQ ID NO 71
<211> LENGTH: 11
<212> TYPE: PRT
<213> ORGANISM: Artificial Sequence
<220> FEATURE:
<223> OTHER INFORMATION: Description of Artificial Sequence:/Note =
      Synthetic Construct

<400> SEQUENCE: 71

Ile Ser Arg Pro Pro Gly Phe Ser Pro Phe Arg
 1               5                  10

<210> SEQ ID NO 72
<211> LENGTH: 10
<212> TYPE: PRT
<213> ORGANISM: Artificial Sequence
<220> FEATURE:
<223> OTHER INFORMATION: Description of Artificial Sequence:/Note =
      Synthetic Construct

<400> SEQUENCE: 72

Lys Arg Pro His Gly Phe Ser Pro Phe Arg
 1               5                  10

<210> SEQ ID NO 73
<211> LENGTH: 9
<212> TYPE: PRT
<213> ORGANISM: Artificial Sequence
<220> FEATURE:
<223> OTHER INFORMATION: Description of Artificial Sequence:/Note =
      Synthetic Construct
<220> FEATURE:
<221> NAME/KEY: VARIANT
<222> LOCATION: 5
<223> OTHER INFORMATION: Xaa = P-Chloro-phenylalanine
<220> FEATURE:
<221> NAME/KEY: VARIANT
<222> LOCATION: 8
<223> OTHER INFORMATION: Xaa = P-Chloro-phenylalanine

<400> SEQUENCE: 73

Arg Pro Pro Gly Xaa Ser Pro Xaa Arg
 1               5

<210> SEQ ID NO 74
<211> LENGTH: 3
<212> TYPE: PRT
<213> ORGANISM: Artificial Sequence
<220> FEATURE:
<223> OTHER INFORMATION: Description of Artificial Sequence:/Note =
      Synthetic Construct
```

```
<400> SEQUENCE: 74

Arg Pro Pro
1

<210> SEQ ID NO 75
<211> LENGTH: 5
<212> TYPE: PRT
<213> ORGANISM: Artificial Sequence
<220> FEATURE:
<223> OTHER INFORMATION: Description of Artificial Sequence:/Note =
      Synthetic Construct

<400> SEQUENCE: 75

Arg Pro Pro Gly Phe
1               5

<210> SEQ ID NO 76
<211> LENGTH: 6
<212> TYPE: PRT
<213> ORGANISM: Artificial Sequence
<220> FEATURE:
<223> OTHER INFORMATION: Description of Artificial Sequence:/Note =
      Synthetic Construct

<400> SEQUENCE: 76

Arg Pro Pro Gly Phe Ser
1               5

<210> SEQ ID NO 77
<211> LENGTH: 7
<212> TYPE: PRT
<213> ORGANISM: Artificial Sequence
<220> FEATURE:
<223> OTHER INFORMATION: Description of Artificial Sequence:/Note =
      Synthetic Construct

<400> SEQUENCE: 77

Arg Pro Pro Gly Phe Ser Pro
1               5

<210> SEQ ID NO 78
<211> LENGTH: 6
<212> TYPE: PRT
<213> ORGANISM: Artificial Sequence
<220> FEATURE:
<223> OTHER INFORMATION: Description of Artificial Sequence:/Note =
      Synthetic Construct

<400> SEQUENCE: 78

Pro Pro Gly Phe Ser Pro
1               5

<210> SEQ ID NO 79
<211> LENGTH: 8
<212> TYPE: PRT
<213> ORGANISM: Artificial Sequence
<220> FEATURE:
<223> OTHER INFORMATION: Description of Artificial Sequence:/Note =
      Synthetic Construct

<400> SEQUENCE: 79

Pro Pro Gly Phe Ser Pro Phe Arg
1               5

<210> SEQ ID NO 80
<211> LENGTH: 10
<212> TYPE: PRT
```

```
<213> ORGANISM: Artificial Sequence
<220> FEATURE:
<223> OTHER INFORMATION: Description of Artificial Sequence:/Note =
      Synthetic Construct
<220> FEATURE:
<221> NAME/KEY: VARIANT
<222> LOCATION: 1
<223> OTHER INFORMATION: Xaa = D Isomer of arginine
<220> FEATURE:
<221> NAME/KEY: VARIANT
<222> LOCATION: 4
<223> OTHER INFORMATION: Xaa = Hydroxyproline
<220> FEATURE:
<221> NAME/KEY: VARIANT
<222> LOCATION: 6
<223> OTHER INFORMATION: Xaa = Tetra hydro isoquinoline 3' carboxylic
      acid
<220> FEATURE:
<221> NAME/KEY: VARIANT
<222> LOCATION: 8
<223> OTHER INFORMATION: Xaa = D Isomer of alpha-amino-2-indanacetic
      acid
<220> FEATURE:
<221> NAME/KEY: VARIANT
<222> LOCATION: 9
<223> OTHER INFORMATION: Xaa = Octahydro indo 2' carboxylic acid

<400> SEQUENCE: 80

Xaa Arg Pro Xaa Gly Xaa Ser Xaa Xaa Arg
 1               5                  10

<210> SEQ ID NO 81
<211> LENGTH: 10
<212> TYPE: PRT
<213> ORGANISM: Artificial Sequence
<220> FEATURE:
<223> OTHER INFORMATION: Description of Artificial Sequence:/Note =
      Synthetic Construct
<220> FEATURE:
<221> NAME/KEY: VARIANT
<222> LOCATION: 1
<223> OTHER INFORMATION: Xaa = D Isomer of arginine
<220> FEATURE:
<221> NAME/KEY: VARIANT
<222> LOCATION: 4
<223> OTHER INFORMATION: Xaa = Hydroxyproline
<220> FEATURE:
<221> NAME/KEY: VARIANT
<222> LOCATION: 6
<223> OTHER INFORMATION: Xaa = Alpha-amino-2-indanacetic acid
<220> FEATURE:
<221> NAME/KEY: VARIANT
<222> LOCATION: 8
<223> OTHER INFORMATION: Xaa = D Isomer of alpha-amino-2-indanacetic
      acid
<220> FEATURE:
<221> NAME/KEY: VARIANT
<222> LOCATION: 9
<223> OTHER INFORMATION: Xaa = Octahydro indo 2' carboxylic acid

<400> SEQUENCE: 81

Xaa Arg Pro Xaa Gly Xaa Ser Xaa Xaa Arg
 1               5                  10

<210> SEQ ID NO 82
<211> LENGTH: 11
<212> TYPE: PRT
<213> ORGANISM: Artificial Sequence
<220> FEATURE:
<223> OTHER INFORMATION: Description of Artificial Sequence:/Note =
      Synthetic Construct

<400> SEQUENCE: 82

Ile Ser Arg Pro Pro Gly Phe Ser Pro Phe Arg
```

```
<210> SEQ ID NO 83
<211> LENGTH: 10
<212> TYPE: PRT
<213> ORGANISM: Artificial Sequence
<220> FEATURE:
<223> OTHER INFORMATION: Description of Artificial Sequence:/Note =
      Synthetic Construct

<400> SEQUENCE: 83

Lys Arg Pro Pro Gly Trp Ser Pro Leu Arg
1               5                   10

<210> SEQ ID NO 84
<211> LENGTH: 9
<212> TYPE: PRT
<213> ORGANISM: Artificial Sequence
<220> FEATURE:
<223> OTHER INFORMATION: Description of Artificial Sequence:/Note =
      Synthetic Construct

<400> SEQUENCE: 84

Arg Pro Pro Gly Phe Thr Pro Phe Arg
1               5

<210> SEQ ID NO 85
<211> LENGTH: 9
<212> TYPE: PRT
<213> ORGANISM: Artificial Sequence
<220> FEATURE:
<223> OTHER INFORMATION: Description of Artificial Sequence:/Note =
      Synthetic Construct

<400> SEQUENCE: 85

Arg Pro Pro Gly Phe Ser Pro Phe Arg
1               5

<210> SEQ ID NO 86
<211> LENGTH: 10
<212> TYPE: PRT
<213> ORGANISM: Artificial Sequence
<220> FEATURE:
<223> OTHER INFORMATION: Description of Artificial Sequence:/Note =
      Synthetic Construct

<400> SEQUENCE: 86

Asp Arg Val Tyr Ile His Pro Phe His Leu
1               5                   10

<210> SEQ ID NO 87
<211> LENGTH: 8
<212> TYPE: PRT
<213> ORGANISM: Artificial Sequence
<220> FEATURE:
<223> OTHER INFORMATION: Description of Artificial Sequence:/Note =
      Synthetic Construct

<400> SEQUENCE: 87

Asp Arg Val Tyr Ile His Pro Phe
1               5

<210> SEQ ID NO 88
<211> LENGTH: 7
<212> TYPE: PRT
<213> ORGANISM: Artificial Sequence
<220> FEATURE:
<223> OTHER INFORMATION: Description of Artificial Sequence:/Note =
```

Synthetic Construct

<400> SEQUENCE: 88

Arg Val Tyr Ile His Pro Phe
1               5

<210> SEQ ID NO 89
<211> LENGTH: 360
<212> TYPE: PRT
<213> ORGANISM: Artificial Sequence
<220> FEATURE:
<223> OTHER INFORMATION: Description of Artificial Sequence:/Note =
      Synthetic Construct

<400> SEQUENCE: 89

Gly Asn Ser Thr Leu Ala Thr Thr Ser Lys Asn Ile Thr Ser Gly Leu
1               5                   10                  15

His Phe Gly Leu Val Asn Ile Ser Gly Asn Asn Glu Ser Thr Leu Asn
                20                  25                  30

Cys Ser Gln Lys Pro Ser Asp Lys His Leu Asp Ala Ile Pro Ile Leu
            35                  40                  45

Tyr Tyr Ile Ile Phe Val Ile Gly Phe Leu Asn Ile Val Val Val Thr
50                  55                  60

Leu Phe Cys Cys Gln Lys Gly Pro Lys Val Ser Ser Ile Tyr Ile
65                  70                  75                  80

Phe Asn Leu Ala Val Ala Asp Leu Leu Leu Ala Thr Leu Pro Leu
                85                  90                  95

Trp Ala Thr Tyr Tyr Ser Tyr Arg Tyr Asp Trp Leu Phe Gly Pro Val
                100                 105                 110

Met Cys Lys Val Phe Gly Ser Phe Leu Thr Leu Asn Met Phe Ala Ser
                115                 120                 125

Ile Phe Phe Ile Thr Cys Met Ser Val Asp Arg Tyr Gln Ser Val Ile
130                 135                 140

Tyr Pro Phe Leu Ser Gln Arg Arg Asn Pro Trp Gln Ala Ser Tyr Ile
145                 150                 155                 160

Val Pro Leu Val Trp Cys Met Ala Cys Leu Ser Ser Leu Pro Thr Phe
                165                 170                 175

Tyr Phe Arg Asp Val Arg Thr Ile Glu Tyr Leu Gly Val Asn Ala Cys
                180                 185                 190

Ile Met Ala Phe Pro Pro Glu Lys Tyr Ala Gln Trp Ser Ala Gly Ile
                195                 200                 205

Ala Leu Met Lys Asn Ile Leu Gly Phe Ile Ile Pro Leu Ile Phe Ile
210                 215                 220

Ala Thr Cys Tyr Phe Gly Ile Arg Lys His Leu Leu Lys Thr Asn Ser
225                 230                 235                 240

Tyr Gly Lys Asn Arg Ile Thr Arg Asp Gln Val Leu Lys Met Ala Ala
                245                 250                 255

Ala Val Val Leu Ala Phe Ile Ile Cys Trp Leu Pro Phe His Val Leu
                260                 265                 270

Thr Phe Leu Asp Ala Leu Ala Trp Met Gly Val Ile Asn Ser Cys Glu
                275                 280                 285

Val Ile Ala Val Ile Asp Leu Ala Leu Pro Phe Ala Ile Leu Leu Gly
                290                 295                 300

Phe Thr Asn Ser Cys Val Asn Pro Phe Leu Tyr Cys Phe Val Gly Asn
305                 310                 315                 320

Arg Phe Gln Gln Lys Leu Arg Ser Val Phe Arg Val Pro Ile Thr Trp

```
                        325                 330                 335
Leu Gln Gly Lys Arg Glu Ser Met Ser Cys Arg Lys Ser Ser Ser Leu
            340                 345                 350

Arg Glu Met Glu Thr Phe Val Ser
        355                 360

<210> SEQ ID NO 90
<211> LENGTH: 9
<212> TYPE: PRT
<213> ORGANISM: Artificial Sequence
<220> FEATURE:
<223> OTHER INFORMATION: Description of Artificial Sequence:/Note =
      Synthetic Construct
<220> FEATURE:
<221> NAME/KEY: VARIANT
<222> LOCATION: 3
<223> OTHER INFORMATION: Xaa = Hydroxyproline
<220> FEATURE:
<221> NAME/KEY: VARIANT
<222> LOCATION: 5
<223> OTHER INFORMATION: Xaa = Beta - [2-Thienyl] alanine
<220> FEATURE:
<221> NAME/KEY: VARIANT
<222> LOCATION: 8
<223> OTHER INFORMATION: Xaa = Tyr (Me)
<220> FEATURE:
<221> NAME/KEY: VARIANT
<222> LOCATION: 9
<223> OTHER INFORMATION: Xaa = psi (CH2NH) -Arginine

<400> SEQUENCE: 90

Arg Pro Xaa Gly Xaa Ser Pro Xaa Xaa
 1               5

<210> SEQ ID NO 91
<211> LENGTH: 9
<212> TYPE: PRT
<213> ORGANISM: Artificial Sequence
<220> FEATURE:
<223> OTHER INFORMATION: Description of Artificial Sequence:/Note =
      Synthetic Construct
<220> FEATURE:
<221> NAME/KEY: VARIANT
<222> LOCATION: 1
<223> OTHER INFORMATION: Xaa = 7-methoxycoumarin-4-acetyl-arginine
<220> FEATURE:
<221> NAME/KEY: VARIANT
<222> LOCATION: 9
<223> OTHER INFORMATION: Xaa = 2,4 dinitrophenyl lysine

<400> SEQUENCE: 91

Xaa Pro Pro Gly Phe Ser Ala Phe Xaa
 1               5               9

<210> SEQ ID NO 92
<211> LENGTH: 10
<212> TYPE: PRT
<213> ORGANISM: Artificial Sequence
<220> FEATURE:
<223> OTHER INFORMATION: Description of Artificial Sequence:/Note =
      Synthetic Construct
<220> FEATURE:
<221> NAME/KEY: VARIANT
<222> LOCATION: 1
<223> OTHER INFORMATION: Xaa = D isomer of arginine
<220> FEATURE:
<221> NAME/KEY: VARIANT
<222> LOCATION: 4
<223> OTHER INFORMATION: Xaa = Hydroxyproline
<220> FEATURE:
<221> NAME/KEY: VARIANT
<222> LOCATION: 8
```

```
<223> OTHER INFORMATION: Xaa = D isomer of phenylalanine

<400> SEQUENCE: 92

Xaa Arg Pro Xaa Gly Phe Ser Xaa Leu Arg
 1               5                   10

<210> SEQ ID NO 93
<211> LENGTH: 10
<212> TYPE: PRT
<213> ORGANISM: Artificial Sequence
<220> FEATURE:
<223> OTHER INFORMATION: Description of Artificial Sequence:/Note =
      Synthetic Construct
<220> FEATURE:
<221> NAME/KEY: VARIANT
<222> LOCATION: 1
<223> OTHER INFORMATION: Xaa = D isomer of arginine
<220> FEATURE:
<221> NAME/KEY: VARIANT
<222> LOCATION: 4
<223> OTHER INFORMATION: Xaa = Hydroxyproline
<220> FEATURE:
<221> NAME/KEY: VARIANT
<222> LOCATION: 8
<223> OTHER INFORMATION: Xaa = D isomer of phenylalanine

<400> SEQUENCE: 93

Xaa Arg Pro Xaa Gly Phe Ser Xaa Phe Arg
 1               5                   10

<210> SEQ ID NO 94
<211> LENGTH: 10
<212> TYPE: PRT
<213> ORGANISM: Artificial Sequence
<220> FEATURE:
<223> OTHER INFORMATION: Description of Artificial Sequence:/Note =
      Synthetic Construct
<220> FEATURE:
<221> NAME/KEY: VARIANT
<222> LOCATION: 1
<223> OTHER INFORMATION: Xaa = D isomer of arginine
<220> FEATURE:
<221> NAME/KEY: VARIANT
<222> LOCATION: 4
<223> OTHER INFORMATION: Xaa = Hydroxyproline
<220> FEATURE:
<221> NAME/KEY: VARIANT
<222> LOCATION: 6
<223> OTHER INFORMATION: Xaa = Beta-[2-Thienyl]alanine
<220> FEATURE:
<221> NAME/KEY: VARIANT
<222> LOCATION: 8
<223> OTHER INFORMATION: Xaa = D isomer of phenylalanine
<220> FEATURE:
<221> NAME/KEY: VARIANT
<222> LOCATION: 9
<223> OTHER INFORMATION: Xaa = Beta-[2-Thienyl]alanine

<400> SEQUENCE: 94

Xaa Arg Pro Xaa Gly Xaa Ser Xaa Xaa Arg
 1               5                   10

<210> SEQ ID NO 95
<211> LENGTH: 9
<212> TYPE: PRT
<213> ORGANISM: Artificial Sequence
<220> FEATURE:
<223> OTHER INFORMATION: Description of Artificial Sequence:/Note =
      Synthetic Construct
<220> FEATURE:
<221> NAME/KEY: VARIANT
<222> LOCATION: 1
<223> OTHER INFORMATION: Xaa = Kallidin H-lysine
```

```
<400> SEQUENCE: 95

Xaa Arg Pro Pro Gly Phe Ser Pro Leu
1               5

<210> SEQ ID NO 96
<211> LENGTH: 11
<212> TYPE: PRT
<213> ORGANISM: Artificial Sequence
<220> FEATURE:
<223> OTHER INFORMATION: Description of Artificial Sequence:/Note =
      Synthetic Construct

<400> SEQUENCE: 96

Ala Glu Phe Leu Ala Glu Gly Gly Gly Pro Arg
1               5                   10

<210> SEQ ID NO 97
<211> LENGTH: 11
<212> TYPE: PRT
<213> ORGANISM: Artificial Sequence
<220> FEATURE:
<223> OTHER INFORMATION: Description of Artificial Sequence:/Note =
      Synthetic Construct

<400> SEQUENCE: 97

Gly Glu Phe Leu Ala Glu Gly Gly Gly Pro Arg
1               5                   10

<210> SEQ ID NO 98
<211> LENGTH: 7
<212> TYPE: PRT
<213> ORGANISM: Artificial Sequence
<220> FEATURE:
<223> OTHER INFORMATION: Description of Artificial Sequence:/Note =
      Synthetic Construct

<400> SEQUENCE: 98

Ala Glu Gly Gly Gly Pro Arg
1               5

<210> SEQ ID NO 99
<211> LENGTH: 5
<212> TYPE: PRT
<213> ORGANISM: Artificial Sequence
<220> FEATURE:
<223> OTHER INFORMATION: Description of Artificial Sequence:/Note =
      Synthetic Construct

<400> SEQUENCE: 99

Gly Gly Gly Pro Arg
1               5

<210> SEQ ID NO 100
<211> LENGTH: 11
<212> TYPE: PRT
<213> ORGANISM: Artificial Sequence
<220> FEATURE:
<223> OTHER INFORMATION: Description of Artificial Sequence:/Note =
      Synthetic Construct

<400> SEQUENCE: 100

Phe Glu Phe Leu Ala Glu Gly Gly Gly Val Arg
1               5                   10

<210> SEQ ID NO 101
<211> LENGTH: 6
```

```
-continued

<212> TYPE: PRT
<213> ORGANISM: Artificial Sequence
<220> FEATURE:
<223> OTHER INFORMATION: Description of Artificial Sequence:/Note =
      Synthetic Construct

<400> SEQUENCE: 101

Ala Gly Gly Gly Val Arg
 1               5

<210> SEQ ID NO 102
<211> LENGTH: 5
<212> TYPE: PRT
<213> ORGANISM: Artificial Sequence
<220> FEATURE:
<223> OTHER INFORMATION: Description of Artificial Sequence:/Note =
      Synthetic Construct

<400> SEQUENCE: 102

Phe Gly Gly Val Arg
 1               5

<210> SEQ ID NO 103
<211> LENGTH: 4
<212> TYPE: PRT
<213> ORGANISM: Artificial Sequence
<220> FEATURE:
<223> OTHER INFORMATION: Description of Artificial Sequence:/Note =
      Synthetic Construct

<400> SEQUENCE: 103

Ala Gly Val Arg
 1

<210> SEQ ID NO 104
<211> LENGTH: 4
<212> TYPE: PRT
<213> ORGANISM: Artificial Sequence
<220> FEATURE:
<223> OTHER INFORMATION: Description of Artificial Sequence:/Note =
      Synthetic Construct

<400> SEQUENCE: 104

Phe Gly Val Arg
 1
```